US011515003B2

(12) United States Patent
Sun et al.

(10) Patent No.: US 11,515,003 B2
(45) Date of Patent: Nov. 29, 2022

(54) COPY NUMBER ALTERATION AND REFERENCE GENOME MAPPING

(71) Applicant: Sequenom, Inc., San Diego, CA (US)

(72) Inventors: Youting Sun, San Diego, CA (US); Sung Kyun Kim, San Diego, CA (US); Mathias Ehrich, San Diego, CA (US); Christopher Ellison, San Diego, CA (US); Taylor Jensen, San Diego, CA (US); Amin Mazloom, San Diego, CA (US)

(73) Assignee: Sequenom, Inc., San Diego, CA (US)

(*) Notice: Subject to any disclaimer, the term of this patent is extended or adjusted under 35 U.S.C. 154(b) by 947 days.

(21) Appl. No.: 15/661,942

(22) Filed: Jul. 27, 2017

(65) Prior Publication Data

US 2018/0032666 A1 Feb. 1, 2018

Related U.S. Application Data

(60) Provisional application No. 62/481,528, filed on Apr. 4, 2017, provisional application No. 62/367,554, filed on Jul. 27, 2016.

(51) Int. Cl.
*G16B 20/10* (2019.01)
*G16B 20/00* (2019.01)
*G16B 20/20* (2019.01)
*G16B 10/00* (2019.01)

(52) U.S. Cl.
CPC ............ *G16B 20/10* (2019.02); *G16B 20/00* (2019.02); *G16B 20/20* (2019.02); *G16B 10/00* (2019.02)

(58) Field of Classification Search
None
See application file for complete search history.

(56) References Cited

U.S. PATENT DOCUMENTS

| | | |
|---|---|---|
| 6,927,028 B2 | 8/2005 | Dennis et al. |
| 2005/0112590 A1 | 5/2005 | Boom et al. |
| 2009/0317818 A1 | 12/2009 | Ehrich et al. |
| 2010/0105049 A1 | 4/2010 | Ehrich et al. |
| 2011/0224087 A1 | 9/2011 | Quake et al. |
| 2013/0012399 A1 | 1/2013 | Myers et al. |
| 2013/0288244 A1 | 10/2013 | Deciu et al. |
| 2013/0338933 A1 | 12/2013 | Deciu et al. |
| 2014/0180594 A1 | 6/2014 | Kim et al. |

FOREIGN PATENT DOCUMENTS

| | | |
|---|---|---|
| WO | 2006/056480 A2 | 6/2006 |
| WO | 2007/140417 A2 | 12/2007 |
| WO | 2007/147063 A2 | 12/2007 |
| WO | 2009/032779 A2 | 3/2009 |
| WO | 2009/032781 A2 | 3/2009 |
| WO | 2010/033639 A2 | 3/2010 |
| WO | 2011/034631 A1 | 3/2011 |
| WO | 2011/143659 A2 | 11/2011 |
| WO | 2013/052907 A2 | 4/2013 |
| WO | 2013/052913 A2 | 4/2013 |
| WO | 2013/055817 A1 | 4/2013 |
| WO | 2013/109981 A1 | 7/2013 |
| WO | 2013/177086 A1 | 11/2013 |
| WO | 2013/192562 A1 | 12/2013 |
| WO | 2014/055774 A1 | 4/2014 |
| WO | 2014/116598 A2 | 7/2014 |
| WO | 2014/190286 A2 | 11/2014 |
| WO | 2014/205401 A1 | 12/2014 |
| WO | 2015/051163 A2 | 4/2015 |
| WO | 2015/054080 A1 | 4/2015 |
| WO | 2015/138774 A1 | 9/2015 |
| WO | 2015/183872 A1 | 12/2015 |
| WO | 2016/019042 A2 | 2/2016 |
| WO | 2016/057901 A1 | 4/2016 |

OTHER PUBLICATIONS

Deutsch, Samuel, et al. "Detection of aneuploidies by paralogous sequence quantification." Journal of Medical Genetics 41.12 (2004): 908-915.*

Klambauer, Günter, et al. "cn. MOPS: mixture of Poissons for discovering copy number variations in next-generation sequencing data with a low false discovery rate." Nucleic acids research 40.9 (2012): e69-e69.*

Ringnér, Markus. "What is principal component analysis?." Nature biotechnology 26.3 (2008): 303-304.*

Wellcome Trust Case Control Consortium. "Genome-wide association study of copy number variation in 16,000 cases of eight common diseases and 3,000 shared controls." Nature 464.7289 (2010): 713, 25 pages plus 137 pages of Supplementary Materials for 162 pages total.*

Alkan, C. et al., "Personalized Copy-Number and Segmental Duplication Maps using Next-Generation Sequencing", Nat. Genet., 41(10):1061-1067 (2009).

(Continued)

*Primary Examiner* — G Steven Vanni
(74) *Attorney, Agent, or Firm* — Kilpatrick Townsend & Stockton LLP

(57) ABSTRACT

Technology provided herein relates in part to methods, processes, machines and apparatuses for non-invasive assessment of genomic nucleic acid instability and genomic nucleic acid stability. The method comprises providing a set of genomic portions each coupled to a copy number alteration quantification for a test sample, wherein the genomic portions comprises portions of a reference genome to which sequence reads obtained for nucleic acid from a test sample obtained from the subject have been mapped, and the copy number alteration quantification coupled to each genomic portion has been determined from a quantification of sequence reads mapped to the genomic portion; and determining, by a computing device, presence or absence of genomic instability for the subject according to the copy number alteration quantifications coupled to the genomic portions.

24 Claims, 25 Drawing Sheets

(56) References Cited

OTHER PUBLICATIONS

Chan, K.C. et al., "Size Distributions of Maternal and Fetal DNA in Maternal Plasma", Clinical Chemistry, 50(1):88-92 (2004).
De Maesschalck, R. et al., The Mahalanobis distance, Chemometrics and Intelligent Laboratory Systems 50:1-18 (2000).
Dowdy and Wearden, "Statistics for Research," Wley, ISBN 0471-08602-9:230 (1983).
Haar, A., "On the Theory of Orthogonal Function Systems", Matt. Ann., 69:331-371 (1910).
Homer, N. et al., "BFAST: An Alignment Tool for Large Scale Genome Resequencing", PLoS One, 4(11):e7767 (2009) 10 pages.
Hsu, L. et al., "Denoising array-based comparative genomic hybridization data using wavelets", Biostatistics, 6(2):211-226 (2005).
Jensen, T. et al., High-Throughput Massively Parallel Sequencing for Fetal Aneuploidy Detection from Maternal Plasma, *PLoS ONE* 8(3):e57381 (2013).
Langmead, B et al., "Ultrafast and memory-efficient alignment of short DNA sequences to the human genome", Genome Biology, 10(3):25.1-25.10 (2009).
Leek, J. and Storey, J., "Capturing Heterogeneity in Gene Expression Studies by Surrogate Variable Analysis", PLoS Genet., 3(9):1724-1735 (2007).
Lefkowitz, R et al., "Clinical validation of noninvasive prenatal test for genomewide detection of fetal copy number variants", Am. J. Obstet. Gynecol., 215:227.e1-16 (2016).
Li, R., et al., "SOAP2: an improved ultrafast tool for short read alignment", Bioinformatics, 25(15):1966-1967 (2009).
Li, H. and Durbin, R., "Fast and accurate short read alignment with Burrows-Wheeler transform", Bioinformatics, 25(14): 1754-1760 (2009).
Lo, Y., "Recent Advances in Fetal Nucleic Acids in Maternal Plasma", J. Histochem. Cytochem., 53(3):293-296 (2005).
Lo, Y.M. et al., "Maternal Plasma DNA Sequencing Reveals the Genome-Wide Genetic and Mutational Profile of the Fetus", Science Translational Medicine, 2(61):1-13 (2010).
Nguyen, N. et al., "Denoising of Array-Based DNA Copy Number Data Using the Dual-tree Complex Wavelet Transform", Proceedings of the 7th IEEE International Conference, Boston MA, on Oct. 14-17, 2007, pp. 137-144.
Olshen, A. et al., "Circular binary segmentation for the analysis of array-based DNA copy number data", Biostatistics, 5(4):557-572 (2004).
Palomaki, G. et al., "DNA sequencing of maternal plasma reliably identifies trisomy 18 and trisomy 13 as well as Down syndrome: an international collaborative study", Genet. Med., 14(3):296-305 (2012).
Price, A. et al., "Principal Components Analysis Corrects for Stratification in Genome-wide Association Studies", Nature Genetics, 38(8):904-909 (2006).
Rizk, G. and Lavenier, D., "GASSST: global alignment short sequence search tool", Bioinformatics, 26(20):2534-2540 (2010).
Sambrook, J. and Russell, D., Molecular Cloning: A Laboratory Manual 3rd ed., vol. 1, 2001.
Strachan, T., The Human Genome, BIO Scientific Publishers, 1992.
Venkatraman, E.S., "A faster circular binary segmentation algorithm for the analysis of array CGH data", Bioinformatics, 23(6):657-663 (2007).
Wang, Y. and Wang, S., "A Novel Stationary Wavelet Denoising Algorithm for Array-Based DNA Copy No. Data", Int. J. Bioinformatics Research and Applications, 3(2):206-222 (2007).
Zhao, C et al., Detection of Fetal Subchromosomal Abnormalities by Sequencing Circulating Cell-Free DNA from Maternal Plasma, Clin. Chem., 61(4):608-616 (2015).

\* cited by examiner

COPY NUMBER ALTERATION AND REFERENCE GENOME MAPPING

RELATED PATENT APPLICATION

This application claims the benefit of U.S. provisional patent application No. 62/367,554, filed on Jul. 27, 2016 and U.S. provisional patent application No. 62/481,528, filed Apr. 4, 2017. The entire contents of the foregoing provisional patent applications are incorporated herein in their entirety for all purposes.

FIELD

Technology provided herein relates in part to methods, machines and apparatuses for non-invasive assessment of genomic nucleic acid instability and genomic nucleic acid stability.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on 24 chromosomes (i.e., 22 autosomes, an X chromosome and a Y chromosome; see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations and/or genetic alterations. Certain genetic variations and/or genetic alterations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations and/or genetic alterations (e.g., copy number alterations, copy number variations, single nucleotide alterations, single nucleotide variations, chromosome alterations, translocations, deletions, insertions, and the like) or variances can lead to diagnosis of, or determining predisposition to, a particular medical condition. Identifying a genetic variance can result in facilitating a medical decision and/or employing a helpful medical procedure. In certain embodiments, identification of one or more genetic variations and/or genetic alterations involves the analysis of circulating cell-free nucleic acid. Circulating cell-free nucleic acid (CCF-NA), such as circulating cell-free DNA (CCF-DNA) for example, is composed of DNA fragments that originate from cell death and circulate in peripheral blood. High concentrations of CCF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

SUMMARY

Provided herein are automated genomic instability classification processes. Such processes are useful for determining whether genomic nucleic acid for a sample from a subject has genomic nucleic acid instability or genomic nucleic acid stability as determined by the presence, absence, or abundance of copy number alterations.

Provided herein is a method of determining presence or absence of genomic instability for a test subject, comprising providing a set of genomic portions each coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion; and determining, by a computing device, presence or absence of genomic instability for the test subject according to the copy number alteration quantifications coupled to the genomic portions.

In certain aspects, a genomic instability classification process includes providing a set of genomic portions of a reference genome to which sequence reads obtained for sample nucleic acid from a subject have been mapped, and for which the sequence reads mapped to the genomic portions have been quantified; adjusting the quantified sequence reads for each of the genomic portions by an adjustment process that reduces experimental, biological and/or technical bias, thereby providing an adjusted quantification of sequence reads for each of the genomic portions; and generating a genomic instability classification for the test sample according to the adjusted quantification of sequence reads for the genomic portions. In some embodiments, genomic portions are filtered or otherwise modified to reduce technical, biological and/or experimental bias. In some embodiments, the generating includes modifying the adjusted quantification of sequence reads according to a baseline adjusted quantification of sequence reads for each of the genomic portions, thereby providing a modified product or absolute value of a modified product for each of the genomic portions. The modified product or absolute value of a modified product for each of the genomic portions sometimes is generated by subtracting the baseline adjusted quantification of sequence from the adjusted quantification of sequence reads for each of the genomic portions (i.e., the modified product is a subtraction product for each of the genomic portions). A genomic instability classification for a test sample can be generated according to the modified products or absolute values of the modified products for the genomic portions. In some embodiments, genomic portions on autosomes are used to minimize the impact of the sex of the individual on the data. In some embodiments, the generating includes summing the modified product or absolute value of the modified product for the genomic portions, thereby providing a genomic instability number (GIN).

In some aspects, a genomic instability classification process makes use of a copy number alteration (CNA) quantification coupled to genomic portions of a reference genome as input, and filters portions according to selected features. The features sometimes are (i) genomic portions associated with copy number alterations consistently presented in a reference set of samples, and/or (ii) highly correlated genomic portions. After filtering, a process often classifies the sample as having genomic nucleic acid instability or not having genomic nucleic acid instability. Classification sometimes includes a transformation of the filtered genomic portion CNA quantifications into a reduced set of parameters, and classifies the sample based on the reduced set of parameters. Classification sometimes includes generating a distance or normalized distance from a reduced set of parameters, and classifies the sample based on the distance or the normalized distance.

In certain aspects, a genomic instability classification (e.g., a GIN, a distance) is utilized to identify presence or absence of genomic instability in a nucleic acid sample from a subject. In some aspects, a genomic instability classification (e.g., a GIN, a distance) is utilized to identify a subject having a cell proliferative condition having a likelihood of responding to a particular therapy that can be administered to the subject to treat the cell proliferative condition. In certain aspects, a genomic instability classification (e.g., a GIN, a distance) is utilized to monitor efficacy of a therapy administered to a subject for treating a cell proliferative condition, and can be utilized to determine whether the therapy should be continued or modified (e.g., dosage should be increased or decreased; therapy duration should be shortened or lengthened) or whether a subject should be taken off the therapy and another therapy should be administered.

Also provided are systems, machines and computer program products that carry out processes, or parts of processes, described herein. In some embodiments, the disclosure provides a system comprising: one or more processors and non-transitory machine readable storage medium; a set of genomic portions each coupled to a copy number alteration quantification for a test sample, wherein the genomic portions comprise portions of a reference genome to which sequence reads obtained for sample nucleic acid from the test subject have been mapped, the copy number alteration quantification coupled to each genomic portion has been determined from a quantification of sequence reads mapped to the genomic portion, and the set of genomic portions are stored on the non-transitory machine readable storage medium; and program instructions to determine a presence or absence of genomic instability for the test subject according to the copy number alteration quantifications coupled to the filtered genomic portions, wherein the program instructions are stored on the non-transitory machine readable storage medium for execution by the one or more processors.

In some embodiments, the disclosure provides a non-transitory machine readable storage medium comprising: a set of genomic portions each coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion; and program instructions that when executed by one or more processors cause the one or more processors to perform a method comprising: determining presence or absence of genomic instability for the test subject according to the copy number alteration qualifications coupled to the genomic portions.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 19 shows a fluctuation in GIN values for a cutaneous squamous cell carcinoma (cSCC) patient treated with Pembrolizumab, indicating a response to therapy.

FIG. 20 shows a fluctuation in GIN values for a colorectal adenocarcinoma patient treated with Nivolumab and radiation, consistent with disease progression.

FIG. 21 shows low GIN values for a melanoma patient treated in which no CNAs were detected by sequencing Circulating cell-free DNA (ccf-DNA).

FIG. 22 shows a fluctuation in GIN values for a patient having metastatic ovarian cancer involving liver treated with Nivolumab and radiation, consistent with progression, and then treated with Carboplatin and Taxol, consistent with a clinical response to the latter therapy.

FIG. 23 to FIG. 25 show GIN values for fourteen (14) cancer patients at different times during immunotherapy targeting immune checkpoints.

DETAILED DESCRIPTION

Figure 1:
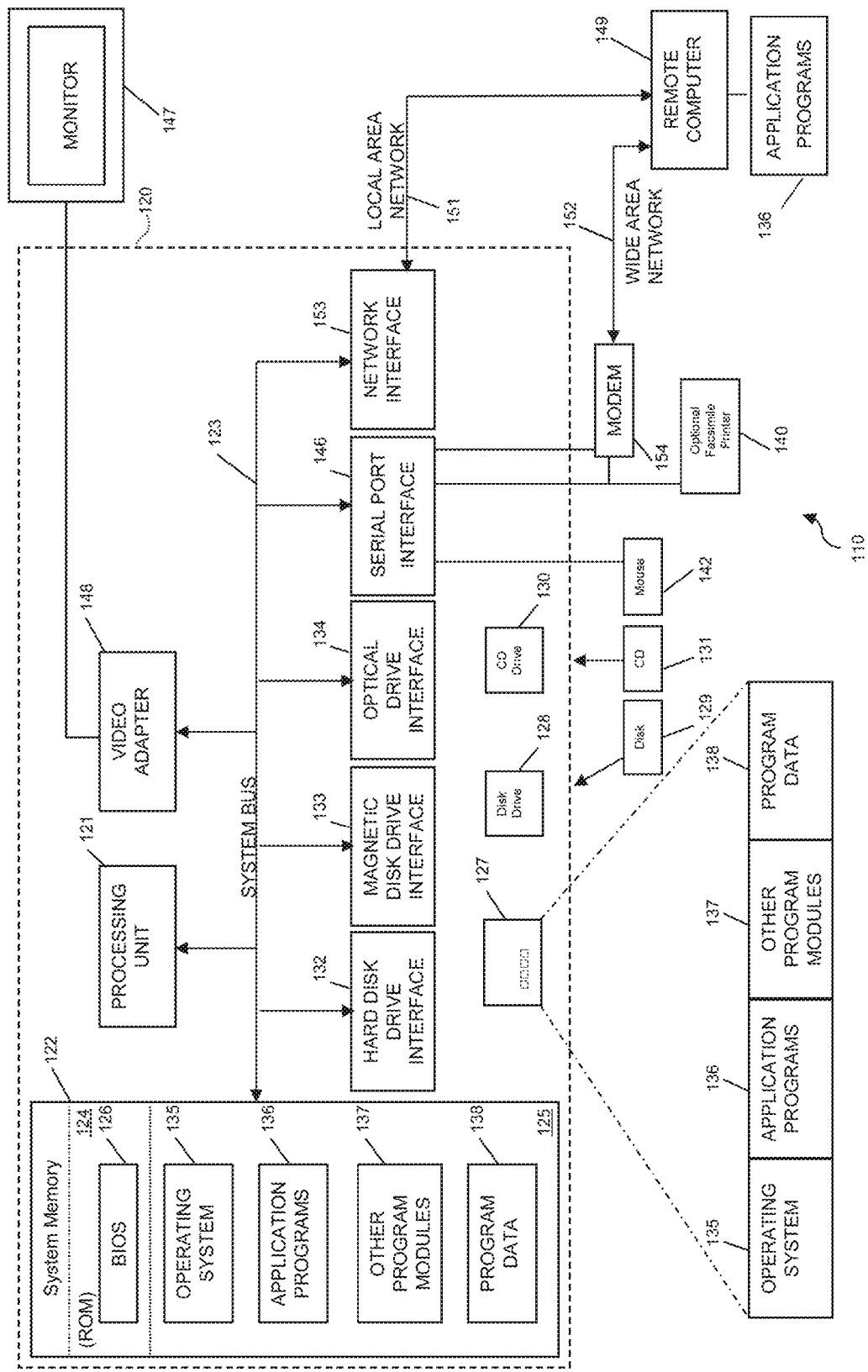
FIG. 1 shows an illustrative embodiment of a system in which certain embodiments of the technology may be implemented.

Provided herein are automated classification processes useful for determining whether a genomic nucleic acid for a sample from a subject has genomic nucleic acid instability or genomic nucleic acid stability. Genomic nucleic acid instability is relative within a population of individuals, and generally is identified in a fraction of a population. Genomic nucleic acid from a sample having genomic instability generally includes two (2) or more copy number alterations (CNAs) that are at least 0.5 megabases in length, and sometimes includes at least three (3) or more, at least four (4) or more, at least five (5) or more, at least six (6) or more, or at least seven (7) or more such CNAs.

Classifying genomic instability sometimes includes determining for a nucleic acid sample from a subject a genomic instability score, measure, assessment or value (e.g., a GIN or distance described herein). In some embodiments, classifying genomic instability includes determining presence or absence of genomic instability for a nucleic acid sample from a subject.

Samples from subjects classified as having genomic nucleic acid instability can be identified and sometimes are treated as cancer candidates (e.g., subjects who have cancer or are predisposed to cancer). A health care professional to whom a genomic nucleic acid instability classification is transmitted for a test sample from a subject may communicate the classification result to the subject, may recommend one or more cancer-directed diagnostic tests to the subject, and/or may recommend a cancer treatment to the subject according to the classification and/or the outcome of the cancer-directed diagnostic tests. Genomic nucleic acid instability and genomic nucleic acid stability sometimes are referred to herein as "genomic instability" and "genomic stability," respectively. A classification process that determines presence or absence of genomic instability for a sample sometimes is referred to herein as a "genomic instability classification process."

Samples from subjects diagnosed has having a cell proliferative condition, or are suspected of having a cell proliferative condition, can be subjected to a genomic instability classification process. A genomic instability classification (e.g., a GIN, a distance) sometimes is utilized to identify a subject who may respond to a particular therapy that can be administered to the subject to treat a cell proliferative condition. A genomic instability classification (e.g., a GIN, a distance) sometimes is utilized to monitor efficacy of a therapy administered to a subject for treating a cell proliferative condition, and can be utilized to determine whether the therapy should be continued or modified (e.g., dosage should be increased or decreased; therapy duration should be shortened or lengthened) or whether a subject should be taken off the therapy and another therapy should be administered instead.

Provided in certain embodiments are methods for classifying genomic instability for a test sample from a subject (e.g., quantifying genomic instability for a test sample from a subject), that include (a) providing a set of genomic portions each coupled to a CNA quantification for a test sample, where: the genomic portions comprise portions of a reference genome to which sequence reads obtained for sample nucleic acid from the test subject have been mapped, and the CNA quantification coupled to each genomic portion has been determined from a quantification of sequence reads mapped to the genomic portion; (b) filtering from the set of genomic portions a subset of portions having or not having one or more selected features, thereby generating a set of filtered genomic portions not containing the subset of portions having the selected features or containing the subset of portions having the selected features; and (c) generating a classification for the sample from the test subject for the presence or absence of genomic nucleic acid instability from the filtered set of genomic portions. Non-limiting examples of features include (i) genomic portions associated with copy number alterations consistently presented in reference samples classified as not having genomic nucleic acid instability, and (ii) genomic portions identified as being representative by a clustering process performed using CNA quantifications coupled to genomic portions for multiple reference samples.

In certain embodiments, generating a classification includes transforming the set of filtered genomic portions to a reduced set of parameters, which parameters in the reduced set are different than parameters of the set of filtered genomic portions, and determining presence or absence of genomic instability for the test subject according to the reduced set of parameters. In some embodiments, generating a classification includes generating a distance for the test subject from the CNA quantifications coupled to the set of filtered genomic portions, or generating a distance for the test subject from the reduced set of parameters, and determining presence or absence of genomic instability for the test subject according to the distance. The distance sometimes is a normalized distance.

Figure 9:
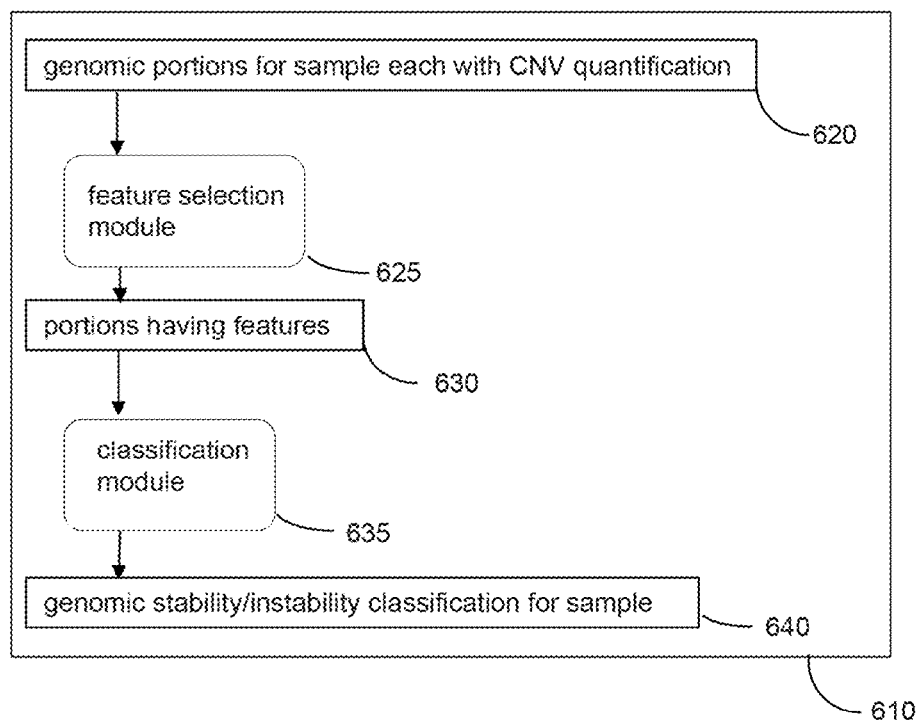
FIG. 9 shows one embodiment of the technology of classifying genomic instability.

A non-limiting embodiment of a genomic stability/instability classification process is illustrated as process 610 in FIG. 9. Genomic portions 620 for a sample (e.g., a test sample) each coupled to a CNA quantification (e.g., segment z-score) are reduced by feature selection module 625, which generates a reduced set of genomic portions 630 having the feature(s). In some embodiments, feature selection module 626 generates a reduced set of genomic portions 631 not having the feature(s) (not shown in FIG. 9). Each of the genomic portions in reduced set 630 often is coupled to a CNA quantification. The reduced set of genomic portions 630 often are input for classification module 635, which provides a genomic stability classification or genomic instability classification 640 for the sample.

In certain embodiments, a genomic instability classification is provided for sample nucleic acid from a subject by a method that includes: (a) providing a set of genomic portions of a reference genome to which sequence reads obtained for sample nucleic acid from a subject have been mapped, and for which the sequence reads mapped to the genomic portions have been quantified; (b) adjusting the quantified sequence reads for each of the genomic portions by an adjustment process that reduces experimental, biological and/or technical bias, thereby providing an adjusted quantification of sequence reads for each of the genomic portions; and (c) generating a genomic instability classification for the test sample according to the adjusted quantification of sequence reads for the genomic portions.

In some embodiments, the generating in (c) includes modifying the adjusted quantification of sequence reads for each of the genomic portions according to a baseline adjusted quantification of sequence reads, thereby providing a modified product for each of the genomic portions. In certain embodiments, the generating in (c) includes subtracting a baseline adjusted quantification of sequence reads from the adjusted quantification of sequence reads for each of the genomic portions, thereby providing a subtraction product for each of the genomic portions. In some embodiments a method includes determining the absolute value of the modified product (e.g., the subtraction product) for each of the genomic portions. In some embodiments, the baseline is an average adjusted quantification of sequence reads. Sometimes the average is a mean, median or mode of the adjusted quantifications of sequence reads for the genomic portions. In some embodiments, the baseline is a centered value based on adjusted quantifications of sequence reads for the genomic portions ("centered value"), and sometimes the baseline is a value representative of adjusted quantifications for genomic portions not associated with a copy number variation ("representative value"). In certain embodiments, a method includes scaling the adjusted quantifications of sequence reads, modified products or absolute values of the modified product for the genomic portions to the average, centered value or representative value.

In some embodiments, the generating in (c) includes summing the quantifications of sequence reads, modified products, or absolute value of the modified products for the genomic portions, thereby providing a genomic instability number. In certain embodiments, a nucleic acid sample is sequenced by a genome-wide sequencing process at about 1-fold or less coverage (e.g., about 0.5-fold or less coverage, about 0.30-fold or less coverage, about 0.25-fold or less coverage). In some embodiments, sequence read quantifications are normalized and adjusted for each genomic portion (e.g., in a bin-wise manner) by a process that includes one or more of (i) a GC normalization process (e.g., a GC-LOESS normalization process), (ii) a principal component normalization process, and (iii) a smoothing process (e.g., LOESS). In some embodiments, (ii) is performed after (i) and (iii) is performed after (ii). In some embodiments, normalized/adjusted sequence read quantifications, modified products or absolute values of modified products for a majority of genomic portions (e.g., bins) in autosomes or the genome are summed (e.g., about 75% to about 95% of genomic or autosomal portions (e.g., bins); about 80% to about 90% of genomic or autosome portions (e.g., bins)). Without being limited by theory, the magnitude of the genomic instability number often is based on the number of copy number variations in the sample nucleic acid, the magnitude of the copy number variations in the sample nucleic acid, and the portion of nucleic acid in the sample nucleic acid bearing each of the copy number variations. A genomic instability classification sometimes is based on the genomic instability number, and in some embodiments, is the genomic instability number. In some embodiments, presence of genomic instability is classified according to a genomic instability number above a cutoff value; and absence of genomic instability is classified according to a genomic instability number below the cutoff value.

In one aspect, the disclosure provides method of determining presence or absence of genomic instability for a test subject, comprising: providing a set of genomic portions each coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion; and determining, by a computing device, presence or absence of genomic instability for the test subject according to the copy number alteration quantifications coupled to the genomic portions.

In some embodiments, the method further comprises filtering, by the computing device, from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and/or the second subset of portions.

In some embodiments, the method further comprises adjusting, by the computing device, the quantified sequence reads for each of the genomic portions by an adjustment process that reduces experimental bias, thereby providing an adjusted quantification of sequence reads for each of the genomic portions. In some embodiments, the method further comprises generating, by the computing device, a genomic instability classification for the test sample according to the adjusted quantification of sequence reads for the genomic portions.

In some embodiments, the determining comprises: transforming the set of genomic portions to a reduced set of parameters, wherein the transforming comprises performing a principal component transformation of the set of genomic portions that yields principal components for the test sample, and determining a distance between the principal components of the test sample from a common principal component origin. In some embodiments, the reduced set of parameters contains fewer dimensions than dimensions of the set of filtered genomic portions.

In some embodiments, the distance is a normalized distance generated according to variance of principal components for a set of training samples, and determining the presence or absence of genomic instability is based on the normalized distance. In some embodiments, the set of training samples comprises or consists of samples classified as not having genomic instability. In some embodiments, the performing the principal component transformation forms a principal component space.

In some embodiments, the test sample is determined as comprising a cancer when the distance of the sample from the common principal component origin shared by a plurality of samples in the principal component space is greater than a pre-determined threshold. In some embodiments, the distance is a Mahalanobis distance and the threshold is greater than 300, or greater than 400, greater than 450, or about 500.

In some embodiments, the test sample is determined as comprising trisomy 21, trisomy 18 or trisomy 13, when the sample is among a group of samples that follow a distinct pattern, wherein the distinct pattern is a vector in a two dimensional principal component space, a plane in a three dimensional principal component space, or a hyperplane in a n-dimension principal component space.

In some embodiments, the clustering used in the methods, systems, or non-transitory machine readable storage medium may comprise: generating, by the computing device, a matrix comprising the genomic portions and the samples in the reference set of samples; generating, by the computing device, pair-wise correlation values from the matrix, wherein there is one correlation value for each pair of the portions; and clustering, by the computing device, the portions into groups according to the correlation values.

In some embodiments, the copy number alteration quantification coupled to each of the genomic portions for the test sample is obtained by a process comprising a segmentation process. In some embodiments, the segmentation process comprises a circular binary segmentation (CBS) process. In some embodiments, the copy number alteration quantification is a z-score. In some cases, the z-score for each genomic portion is the z-score for a segment identified by the segmentation process that includes the genomic portion. In some cases, the z-score is determined according to:

$$z\text{-score}=(Sscr-Smcr)/MAD$$

wherein:
  the Sscr is a test sample count representation of a segment, and the Sscr is the total normalized counts in the segment divided by the total normalized autosome counts for the test sample;
  the Smcr is a median count representation for the segment generated for a reference set of samples; and
  the MAD is a median absolute deviation determined for the count representation of the segment for the reference set of samples.

In some embodiments, the generating a genomic instability classification comprises modifying the adjusted quantification of sequence reads according to a baseline adjusted quantification of sequence reads for each of the genomic portions, thereby providing a modified product for each of the genomic portions. In some embodiments, the generating a genomic instability classification comprises subtracting a baseline adjusted quantification of sequence reads from the adjusted quantification of sequence reads for each of the genomic portions, thereby providing a subtraction product for each of the genomic portions. In some embodiments the method further comprising determining by a computing device, the absolute value of the modified product or the subtraction product for each of the genomic portions. The baseline may be (i) an average adjusted quantification of sequence reads for the genomic portions, (ii) a centered value of the adjusted quantification of sequence reads for the genomic portions, or (iii) a representative value of the adjusted quantification of sequence reads for the genomic portions. In some embodiments, the method further comprises scaling, by a computing device, the adjusted quantification of sequence reads for the genomic portions to the average, centered value or representative value.

In some embodiments, the generating a genomic instability classification comprises summing the modified products, absolute values of the modified products, subtraction products or absolute values of the subtraction products for the genomic portions, thereby providing a genomic instability number. In some embodiments the adjusting comprises normalizing the quantification of sequence reads by a guanine-cytosine (GC) normalizing process that generates a GC normalized quantification of sequence reads for each of the genomic portions, whereby the adjusted quantification of sequence reads in (b) is the GC normalized quantification of sequence reads.

In some embodiments, the subject is diagnosed with a cell proliferative condition according to the genomic instability classification, and the subject is selected for a treatment of the cell proliferative condition according to the genomic instability classification.

In some embodiments, the genomic instability classification is generated for the subject at two or more time points during the treatment, and (i) the subject is identified as a responder to the treatment if after a time point of about 6 weeks to about 8 weeks of treatment the genomic instability classification is less than a threshold value, or (ii) the subject is identified as a non-responder to the treatment if after the time point of treatment the genomic instability classification is greater than the threshold value. In some embodiments, the cell proliferative disorder is a cancer. In some embodiments, the treatment comprises administering at least one of an immunotherapeutic or a checkpoint inhibitor.

In some embodiments, the sample nucleic acid from the subject is circulating cell free nucleic acid.

In another aspect, the disclosure provides a system comprising: one or more processors and non-transitory machine readable storage medium; a set of genomic portions each coupled to a copy number alteration quantification for a test sample, wherein the genomic portions comprise portions of a reference genome to which sequence reads obtained for sample nucleic acid from the test subject have been mapped, the copy number alteration quantification coupled to each genomic portion has been determined from a quantification of sequence reads mapped to the genomic portion, and the set of genomic portions are stored on the non-transitory machine readable storage medium; and program instructions to determine a presence or absence of genomic instability for the test subject according to the copy number alteration quantifications coupled to the filtered genomic portions, wherein the program instructions are stored on the non-transitory machine readable storage medium for execution by the one or more processors.

In some embodiments, the system comprises: program instructions to filter from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and the second subset of portions wherein the program instructions are stored on the non-transitory machine readable storage medium for execution by the one or more processors.

In some embodiments, the system comprises program instructions for transforming the set of filtered genomic portions to a reduced set of parameters, wherein the transforming comprises performing a principal component transformation that yields principal components for the test sample, and determining a distance from a common principal component origin for the test sample; and program instructions for determining a distance between the principal components of the test sample from a common principal component origin wherein the program instructions are stored on the non-transitory machine readable storage medium for execution by the one or more processors.

In some embodiments, the system further comprises program instructions to adjust the quantified sequence reads for each of the genomic portions by an adjustment process that reduces experimental bias, wherein the adjustment process generates a normalized quantification of sequence reads for each of the genomic portions wherein the program instructions are stored on the non-transitory machine readable storage medium for execution by the one or more processors.

In some embodiments, the system further comprises program instructions to generate a genomic instability classification for the test sample according to the normalized quantification of sequence reads for each of the genomic portions, wherein the program instructions are stored on the non-transitory machine readable storage medium for execution by the one or more processors.

In some embodiments, the system further comprises program instructions to reduce experimental bias is according to a GC normalized quantification of sequence reads.

In another aspect, the system comprise a non-transitory machine readable storage medium comprising: a set of genomic portions each coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion; and program instructions that when executed by one or more processors cause the one or more processors to perform a method comprising: determining presence or absence of genomic instability for the test subject according to the copy number alteration qualifications coupled to the genomic portions.

In some embodiments, the non-transitory machine readable storage medium further comprises:
program instructions that when executed by one or more processors cause the one or more processors to perform a method comprising filtering from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and the second subset of portions.

In some embodiments, the non-transitory machine readable storage medium further comprises:
program Instructions for transforming a set of genomic portions to a reduced set of parameters, wherein the transforming comprises:
performing a principal component transformation that yields principal components for the test sample,
determining a distance from a common principal component origin for the test sample; and
determining a distance between the principal components of the test sample from a common principal component origin.

In some embodiments, the non-transitory machine readable storage medium further comprises: program instructions that when executed by one or more processors cause the one or more processors to perform a method comprising adjusting the quantified sequence reads for each of the genomic portions by an adjustment process that reduces experimental bias, wherein the adjustment process generates a normalized quantification of sequence reads for each of the genomic portions.

In some embodiments, the non-transitory machine readable storage medium comprises program instructions that when executed by one or more processors cause the one or more processors to perform a method comprising generating a genomic instability classification for the test sample according to the normalized quantification of sequence reads for each of the genomic portions.

In some embodiments, the instructions to reduce experimental bias is according to a GC normalized quantification of sequence reads.

Sequence Read Quantification

A genomic portion sequence read quantification (i.e., a sequence read quantification coupled to a genomic portion) often is a read count and sometimes is a read density. Each reference genome portion is referred to herein as a genomic portion to which one or more sequence reads have been mapped in a mapping process performed after sequence reads for a sample have been obtained. A genomic portion sometimes is referred to as a "bin" or "window." Genomic portions sometimes are of fixed length, sometimes are of equal length, sometimes are about 1 kilobase to about 1,000 kilobases in length (e.g., about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900 kilobases in length), sometimes are of unequal length (e.g., at least two of the genomic portions are of unequal length), sometimes do not overlap (e.g., the 3' ends of the genomic portions sometimes abut the 5' ends of adjacent genomic portions), and/or sometimes overlap (e.g., at least two of the genomic portions overlap). In some embodiments, genomic portions are of fixed length, are of a substantially equal length of about 50 kilobases, and do not overlap.

Sequence reads can be generated by any suitable sequencing process applied to nucleic acid extracted form a sample. Nucleic acid can be extracted from a biological sample obtained from a subject, as described herein. A subject sometimes is female or male (e.g., human female or human male), and a female can be a pregnant female at any suitable stage of pregnancy (e.g., first, second or third trimester). Extracted nucleic acid from the test subject sometimes is circulating cell free nucleic acid, and circulating cell free nucleic acid sometimes is from a blood plasma, blood serum or urine sample from a test subject. Extracted circulating cell free nucleic acid sometimes is not manipulated prior to performing a sequencing process (e.g., the cell free nucleic acid often is not cleaved by an exonuclease or endonuclease). A sequencing process utilized often is a genome-wide sequencing process, and in some embodiments is a targeted sequencing process (e.g., a processes that sequences a subset of all nucleic acid in a sample). A sequencing process utilized sometimes includes sequencing by synthesis. Depth of sequencing or sequencing coverage sometimes is about 0.01-fold to about 1,000-fold (e.g., 0.02-fold, 0.03-fold, 0.04-fold, 0.05-fold, 0.06-fold, 0.07-fold, 0.08-fold, 0.09-fold, 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold).

In certain embodiments, read quantifications for the genomic portions are normalized or adjusted by a process that reduces or removes the effect(s) of one or more biases (e.g., experimental bias(es)). A process that normalizes or adjusts read quantifications sometimes normalizes or adjusts read quantification at a genomic portion level (e.g., at a bin level) and sometimes a process normalizes or adjusts read quantifications for multiple bins. In some embodiments, normalizing or adjusting read quantifications for genomic portions includes normalizing according to guanine-cytosine (GC) content (e.g., GC percentage). Any suitable GC normalization process can be utilized, non-limiting examples of which include LOESS, LOESS with repeat masking (GCRM) and GC bias coefficient-based correction according to multiple samples (see, e.g., Alkan et al., Nat. Genet. 41:1061-1067 (2009); Palomaki et al., Genet. Med. 14: 296-305 (2012); International patent application no. PCT/US2012/059123 filed on Oct. 5, 2012 and published as WO 2013/052913 on Apr. 11, 2013). In some embodiments, bias effects are reduced by a process that includes transforming genomic portion read quantifications (e.g., GC normalized genomic portion read quantifications) into principal components. Any suitable principal component transformation process can be utilized, non-limiting examples of which are described herein (e.g., singular value decomposition (SVD) principal component transformation, Eigen decomposition principal component transformation). In certain embodiments, genomic portion sequence read quantifications are normalized or adjusted by first reducing GC bias by LOESS and then reducing residual bias by principal component analysis (PCA), which is referred to herein as SPCA (see, e.g., International patent application no. PCT/US2014/058885 filed on Oct. 2, 2014 and published as WO 2015/051163 on Apr. 9, 2015). In certain embodiments, genomic portion sequence read quantifications are normalized or adjusted by SPCA followed by a secondary GC bias normalization/adjustment process (e.g., secondary LOESS).

In certain PCA embodiments, principal components are utilized to generate a set of weights, one for each genomic portion, that are multiplied against genomic portion read quantifications to yield normalized read quantifications. In some PCA embodiments, principal components are utilized to generate predicted genomic portion read quantifications. Predicted read quantifications sometimes are obtained by a process that includes: (a) performing PCA using genomic portion read quantifications from a training set of samples, thereby generating principal components; (b) optionally selecting a subset of the principal components generated in (a); (c) estimating regression coefficients from all of the principal components generated in (a) or from the subset of principal components provided in (b); and (d) running a regression on genomic portion read quantifications for a test sample using the regression coefficients estimated in (c); whereby a PCA-predicted genomic portion read quantifications can be obtained from the regression. In some embodiments, the regression is a multivariate linear regression. The PCA-predicted genomic portion read quantifications can be subtracted from the experimentally derived read quantification for the same genomic portion for a test sample, thereby providing PCA-adjusted genomic portion read quantifications for the test sample.

In some embodiments certain genomic portions are filtered prior to, or after, normalization. Filtering, when implemented, sometimes is based on mappability, repeat masking, or a combination thereof. In certain embodiments, filtering is based on variability of genomic portion read quantifications (i.e., inconsistently mapped reads), and/or consistently no reads mapped to certain genomic portions, for a reference set of samples.

Copy Number Alteration Quantification

Genomic portion copy number alteration (CNA) quantifications sometimes are utilized as input for automated classification processes described herein. A CNA quantification sometimes is derived from a quantification of sequence reads mapped to each genomic portion. Genomic portion CNA quantifications (e.g., a CNA quantification coupled to each genomic portion) for a test sample sometimes is obtained by a process comprising segmentation. A segment sometimes includes multiple genomic portions. A segmentation process sometimes provides a start and end position for each segment, a CNA quantification for the segment, and optionally a measure of confidence for the segment. Any suitable segmentation process may be utilized, including without limitation a circular binary segmentation (CBS) process. Other processes could be utilized instead of, or in addition to, CBS, non-limiting examples of which include wavelet segmentation (e.g., Haar wavelet segmentation), Fourier transformation, sliding window z-scores, and Markov chain models.

In some embodiments, a CNA quantification is a z-score. A z-score sometimes is for a segment, and sometimes is assigned to each genomic portion included in a segment. In some embodiments, a z-score is determined according to $$z\text{-score}=(S_{scr}-S_{mcr})/\text{MAD}$$

where $S_{scr}$ is a test sample count representation of a segment, $S_{scr}$ is the total normalized counts in the segment divided by the total normalized autosome counts for the test sample, $S_{mcr}$ is a median count representation for the segment generated for a reference set of samples, and MAD is a median absolute deviation determined for the count representation of the segment for the reference set of samples. Non-limiting examples of methodology useful for generating z-score copy number quantifications based on CBS segmentation are described in Zhao et al., Clin. Chem. 61:4: 608-616 (2015); Lefkowitz et al., American Journal of Obstetrics & Gynecology 1.e1 (2016); and International patent application no. PCT/US2014/039389 filed on May 23, 2014 and published as WO 2014/190286 on Nov. 27, 2014. Instead of z-scores, other genomic portion CNA quantifications may be utilized, non-limiting examples of which include normal scores, z-values, standardized variables and t-statistics.

One or more or all steps for generating genomic portion CNA quantifications can be performed by an apparatus that includes memory and a processor (e.g., a computer). Genomic portion read quantifications for a test sample sometimes are stored in memory. In some embodiments, instructions for normalizing genomic portion read quantifications, and/or resulting normalized genomic portion read quantifications for a test sample, are stored in memory and are accessible to a processor. In certain embodiments, instructions for segmenting normalized genomic portion read quantifications are stored in memory and are accessible to a processor. In some embodiments, resulting start and end positions for each segment, a confidence value for each segment, and/or a CNA quantification value for each segment, for a test sample, are stored in memory and are accessible to a processor. Programming instructions (e.g., module programming instructions) sometimes are in R programming language, and sometimes features of programming instructions for performing methods described herein are selected from the "stats" R package (e.g., "loess" for local polynomial regression fitting, function "prcomp" for principal components analysis, function "lm" for fitting linear models, and function "predict" for model predictions), "plyr" R package and/or "DNAcopy" R package.

Feature Selection

In certain embodiments, filtering comprises at least one filtering processes and sometimes two or more filtering processes. Genomic portions for filtering often are identified as having or not having one or more particular features. Genomic portions having one or more particular features sometimes are filtered away, leaving genomic portions not having the particular feature(s) as filtered genomic portions. Genomic portions not having one or more particular features sometimes are filtered away, leaving genomic portions having the particular feature(s) as filtered genomic portions. Each of the filtered genomic portions often is coupled to a CNA quantification. Features often are characteristics pertaining to CNA quantifications, and sometimes are one or more of the following: (i) CNA z-score absolute value less than a particular level (e.g., |z-score| between 0 and 3 or between 0 and x, where x is an integer between 1 and 5 (e.g., x is 2, 3 or 4) or where x is an intermediate fractional value between 1 and 5 (e.g., x is 2.9, 2.91, 3.09 or 3.1)); (ii) CNA confidence value less than a particular level (e.g., less than 0.99); (iii) affected CNA size less than a particular size threshold (e.g., less than 0.5 megabases); (iv) CNA is located on one or more particular chromosomes (e.g., chromosome 19); (v) CNA consistently presented in a reference set of samples not classified as having genomic nucleic acid instability; and (vi) genomic portions other than a representative genomic portion for a genomic portion cluster identified according to genomic portion CNA quantifications.

Filtering sometimes includes filtering from a set of genomic portions (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and/or the second subset of portions. In some embodiments, filtering consists essentially of filtering from the set of genomic portions (i) a first subset of portions associated with copy number alterations consistently presented in a reference set of samples, and (ii) a second subset of portions other than representative portions derived from groups of portions identified by a clustering process applied to a reference set of samples, thereby generating a set of filtered genomic portions not containing the first subset of portions and the second subset of portions. For the filtering process in the previous sentence, "consists essentially of" refers to a process that includes sub-processes (i) and (ii), which may also include one or more other sub-processes (referred to as "additional sub-processes") that influence a resulting classification less than sub-processes (i) and (ii). Determining whether additional sub-processes influence a resulting classification less than sub-processes (i) and (ii) can be determined by assessing classification performance (e.g., sensitivity and/or specificity) when sub-processes (i) and (ii) are utilized with and without the additional sub-processes.

For embodiments in which filtering is based on CNAs consistently presented in a reference set of samples, any suitable identification process can be utilized. Such consistently presented CNAs sometimes occur a certain number of times in a reference set of samples or in a certain percentage of samples in a reference set of samples. For example, a CNA may be determined as being consistently presented in a reference set of samples when the CNA presents about 1.1 or more times per 1000 reference samples (e.g., about 1.2, 1.25, 1.3, 1.35, 1.4, 1.45, 1.5, 1.55, 1.6, 1.65, 1.7, 1.75, 1.8, 1.85, 1.9, 1.95, 2, 3, 4, 5, 6, 7, 8, 9, 10, 11, 12, 13, 14, 15, 16, 17, 18, 19 or 20 or more times per 1000 reference samples), or when the CNA presents in about 0.05% or more of the samples in the reference set of samples (e.g., about 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 4, 5, 6, 7, 8, 9, 10% or more of a group of reference samples). For identifying CNA that are consistently presented, a reference set of samples utilized often includes samples classified as not having genomic instability, and often a reference set of samples utilized consists of samples classified as not having genomic instability. Genomic portions having genomic positions overlapping with genomic positions of the consistently presented CNAs often are selected as being associated with the consistently presented CNAs.

Identifying genomic portions associated with consistently presented CNAs generally is based on criteria different than identifying genomic portions associated with mappability issues. Genomic portions associated with mappability issues often contain repeated sequences. Genomic portions associated with mappability issues therefore often are selected for filtering based on whether a read maps to multiple genomic portions. In contrast, genomic portions associated with consistently presented CNA regions generally are not identified by observing whether a read maps to more than one genomic portion. Rather, CNA regions that present consistently (e.g., present a particular number of times in a group of samples or present in a particular percentage of samples) are observed and genomic portions that span the CNA are identified for filtering.

After genomic portions associated with consistently presented CNAs are selected, genomic portion CNA quantifications from a test sample often are removed from genomic portion CNA quantifications for a test sample by a filter. Such filtering embodiments result in a reduced set of filtered genomic portion CNA quantifications not associated with CNAs consistently presented in a reference set of samples classified as not having genomic nucleic acid instability. As an alternative to filtering, CNA quantifications coupled with genomic portions deemed associated with consistently presented CNAs are assigned a weight lower than CNA quantifications coupled to genomic portions not associated with consistently presented CNAs. Any suitable weighting process can be utilized, and non-limiting examples of weighting processes include weighting the genomic portions by one-CNA consistency. After genomic portions are identified as being associated with consistently presented CNAs according to a group of reference samples, such genomic portions can be consistently filtered for a series of test samples, or a lower weighting can be applied consistently for a series of test samples.

For embodiments in which non-representative genomic portions are removed by a filter according to representative genomic portions identified by a clustering process, any suitable clustering process can be utilized to identify genomic portion clusters. Clustering processes typically are performed using genomic portion CNA quantifications as input. Non-limiting examples of clustering processes include, connectivity clustering (e.g., hierarchical clustering based on distance connectivity, graph nodes clustering based on edge connectivity), centroid clustering (e.g., k-means clustering that characterizes each cluster by a single mean vector), distribution clustering (e.g., clusters modeled by statistical distributions, such as multivariate normal distributions), density clustering (e.g., clusters identified as connected dense regions in the data space), subspace clustering (e.g., bi-clustering, co-clustering, two-mode-clustering), group clustering, graph-based clustering (e.g., clustering identified by a subset of nodes in a graph). For connectivity clustering, non-limiting examples of parameters that can be utilized for identifying clusters include Euclidean distance, squared Euclidean distance, pairwise similarity value and/or pairwise dissimilarity value, Manhattan distance, Pearson correlation coefficient, squared Pearson correlation coefficient, Chebychev distance, and Spearman coefficient.

For identifying representative genomic portions by a clustering process, a reference set of samples utilized often includes samples classified as not having genomic instability, and often a reference set of samples utilized consists of samples classified as not having genomic instability. The same reference set of samples sometimes is utilized for clustering and for identifying consistently presented CNAs.

In certain embodiments, graph-based connectivity clustering is utilized to cluster genomic portion CNA quantifications for reference samples, and pairwise similarity values and/or pairwise dissimilarity values are generated and analyzed, yielding correlation values for genomic portion CNA quantification pairs (see, e.g., Dowdy and Wearden, "Statistics for Research," Wiley, ISBN 0-471-08602-9:230 (1983)). A cutoff correlation value often is assigned, which often is greater than 0.90 (e.g., correlation value of 0.95, 0.96, 0.07, 0.98, 0.99, 0.995, 0.999 or greater), where genomic portions correlated by a correlation value equal to or greater than the cutoff value often are correlated or connected in the corresponding graph. In a graph, each node represents a genomic portion and each edge represents a strong correlation (e.g. correlation value greater than 0.9). Nodes that are connected are clustered together. The "graph.ajacency" function from the "igraph" R package can be used to create a graph from the binarized correlation matrix (or adjacency matrix) and the "clusters" function from the same R package can be used to identify and cluster connected components of a graph, in some embodiments. A clustering process can yield non-clustered stand-alone genomic portions and genomic portion clusters, where the clusters can include two genomic portions or three or more genomic portions (e.g., clusters can include 2, 3, 4, 5, 6, 7, 8, 9, 10 or more genomic portions).

One representative genomic portion often is selected from each cluster, and the representative genomic portions often are combined with the non-clustered genomic portions and collectively are considered representative genomic portions. Non-representative genomic portions often are removed from test sample genomic portions by a filter, and such genomic portions and their coupled CNA quantifications are removed for further analysis. In certain embodiments, a CNA quantification for each genomic portion is assigned a weight. Any suitable weighting process can be utilized, and a non-limiting example of a weighting process includes weighting each genomic portion by the reciprocal of its cluster size, where a cluster size is defined as the number of genomic portions in a correlation cluster. After genomic portions are identified as representative by a clustering process, such genomic portions can be consistently applied by a filter for a series of test samples, or a weighting can be applied consistently for a series of test samples.

In certain embodiments, a clustering process includes (A) providing a set of genomic portions each coupled to a CNA quantification for each sample in the reference set of samples, where: the genomic portions comprise portions of a reference genome to which sequence reads obtained for nucleic acid from each sample in the reference set of samples have been mapped, and the CNA quantification coupled to each genomic portion has been determined from a quantification of sequence reads mapped to the genomic portion; (B) clustering genomic portions according to the CNA quantification coupled to each of the portions for each sample in the reference set of samples, thereby generating groups of portions, and (C) selecting a representative genomic portion from each of the groups. In some embodiments, a clustering process includes, prior to (A), removing from the set of genomic portions a first subset of portions associated with copy number alterations consistently presented in the reference set of samples, thereby providing a set of filtered genomic portions for each sample in the reference set of samples, and performing (B) and (C) on the set of filtered genomic portions. In certain embodiments, the clustering process includes generating a matrix comprising CNA quantifications for the genomic portions for the samples in the reference set of samples; generating pair-wise correlation values from the matrix, where there is one correlation value for each pair of the genomic portions; and clustering the genomic portions into groups according to the correlation values. Each of the groups sometimes consists of portions that are correlated to one another according to the correlation value for each pair, and sometimes each of the groups consists of portions correlated with a correlation value of 0.999 or greater.

One or more or all steps for filtering can be performed by an apparatus that includes memory and a processor (e.g., a computer). Filtering features sometimes are stored in memory and are accessible to a processor. In some embodiments, instructions for filtering according to the features, and providing a set of filtered genomic portions coupled with CNA quantifications based on features, are stored in memory and are accessible to a processor. A cluster feature cutoff value sometimes is stored in memory and is accessible to a processor. In some embodiments, instructions for clustering and selecting representative genomic portions are stored in memory and are accessible to a processor. The R package "Matrix" can be utilized for filtering based on consistently presented CNAs in normal samples, and the R package "igraph" can be used for filtering based on selecting representative bins from clusters, in certain embodiments.

Figure 10:
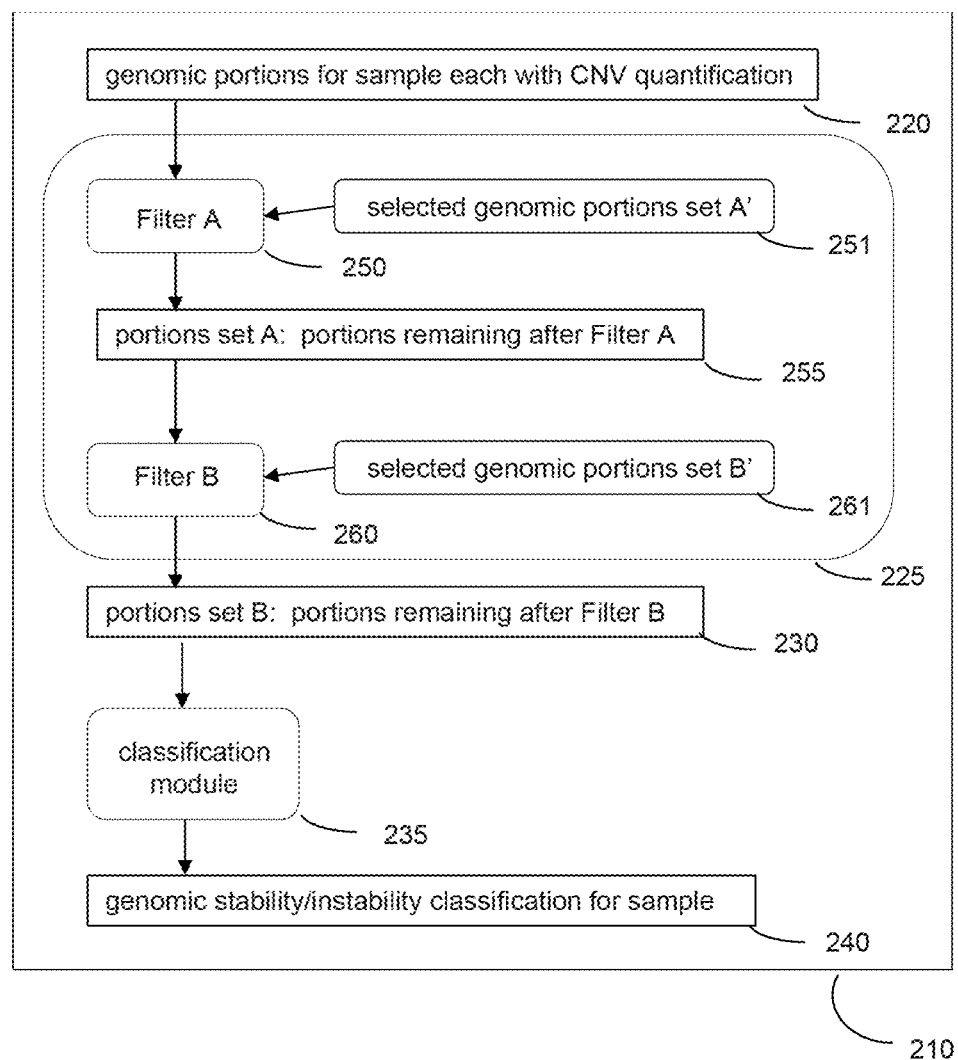
FIG. 10 shows one embodiment of the technology of classifying genomic instability.

An embodiment of a genomic stability/instability classification process is illustrated as process 210 in FIG. 10. Genomic portions 220 for a sample (e.g., a test sample) coupled to a CNA quantification (e.g., segment z-score) are reduced by feature selection module 225, which generates a reduced set of genomic portions 230 having or not having selected features. Feature selection module 225 includes a first filter 250 (i.e., filter A) that reduces the set of genomic portions 220 into a reduced set of genomic portions 255 that have or do not have features applied by the first filter 250. Feature selection module 225 also includes a second filter 260 (i.e., filter B) that reduces the set of genomic portions 255 reduced by filter A into the reduced set of genomic portions 230 that have or do not have features applied by the second filter 260. Each of the genomic portions in reduced set 230 is coupled to a CNA quantification. The reduced set of genomic portions 230 are input for classification module 235, which provides a genomic stability classification or genomic instability classification 240 for the sample. When a filter removes one or more genomic portions it often removes CNA quantifications coupled with those genomic portions.

In certain embodiments of process 210, first filter 250 removes selected genomic portions 251 in set A' from genomic portions 220 and yields the reduced set of genomic portions 255. Genomic portions 251 in set A' often are associated with CNAs consistently presented in a reference set of samples not classified as having genomic nucleic acid instability, and genomic portions 251 in set A' often are pre-selected as having this feature from the reference set of samples and are applied to each test sample. In some embodiments of process 210, first filter 250 also removes genomic portions having one or more of the following features from the set of genomic portions 220: (i) CNA z-score absolute value less than a particular level (e.g., |z-score| between 0 and 3 or between 0 and x, where x is an integer between 1 and 5 (e.g., x is 2, 3 or 4) or where x is an intermediate fractional value between 1 and 5 (e.g., x is 2.9, 2.91, 3.09 or 3.1)); (ii) CNA confidence less than a particular level (e.g., less than 0.99); (iii) affected CNA size less than a particular size threshold (e.g., less than 0.5 megabases); and (iv) CNA is located on one or more particular chromosomes (e.g., chromosome 19).

In some embodiments of process 210, second filter 260 retains within genomic portions 255 selected genomic portions 261 in set B' and removes genomic portions in set 255 that are not in set B' to generate the reduced set of genomic portions 230. Genomic portions 261 in set B' often are representative genomic portions identified by a clustering process described herein (e.g., process embodiment 563 illustrated in FIG. 13), and genomic portions 261 in set B' often are pre-selected as being representative according to the reference set of samples and are applied to each test sample.

Figure 13:
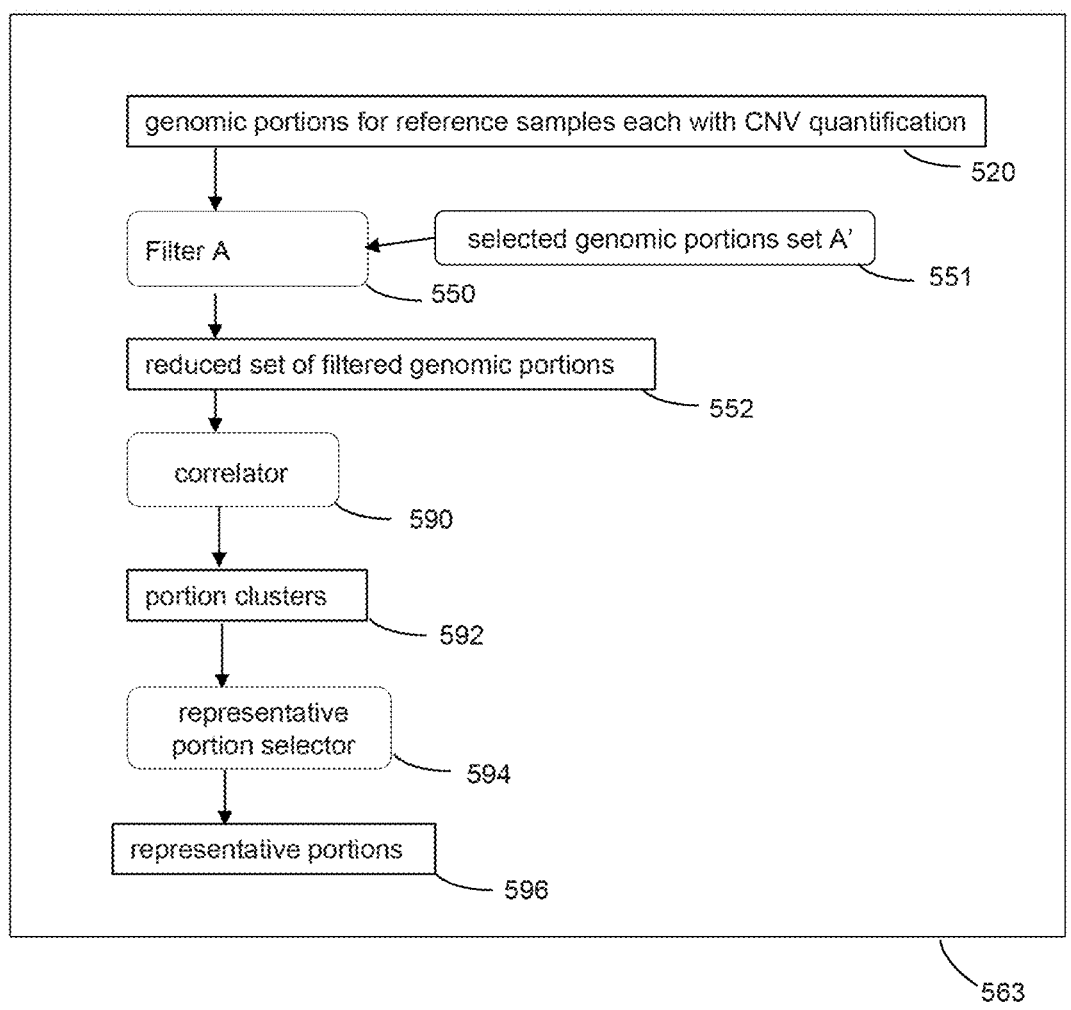
FIG. 13 shows one embodiment of the technology of classifying genomic instability.

An embodiment of a process for identifying representative genomic portions utilized for filtering (e.g., a process that can be used to select genomic portions 261 utilized by filter 260 in process 210) is process 563 illustrated in FIG. 13. In process 563, filter 550 removes genomic portions 551 in set A' having one or more selected features from genomic portions 520 for reference samples. In certain embodiments, genomic portions 251 in set A' are associated with CNA consistently presented in a reference set of samples classified as not having genomic nucleic acid instability, and genomic portions 251 in set A' often are pre-selected as having this feature from the reference set of samples and are applied to each test sample. In some embodiments of process 563, first filter 550 also removes genomic portions having one or more of the following features from the set of genomic portions 520 for reference samples: (i) CNA z-score absolute value less than a particular level (e.g., |z-score| between 0 and 3 or between 0 and x, where x is an integer between 1 and 5 (e.g., x is 2, 3 or 4) or where x is an intermediate fractional value between 1 and 5 (e.g., x is 2.9, 2.91, 3.09 or 3.1)); (ii) CNA confidence less than a particular level (e.g., less than 0.99); (iii) affected CNA size less than a particular size threshold (e.g., less than 0.5 megabases); and (iv) CNA is located on one or more particular chromosomes (e.g., chromosome 19). Filter 550 removes a sub-set of genomic portions from reference sample genomic portions 520 as described, and yields a reduced set of filtered genomic portions 552 in process 563.

Process 563 also generates genomic portion clusters 592 from the reduced set of genomic portions 552 by operation of correlator 590. Correlator 590 sometimes performs a graph based connectivity clustering process in which pairwise similarity values and/or pairwise dissimilarity values are generated and analyzed, yielding correlation values for genomic portion pairs, and clusters are identified according to the correlation values (e.g., genomic portion pairs having correlation values of 0.999 or greater are clustered). Representative portion selector 594 then selects representative portions from clusters 592, often combines such genomic portions with non-clustered genomic portions, and thereby identifies representative genomic portions 596. Representative portion selector 594 sometimes identifies a representative portion from a cluster based on the location of the genomic portion in the genome (e.g., the most 5' genomic portion sometimes is selected from a cluster of genomic portions). Representative portions 596 sometimes are utilized as selected genomic portions 261 by filter 260 in process 210.

Transformation into Fewer Parameters

After filtering, a classification process often includes transforming the set of filtered genomic portions and coupled CNA quantification (e.g., CNA quantification coupled to genomic portions remaining after selected genomic portions are removed, or weighted CNA quantifications coupled to each genomic portion) to a reduced set of parameters, which parameters in the reduced set are different than parameters of the set of filtered genomic portions and coupled CNA quantifications. The reduced set of parameters often contains fewer dimensions than dimensions of the set of filtered genomic portions and coupled CNA quantifications.

A transformation process sometimes includes performing a principal component transformation that yields principal component values for a test sample. Any suitable principal component transformation process can be utilized, non-limiting examples of which include singular value decomposition (SVD) principal component transformation and Eigen decomposition principal component transformation. A principal component transformation processes often is performed for the test sample with input principal component portion weights obtained from a set of training samples (see, e.g., Price et al., Nat. Genet. 38: 904-909 (2006); Leek et al., PLoS Genet 3:1724-1735 (2007) and International patent application no. PCT/US2014/058885 filed on Oct. 2, 2014 and published as WO 2015/051163 on Apr. 9, 2015. In some embodiments, input principal component portion weights from the set of training samples are obtained by a process that includes (A) providing a set of genomic portions each coupled to a CNA quantification for each training sample in the set of training samples, where: the genomic portions comprise portions of a reference genome to which sequence reads obtained for nucleic acid from each training sample have been mapped, and the CNA quantification coupled to each genomic portion has been determined from a quantification of sequence reads mapped to the genomic portion; (B) filtering from the set of genomic portions a subset of portions having selected features, thereby generating a set of filtered genomic portions not containing the subset of portions having the selected features; and (C) performing a principal component transformation on the set of filtered genomic portions that yields principal component portion weights from the training set of samples. The weights are obtained from the eigenvectors of a covariance matrix of the training samples by performing a singular value decomposition (SVD) process, in some embodiments.

In certain embodiments, a principal component transformation includes generating a matrix comprising the training samples and the set of filtered genomic portions for the training samples; and performing the principal component transformation on the matrix. In some embodiments, part (C) yields a weight for each portion for each principal component. The filtering in (B) sometimes includes removing from the set of genomic portions for the training samples: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and/or the second subset of portions, as described above.

A set of training samples often includes, or consists of, samples classified as not having genomic instability (e.g., euploid samples not having a chromosome trisomy or other significant duplication or deletion). A set of training samples sometimes includes one or more samples classified as having genomic instability and sometimes samples classified as having at least one chromosome trisomy. A reference set of samples (i.e., a set of reference samples) utilized for identifying genomic portions for filtering, as described above, often consists of samples classified as not having genomic instability (e.g., euploid samples not having a chromosome trisomy or other significantly large duplication or deletion).

In embodiments for which a reduced set of parameters is generated by a transformation (e.g., principal components), a classification process sometimes includes determining a distance for each test sample based on the reduced set of parameters, and presence or absence of genomic instability is classified according to the distance. For example, a distance sometimes is determined from a common principal component origin for a test sample, and the presence or absence of genomic instability is classified according to the distance. The distance sometimes is a Euclidean distance determined from the common origin for principal component values. The distance sometimes is a normalized distance determined from the common origin for principal component values, and presence or absence of genomic instability is classified according to the normalized distance. In some embodiments, the distance is generated using at least 3, e.g., at least 4, at least 5 or more principal component values. A normalized distance sometimes takes into account variance of principal components for multiple samples (e.g., a set of training samples). In some embodiments, a normalized distance utilized for a classification is a Mahalanobis distance (see, e.g., De Maesschalck et al., Chemometrics and Intelligent Laboratory Systems 50: 1-18 (2000) and Gnanadesikan et al., Biometrics 28: 81-124 (1972)). A Mahalanobis distance for a test sample sometimes is a normalized Euclidian distance and sometimes is equal to a Euclidian distance. Non-limiting examples of other types of distances that can be determined and utilized for a classification system include Bhattacharyya distance, Hamming distance, Hellinger distance, a distance obtained from Bregman divergence, and a distance determined from similarity learning. A Mahalanobis distance (d) can be determined according to the following relation:

$$d = \sqrt{(x-\mu)C^T(x-\mu)}$$

where x represents the principal component values of the sample, and where $\mu$ and C represent the mean and covariance matrix of the principal component values of all the training samples. Thus, a Mahalanobis distance can be determined according to a mean and covariance of principal components, in certain embodiments.

In some embodiments, a distance or normalized distance is determined for a test sample using a sub-group of the principal components (i.e., principal component values), and sometimes the sub-group of principal components are top-ranked principal components. A sub-group of principal components can be determined using any suitable ranking process, a non-limiting example of which includes generating a co-variance matrix containing CNA quantifications for multiple samples (e.g., samples are in rows and CNA quantifications for genomic portions are in columns), determining corresponding eigenvalues for the matrix, and ranking the eigenvalues. In certain embodiments, a sub-group of principal components includes about 10 to about 30 principal components (e.g., about 11, 12, 13, 14, 15, 16, 17, 18, 19, 20, 21, 22, 23, 24, 25, 26, 27, 28, 29 principal components).

Figure 16A:
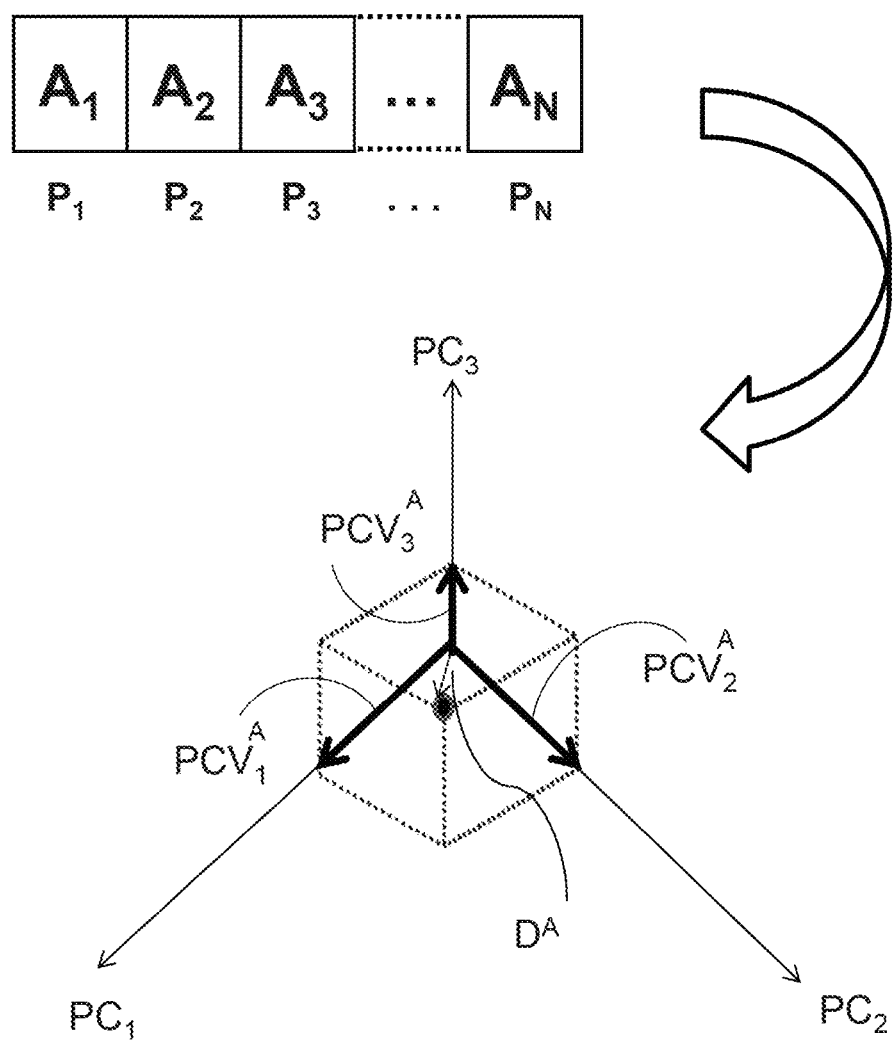
FIG. 16A and FIG. 16B conceptually illustrate transformation of bin counts into fewer parameters, using a principal component transformation (represented by the open arrow), for an illustrative sample not having significant genomic instability and for an illustrative sample having significant genomic instability, respectively. The distance $D^A$ is smaller than a predetermined threshold and $D^B$ is greater than the threshold.
Figure 16B:
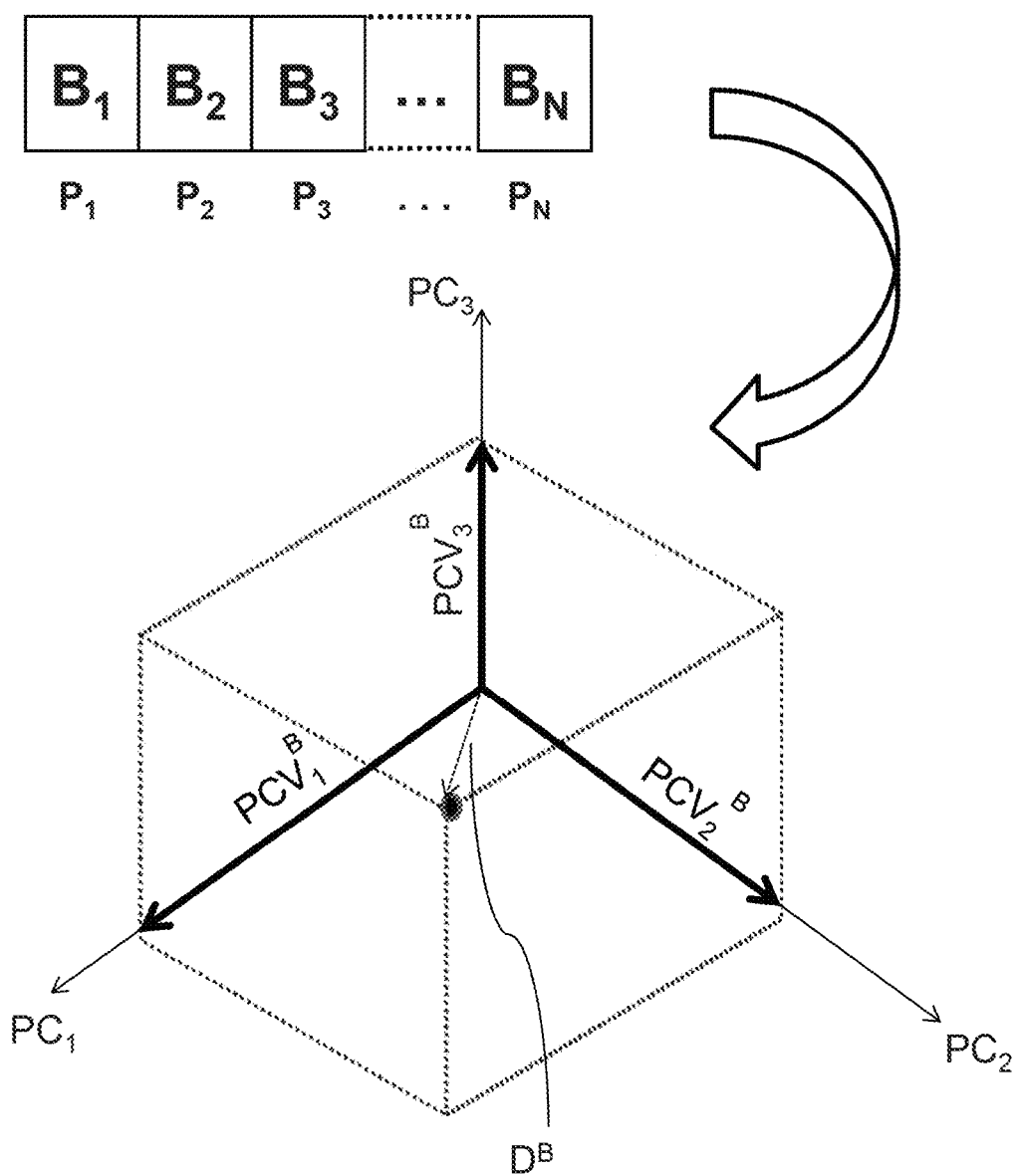

Principal component transformation and distances are graphically illustrated in three dimensions in FIG. 16A and FIG. 16B for two illustrative test samples. Principal component values and a distance (e.g., normalized distance) for test sample A, which does not have significant genomic instability, are shown in FIG. 16A. CNA quantifications $A_1$, $A_2$, $A_3$ through $A_N$ coupled to genomic portions $P_1$, $P_2$, $P_3$ through $P_N$, respectively, are shown for test sample A. The genomic portions and coupled CNA quantifications were transformed into principal component space, which transformation is represented by the open arrow. Principal component values were determined for each principal component for test sample A, $PCV_1^A$, $PCV_2^A$ and $PCV_3^A$, taking into account principal component weights obtained from a training set of samples. Three principal component values are shown for the three principal components $PC_1$, $PC_2$ and $PC_3$, although more principal component values typically are generated as part of the transformation and contribute to a multidimensional principal component space having more than three dimensions. There are fewer principal components generated by the transformation than the number of genomic portions (i.e., $P_1$ to $P_N$) and CNA quantifications (i.e., $A_1$ to $A_N$) used as input for the transformation, the principal component parameters are different than the genomic portion and CNA quantification input parameters, and the principal component space can be viewed as a higher dimensional space than the genomic portion/CNA quantification space. The reduced set of principal component value parameters are different than the input CNA quantification/ genomic portion parameters. The number of principal component values equals the number of principal components for the sample, and more than three principal component values often are selected and utilized to generate a distance (e.g., about 10 to about 30 principal component values often are utilized). Distance $D_A$ was determined from the principal component origin according to the selected principal component values generated for test sample A.

Principal component values and a distance (e.g., normalized distance) for test sample B, which has significant genomic instability, are shown in FIG. 16B. CNA quantifications $B_1$, $B_2$, $B_3$ through $B_N$, coupled to genomic portions $P_1$, $P_2$, $P_3$ through $P_N$, respectively, are shown for test sample B. The genomic portions and coupled CNA quantifications were transformed into principal component space, which transformation is represented by the open arrow. Principal component values were determined for each principal component for test sample B, $PCV_1^B$, $PCV_2^B$ and $PCV_3^B$, taking into account the same principal component weights used for test sample A obtained from the training set of samples. As with test sample A, three principal component values are shown for the three principal components $PC_1$, $PC_2$ and $PC_3$, although more principal component values typically are generated as part of the transformation and contribute to a multidimensional principal component space having more than three dimensions. Also, as with test sample A, there are fewer principal components generated by the transformation than the number of genomic portions (i.e., $P_1$ to $P_N$) and CNA quantifications (i.e., $B_1$ to $B_N$) used as input for the transformation, the principal component parameters are different than the genomic portion and CNA quantification input parameters, and the principal component space can be viewed as a higher dimensional space than the genomic portion/CNA quantification space. The number of principal component values equals the number of principal components for the sample, and the same number of principal component values selected and utilized to generate distance $D_A$ for test sample A were utilized to generate distance $D_B$ for test sample B. As with test sample A, distance $D_B$ was determined from the principal component origin according to the selected principal component values generated for test sample B.

As test sample B has significant genomic nucleic acid instability and test sample A does not, there often is a greater number of genomic portions with larger CNA quantifications for test sample B than for test sample A. A greater number of genomic portions with larger CNA quantifications for test sample B results in one or more $PCV^B$ values being larger than counterpart $PCV^A$ values, which results in distance $D_B$ being larger than distance $D_A$. As graphically illustrated in FIG. 16A and FIG. 16B, classification processes described herein can sequentially reduce a significant number of CNA quantification and genomic portion parameters for a test sample into one parameter, a distance (e.g., a normalized distance), that serves as a proxy for test sample genomic nucleic acid instability or stability. For example, test sample B can be classified for the presence of genomic nucleic acid instability if distance $D_B$ is greater than a cutoff value predetermined from distances ascertained for samples known to have genomic instability and samples known to not have genomic instability. Also, for example, test sample A can be classified for the absence of genomic nucleic acid instability if distance $D_A$ is less than the cutoff value predetermined from distances ascertained for samples known to have genomic instability and samples known to not have genomic instability.

In certain embodiments, principal components obtained from a principal component analysis (PCA) can be utilized to adjust CNA quantifications coupled to genomic portions for a test sample. In some embodiments, a PCA-predicted CNA quantification for each genomic portion (e.g., filtered genomic portion) for a test sample is generated. PCA-predicted CNA quantifications can be generated by performing PCA regression using genomic portion CNA quantifications from a training set of samples. In certain embodiments, a PCA regression includes the following: (a) performing PCA using genomic portion CNA quantifications from a training set of samples, thereby generating principal components; (b) optionally selecting a subset of the principal components; (c) estimating regression coefficients from all of the principal components or the subset of principal components; and (d) running a regression on CNA quantifications coupled to genomic portions for a test sample using the regression coefficients estimated in (c); whereby a PCA-predicted CNA quantification for each genomic portion can be obtained from the regression line. In some embodiments, the regression is a multivariate linear regression. The PCA-predicted CNA quantification for each genomic portion can be subtracted from the experimentally derived CNA quantification for the same genomic portion for a test sample, thereby providing a PCA-adjusted CNA quantification for each genomic portion for the test sample. PCA-adjusted CNA quantifications coupled to genomic portions, or an average thereof (e.g., mean, median, mean), can be used for classification in certain embodiments.

One or more or all steps performed for a transformation resulting in fewer parameters can be performed by an apparatus that includes memory and a processor (e.g., a computer). Instructions for transforming CNA quantifications coupled to genomic portions (e.g., principal component transformation) sometimes are stored in memory and are accessible to a processor. In some embodiments, instructions for generating a distance (e.g., a normalized distance) from parameters resulting from a transformation (e.g., generating a Mahalanobis distance from principal components generated for a test sample) are stored in memory and are accessible to a processor. In some embodiments, the R package "irlba" can be used for efficient singular value decomposition (SVD), and the R package "Matrix" can be used for matrix operations. The function "mahalanobis" from the R package "stats" can be used to generate Mahalanobis distance calculations, in certain embodiments.

Figure 11:
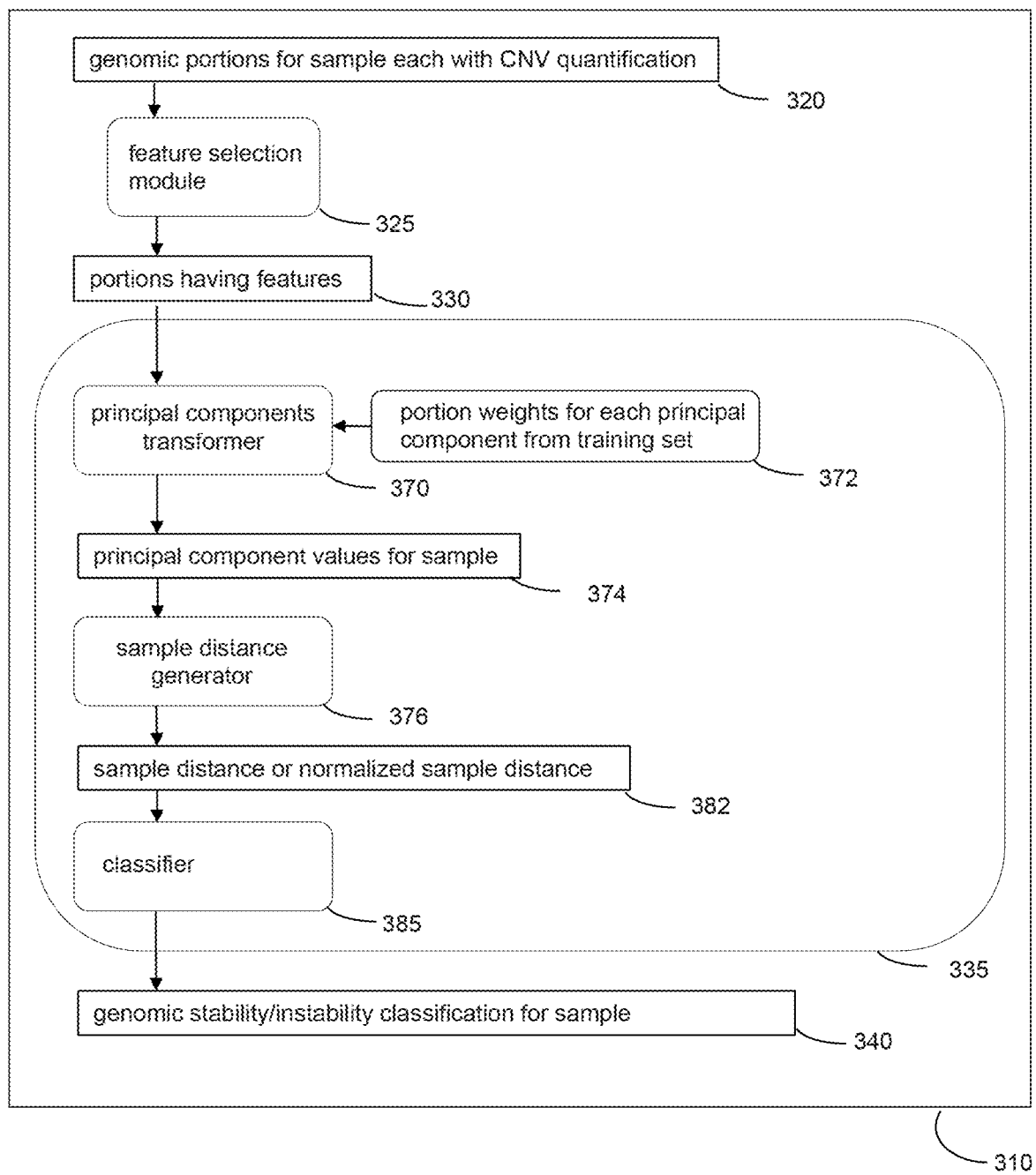
FIG. 11 shows one embodiment of the technology of classifying genomic instability.

An embodiment of a genomic stability/instability classification process is illustrated as process 310 in FIG. 11. Genomic portions 320 for a sample (e.g., a test sample) each coupled to a CNA quantification (e.g., segment z-score) are reduced by feature selection module 325, which generates a reduced set of genomic portions 330 having the feature(s). In some embodiments, feature selection module 326 generates a reduced set of genomic portions 331 not having the feature(s) (not shown in FIG. 11). Each of the genomic portions in reduced set 330 is coupled to a CNA quantification. The reduced set of genomic portions 330 are input for classification module 335, which provides a genomic stability classification or genomic instability classification 340 for the sample. Classification module 335 shown in process 310 generates principal component values 374 from the CNA quantifications coupled to the reduced set of genomic portions 330 by principal component transformer 370. The principal component transformer 370 utilizes genomic portion weights 372 for each principal component obtained from a training set of samples to generate principal component values 374 for a test sample. Classification module 335 also generates a sample distance or normalized sample distance 382 from the principal component values 374 by sample distance generator 376. Classification module 335 generates the genomic stability classification or genomic instability classification 340 for the sample by classifier 385 utilizing the distance or normalized distance 382 as input.

In certain embodiments of classification module 335, (i) principal component transformer 370 performs a singular value decomposition (SVD) principal component transformation, (ii) normalized sample distance 382 is a Mahalanobis distance, (iii) classifier 385 generates classification 340 in conjunction with a normalized distance cutoff value (e.g., a Mahalanobis distance cutoff value) selected by performing process 310 on a training set of samples containing samples having genomic instability and samples not having genomic instability, and (iv) combinations of two or three of (i), (ii) and (iii).

Figure 12:
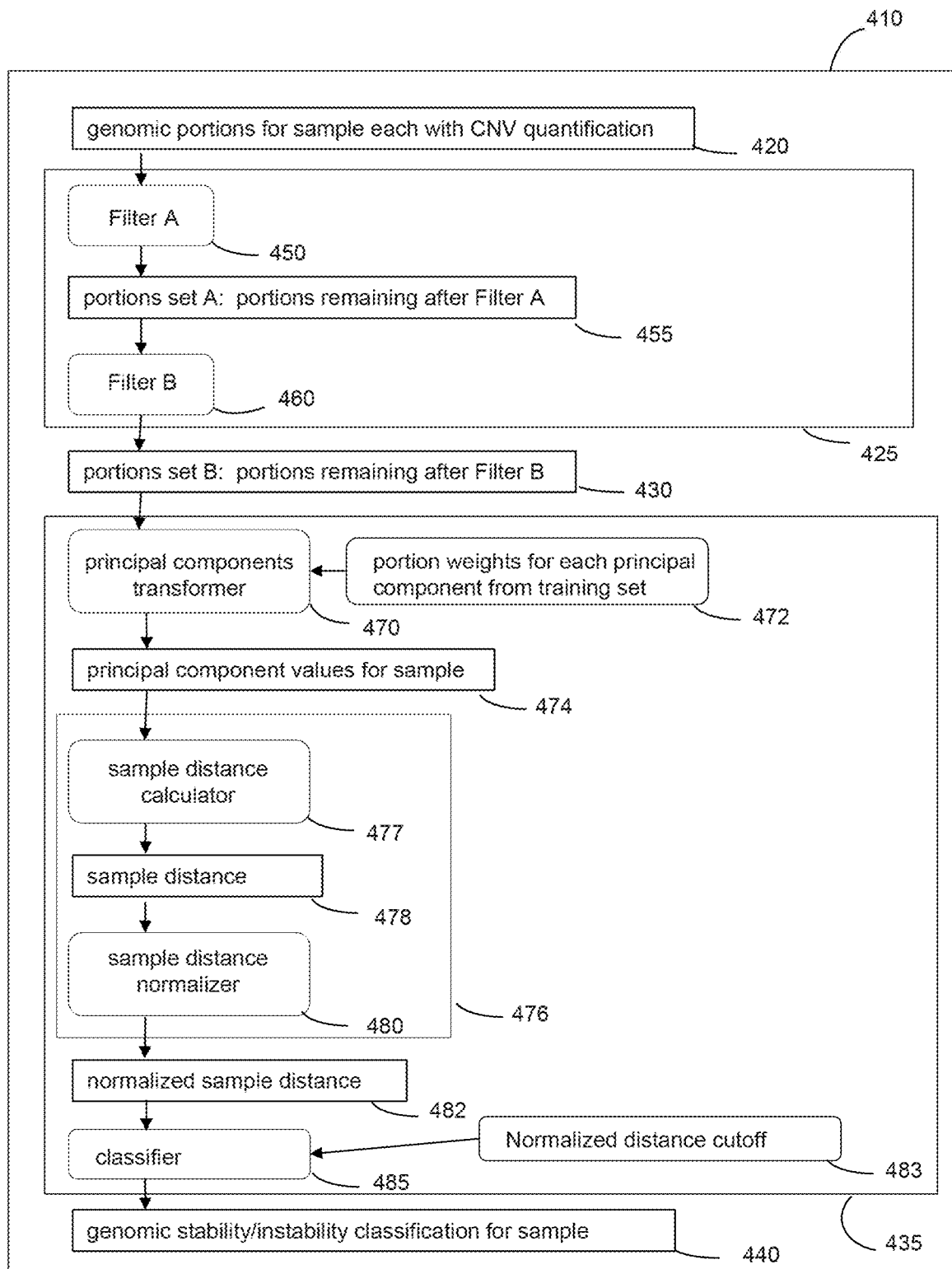
FIG. 12 shows one embodiment of the technology of classifying genomic instability.

Another embodiment of a genomic stability/instability classification process is illustrated as process 410 in FIG. 12. Genomic portions 420 for a sample (e.g., a test sample) each coupled to a CNA quantification (e.g., segment z-score) are reduced by feature selection module 425, which generates a reduced set of genomic portions 430 having the feature(s). Genomic portions 420 for a sample (e.g., a test sample)

coupled to a CNA quantification (e.g., segment z-score) are reduced by feature selection module 425, which generates a reduced set of genomic portions 430 having or not having the selected features. Feature selection module 425 includes a first filter 450 (i.e., filter A) that reduces the set of genomic portions 420 into a reduced set of genomic portions 455 that have or do not have features applied by the first filter 450. Feature selection module 425 also includes a second filter 460 (i.e., filter B) that reduces the set of genomic portions 455 reduced by filter A into the reduced set of genomic portions 430 that have or do not have features applied by the second filter 460. In certain embodiments, the first filter 450 and the second filter 460 filter each independently filter according to (i) consistent CNA presentation in a reference set of samples not having genomic nucleic acid instability, and (ii) representative genomic portions identified by a clustering process performed using a reference set of samples, in either order. Each of the genomic portions in reduced set 430 is coupled to a CNA quantification.

In certain embodiments of process 410, first filter 450 sometimes operates as certain filter 250 embodiments described herein. In such embodiments, filter 450 removes selected genomic portions 251 in set A' as described herein from genomic portions 420, and thereby yields the reduced set of genomic portions 455. In some embodiments of process 410, second filter 460 operates as certain filter 260 embodiments described herein. In such embodiments, filter 460 retains within genomic portions 455 selected genomic portions 261 in set B', removes genomic portions in set 455 that are not in set B', and thereby generates the reduced set of genomic portions 430.

In process embodiment 410, the reduced set of genomic portions 430 are input for classification module 435, which provides a genomic stability classification or genomic instability classification 440 for the sample. Classification module 435 shown in process 410 generates principal component values 474 from the CNA quantifications coupled to the reduced set of genomic portions 430 by principal component transformer 470. The principal component transformer 370 utilizes portion weights 472 for each principal component obtained from a training set of samples to generate principal component values 474 for a test sample. Classification module 335 also generates a normalized sample distance 482 from principal component values 374 by sample distance generator 476. Sample distance generator 476 generates a sample distance 478 by a sample distance calculator 477 and generates the normalized sample distance 482 by operation of a sample distance normalizer 480 on sample distance 478, in process embodiment 410. Classification module 435 generates the genomic stability classification or genomic instability classification 440 for the sample by classifier 485 utilizing the distance or normalized distance 482 as input in conjunction with a predetermined normalized distance cutoff value 483.

In certain embodiments of classification module 435, (i) principal component transformer 470 performs a singular value decomposition (SVD) principal component transformation, (ii) normalized sample distance 482 is a Mahalanobis distance, (iii) sample distance 478 is a Euclidian distance, (iv) normalized distance cutoff 483 is a Mahalanobis distance cutoff value selected by performing process 410 on a training set of samples containing samples having genomic instability and samples not having genomic instability, and (v) combinations of two or more of (i) to (iv).

Figure 14:
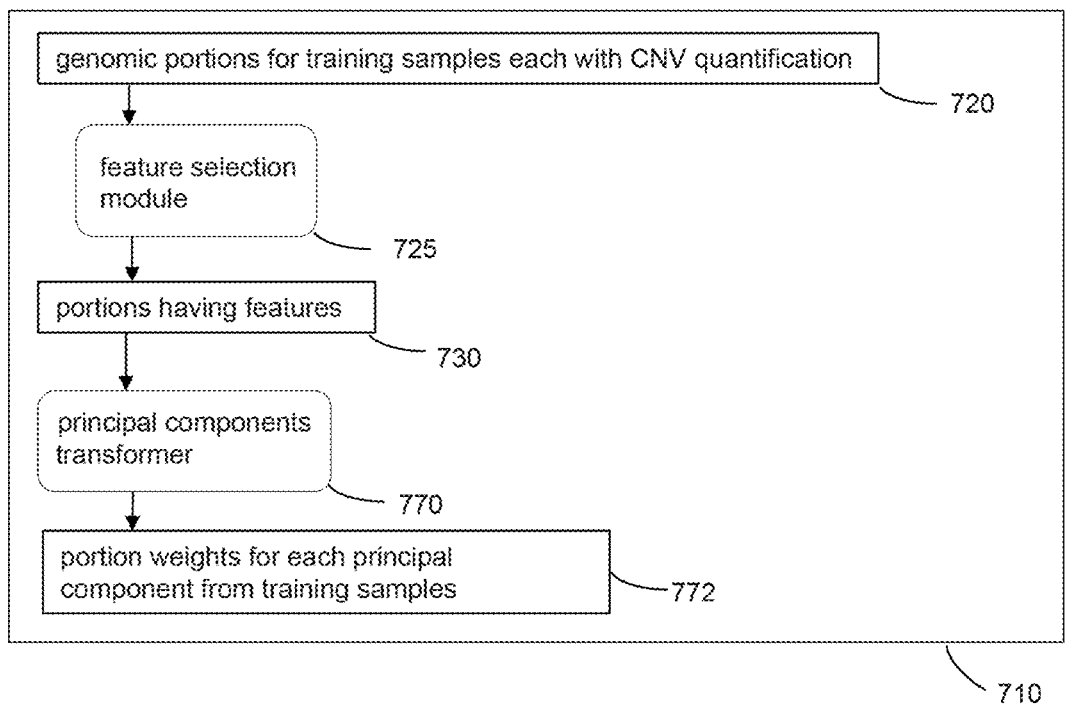
FIG. 14 shows one embodiment of the technology of classifying genomic instability.

In some embodiments, process 710 as illustrated in FIG. 14 is utilized to generate portion weights 372 utilized by principal component transformer 370 in process 310, or is utilized to generate portion weights 472 utilized by principal component transformer 470 in process 410. In process 710, genomic portions 720 for training samples, each coupled to a CNA quantification, are filtered according to one or more features by a feature selection module 725, resulting in a reduced set of filtered genomic portions 730. The reduced set of filtered genomic portions 730 and coupled CNA quantifications are transformed by a principal component transformer 770 into genomic portion weights 772. The genomic portion weights 772 from a training set of samples sometimes are utilized as genomic portion weights 372 or as genomic portion weights 472 applied to test samples.

Figure 15:
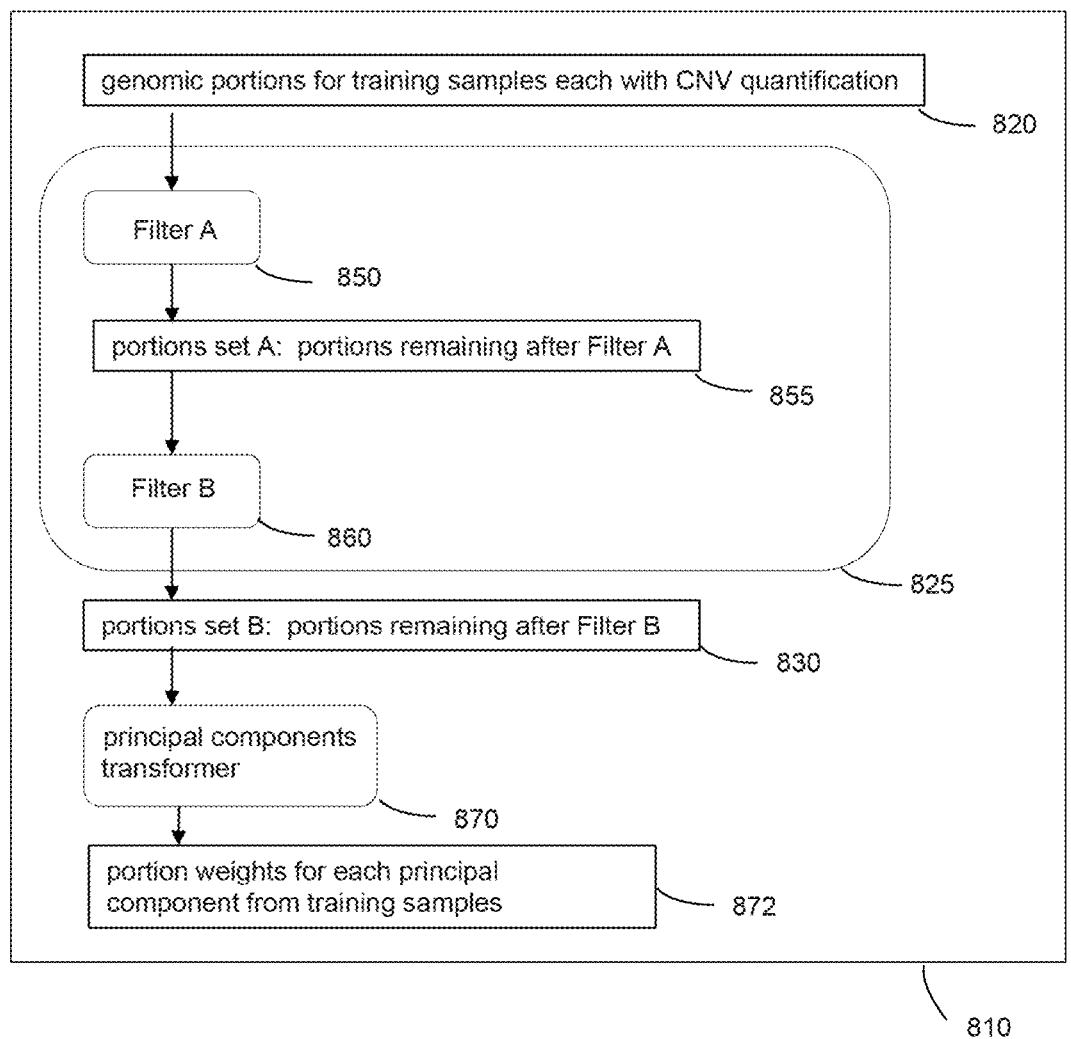
FIG. 15 shows non-limiting embodiments of the technology of classifying genomic instability.

In certain embodiments, process 810 as illustrated in FIG. 15 is utilized to generate portion weights 372 utilized by principal component transformer 370 in process 310, or is utilized to generate portion weights 472 utilized by principal component transformer 470 in process 410. In process 810, genomic portions 820 for training samples, each coupled to a CNA quantification, are filtered according to one or more features by a feature selection module 825, resulting in a reduced set of filtered genomic portions 830. In certain feature selection module 825 embodiments, first filter 850 sometimes operates as certain filter 250 embodiments described herein. In such embodiments, filter 850 removes selected genomic portions 251 in set A' as described herein from genomic portions 820, and thereby yields the reduced set of genomic portions 855. In some feature selection module 825 embodiments, second filter 860 operates as certain filter 260 embodiments described herein. In such embodiments, filter 860 retains within genomic portions 855 selected genomic portions 261 in set B', removes genomic portions in set 855 that are not in set B', and thereby generates the reduced set of filtered genomic portions 830. The reduced set of filtered genomic portions 830 and coupled CNA quantifications are transformed by a principal component transformer 870 into genomic portion weights 872. The genomic portion weights 872 from a training set of samples sometimes are utilized as genomic portion weights 372 or as genomic portion weights 472 applied to test samples.

Classifying Presence or Absence of Genomic Instability

A classification process generally classifies presence or absence of genomic instability based on genomic portion CNA quantifications resulting from filtering or weighting according to certain features. As described herein, a classification process can include generating a reduced set of parameters after transforming the CNA quantifications and coupled genomic portions into the reduced set of parameters, and the classification can be generated according to the reduced set of parameters. Also, as described herein, a classification process can include generating a distance or normalized distance determined for CNA quantifications coupled to genomic portions, or determined for a reduced set of parameters, and the classification can be generated according to the distance or normalized distance. One or more alternative classification processes for determining presence or absence of genomic instability can be applied to CNA quantifications resulting from a filtering or weighting as described herein. Non-limiting examples of alternative classification processes include artificial neural network (ANN), random forest, support vector machine (SVM), and k-nearest neighbor (KNN) classification processes, for example. As results of the improved features of the methods disclosed herein, a laboratory director typically can make this type of classification of genomic instability by visual inspection at a rate of about two (2) samples per minute (i.e., one sample every 30 seconds). The classification system here can make this type of classification at a rate of 100 samples per second when running on a standard desktop computer.

A classification sometimes is generated by comparing a parameter determined for a test sample to a cutoff value. Non-limiting examples of a parameter for a test sample include CNA quantifications resulting from filtering or weighting according to certain features described herein (e.g., an average CNA quantification (e.g., mean, median, mode CNA quantification) for a set of filtered genomic portions for a test sample); a reduced set of parameters (e.g., principal component values); principal component adjusted CNA quantifications (e.g., average adjusted CNA quantification (e.g., mean, median, mode adjusted CNA quantification) for a set of filtered genomic portions); a distance determined from CNA quantifications or reduced set of parameters (e.g., Euclidian distance generated from the reduced set of parameters); and a normalized distance determined from the CNA quantifications or reduced set of parameters (e.g., Mahalanobis distance generated from the reduced set of parameters). A suitable cutoff value for discriminating between samples having genomic nucleic acid instability and samples not having genomic nucleic acid instability can be determined by performing the feature filtering and classification processes described herein consistently on a training set of samples, where the training set includes samples known to have genomic instability and samples known to not have genomic instability. The cutoff value determined for a parameter for the training set of samples then can be applied consistently to the same parameter obtained for each test sample. In certain embodiments, a classification process includes determining the presence of genomic instability for the test subject according to a normalized distance above a cutoff value; and determining the absence of genomic instability for the test subject according to a normalized distance below the cutoff value. A Mahalanobis distance cutoff value of about 300 to about 700 (e.g., Mahalanobis cutoff value of about 300, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650) can be used in certain classification embodiments.

Classification performance can be assessed in any suitable manner. In some embodiments, classification performance is assessed by determining a sensitivity and/or specificity for classification of multiple samples with known genomic stability and genomic instability. In certain embodiments, a classification processes described herein is characterized by a sensitivity of about 90% or greater (e.g., sensitivity of 85, 86, 87, 88, 89, 90, 91, 92, 93, 94, 95, 96, 97, 98, 99, 99.5, 99.9% or greater) and/or independently by a specificity of about 90% or greater (e.g., specificity of 85, 86, 87, 88, 89, 90, 91, 92, 93, 94, 95, 96, 97, 98, 99, 99.5, 99.9% or greater).

A genomic stability or instability classification provided by a process described herein can be included in a laboratory test report. A laboratory test report may include only the genomic stability or instability classification, or may include other information (e.g., prenatal diagnostic test information (e.g., chromosome trisomy classification and/or sub-chromosome CNA classification); cancer diagnostic test information (e.g., presence or absence of one or more specific single nucleotide variations or copy number alterations)). Samples from subjects classified as having genomic nucleic acid instability can be identified and treated as cancer candidates (e.g., subjects who have cancer or are likely to have cancer in the future). A health care professional to whom a genomic instability classification is transmitted for a test sample from a subject may communicate the classification result to the subject, may recommend one or more cancer-directed diagnostic tests to the subject, and/or may recommend a cancer treatment to the subject according to the classification and/or the outcome of the one or more cancer-directed diagnostic tests.

One or more or all steps for classifying presence or absence of genomic instability can be performed by an apparatus that includes memory and a processor (e.g., a computer). A cutoff value for a parameter (e.g., normalized distance cutoff value) sometimes is stored in memory, is accessible to a processor, and can be applied by the processor for a determination by the processor as to whether the parameter obtained for a test sample is greater than, equal to, or less than the cutoff value. In certain embodiments, instructions for performing a determination as to whether the parameter obtained for a test sample is greater than, equal to, or less than the cutoff value are stored in memory and are accessible to a processor. In some embodiments, instructions for generating a report that contains a classification result are stored in memory and are accessible to a processor. When performed by an apparatus that includes memory and a processor, a classification process can be performed at a rate of about 80 determinations or more per second (e.g., about 70, 75, 80, 85, 90, 95, 100, 105, 110, 120, 125, 150, 200, 300, 400 or more determinations per second). Such a classification rate can be determined from the time that feature filtering is applied by a classification process to CNA quantifications for test samples.

Uses of Genomic Instability Classifications in Therapeutic Settings

Genomic instability classifications can be used in therapeutic settings. For example, a liquid sample containing cell-free nucleic acid (e.g., a liquid biopsy) can be obtained from a subject having, diagnosed with and/or suspected of having a medical condition or disorder, and can be utilized to generate a genomic instability classification. A genomic instability classification generated for a sample can be utilized to identify a subject having a higher probability of responding to a particular treatment of the medical condition or disorder. In certain embodiments, a method is applicable to a subject diagnosed with, or is suspected of having, a cell proliferative condition, and the subject is selected for a treatment of the cell proliferative condition according to a genomic instability classification.

A genomic instability classification generated for a sample also can be utilized to determine whether a particular treatment of the medical disorder or condition is effective, is not effective, is detrimental to the subject's health, should be continued or should be modified. Non-limiting examples of modifications include changing a dose of one or more therapeutics (e.g., increase or decreasing a dosage), changing a dosing regimen of one or more therapeutics or therapies (e.g., more frequent or less frequent administration), delaying to accelerating a time period for beginning or administering a therapy, and starting or discontinuing a therapy. In certain embodiments, a method is applicable to a subject diagnosed with, or is suspected of having, a cell proliferative condition and is undergoing a treatment of the cell proliferative condition, and the subject is identified as a responder or non-responder to the treatment according to a genomic instability classification. A genomic instability classification sometimes is generated for a subject at two or more time points during a treatment, and sometimes a genomic instability classification is a genomic instability number or is based on a genomic instability number. In some embodiments, a subject is identified as a responder to a treatment (e.g., a responder to an immunotherapy treatment (e.g., a responder to a checkpoint inhibitor treatment)) if after a time point of about 6 weeks to about 8 weeks of treatment the genomic instability classification is less than a threshold value (e.g., about 5, 6, 7, 8, 9 weeks); or the subject is identified as a non-responder to the treatment if after the time point of treatment the genomic instability classification is greater than the threshold value.

A cell proliferative disorder sometimes is a cancer (e.g., a tumor cancer; a solid tumor cancer), and non-limiting examples of cell proliferative conditions (i.e., also referred to as cell proliferative disorders) and cancers are described in the section entitled "Medical disorders and medical conditions" herein. A treatment sometimes includes administering an immunotherapy. Non-limiting examples of immunotherapies are active, passive or hybrid (active and passive) immunotherapies. Non-limiting examples of immunotherapies include adoptive T-cell therapy and administration of interleukin-2, interferon-alpha, polysaccharide-K and antibody therapeutics. Non-limiting examples of antibody therapeutics are antibodies that specifically bind to CD20, CD274, CD279, CD47, GD2, CD52, CD-L1, CTLA4, and PD-1. A class of antibody therapeutics include checkpoint inhibitors, non-limiting examples of which include antibodies that specifically bind to CTLA-4 (e.g., ipilimumab), PD-1 (e.g., nivolumab, pembrolizumab, BGB-A317) or PD-L1 (e.g., atezolizumab, avelumab, durvalumab).

Samples

Provided herein are systems, methods and products for analyzing nucleic acids. In some embodiments, nucleic acid fragments in a mixture of nucleic acid fragments are analyzed. Nucleic acid fragments may be referred to as nucleic acid templates, and the terms may be used interchangeably herein. A mixture of nucleic acids can comprise two or more nucleic acid fragment species having the same or different nucleotide sequences, different fragment lengths, different origins (e.g., genomic origins, fetal vs. maternal origins, cell or tissue origins, cancer vs. non-cancer origin, tumor vs. non-tumor origin, sample origins, subject origins, and the like), or combinations thereof.

Nucleic acid or a nucleic acid mixture utilized in systems, methods and products described herein often is isolated from a sample obtained from a subject (e.g., a test subject). A subject can be any living or non-living organism, including but not limited to a human, a non-human animal, a plant, a bacterium, a fungus, a protest or a pathogen. Any human or non-human animal can be selected, and may include, for example, mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, an infant, a child, an adult). A subject may be a cancer patient, a patient suspected of having cancer, a patient in remission, a patient with a family history of cancer, and/or a subject obtaining a cancer screen. In some embodiments, a test subject is a female. In some embodiments, a test subject is a human female. In some embodiments, a test subject is a male. In some embodiments, a test subject is a human male.

Nucleic acid may be isolated from any type of suitable biological specimen or sample (e.g., a test sample). A sample or test sample can be any specimen that is isolated or obtained from a subject or part thereof (e.g., a human subject, a pregnant female, a cancer patient, a fetus, a tumor). A sample sometimes is from a pregnant female subject bearing a fetus at any stage of gestation (e.g., first, second or third trimester for a human subject), and sometimes is from a post-natal subject. A sample sometimes is from a pregnant subject bearing a fetus that is euploid for all chromosomes, and sometimes is from a pregnant subject bearing a fetus having a chromosome aneuploidy (e.g., one, three (i.e., trisomy (e.g., T21, T18, T13)), or four copies of a chromosome) or other genetic variation. Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo; cancer biopsy), celocentesis sample, cells (blood cells, placental cells, embryo or fetal cells, fetal nucleated cells or fetal cellular remnants, normal cells, abnormal cells (e.g., cancer cells)) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. A fluid or tissue sample from which nucleic acid is extracted may be acellular (e.g., cell-free). In some embodiments, a fluid or tissue sample may contain cellular elements or cellular remnants. In some embodiments, fetal cells or cancer cells may be included in the sample.

A sample can be a liquid sample. A liquid sample can comprise extracellular nucleic acid (e.g., circulating cell-free DNA). Non-limiting examples of liquid samples, include, blood or a blood product (e.g., serum, plasma, or the like), urine, biopsy sample (e.g., liquid biopsy for the detection of cancer), a liquid sample described above, the like or combinations thereof. In certain embodiments, a sample is a liquid biopsy, which generally refers to an assessment of a liquid sample from a subject for the presence, absence, progression or remission of a disease (e.g., cancer). A liquid biopsy can be used in conjunction with, or as an alternative to, a sold biopsy (e.g., tumor biopsy). In certain instances, extracellular nucleic acid is analyzed in a liquid biopsy.

In some embodiments, a biological sample may be blood, plasma or serum. The term "blood" encompasses whole blood, blood product or any fraction of blood, such as serum, plasma, buffy coat, or the like as conventionally defined. Blood or fractions thereof often comprise nucleosomes. Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3 to 40 milliliters, between 5 to 50 milliliters) often is collected and can be stored according to standard procedures prior to or after preparation.

An analysis of nucleic acid found in a subject's blood may be performed using, e.g., whole blood, serum, or plasma. An analysis of fetal DNA found in maternal blood, for example, may be performed using, e.g., whole blood, serum, or plasma. An analysis of tumor DNA found in a patient's blood, for example, may be performed using, e.g., whole blood, serum, or plasma. Methods for preparing serum or plasma from blood obtained from a subject (e.g., a maternal subject; cancer patient) are known. For example, a subject's blood (e.g., a pregnant woman's blood; cancer patient's blood) can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for nucleic acid extraction. In addition to the acellular portion of the whole blood, nucleic acid may also be recovered from the cellular fraction, enriched in the buffy coat portion, which can be obtained following centrifugation of a whole blood sample from the subject and removal of the plasma.

A sample may be heterogeneous. For example, a sample may include more than one cell type and/or one or more nucleic acid species. In some instances, a sample may include (i) fetal cells and maternal cells, (ii) cancer cells and non-cancer cells, and/or (iii) pathogenic cells and host cells. In some instances, a sample may include (i) cancer and non-cancer nucleic acid, (ii) pathogen and host nucleic acid, (iii) fetal derived and maternal derived nucleic acid, and/or more generally, (iv) mutated and wild-type nucleic acid. In some instances, a sample may include a minority nucleic acid species and a majority nucleic acid species, as described in further detail below. In some instances, a sample may include cells and/or nucleic acid from a single subject or may include cells and/or nucleic acid from multiple subjects.

Cell Types

As used herein, a "cell type" refers to a type of cell that can be distinguished from another type of cell. Extracellular nucleic acid can include nucleic acid from several different cell types. Non-limiting examples of cell types that can contribute nucleic acid to circulating cell-free nucleic acid include liver cells (e.g., hepatocytes), lung cells, spleen cells, pancreas cells, colon cells, skin cells, bladder cells, eye cells, brain cells, esophagus cells, cells of the head, cells of the neck, cells of the ovary, cells of the testes, prostate cells, placenta cells, epithelial cells, endothelial cells, adipocyte cells, kidney/renal cells, heart cells, muscle cells, blood cells (e.g., white blood cells), central nervous system (CNS) cells, the like and combinations of the foregoing. In some embodiments, cell types that contribute nucleic acid to circulating cell-free nucleic acid analyzed include white blood cells, endothelial cells and hepatocyte liver cells. Different cell types can be screened as part of identifying and selecting nucleic acid loci for which a marker state is the same or substantially the same for a cell type in subjects having a medical condition and for the cell type in subjects not having the medical condition, as described in further detail herein.

A particular cell type sometimes remains the same or substantially the same in subjects having a medical condition and in subjects not having a medical condition. In a non-limiting example, the number of living or viable cells of a particular cell type may be reduced in a cell degenerative condition, and the living, viable cells are not modified, or are not modified significantly, in subjects having the medical condition.

A particular cell type sometimes is modified as part of a medical condition and has one or more different properties than in its original state. In a non-limiting example, a particular cell type may proliferate at a higher than normal rate, may transform into a cell having a different morphology, may transform into a cell that expresses one or more different cell surface markers and/or may become part of a tumor, as part of a cancer condition. In embodiments for which a particular cell type (i.e., a progenitor cell) is modified as part of a medical condition, the marker state for each of the one or more markers assayed often is the same or substantially the same for the particular cell type in subjects having the medical condition and for the particular cell type in subjects not having the medical condition. Thus, the term "cell type" sometimes pertains to a type of cell in subjects not having a medical condition, and to a modified version of the cell in subjects having the medical condition. In some embodiments, a "cell type" is a progenitor cell only and not a modified version arising from the progenitor cell. A "cell type" sometimes pertains to a progenitor cell and a modified cell arising from the progenitor cell. In such embodiments, a marker state for a marker analyzed often is the same or substantially the same for a cell type in subjects having a medical condition and for the cell type in subjects not having the medical condition.

In certain embodiments, a cell type is a cancer cell. Certain cancer cell types include, for example, leukemia cells (e.g., acute myeloid leukemia, acute lymphoblastic leukemia, chronic myeloid leukemia, chronic lymphoblastic leukemia); cancerous kidney/renal cells (e.g., renal cell cancer (clear cell, papillary type 1, papillary type 2, chromophobe, oncocytic, collecting duct), renal adenocarcinoma, hypernephroma, Wilm's tumor, transitional cell carcinoma); brain tumor cells (e.g., acoustic neuroma, astrocytoma (grade I: pilocytic astrocytoma, grade II: low-grade astrocytoma, grade III: anaplastic astrocytoma, grade IV: glioblastoma (GBM)), chordoma, cns lymphoma, craniopharyngioma, glioma (brain stem glioma, ependymoma, mixed glioma, optic nerve glioma, subependyoma), medulloblastoma, meningioma, metastatic brain tumors, oligodendroglioma, pituitary tumors, primitive neuroectodermal (PNET), schwannoma, juvenile pilocytic astrocytoma (JPA), pineal tumor, rhabdoid tumor).

Different cell types can be distinguished by any suitable characteristic, including without limitation, one or more different cell surface markers, one or more different morphological features, one or more different functions, one or more different protein (e.g., histone) modifications and one or more different nucleic acid markers. Non-limiting examples of nucleic acid markers include single-nucleotide polymorphisms (SNPs), methylation state of a nucleic acid locus, short tandem repeats, insertions (e.g., microinsertions), deletions (microdeletions) the like and combinations thereof. Non-limiting examples of protein (e.g., histone) modifications include acetylation, methylation, ubiquitylation, phosphorylation, sumoylation, the like and combinations thereof.

As used herein, the term a "related cell type" refers to a cell type having multiple characteristics in common with another cell type. In related cell types, 75% or more cell surface markers sometimes are common to the cell types (e.g., about 80%, 85%, 90% or 95% or more of cell surface markers are common to the related cell types).

Nucleic Acid

Provided herein are methods for analyzing nucleic acid. The terms "nucleic acid," "nucleic acid molecule," "nucleic acid fragment," and "nucleic acid template" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by a fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, virus, bacterium, autonomously replicating sequence (ARS), mitochondria, centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense," "plus" strand or "minus" strand, "forward" reading frame or "reverse" reading frame) and double-stranded polynucleotides. The term "gene" refers to a section of DNA involved in producing a polypeptide chain; and generally includes regions preceding and following the coding region (leader and trailer) involved in the transcription/translation of the gene product and the regulation of the transcription/translation, as well as intervening sequences (introns) between individual coding regions (exons). A nucleotide or base generally refers to the purine and pyrimidine molecular units of nucleic acid (e.g., adenine (A), thymine (T), guanine (G), and cytosine (C)). For RNA, the base thymine is replaced with uracil. Nucleic acid length or size may be expressed as a number of bases.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be derived from one or more sources (e.g., biological sample, blood, cells, serum, plasma, buffy coat, urine, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Ws.), and GFX™ Genomic Blood DNA Purification Kit (Amersham, Piscataway, N.J.), the like or combinations thereof.

In some embodiments, nucleic acid is extracted from cells using a cell lysis procedure. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. In some instances, a high salt and/or an alkaline lysis procedure may be utilized.

Nucleic acids can include extracellular nucleic acid in certain embodiments. The term "extracellular nucleic acid" as used herein can refer to nucleic acid isolated from a source having substantially no cells and also is referred to as "cell-free" nucleic acid, "circulating cell-free nucleic acid" (e.g., CCF fragments, ccf DNA) and/or "cell-free circulating nucleic acid." Extracellular nucleic acid can be present in and obtained from blood (e.g., from the blood of a human subject). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder"). In some embodiments, sample nucleic acid from a test subject is circulating cell-free nucleic acid. In some embodiments, circulating cell free nucleic acid is from blood plasma or blood serum from a test subject.

Extracellular nucleic acid can include different nucleic acid species, and therefore is referred to herein as "heterogeneous" in certain embodiments. For example, blood serum or plasma from a person having cancer can include nucleic acid from cancer cells (e.g., tumor, neoplasia) and nucleic acid from non-cancer cells. In another example, blood serum or plasma from a pregnant female can include maternal nucleic acid and fetal nucleic acid. In some instances, cancer or fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is cancer or fetal nucleic acid).

At least two different nucleic acid species can exist in different amounts in extracellular nucleic acid and sometimes are referred to as minority species and majority species. In certain instances, a minority species of nucleic acid is from an affected cell type (e.g., cancer cell, wasting cell, cell attacked by immune system). In certain embodiments, a genetic variation or genetic alteration (e.g., copy number alteration, copy number variation, single nucleotide alteration, single nucleotide variation, chromosome alteration, and/or translocation) is determined for a minority nucleic acid species. In certain embodiments, a genetic variation or genetic alteration is determined for a majority nucleic acid species. Generally it is not intended that the terms "minority" or "majority" be rigidly defined in any respect. In one aspect, a nucleic acid that is considered "minority," for example, can have an abundance of at least about 0.1% of the total nucleic acid in a sample to less than 50% of the total nucleic acid in a sample. In some embodiments, a minority nucleic acid can have an abundance of at least about 1% of the total nucleic acid in a sample to about 40% of the total nucleic acid in a sample. In some embodiments, a minority nucleic acid can have an abundance of at least about 2% of the total nucleic acid in a sample to about 30% of the total nucleic acid in a sample. In some embodiments, a minority nucleic acid can have an abundance of at least about 3% of the total nucleic acid in a sample to about 25% of the total nucleic acid in a sample. For example, a minority nucleic acid can have an abundance of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% of the total nucleic acid in a sample. In some instances, a minority species of extracellular nucleic acid sometimes is about 1% to about 40% of the overall nucleic acid (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% of the nucleic acid is minority species nucleic acid). In some embodiments, the minority nucleic acid is extracellular DNA. In some embodiments, the minority nucleic acid is extracellular DNA from apoptotic tissue. In some embodiments, the minority nucleic acid is extracellular DNA from tissue affected by a cell proliferative disorder. In some embodiments, the minority nucleic acid is extracellular DNA from a tumor cell. In some embodiments, the minority nucleic acid is extracellular fetal DNA.

In another aspect, a nucleic acid that is considered "majority," for example, can have an abundance greater than 50% of the total nucleic acid in a sample to about 99.9% of the total nucleic acid in a sample. In some embodiments, a majority nucleic acid can have an abundance of at least about 60% of the total nucleic acid in a sample to about 99% of the total nucleic acid in a sample. In some embodiments, a majority nucleic acid can have an abundance of at least about 70% of the total nucleic acid in a sample to about 98% of the total nucleic acid in a sample. In some embodiments, a majority nucleic acid can have an abundance of at least about 75% of the total nucleic acid in a sample to about 97% of the total nucleic acid in a sample. For example, a majority nucleic acid can have an abundance of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the total nucleic acid in a sample. In some embodiments, the majority nucleic acid is extracellular DNA. In some embodiments, the majority nucleic acid is extracellular maternal DNA. In some embodiments, the majority nucleic acid is DNA from healthy tissue. In some embodiments, the majority nucleic acid is DNA from non-tumor cells.

In some embodiments, a minority species of extracellular nucleic acid is of a length of about 500 base pairs or less (e.g., about 80, 85, 90, 91, 92, 93, 94, 95, 96, 97, 98, 99 or 100% of minority species nucleic acid is of a length of about 500 base pairs or less). In some embodiments, a minority species of extracellular nucleic acid is of a length of about 300 base pairs or less (e.g., about 80, 85, 90, 91, 92, 93, 94, 95, 96, 97, 98, 99 or 100% of minority species nucleic acid is of a length of about 300 base pairs or less). In some embodiments, a minority species of extracellular nucleic acid is of a length of about 250 base pairs or less (e.g., about 80, 85, 90, 91, 92, 93, 94, 95, 96, 97, 98, 99 or 100% of minority species nucleic acid is of a length of about 250 base pairs or less). In some embodiments, a minority species of extracellular nucleic acid is of a length of about 200 base pairs or less (e.g., about 80, 85, 90, 91, 92, 93, 94, 95, 96, 97, 98, 99 or 100% of minority species nucleic acid is of a length of about 200 base pairs or less). In some embodiments, a minority species of extracellular nucleic acid is of a length of about 150 base pairs or less (e.g., about 80, 85, 90, 91, 92, 93, 94, 95, 96, 97, 98, 99 or 100% of minority species nucleic acid is of a length of about 150 base pairs or less). In some embodiments, a minority species of extracellular nucleic acid is of a length of about 100 base pairs or less (e.g., about 80, 85, 90, 91, 92, 93, 94, 95, 96, 97, 98, 99 or 100% of minority species nucleic acid is of a length of about 100 base pairs or less). In some embodiments, a minority species of extracellular nucleic acid is of a length of about 50 base pairs or less (e.g., about 80, 85, 90, 91, 92, 93, 94, 95, 96, 97, 98, 99 or 100% of minority species nucleic acid is of a length of about 50 base pairs or less).

Nucleic acid may be provided for conducting methods described herein with or without processing of the sample(s) containing the nucleic acid. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample.

A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, small fragments of fetal nucleic acid (e.g., 30 to 500 bp fragments) can be purified, or partially purified, from a mixture comprising both fetal and maternal nucleic acid fragments. In certain examples, nucleosomes comprising smaller fragments of fetal nucleic acid can be purified from a mixture of larger nucleosome complexes comprising larger fragments of maternal nucleic acid. In certain examples, cancer cell nucleic acid can be purified from a mixture comprising cancer cell and non-cancer cell nucleic acid. In certain examples, nucleosomes comprising small fragments of cancer cell nucleic acid can be purified from a mixture of larger nucleosome complexes comprising larger fragments of non-cancer nucleic acid. In some embodiments, nucleic acid is provided for conducting methods described herein without prior processing of the sample(s) containing the nucleic acid. For example, nucleic acid may be analyzed directly from a sample without prior extraction, purification, partial purification, and/or amplification.

In some embodiments nucleic acids, such as, for example, cellular nucleic acids, are sheared or cleaved prior to, during or after a method described herein. The term "shearing" or "cleavage" generally refers to a procedure or conditions in which a nucleic acid molecule, such as a nucleic acid template gene molecule or amplified product thereof, may be severed into two (or more) smaller nucleic acid molecules. Such shearing or cleavage can be sequence specific, base specific, or nonspecific, and can be accomplished by any of a variety of methods, reagents or conditions, including, for example, chemical, enzymatic, physical shearing (e.g., physical fragmentation). Sheared or cleaved nucleic acids may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs.

Sheared or cleaved nucleic acids can be generated by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 2005/0112590, the like or combinations thereof. The average, mean or nominal length of the resulting nucleic acid fragments can be controlled by selecting an appropriate fragment-generating method.

The term "amplified" as used herein refers to subjecting a target nucleic acid in a sample to a process that linearly or exponentially generates amplicon nucleic acids having the same or substantially the same nucleotide sequence as the target nucleic acid, or part thereof. In certain embodiments the term "amplified" refers to a method that comprises a polymerase chain reaction (PCR). In certain instances, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule).

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a sequence analysis.

Enriching Nucleic Acids

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, cancer nucleic acid, patient nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, cancer or fetal nucleic acid. In certain embodiments, a method for determining fraction of cancer cell nucleic acid or fetal fraction also can be used to enrich for cancer or fetal nucleic acid. In certain embodiments, nucleic acid from normal tissue (e.g., non-cancer cells) is selectively removed (partially, substantially, almost completely or completely) from the sample. In certain embodiments, maternal nucleic acid is selectively removed (partially, substantially, almost completely or completely) from the sample. In certain embodiments, enriching for a particular low copy number species nucleic acid (e.g., cancer or fetal nucleic acid) may improve quantitative sensitivity. Methods for enriching a sample for a particular species of nucleic acid are described, for example, in U.S. Pat. No. 6,927,028, International Patent Application Publication No. WO 2007/140417, International Patent Application Publication No. WO 2007/147063, International Patent Application Publication No. WO 2009/032779, International Patent Application Publication No. WO 2009/032781, International Patent Application Publication No. WO 2010/033639, International Patent Application Publication No.

WO 2011/034631, International Patent Application Publication No. WO 2006/056480, and International Patent Application Publication No. WO 2011/143659, the entire content of each is incorporated herein by reference, including all text, tables, equations and drawings.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art.

Non-limiting examples of methods for enriching for a nucleic acid subpopulation in a sample include methods that exploit epigenetic differences between nucleic acid species (e.g., methylation-based fetal nucleic acid enrichment methods described in U.S. Patent Application Publication No. 2010/0105049, which is incorporated by reference herein); restriction endonuclease enhanced polymorphic sequence approaches (e.g., such as a method described in U.S. Patent Application Publication No. 2009/0317818, which is incorporated by reference herein); selective enzymatic degradation approaches; massively parallel signature sequencing (MPSS) approaches; amplification (e.g., PCR)-based approaches (e.g., loci-specific amplification methods, multiplex SNP allele PCR approaches; universal amplification methods); pull-down approaches (e.g., biotinylated ultramer pull-down methods); extension and ligation-based methods (e.g., molecular inversion probe (MIP) extension and ligation); and combinations thereof.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments often are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from a nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a part or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome). In certain embodiments, a hybridization-based method (e.g., using oligonucleotide arrays) can be used to enrich for nucleic acid sequences from certain chromosomes (e.g., a potentially aneuploid chromosome, reference chromosome or other chromosome of interest), genes or regions of interest thereof. Thus, in some embodiments, a nucleic acid sample is optionally enriched by capturing a subset of fragments using capture oligonucleotides complementary to, for example, selected genes in sample nucleic acid. In certain instances, captured fragments are amplified. For example, captured fragments containing adapters may be amplified using primers complementary to the adapter oligonucleotides to form collections of amplified fragments, indexed according to adapter sequence. In some embodiments, nucleic acid is enriched for fragments from a select genomic region (e.g., chromosome, a gene) by amplification of one or more regions of interest using oligonucleotides (e.g., PCR primers) complementary to sequences in fragments containing the region(s) of interest, or part(s) thereof.

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain instances, length-based separation approaches can include selective sequence tagging approaches, fragment circularization, chemical treatment (e.g., formaldehyde, polyethylene glycol (PEG) precipitation), mass spectrometry and/or size-specific nucleic acid amplification, for example.

Nucleic Acid Quantification

The amount of nucleic acid (e.g., concentration, relative amount, absolute amount, copy number, and the like) in a sample may be determined. The amount of a minority nucleic acid (e.g., concentration, relative amount, absolute amount, copy number, and the like) in nucleic acid is determined in some embodiments. In certain embodiments, the amount of a minority nucleic acid species in a sample is referred to as "minority species fraction." In some embodiments "minority species fraction" refers to the fraction of a minority nucleic acid species in circulating cell-free nucleic acid in a sample (e.g., a blood sample, a serum sample, a plasma sample, a urine sample) obtained from a subject.

The amount of a minority nucleic acid in extracellular nucleic acid can be quantified and used in conjunction with a method provided herein. Thus, in certain embodiments, methods described herein comprise an additional step of determining the amount of a minority nucleic acid. The amount of a minority nucleic acid can be determined in a sample from a subject before or after processing to prepare sample nucleic acid. In certain embodiments, the amount of a minority nucleic acid is determined in a sample after sample nucleic acid is processed and prepared, which amount is utilized for further assessment. In some embodiments, an outcome comprises factoring the minority species fraction in the sample nucleic acid (e.g., adjusting counts, removing samples, making a call or not making a call).

A determination of minority species fraction can be performed before, during, or at any one point in a method described herein, or after certain methods described herein (e.g., detection of a genetic variation or genetic alteration). For example, to conduct a genetic variation/genetic alteration determination method with a certain sensitivity or specificity, a minority nucleic acid quantification method may be implemented prior to, during or after genetic variation/genetic alteration determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more minority nucleic acid. In some embodiments, samples determined as having a certain threshold amount of minority nucleic acid (e.g., about 15% or more minority nucleic acid; about 4% or more minority nucleic acid) are further analyzed for a genetic variation/genetic alteration, or the presence or absence of a genetic variation/genetic alteration, for example. In certain embodiments, determinations of, for example, a genetic variation or genetic alteration are selected (e.g., selected and communicated to a patient) only for samples having a certain threshold amount of a minority nucleic acid (e.g., about 15% or more minority nucleic acid; about 4% or more minority nucleic acid).

The amount of cancer cell nucleic acid (e.g., concentration, relative amount, absolute amount, copy number, and the like) in nucleic acid is determined in some embodiments. In certain instances, the amount of cancer cell nucleic acid in a sample is referred to as "fraction of cancer cell nucleic acid," and sometimes is referred to as "cancer fraction" or "tumor fraction." In some embodiments "fraction of cancer cell nucleic acid" refers to the fraction of cancer cell nucleic acid in circulating cell-free nucleic acid in a sample (e.g., a blood sample, a serum sample, a plasma sample, a urine sample) obtained from a subject.

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction." In some embodiments "fetal fraction" refers to the fraction of fetal nucleic acid in circulating cell-free nucleic acid in a sample (e.g., a blood sample, a serum sample, a plasma sample, a urine sample) obtained from a pregnant female. Certain methods described herein or known in the art for determining fetal fraction can be used for determining a fraction of cancer cell nucleic acid and/or a minority species fraction.

In certain instances, fetal fraction may be determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation) between mother and fetus, or fetal RNA markers in maternal blood plasma (see e.g., Lo, 2005, Journal of Histochemistry and Cytochemistry 53 (3): 293-296)). Determination of fetal fraction sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample.

In certain embodiments, a minority species fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method for determining fetal fraction, for example, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome.

A minority species fraction can be determined, in some embodiments, using methods that incorporate information derived from chromosomal aberrations as described, for example, in International Patent Application Publication No. WO2014/055774, which is incorporated by reference herein. A minority species fraction can be determined, in some embodiments, using methods that incorporate information derived from sex chromosomes as described, for example, in U.S. Patent Application Publication No. 2013/0288244 and U.S. Patent Application Publication No. 2013/0338933, each of which is incorporated by reference herein.

A minority species fraction can be determined in some embodiments using methods that incorporate fragment length information (e.g., fragment length ratio (FLR) analysis, fetal ratio statistic (FRS) analysis as described in International Patent Application Publication No. WO 2013/177086, which is incorporated by reference herein). Cell-free fetal nucleic acid fragments generally are shorter than maternally-derived nucleic acid fragments (see e.g., Chan et al. (2004) Clin. Chem. 50:88-92; Lo et al. (2010) Sci. Transl. Med. 2:61ra91). Thus, fetal fraction can be determined, in some embodiments, by counting fragments under a particular length threshold and comparing the counts, for example, to counts from fragments over a particular length threshold and/or to the amount of total nucleic acid in the sample. Methods for counting nucleic acid fragments of a particular length are described in further detail in International Patent Application Publication No. WO 2013/177086.

A minority species fraction can be determined, in some embodiments, according to portion-specific fraction estimates (e.g., as described in International Patent Application Publication No. WO 2014/205401, which is incorporated by reference herein). Without being limited to theory, the amount of reads from fetal CCF fragments (e.g., fragments of a particular length, or range of lengths) often map with ranging frequencies to portions (e.g., within the same sample, e.g., within the same sequencing run). Also, without being limited to theory, certain portions, when compared among multiple samples, tend to have a similar representation of reads from fetal CCF fragments (e.g., fragments of a particular length, or range of lengths), and that the representation correlates with portion-specific fetal fractions (e.g., the relative amount, percentage or ratio of CCF fragments originating from a fetus). Portion-specific fetal fraction estimates generally are determined according to portion-specific parameters and their relation to fetal fraction.

In some embodiments, the determination of minority species fraction (e.g., fraction of cancer cell nucleic acid; fetal fraction) is not required or necessary for identifying the presence or absence of a genetic variation or genetic alteration. In some embodiments, identifying the presence or absence of a genetic variation or genetic alteration does not require a sequence differentiation of a minority nucleic acid versus a majority nucleic acid. In certain embodiments, this is because the summed contribution of both minority and majority sequences in a particular chromosome, chromosome portion or part thereof is analyzed. In some embodiments, identifying the presence or absence of a genetic variation or genetic alteration does not rely on a priori sequence information that would distinguish minority nucleic acid from majority nucleic acid.

Nucleic Acid Library

In some embodiments a nucleic acid library is a plurality of polynucleotide molecules (e.g., a sample of nucleic acids) that are prepared, assembled and/or modified for a specific process, non-limiting examples of which include immobilization on a solid phase (e.g., a solid support, a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments, a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adapters. In some embodiments, a library of nucleic acids comprises one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments, a polynucleotide of known sequence comprises a universal sequence. A universal sequence is a specific nucleotide sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using cell-free DNA).

In certain embodiments, a ligation-based library preparation method is used (e.g., ILLUMINA TRUSEQ, Illumina, San Diego Calif.). Ligation-based library preparation methods often make use of an adapter (e.g., a methylated adapter) design which can incorporate an index sequence (e.g., a sample index sequence to identify sample origin for a nucleic acid sequence) at the initial ligation step and often can be used to prepare samples for single-read sequencing, paired-end sequencing and multiplexed sequencing. For example, nucleic acids (e.g., fragmented nucleic acids or cell-free DNA) may be end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides.

In some embodiments nucleic acid library preparation comprises ligating an adapter oligonucleotide (e.g., to a sample nucleic acid, to a sample nucleic acid fragment, to a template nucleic acid). Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). In some embodiments, an adapter oligonucleotide comprises one or more of primer annealing polynucleotide (e.g., for annealing to flow cell attached oligonucleotides and/or to free amplification primers), an index polynucleotide (e.g., sample index sequence for tracking nucleic acid from different samples; also referred to as a sample ID), and a barcode polynucleotide (e.g., single molecule barcode (SMB) for tracking individual molecules of sample nucleic acid that are amplified prior to sequencing; also referred to as a molecular barcode). In some embodiments, a primer annealing component of an adapter oligonucleotide comprises one or more universal sequences (e.g., sequences complementary to one or more universal amplification primers). In some embodiments, an index polynucleotide (e.g., sample index; sample ID) is a component of an adapter oligonucleotide. In some embodiments, an index polynucleotide (e.g., sample index; sample ID) is a component of a universal amplification primer sequence.

In some embodiments, adapter oligonucleotides when used in combination with amplification primers (e.g., universal amplification primers) are designed generate library constructs comprising one or more of: universal sequences, molecular barcodes, sample ID sequences, spacer sequences, and a sample nucleic acid sequence. In some embodiments, adapter oligonucleotides when used in combination with universal amplification primers are designed generate library constructs comprising an ordered combination of one or more of: universal sequences, molecular barcodes, sample ID sequences, spacer sequences, and a sample nucleic acid sequence. For example, a library construct may comprise a first universal sequence, followed by a second universal sequence, followed by first molecular barcode, followed by a spacer sequence, followed by a template sequence (e.g., sample nucleic acid sequence), followed by a spacer sequence, followed by a second molecular barcode, followed by a third universal sequence, followed by a sample ID, followed by a fourth universal sequence. In some embodiments, adapter oligonucleotides when used in combination with amplification primers (e.g., universal amplification primers) are designed generate library constructs for each strand of a template molecule (e.g., sample nucleic acid molecule). In some embodiments, adapter oligonucleotides are duplex adapter oligonucleotides.

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein, an enzyme, an antibody or part thereof, a linker, a member of a binding pair, the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method, apparatus or machine, non-limiting examples of which include flow cytometry, quantitative polymerase chain reaction (qPCR), gel electrophoresis, a luminometer, a fluorometer, a spectrophotometer, a suitable genechip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a transposon-based library preparation method is used (e.g., EPICENTRE NEXTERA, Epicentre, Madison, Wis.). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments, a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support. In some embodiments, modified nucleic acid (e.g., nucleic acid modified by addition of adapters) is amplified.

In some embodiments, solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., U.S. Patent Application Publication No. 2013/0012399), the like or combinations thereof.

Nucleic Acid Sequencing and Processing

Methods provided herein generally include nucleic acid sequencing and analysis. In some embodiments, nucleic acid is sequenced and the sequencing product (e.g., a collection of sequence reads) is processed prior to, or in conjunction with, an analysis of the sequenced nucleic acid. For example, sequence reads may be processed according to one or more of the following: aligning, mapping, filtering portions, selecting portions, counting, normalizing, weighting, generating a profile, and the like, and combinations thereof. Certain processing steps may be performed in any order and certain processing steps may be repeated. For example, portions may be filtered followed by sequence read count normalization, and, in certain embodiments, sequence read counts may be normalized followed by portion filtering. In some embodiments, a portion filtering step is followed by sequence read count normalization followed by a further portion filtering step. Certain sequencing methods and processing steps are described in further detail below.

Sequencing

In some embodiments, nucleic acid (e.g., nucleic acid fragments, sample nucleic acid, cell-free nucleic acid) is sequenced. In certain instances, a full or substantially full sequence is obtained and sometimes a partial sequence is obtained. Nucleic acid sequencing generally produces a collection of sequence reads. As used herein, "reads" (e.g., "a read," "a sequence read") are short nucleotide sequences produced by any sequencing process described herein or known in the art. Reads can be generated from one end of nucleic acid fragments ("single-end reads"), and sometimes are generated from both ends of nucleic acid fragments (e.g., paired-end reads, double-end reads).

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length of about 1000 bp or more. In some embodiments sequence reads are of a mean, median, average or absolute length of about 1500, 2000, 2500, 3000, 3500, 4000, 4500, or 5000 bp or more. In some embodiments, sequence reads are of a mean, median, average or absolute length of about 100 bp to about 200 bp. In some embodiments, sequence reads are of a mean, median or absolute length of about 140 bp to about 160 bp. For example, sequence reads may be of a mean, median, average or absolute length of about 140, 141, 142, 143, 144, 145, 146, 147, 148, 149, 150, 151, 152, 153, 154, 155, 156, 157, 158, 159 or 160 bp.

In some embodiments the nominal, average, mean or absolute length of single-end reads sometimes is about 10 continuous nucleotides to about 250 or more contiguous nucleotides, about 15 contiguous nucleotides to about 200 or more contiguous nucleotides, about 15 contiguous nucleotides to about 150 or more contiguous nucleotides, about 15 contiguous nucleotides to about 125 or more contiguous nucleotides, about 15 contiguous nucleotides to about 100 or more contiguous nucleotides, about 15 contiguous nucleotides to about 75 or more contiguous nucleotides, about 15 contiguous nucleotides to about 60 or more contiguous nucleotides, 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length. In certain embodiments the nominal, average, mean or absolute length of single-end reads is about 20 to about 200 bases, about 100 to about 200 bases, or about 140 to about 160 bases in length. In certain embodiments the nominal, average, mean or absolute length of single-end reads is about 30, 40, 50, 60, 70, 80, 90, 100, 110, 120, 130, 140, 150, 160, 170, 180, 190, or about 200 bases or more in length. In certain embodiments, the nominal, average, mean or absolute length of paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides or about 18 contiguous nucleotides. In certain embodiments, the nominal, average, mean or absolute length of paired-end reads sometimes is about 25 contiguous nucleotides to about 400 contiguous nucleotides or more (e.g., about 25, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 nucleotides in length or more), about 50 contiguous nucleotides to about 350 contiguous nucleotides or more, about 100 contiguous nucleotides to about 325 contiguous nucleotides, about 150 contiguous nucleotides to about 325 contiguous nucleotides, about 200 contiguous nucleotides to about 325 contiguous nucleotides, about 275 contiguous nucleotides to about 310 contiguous nucleotides, about 100 contiguous nucleotides to about 200 contiguous nucleotides, about 100 contiguous nucleotides to about 175 contiguous nucleotides, about 125 contiguous nucleotides to about 175 contiguous nucleotides, and sometimes is about 140 contiguous nucleotides to about 160 contiguous nucleotides. In certain embodiments, the nominal, average, mean, or absolute length of paired-end reads is about 150 contiguous nucleotides, and sometimes is 150 contiguous nucleotides.

In some embodiments, nucleotide sequence reads obtained from a sample are partial nucleotide sequence reads. As used herein, "partial nucleotide sequence reads" refers to sequence reads of any length with incomplete sequence information, also referred to as sequence ambiguity. Partial nucleotide sequence reads may lack information regarding nucleobase identity and/or nucleobase position or order. Partial nucleotide sequence reads generally do not include sequence reads in which the only incomplete sequence information (or in which less than all of the bases are sequenced or determined) is from inadvertent or unintentional sequencing errors. Such sequencing errors can be inherent to certain sequencing processes and include, for example, incorrect calls for nucleobase identity, and missing or extra nucleobases. Thus, for partial nucleotide sequence reads herein, certain information about the sequence is often deliberately excluded. That is, one deliberately obtains sequence information with respect to less than all of the nucleobases or which might otherwise be characterized as or be a sequencing error. In some embodiments, a partial nucleotide sequence read can span a portion of a nucleic acid fragment. In some embodiments, a partial nucleotide sequence read can span the entire length of a nucleic acid fragment. Partial nucleotide sequence reads are described, for example, in International Patent Application Publication No. WO 2013/052907, the entire content of which is incorporated herein by reference, including all text, tables, equations and drawings.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from a sample from a subject can be reads from a mixture of a minority nucleic acid and a majority nucleic acid. For example, sequence reads obtained from the blood of a cancer patient can be reads from a mixture of cancer nucleic acid and non-cancer nucleic acid. In another example, sequence reads obtained from the blood of a pregnant female can be reads from a mixture of fetal nucleic acid and maternal nucleic acid. A mixture of relatively short reads can be transformed by processes described herein into a representation of genomic nucleic acid present in the subject, and/or a representation of genomic nucleic acid present in a tumor or a fetus. In certain instances, a mixture of relatively short reads can be transformed into a representation of a copy number alteration, a genetic variation/genetic alteration or an aneuploidy, for example. In one example, reads of a mixture of cancer and non-cancer nucleic acid can be transformed into a representation of a composite chromosome or a part thereof comprising features of one or both cancer cell and non-cancer cell chromosomes. In another example, reads of a mixture of maternal and fetal nucleic acid can be transformed into a representation of a composite chromosome or a part thereof comprising features of one or both maternal and fetal chromosomes.

In some instances, circulating cell free nucleic acid fragments (CCF fragments) obtained from a cancer patient comprise nucleic acid fragments originating from normal cells (i.e., non-cancer fragments) and nucleic acid fragments originating from cancer cells (i.e., cancer fragments). Sequence reads derived from CCF fragments originating from normal cells (i.e., non-cancerous cells) are referred to herein as "non-cancer reads." Sequence reads derived from CCF fragments originating from cancer cells are referred to herein as "cancer reads." CCF fragments from which non-cancer reads are obtained may be referred to herein as non-cancer templates and CCF fragments from which cancer reads are obtained may be referred herein to as cancer templates.

In some instances, circulating cell free nucleic acid fragments (CCF fragments) obtained from a pregnant female comprise nucleic acid fragments originating from fetal cells (i.e., fetal fragments) and nucleic acid fragments originating from maternal cells (i.e., maternal fragments). Sequence reads derived from CCF fragments originating from a fetus are referred to herein as "fetal reads." Sequence reads derived from CCF fragments originating from the genome of a pregnant female (e.g., a mother) bearing a fetus are referred to herein as "maternal reads." CCF fragments from which fetal reads are obtained are referred to herein as fetal templates and CCF fragments from which maternal reads are obtained are referred herein to as maternal templates.

In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, some or all nucleic acids in a sample are enriched and/or amplified (e.g., non-specifically, e.g., by a PCR based method) prior to or during sequencing. In certain embodiments specific nucleic acid species or subsets in a sample are enriched and/or amplified prior to or during sequencing. In some embodiments, a species or subset of a pre-selected pool of nucleic acids is sequenced randomly. In some embodiments, nucleic acids in a sample are not enriched and/or amplified prior to or during sequencing.

In some embodiments, a representative fraction of a genome is sequenced and is sometimes referred to as "coverage" or "fold coverage." For example, a 1-fold coverage indicates that roughly 100% of the nucleotide sequences of the genome are represented by reads. In some instances, fold coverage is referred to as (and is directly proportional to) "sequencing depth." In some embodiments, "fold coverage" is a relative term referring to a prior sequencing run as a reference. For example, a second sequencing run may have 2-fold less coverage than a first sequencing run. In some embodiments a genome is sequenced with redundancy, where a given region of the genome can be covered by two or more reads or overlapping reads (e.g., a "fold coverage" greater than 1, e.g., a 2-fold coverage). In some embodiments, a genome or a majority of a genome (e.g., genome-wide sequencing) is sequenced with about 0.1-fold to about 100-fold coverage, about 0.2-fold to 20-fold coverage, or about 0.2-fold to about 1-fold coverage (e.g., about 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage). In some embodiments, a genome or a majority of a genome (e.g., genome-wide sequencing) is sequenced with about 0.01-fold to about 100-fold coverage, about 0.1-fold to 20-fold coverage, or about 0.1-fold to about 1-fold coverage (e.g., about 0.015-, 0.02-, 0.03-, 0.04-, 0.05-, 0.06-, 0.07-, 0.08-, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold or greater coverage). In some embodiments, specific parts of a genome (e.g., genomic parts from targeted and/or probe-based methods) are sequenced and fold coverage values generally refer to the fraction of the specific genomic parts sequenced (i.e., fold coverage values do not refer to the whole genome). In some instances, specific genomic parts are sequenced at 1000-fold coverage or more. For example, specific genomic parts may be sequenced at 2000-fold, 5,000-fold, 10,000-fold, 20,000-fold, 30,000-fold, 40,000-fold or 50,000-fold coverage. In some embodiments, sequencing is at about 1,000-fold to about 100,000-fold coverage. In some embodiments, sequencing is at about 10,000-fold to about 70,000-fold coverage. In some embodiments, sequencing is at about 20,000-fold to about 60,000-fold coverage. In some embodiments, sequencing is at about 30,000-fold to about 50,000-fold coverage.

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments, a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane is dependent on the number of unique identifiers utilized during library preparation and/or probe design. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments, sequencing technologies that include the use of nucleic acid imaging technologies (e.g., transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments, MPS sequencing methods utilize a targeted approach, where specific chromosomes, genes or regions of interest are sequenced. In certain embodiments, a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g., Illumina's Genome Analyzer; Genome Analyzer II; HISEQ 2000; HISEQ 2500 (Illumina, San Diego Calif.)). With this technology, millions of nucleic acid (e.g., DNA) fragments can be sequenced in parallel. In one example of this type of sequencing technology, a flow cell is used which contains an optically transparent slide with 8 individual lanes on the surfaces of which are bound oligonucleotide anchors (e.g., adapter primers).

Sequencing by synthesis generally is performed by iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof.

Any suitable MPS method, system or technology platform for conducting methods described herein can be used to obtain nucleic acid sequence reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, U.S. Patent Application Publication No. 2013/0012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, the like or combinations thereof. Other sequencing methods that may be used to conduct methods herein include digital PCR, sequencing by hybridization, nanopore sequencing, chromosome-specific sequencing (e.g., using DANSR (digital analysis of selected regions) technology.

In some embodiments, sequence reads are generated, obtained, gathered, assembled, manipulated, transformed, processed, and/or provided by a sequence module. A machine comprising a sequence module can be a suitable machine and/or apparatus that determines the sequence of a nucleic acid utilizing a sequencing technology known in the art. In some embodiments a sequence module can align, assemble, fragment, complement, reverse complement, and/or error check (e.g., error correct sequence reads).

Mapping Reads

Sequence reads can be mapped and the number of reads mapping to a specified nucleic acid region (e.g., a chromosome or portion thereof) are referred to as counts. Any suitable mapping method (e.g., process, algorithm, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped," as "a mapped sequence read" or as "a mapped read." In certain embodiments, a mapped sequence read is referred to as a "hit" or "count." In some embodiments, mapped sequence reads are grouped together according to various parameters and assigned to particular genomic portions, which are discussed in further detail below.

The terms "aligned," "alignment," or "aligning" generally refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand (e.g., sense or antisense strand). In certain embodiments a nucleic acid sequence is aligned with the reverse complement of another nucleic acid sequence.

Various computational methods can be used to map each sequence read to a portion. Non-limiting examples of computer algorithms that can be used to align sequences include, without limitation, BLAST, BLITZ, FASTA, BOWTIE 1, BOWTIE 2, ELAND, MAQ, PROBEMATCH, SOAP, BWA or SEQMAP, or variations thereof or combinations thereof. In some embodiments, sequence reads can be aligned with sequences in a reference genome. In some embodiments, sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search identified sequences against a sequence database. Search hits can then be used to sort the identified sequences into appropriate portions (described hereafter), for example.

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the website of National Center for Biotechnology Information. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, mappability is assessed for a genomic region (e.g., portion, genomic portion). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

For paired-end sequencing, reads may be mapped to a reference genome by use of a suitable mapping and/or alignment program, non-limiting examples of which include BWA (Li H. and Durbin R. (2009) *Bioinformatics* 25, 1754-60), Novoalign [Novocraft (2010)], Bowtie (Langmead B, et al., (2009) *Genome Biol.* 10:R25), SOAP2 (Li R, et al., (2009) *Bioinformatics* 25, 1966-67), BFAST (Homer N, et al., (2009) *PLoS ONE* 4, e7767), GASSST (Rizk, G. and Lavenier, D. (2010) *Bioinformatics* 26, 2534-2540), and MPscan (Rivals E., et al. (2009) *Lecture Notes in Computer Science* 5724, 246-260), and the like. Paired-end reads may be mapped and/or aligned using a suitable short read alignment program. Non-limiting examples of short read alignment programs include BarraCUDA, BFAST, BLASTN, BLAT, Bowtie, BWA, CASHX, CUDA-EC, CUSHAW, CUSHAW2, drFAST, ELAND, ERNE, GNUMAP, GEM, GensearchNGS, GMAP, Geneious Assembler, iSAAC, LAST, MAQ, mrFAST, mrsFAST, MOSAIK, MPscan, Novoalign, NovoalignCS, Novocraft, NextGENe, Omixon, PALMapper, Partek, PASS, PerM, QPalma, RazerS, REAL, cREAL, RMAP, rNA, RTG, Segemehl, SeqMap, Shrec, SHRiMP, SLIDER, SOAP, SOAP2, SOAP3, SOCS, SSAHA, SSAHA2, Stampy, SToRM, Subread, Subjunc, Taipan, UGENE, VelociMapper, TimeLogic, XpressAlign, ZOOM, the like or combinations thereof. Paired-end reads are often mapped to opposing ends of the same polynucleotide fragment, according to a reference genome. In some embodiments, read mates are mapped independently. In some embodiments, information from both sequence reads (i.e., from each end) is factored in the mapping process. A reference genome is often used to determine and/or infer the sequence of nucleic acids located between paired-end read mates. The term "discordant read pairs" as used herein refers to a paired-end read comprising a pair of read mates, where one or both read mates fail to unambiguously map to the same region of a reference genome defined, in part, by a segment of contiguous nucleotides. In some embodiments discordant read pairs are paired-end read mates that map to unexpected locations of a reference genome. Non-limiting examples of unexpected locations of a reference genome include (i) two different chromosomes, (ii) locations separated by more than a predetermined fragment size (e.g., more than 300 bp, more than 500 bp, more than 1000 bp, more than 5000 bp, or more than 10,000 bp), (iii) an orientation inconsistent with a reference sequence (e.g., opposite orientations), the like or a combination thereof. In some embodiments discordant read mates are identified according to a length (e.g., an average length, a predetermined fragment size) or expected length of template polynucleotide fragments in a sample. For example, read mates that map to a location that is separated by more than the average length or expected length of polynucleotide fragments in a sample are sometimes identified as discordant read pairs. Read pairs that map in opposite orientation are sometimes determined by taking the reverse complement of one of the reads and comparing the alignment of both reads using the same strand of a reference sequence. Discordant read pairs can be identified by any suitable method and/or algorithm known in the art or described herein (e.g., SVDetect, Lumpy, BreakDancer, BreakDancerMax, CREST, DELLY, the like or combinations thereof).

Portions

In some embodiments, mapped sequence reads are grouped together according to various parameters and assigned to particular genomic portions (e.g., portions of a reference genome). A "portion" also may be referred to herein as a "genomic section," "bin," "partition," "portion of a reference genome," "portion of a chromosome" or "genomic portion."

A portion often is defined by partitioning of a genome according to one or more features. Non-limiting examples of certain partitioning features include length (e.g., fixed length, non-fixed length) and other structural features. Genomic portions sometimes include one or more of the following features: fixed length, non-fixed length, random length, non-random length, equal length, unequal length (e.g., at least two of the genomic portions are of unequal length), do not overlap (e.g., the 3' ends of the genomic portions sometimes abut the 5' ends of adjacent genomic portions), overlap (e.g., at least two of the genomic portions overlap), contiguous, consecutive, not contiguous, and not consecutive. Genomic portions sometimes are about 1 to about 1,000 kilobases in length (e.g., about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900 kilobases in length), about 5 to about 500 kilobases in length, about 10 to about 100 kilobases in length, or about 40 to about 60 kilobases in length.

Partitioning sometimes is based on, or is based in part on, certain informational features, such as, information content and information gain, for example. Non-limiting examples of certain informational features include speed and/or convenience of alignment, sequencing coverage variability, GC content (e.g., stratified GC content, particular GC contents, high or low GC content), uniformity of GC content, other measures of sequence content (e.g., fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual portions of a reference genome, and/or a targeted search for particular features. In some embodiments, information content may be quantified using a p-value profile measuring the significance of particular genomic locations for distinguishing between groups of confirmed normal and abnormal subjects (e.g. euploid and trisomy subjects, respectively).

In some embodiments, partitioning a genome may eliminate similar regions (e.g., identical or homologous regions or sequences) across a genome and only keep unique regions. Regions removed during partitioning may be within a single chromosome, may be one or more chromosomes, or may span multiple chromosomes. In some embodiments, a partitioned genome is reduced and optimized for faster alignment, often focusing on uniquely identifiable sequences.

In some embodiments, genomic portions result from a partitioning based on non-overlapping fixed size, which results in consecutive, non-overlapping portions of fixed length. Such portions often are shorter than a chromosome and often are shorter than a copy number variation (or copy number alteration) region (e.g., a region that is duplicated or is deleted), the latter of which can be referred to as a segment. A "segment" or "genomic segment" often includes two or more fixed-length genomic portions, and often includes two or more consecutive fixed-length portions (e.g., about 2 to about 100 such portions (e.g., 2, 3, 4, 5, 6, 7, 8, 9, 10, 11, 12, 13, 14, 15, 16, 17, 18, 19, 20, 25, 30, 35, 40, 45, 50, 60, 70, 80, 90 such portions)).

Multiple portions sometimes are analyzed in groups, and sometimes reads mapped to portions are quantified according to a particular group of genomic portions. Where portions are partitioned by structural features and correspond to regions in a genome, portions sometimes are grouped into one or more segments and/or one or more regions. Non-limiting examples of regions include sub-chromosome (i.e., shorter than a chromosome), chromosome, autosome, sex chromosome and combinations thereof. One or more sub-chromosome regions sometimes are genes, gene fragments, regulatory sequences, introns, exons, segments (e.g., a segment spanning a copy number alteration region; a segment spanning a copy number variation region), microduplications, microdeletions and the like. A region sometimes is smaller than a chromosome of interest or is the same size of a chromosome of interest, and sometimes is smaller than a reference chromosome or is the same size as a reference chromosome.

Filtering and/or Selecting Portions

In some embodiments, one or more processing steps can comprise one or more portion filtering steps and/or portion selection steps. The term "filtering" as used herein refers to removing portions or portions of a reference genome from consideration. In certain embodiments one or more portions are filtered (e.g., subjected to a filtering process) thereby providing filtered portions. In some embodiments a filtering process removes certain portions and retains portions (e.g., a subset of portions). Following a filtering process, retained portions are often referred to herein as filtered portions.

Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or underrepresented sequences, noisy data, the like, or combinations of the foregoing. A filtering process often involves removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or part of a chromosome by a predetermined multiple of the profile variance, and in certain embodiments, a filtering process comprises removing data points from a data set that do not deviate from the mean profile level of a portion, a chromosome or part of a chromosome by a predetermined multiple of the profile variance. In some embodiments, a filtering process is utilized to reduce the number of candidate portions of a reference genome analyzed for the presence or absence of a genetic variation/genetic alteration and/or copy number alteration (e.g., aneuploidy, microdeletion, microduplication). Reducing the number of candidate portions of a reference genome analyzed for the presence or absence of a genetic variation/genetic alteration and/or copy number alteration often reduces the complexity and/or dimensionality of a data set, and sometimes increases the speed of searching for and/or identifying genetic variations/genetic alterations and/or copy number alterations by two or more orders of magnitude.

Portions may be processed (e.g., filtered and/or selected) by any suitable method and according to any suitable parameter. Non-limiting examples of features and/or parameters that can be used to filter and/or select portions include redundant data (e.g., redundant or overlapping mapped reads), non-informative data (e.g., portions of a reference genome with zero mapped counts), portions of a reference genome with over represented or underrepresented sequences, noisy data, counts, count variability, coverage, mappability, variability, a repeatability measure, read density, variability of read density, a level of uncertainty, guanine-cytosine (GC) content, CCF fragment length and/or read length (e.g., a fragment length ratio (FLR), a fetal ratio statistic (FRS)), DNaseI-sensitivity, methylation state, acetylation, histone distribution, chromatin structure, percent repeats, the like or combinations thereof. Portions can be filtered and/or selected according to any suitable feature or parameter that correlates with a feature or parameter listed or described herein. Portions can be filtered and/or selected according to features or parameters that are specific to a portion (e.g., as determined for a single portion according to multiple samples) and/or features or parameters that are specific to a sample (e.g., as determined for multiple portions within a sample). In some embodiments portions are filtered and/or removed according to relatively low mappability, relatively high variability, a high level of uncertainty, relatively long CCF fragment lengths (e.g., low FRS, low FLR), relatively large fraction of repetitive sequences, high GC content, low GC content, low counts, zero counts, high counts, the like, or combinations thereof. In some embodiments portions (e.g., a subset of portions) are selected according to suitable level of mappability, variability, level of uncertainty, fraction of repetitive sequences, count, GC content, the like, or combinations thereof. In some embodiments portions (e.g., a subset of portions) are selected according to relatively short CCF fragment lengths (e.g., high FRS, high FLR). Counts and/or reads mapped to portions are sometimes processed (e.g., normalized) prior to and/or after filtering or selecting portions (e.g., a subset of portions). In some embodiments counts and/or reads mapped to portions are not processed prior to and/or after filtering or selecting portions (e.g., a subset of portions).

In some embodiments, portions may be filtered according to a measure of error (e.g., standard deviation, standard error, calculated variance, p-value, mean absolute error (MAE), average absolute deviation and/or mean absolute deviation (MAD)). In certain instances, a measure of error may refer to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments, portions with a count variability above a pre-determined upper range are filtered (e.g., excluded from consideration). In some embodiments portions with a count variability below a pre-determined lower range are filtered (e.g., excluded from consideration). In some embodiments, portions with a count variability outside a pre-determined range are filtered (e.g., excluded from consideration). In some embodiments portions with a count variability within a pre-determined range are selected (e.g., used for determining the presence or absence of a copy number alteration). In some embodiments, count variability of portions represents a distribution (e.g., a normal distribution). In some embodiments portions are selected within a quantile of the distribution. In some embodiments portions within a 99% quantile of the distribution of count variability are selected.

Sequence reads from any suitable number of samples can be utilized to identify a subset of portions that meet one or more criteria, parameters and/or features described herein. Sequence reads from a group of samples from multiple subjects sometimes are utilized. In some embodiments, the multiple subjects include pregnant females. In some embodiments, the multiple subjects include healthy subjects. In some embodiments, the multiple subjects include cancer patients. One or more samples from each of the multiple subjects can be addressed (e.g., 1 to about 20 samples from each subject (e.g., about 2, 3, 4, 5, 6, 7, 8, 9, 10, 11, 12, 13, 14, 15, 16, 17, 18 or 19 samples)), and a suitable number of subjects may be addressed (e.g., about 2 to about 10,000 subjects (e.g., about 10, 20, 30, 40, 50, 60, 70, 80, 90, 100, 150, 200, 250, 300, 350, 400, 500, 600, 700, 800, 900, 1000, 2000, 3000, 4000, 5000, 6000, 7000, 8000, 9000 subjects)). In some embodiments, sequence reads from the same test sample(s) from the same subject are mapped to portions in the reference genome and are used to generate the subset of portions.

Portions can be selected and/or filtered by any suitable method. In some embodiments portions are selected according to visual inspection of data, graphs, plots and/or charts. In certain embodiments portions are selected and/or filtered (e.g., in part) by a system or a machine comprising one or more microprocessors and memory. In some embodiments portions are selected and/or filtered (e.g., in part) by a non-transitory computer-readable storage medium with an executable program stored thereon, where the program instructs a microprocessor to perform the selecting and/or filtering.

In some embodiments, sequence reads derived from a sample are mapped to all or most portions of a reference genome and a pre-selected subset of portions are thereafter selected. For example, a subset of portions to which reads from fragments under a particular length threshold preferentially map may be selected. Certain methods for pre-selecting a subset of portions are described in U.S. Patent Application Publication No. 2014/0180594, which is incorporated by reference herein. Reads from a selected subset of portions often are utilized in further steps of a determination of the presence or absence of a genetic variation or genetic alteration, for example. Often, reads from portions not selected are not utilized in further steps of a determination of the presence or absence of a genetic variation or genetic alteration (e.g., reads in the non-selected portions are removed or filtered).

In some embodiments portions associated with read densities (e.g., where a read density is for a portion) are removed by a filtering process and read densities associated with removed portions are not included in a determination of the presence or absence of a copy number alteration (e.g., a chromosome aneuploidy, microduplication, microdeletion). In some embodiments a read density profile comprises and/or consists of read densities of filtered portions. Portions are sometimes filtered according to a distribution of counts and/or a distribution of read densities. In some embodiments portions are filtered according to a distribution of counts and/or read densities where the counts and/or read densities are obtained from one or more reference samples. One or more reference samples may be referred to herein as a training set. In some embodiments portions are filtered according to a distribution of counts and/or read densities where the counts and/or read densities are obtained from one or more test samples. In some embodiments portions are filtered according to a measure of uncertainty for a read density distribution. In certain embodiments, portions that demonstrate a large deviation in read densities are removed by a filtering process. For example, a distribution of read densities (e.g., a distribution of average mean, or median read densities) can be determined, where each read density in the distribution maps to the same portion. A measure of uncertainty (e.g., a MAD) can be determined by comparing a distribution of read densities for multiple samples where each portion of a genome is associated with measure of uncertainty. According to the foregoing example, portions can be filtered according to a measure of uncertainty (e.g., a standard deviation (SD), a MAD) associated with each portion and a predetermined threshold. In certain instances, portions comprising MAD values within the acceptable range are retained and portions comprising MAD values outside of the acceptable range are removed from consideration by a filtering process. In some embodiments, according to the foregoing example, portions comprising read densities values (e.g., median, average or mean read densities) outside a pre-determined measure of uncertainty are often removed from consideration by a filtering process. In some embodiments portions comprising read densities values (e.g., median, average or mean read densities) outside an inter-quartile range of a distribution are removed from consideration by a filtering process. In some embodiments portions comprising read densities values outside more than 2 times, 3 times, 4 times or 5 times an inter-quartile range of a distribution are removed from consideration by a filtering process. In some embodiments portions comprising read densities values outside more than 2 sigma, 3 sigma, 4 sigma, 5 sigma, 6 sigma, 7 sigma or 8 sigma (e.g., where sigma is a range defined by a standard deviation) are removed from consideration by a filtering process.

Sequence Read Quantification

Sequence reads that are mapped or partitioned based on a selected feature or variable can be quantified to determine the amount or number of reads that are mapped to one or more portions (e.g., portion of a reference genome), in some embodiments. In certain embodiments the quantity of sequence reads that are mapped to a portion or segment is referred to as a count or read density.

A count often is associated with a genomic portion. In some embodiments a count is determined from some or all of the sequence reads mapped to (i.e., associated with) a portion. In certain embodiments, a count is determined from some or all of the sequence reads mapped to a group of portions (e.g., portions in a segment or region (described herein)).

A count can be determined by a suitable method, operation or mathematical process. A count sometimes is the direct sum of all sequence reads mapped to a genomic portion or a group of genomic portions corresponding to a segment, a group of portions corresponding to a sub-region of a genome (e.g., copy number variation region, copy number alteration region, copy number duplication region, copy number deletion region, microduplication region, microdeletion region, chromosome region, autosome region, sex chromosome region or other chromosomal rearrangement) and/or sometimes is a group of portions corresponding to a genome. A read quantification sometimes is a ratio, and sometimes is a ratio of a quantification for portion(s) in region a to a quantification for portion(s) in region b. Region a sometimes is one portion, segment region, copy number variation region, copy number alteration region, copy number duplication region, copy number deletion region, microduplication region, microdeletion region, chromosome region, autosome region and/or sex chromosome region. Region b independently sometimes is one portion, segment region, copy number variation region, copy number alteration region, copy number duplication region, copy number deletion region, microduplication region, microdeletion region, chromosome region, autosome region, sex chromosome region, a region including all autosomes, a region including sex chromosomes and/or a region including all chromosomes.

In some embodiments, a count is derived from raw sequence reads and/or filtered sequence reads. In certain embodiments a count is determined by a mathematical process. In certain embodiments a count is an average, mean or sum of sequence reads mapped to a genomic portion or group of genomic portions (e.g., genomic portions in a region). In some embodiments, a count is associated with an uncertainty value. A count sometimes is adjusted. A count may be adjusted according to sequence reads associated with a genomic portion or group of portions that have been weighted, removed, filtered, normalized, adjusted, averaged, derived as a mean, derived as a median, added, or combination thereof.

A sequence read quantification sometimes is a read density. A read density may be determined and/or generated for one or more segments of a genome. In certain instances, a read density may be determined and/or generated for one or more chromosomes. In some embodiments a read density comprises a quantitative measure of counts of sequence reads mapped to a segment or portion of a reference genome. A read density can be determined by a suitable process. In some embodiments a read density is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. A read density may be a density estimation derived from a suitable probability density function. A density estimation is the construction of an estimate, based on observed data, of an underlying probability density function. In some embodiments a read density comprises a density estimation (e.g., a probability density estimation, a kernel density estimation). A read density may be generated according to a process comprising generating a density estimation for each of the one or more portions of a genome where each portion comprises counts of sequence reads. A read density may be generated for normalized and/or weighted counts mapped to a portion or segment. In some instances, each read mapped to a portion or segment may contribute to a read density, a value (e.g., a count) equal to its weight obtained from a normalization process described herein. In some embodiments read densities for one or more portions or segments are adjusted. Read densities can be adjusted by a suitable method. For example, read densities for one or more portions can be weighted and/or normalized.

Reads quantified for a given portion or segment can be from one source or different sources. In one example, reads may be obtained from nucleic acid from a subject having cancer or suspected of having cancer. In such circumstances, reads mapped to one or more portions often are reads representative of both healthy cells (i.e., non-cancer cells) and cancer cells (e.g., tumor cells). In certain embodiments, some of the reads mapped to a portion are from cancer cell nucleic acid and some of the reads mapped to the same portion are from non-cancer cell nucleic acid. In another example, reads may be obtained from a nucleic acid sample from a pregnant female bearing a fetus. In such circumstances, reads mapped to one or more portions often are reads representative of both the fetus and the mother of the fetus (e.g., a pregnant female subject). In certain embodiments some of the reads mapped to a portion are from a fetal genome and some of the reads mapped to the same portion are from a maternal genome.

Levels

In some embodiments, a value (e.g., a number, a quantitative value) is ascribed to a level. A level can be determined by a suitable method, operation or mathematical process (e.g., a processed level). A level often is, or is derived from, counts (e.g., normalized counts) for a set of portions. In some embodiments a level of a portion is substantially equal to the total number of counts mapped to a portion (e.g., counts, normalized counts). Often a level is determined from counts that are processed, transformed or manipulated by a suitable method, operation or mathematical process known in the art. In some embodiments a level is derived from counts that are processed and non-limiting examples of processed counts include weighted, removed, filtered, normalized, adjusted, averaged, derived as a mean (e.g., mean level), added, subtracted, transformed counts or combination thereof. In some embodiments a level comprises counts that are normalized (e.g., normalized counts of portions). A level can be for counts normalized by a suitable process, non-limiting examples of which are described herein. A level can comprise normalized counts or relative amounts of counts. In some embodiments a level is for counts or normalized counts of two or more portions that are averaged and the level is referred to as an average level. In some embodiments a level is for a set of portions having a mean count or mean of normalized counts which is referred to as a mean level. In some embodiments a level is derived for portions that comprise raw and/or filtered counts. In some embodiments, a level is based on counts that are raw. In some embodiments a level is associated with an uncertainty value (e.g., a standard deviation, a MAD). In some embodiments a level is represented by a Z-score or p-value.

A level for one or more portions is synonymous with a "genomic section level" herein. The term "level" as used herein is sometimes synonymous with the term "elevation." A determination of the meaning of the term "level" can be determined from the context in which it is used. For example, the term "level," when used in the context of portions, profiles, reads and/or counts often means an elevation. The term "level," when used in the context of a substance or composition (e.g., level of RNA, plexing level) often refers to an amount. The term "level," when used in the context of uncertainty (e.g., level of error, level of confidence, level of deviation, level of uncertainty) often refers to an amount.

Normalized or non-normalized counts for two or more levels (e.g., two or more levels in a profile) can sometimes be mathematically manipulated (e.g., added, multiplied, averaged, normalized, the like or combination thereof) according to levels. For example, normalized or non-normalized counts for two or more levels can be normalized according to one, some or all of the levels in a profile. In some embodiments normalized or non-normalized counts of all levels in a profile are normalized according to one level in the profile. In some embodiments normalized or non-normalized counts of a first level in a profile are normalized according to normalized or non-normalized counts of a second level in the profile.

Non-limiting examples of a level (e.g., a first level, a second level) are a level for a set of portions comprising processed counts, a level for a set of portions comprising a mean, median or average of counts, a level for a set of portions comprising normalized counts, the like or any combination thereof. In some embodiments, a first level and a second level in a profile are derived from counts of portions mapped to the same chromosome. In some embodiments, a first level and a second level in a profile are derived from counts of portions mapped to different chromosomes.

In some embodiments a level is determined from normalized or non-normalized counts mapped to one or more portions. In some embodiments, a level is determined from normalized or non-normalized counts mapped to two or more portions, where the normalized counts for each portion often are about the same. There can be variation in counts (e.g., normalized counts) in a set of portions for a level. In a set of portions for a level there can be one or more portions having counts that are significantly different than in other portions of the set (e.g., peaks and/or dips). Any suitable number of normalized or non-normalized counts associated with any suitable number of portions can define a level.

In some embodiments one or more levels can be determined from normalized or non-normalized counts of all or some of the portions of a genome. Often a level can be determined from all or some of the normalized or non-normalized counts of a chromosome, or part thereof. In some embodiments, two or more counts derived from two or more portions (e.g., a set of portions) determine a level. In some embodiments two or more counts (e.g., counts from two or more portions) determine a level. In some embodiments, counts from 2 to about 100,000 portions determine a level. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a level. In some embodiments counts from about 10 to about 50 portions determine a level. In some embodiments counts from about 20 to about 40 or more portions determine a level. In some embodiments, a level comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more portions. In some embodiments, a level corresponds to a set of portions (e.g., a set of portions of a reference genome, a set of portions of a chromosome or a set of portions of a part of a chromosome).

In some embodiments, a level is determined for normalized or non-normalized counts of portions that are contiguous. In some embodiments portions (e.g., a set of portions) that are contiguous represent neighboring regions of a genome or neighboring regions of a chromosome or gene. For example, two or more contiguous portions, when aligned by merging the portions end to end, can represent a sequence assembly of a DNA sequence longer than each portion. For example two or more contiguous portions can represent of an intact genome, chromosome, gene, intron, exon or part thereof. In some embodiments a level is determined from a collection (e.g., a set) of contiguous portions and/or non-contiguous portions.

Data Processing and Normalization

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or underrepresented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing." Processing can render data more amenable to further analysis, and can generate an outcome in some embodiments. In some embodiments one or more or all processing methods (e.g., normalization methods, portion filtering, mapping, validation, the like or combinations thereof) are performed by a processor, a microprocessor, a computer, in conjunction with memory and/or by a microprocessor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being overrepresented when prepared using PCR-based methods. Methods described herein can reduce or eliminate the contribution of noisy data, and therefore reduce the effect of noisy data on the provided outcome.

The terms "uninformative data," "uninformative portions of a reference genome," and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation or genetic alteration (e.g., a copy number alteration, an aneuploidy, a microduplication, a microdeletion, a chromosomal aberration, and the like). In certain embodiments, a threshold is exceeded by results obtained by methods described herein and a subject is diagnosed with a copy number alteration. A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula described herein.

Any suitable procedure can be utilized for processing data sets described herein. Non-limiting examples of procedures suitable for use for processing data sets include filtering, normalizing, weighting, monitoring peak heights, monitoring peak areas, monitoring peak edges, peak level analysis, peak width analysis, peak edge location analysis, peak lateral tolerances, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., subject gender, subject age, subject ploidy, percent contribution of cancer cell nucleic acid, fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments one or more processing steps can comprise one or more normalization steps. Normalization can be performed by a suitable method described herein or known in the art. In certain embodiments, normalization comprises adjusting values measured on different scales to a notionally common scale. In certain embodiments, normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Normalization sometimes comprises subtraction of one or more data sets by a predetermined variable or formula. Non-limiting examples of normalization methods include portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn and/or combinations thereof. In some embodiments, the determination of a presence or absence of a copy number alteration (e.g., an aneuploidy, a microduplication, a microdeletion) utilizes a normalization method (e.g., portion-wise normalization, normalization by GC content, median count (median bin count, median portion count) normalization, linear and nonlinear least squares regression, LOESS, GC LOESS, LOWESS (locally weighted scatterplot smoothing), principal component normalization, repeat masking (RM), GC-normalization and repeat masking (GCRM), cQn, a normalization method known in the art and/or a combination thereof). Described in greater detail hereafter are certain examples of normalization processes that can be utilized, such as LOESS normalization, principal component normalization, and hybrid normalization methods, for example. Aspects of certain normalization processes also are described, for example, in International Patent Application Publication No. WO 2013/052913 and International Patent Application Publication No. WO 2015/051163, each of which is incorporated by reference herein.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped; normalizing raw count data for one or more selected portions to a median reference count for one or more portions or the chromosome on which a selected portion is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing portions, or portions of a reference genome, with respect to a normalizing value sometimes is referred to as "portion-wise normalization."

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include principal component analysis, decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principal component analysis, linear discriminant analysis, quadratic discriminant analysis, bagging, neural networks, support vector machine models, random forests, classification tree models, K-nearest neighbors, logistic regression and/or smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation/genetic alteration and/or copy number alteration, depending on the status of the reference samples (e.g., positive or negative for a selected copy number alteration). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation/genetic alteration and/or copy number alteration and/or medical condition.

After data sets have been counted, optionally filtered, normalized, and optionally weighted the processed data sets can be further manipulated by one or more filtering and/or normalizing and/or weighting procedures, in some embodiments. A data set that has been further manipulated by one or more filtering and/or normalizing and/or weighting procedures can be used to generate a profile, in certain embodiments. The one or more filtering and/or normalizing and/or weighting procedures sometimes can reduce data set complexity and/or dimensionality, in some embodiments. An outcome can be provided based on a data set of reduced complexity and/or dimensionality. In some embodiments, a profile plot of processed data further manipulated by weighting, for example, is generated to facilitate classification and/or providing an outcome. An outcome can be provided based on a profile plot of weighted data, for example.

Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after levels are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. In certain embodiments, mathematical and/or statistical manipulations include one or more assumptions pertaining to ploidy and/or fraction of a minority species (e.g., fraction of cancer cell nucleic acid; fetal fraction). In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fraction of a minority species (e.g., fraction of cancer cell nucleic acid; fetal fraction).

In some embodiments, analysis and processing of data can include the use of one or more assumptions. A suitable number or type of assumptions can be utilized to analyze or process a data set. Non-limiting examples of assumptions that can be used for data processing and/or analysis include subject ploidy, cancer cell contribution, maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a nucleic acid quantification assay (e.g., fetal quantifier assay (FQA)), assumptions regarding twins (e.g., if 2 twins and only 1 is affected the effective fetal fraction is only 50% of the total measured fetal fraction (similarly for triplets, quadruplets and the like)), cell free DNA (e.g., cfDNA) uniformly covers the entire genome, the like and combinations thereof.

In those instances where the quality and/or depth of mapped sequence reads does not permit an outcome prediction of the presence or absence of a genetic variation/genetic alteration and/or copy number alteration at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

Described in greater detail hereafter are non-limiting examples of processing steps and normalization methods that can be utilized, such as normalizing to a window (static or sliding), weighting, determining bias relationship, LOESS normalization, principal component normalization, hybrid normalization, generating a profile and performing a comparison.

Normalizing to a Window (Static or Sliding)

In certain embodiments, a processing step comprises normalizing to a static window, and in some embodiments, a processing step comprises normalizing to a moving or sliding window. The term "window" as used herein refers to one or more portions chosen for analysis, and sometimes is used as a reference for comparison (e.g., used for normalization and/or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate surrounding portions, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of microdeletions and/or microduplications. In certain embodiments, displaying cumulative sums of one or more portions is used to identify the presence or absence of regions of copy number alteration (e.g., microdeletion, microduplication).

Weighting

In some embodiments, a processing step comprises a weighting. The terms "weighted," "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with underrepresented or low quality sequence data can be "down weighted" to minimize the influence on a data set, whereas selected portions of a reference genome can be "up weighted" to increase the influence on a data set. A non-limiting example of a weighting function is [1/(standard deviation)$^2$]. Weighting portions sometimes removes portion dependencies. In some embodiments one or more portions are weighted by an eigen function (e.g., an eigenfunction). In some embodiments an eigen function comprises replacing portions with orthogonal eigen-portions. A weighting step sometimes is performed in a manner substantially similar to a normalizing step. In some embodiments, a data set is adjusted (e.g., divided, multiplied, added, subtracted) by a predetermined variable (e.g., weighting variable). In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

Bias Relationships

In some embodiments, a processing step comprises determining a bias relationship. For example, one or more relationships may be generated between local genome bias estimates and bias frequencies. The term "relationship" as use herein refers to a mathematical and/or a graphical relationship between two or more variables or values. A relationship can be generated by a suitable mathematical and/or graphical process. Non-limiting examples of a relationship include a mathematical and/or graphical representation of a function, a correlation, a distribution, a linear or non-linear equation, a line, a regression, a fitted regression, the like or a combination thereof. Sometimes a relationship comprises a fitted relationship. In some embodiments a fitted relationship comprises a fitted regression. Sometimes a relationship comprises two or more variables or values that are weighted. In some embodiments a relationship comprise a fitted regression where one or more variables or values of the relationship a weighted. Sometimes a regression is fitted in a weighted fashion. Sometimes a regression is fitted without weighting. In certain embodiments, generating a relationship comprises plotting or graphing.

In certain embodiments, a relationship is generated between GC densities and GC density frequencies. In some embodiments generating a relationship between (i) GC densities and (ii) GC density frequencies for a sample provides a sample GC density relationship. In some embodiments generating a relationship between (i) GC densities and (ii) GC density frequencies for a reference provides a reference GC density relationship. In some embodiments, where local genome bias estimates are GC densities, a sample bias relationship is a sample GC density relationship and a reference bias relationship is a reference GC density relationship. GC densities of a reference GC density relationship and/or a sample GC density relationship are often representations (e.g., mathematical or quantitative representation) of local GC content.

In some embodiments a relationship between local genome bias estimates and bias frequencies comprises a distribution. In some embodiments a relationship between local genome bias estimates and bias frequencies comprises a fitted relationship (e.g., a fitted regression). In some embodiments a relationship between local genome bias estimates and bias frequencies comprises a fitted linear or non-linear regression (e.g., a polynomial regression). In certain embodiments a relationship between local genome bias estimates and bias frequencies comprises a weighted relationship where local genome bias estimates and/or bias frequencies are weighted by a suitable process. In some embodiments a weighted fitted relationship (e.g., a weighted fitting) can be obtained by a process comprising a quantile regression, parameterized distributions or an empirical distribution with interpolation. In certain embodiments a relationship between local genome bias estimates and bias frequencies for a test sample, a reference or part thereof, comprises a polynomial regression where local genome bias estimates are weighted. In some embodiments a weighed fitted model comprises weighting values of a distribution. Values of a distribution can be weighted by a suitable process. In some embodiments, values located near tails of a distribution are provided less weight than values closer to the median of the distribution. For example, for a distribution between local genome bias estimates (e.g., GC densities) and bias frequencies (e.g., GC density frequencies), a weight is determined according to the bias frequency for a given local genome bias estimate, where local genome bias estimates comprising bias frequencies closer to the mean of a distribution are provided greater weight than local genome bias estimates comprising bias frequencies further from the mean.

In some embodiments, a processing step comprises normalizing sequence read counts by comparing local genome bias estimates of sequence reads of a test sample to local genome bias estimates of a reference (e.g., a reference genome, or part thereof). In some embodiments, counts of sequence reads are normalized by comparing bias frequencies of local genome bias estimates of a test sample to bias frequencies of local genome bias estimates of a reference. In some embodiments counts of sequence reads are normalized by comparing a sample bias relationship and a reference bias relationship, thereby generating a comparison.

Counts of sequence reads may be normalized according to a comparison of two or more relationships. In certain embodiments two or more relationships are compared thereby providing a comparison that is used for reducing local bias in sequence reads (e.g., normalizing counts). Two or more relationships can be compared by a suitable method. In some embodiments a comparison comprises adding, subtracting, multiplying and/or dividing a first relationship from a second relationship. In certain embodiments comparing two or more relationships comprises a use of a suitable linear regression and/or a non-linear regression. In certain embodiments comparing two or more relationships comprises a suitable polynomial regression (e.g., a $3^{rd}$ order polynomial regression). In some embodiments a comparison comprises adding, subtracting, multiplying and/or dividing a first regression from a second regression. In some embodiments two or more relationships are compared by a process comprising an inferential framework of multiple regressions. In some embodiments two or more relationships are compared by a process comprising a suitable multivariate analysis. In some embodiments two or more relationships are compared by a process comprising a basis function (e.g., a blending function, e.g., polynomial bases, Fourier bases, or the like), splines, a radial basis function and/or wavelets.

In certain embodiments a distribution of local genome bias estimates comprising bias frequencies for a test sample and a reference is compared by a process comprising a polynomial regression where local genome bias estimates are weighted. In some embodiments a polynomial regression is generated between (i) ratios, each of which ratios comprises bias frequencies of local genome bias estimates of a reference and bias frequencies of local genome bias estimates of a sample and (ii) local genome bias estimates. In some embodiments a polynomial regression is generated between (i) a ratio of bias frequencies of local genome bias estimates of a reference to bias frequencies of local genome bias estimates of a sample and (ii) local genome bias estimates. In some embodiments a comparison of a distribution of local genome bias estimates for reads of a test sample and a reference comprises determining a log ratio (e.g., a log 2 ratio) of bias frequencies of local genome bias estimates for the reference and the sample. In some embodiments a comparison of a distribution of local genome bias estimates comprises dividing a log ratio (e.g., a log 2 ratio) of bias frequencies of local genome bias estimates for the reference by a log ratio (e.g., a log 2 ratio) of bias frequencies of local genome bias estimates for the sample.

Normalizing counts according to a comparison typically adjusts some counts and not others. Normalizing counts sometimes adjusts all counts and sometimes does not adjust any counts of sequence reads. A count for a sequence read sometimes is normalized by a process that comprises determining a weighting factor and sometimes the process does not include directly generating and utilizing a weighting factor. Normalizing counts according to a comparison sometimes comprises determining a weighting factor for each count of a sequence read. A weighting factor is often specific to a sequence read and is applied to a count of a specific sequence read. A weighting factor is often determined according to a comparison of two or more bias relationships (e.g., a sample bias relationship compared to a reference bias relationship). A normalized count is often determined by adjusting a count value according to a weighting factor. Adjusting a count according to a weighting factor sometimes includes adding, subtracting, multiplying and/or dividing a count for a sequence read by a weighting factor. A weighting factor and/or a normalized count sometimes are determined from a regression (e.g., a regression line). A normalized count is sometimes obtained directly from a regression line (e.g., a fitted regression line) resulting from a comparison between bias frequencies of local genome bias estimates of a reference (e.g., a reference genome) and a test sample. In some embodiments each count of a read of a sample is provided a normalized count value according to a comparison of (i) bias frequencies of a local genome bias estimates of reads compared to (ii) bias frequencies of a local genome bias estimates of a reference. In certain embodiments, counts of sequence reads obtained for a sample are normalized and bias in the sequence reads is reduced.

LOESS Normalization

In some embodiments, a processing step comprises a LOESS normalization. LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relationship between fragment count (e.g., sequence reads, counts) and GC composition for portions of a reference genome. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

Principal Component Analysis

In some embodiments, a processing step comprises a principal component analysis (PCA). In some embodiments, sequence read counts (e.g., sequence read counts of a test sample) is adjusted according to a principal component analysis (PCA). In some embodiments a read density profile (e.g., a read density profile of a test sample) is adjusted according to a principal component analysis (PCA). A read density profile of one or more reference samples and/or a read density profile of a test subject can be adjusted according to a PCA. Removing bias from a read density profile by a PCA related process is sometimes referred to herein as adjusting a profile. A PCA can be performed by a suitable PCA method, or a variation thereof. Non-limiting examples of a PCA method include a canonical correlation analysis (CCA), a Karhunen-Loève transform (KLT), a Hotelling transform, a proper orthogonal decomposition (POD), a singular value decomposition (SVD) of X, an eigenvalue decomposition (EVD) of XTX, a factor analysis, an Eckart-Young theorem, a Schmidt-Mirsky theorem, empirical orthogonal functions (EOF), an empirical eigenfunction decomposition, an empirical component analysis, quasiharmonic modes, a spectral decomposition, an empirical modal analysis, the like, variations or combinations thereof. A PCA often identifies and/or adjusts for one or more biases in a read density profile. A bias identified and/or adjusted for by a PCA is sometimes referred to herein as a principal component. In some embodiments one or more biases can be removed by adjusting a read density profile according to one or more principal component using a suitable method. A read density profile can be adjusted by adding, subtracting, multiplying and/or dividing one or more principal components from a read density profile. In some embodiments, one or more biases can be removed from a read density profile by subtracting one or more principal components from a read density profile. Although bias in a read density profile is often identified and/or quantitated by a PCA of a profile, principal components are often subtracted from a profile at the level of read densities. A PCA often identifies one or more principal components. In some embodiments a PCA identifies a $1^{st}$, $2^{nd}$, $3^{rd}$, $4^{th}$, $5^{th}$, $6^{th}$, $7^{th}$, $8^{th}$, $9^{th}$, and a $10^{th}$ or more principal components. In certain embodiments, 1, 2, 3, 4, 5, 6, 7, 8, 9, 10 or more principal components are used to adjust a profile. In certain embodiments, 5 principal components are used to adjust a profile. Often, principal components are used to adjust a profile in the order of appearance in a PCA. For example, where three principal components are subtracted from a read density profile, a $1^{st}$, $2^{nd}$ and $3^{rd}$ principal component are used. Sometimes a bias identified by a principal component comprises a feature of a profile that is not used to adjust a profile. For example, a PCA may identify a copy number alteration (e.g., an aneuploidy, microduplication, microdeletion, deletion, translocation, insertion) and/or a gender difference as a principal component. Thus, in some embodiments, one or more principal components are not used to adjust a profile. For example, sometimes a $1^{st}$, $2^{nd}$ and $4^{th}$ principal component are used to adjust a profile where a $3^{rd}$ principal component is not used to adjust a profile.

A principal component can be obtained from a PCA using any suitable sample or reference. In some embodiments principal components are obtained from a test sample (e.g., a test subject). In some embodiments principal components are obtained from one or more references (e.g., reference samples, reference sequences, a reference set). In certain instances, a PCA is performed on a median read density profile obtained from a training set comprising multiple samples resulting in the identification of a $1^{st}$ principal component and a $2^{nd}$ principal component. In some embodiments, principal components are obtained from a set of subjects devoid of a copy number alteration in question. In some embodiments, principal components are obtained from a set of known euploids. Principal component are often identified according to a PCA performed using one or more read density profiles of a reference (e.g., a training set). One or more principal components obtained from a reference are often subtracted from a read density profile of a test subject thereby providing an adjusted profile.

Hybrid Normalization

In some embodiments, a processing step comprises a hybrid normalization method. A hybrid normalization method may reduce bias (e.g., GC bias), in certain instances. A hybrid normalization, in some embodiments, comprises (i) an analysis of a relationship of two variables (e.g., counts and GC content) and (ii) selection and application of a normalization method according to the analysis. A hybrid normalization, in certain embodiments, comprises (i) a regression (e.g., a regression analysis) and (ii) selection and application of a normalization method according to the regression. In some embodiments counts obtained for a first sample (e.g., a first set of samples) are normalized by a different method than counts obtained from another sample (e.g., a second set of samples). In some embodiments counts obtained for a first sample (e.g., a first set of samples) are normalized by a first normalization method and counts obtained from a second sample (e.g., a second set of samples) are normalized by a second normalization method. For example, in certain embodiments a first normalization method comprises use of a linear regression and a second normalization method comprises use of a non-linear regression (e.g., a LOESS, GC-LOESS, LOWESS regression, LOESS smoothing).

In some embodiments a hybrid normalization method is used to normalize sequence reads mapped to portions of a genome or chromosome (e.g., counts, mapped counts, mapped reads). In certain embodiments raw counts are normalized and in some embodiments adjusted, weighted, filtered or previously normalized counts are normalized by a hybrid normalization method. In certain embodiments, levels or Z-scores are normalized. In some embodiments counts mapped to selected portions of a genome or chromosome are normalized by a hybrid normalization approach. Counts can refer to a suitable measure of sequence reads mapped to portions of a genome, non-limiting examples of which include raw counts (e.g., unprocessed counts), normalized counts (e.g., normalized by LOESS, principal component, or a suitable method), portion levels (e.g., average levels, mean levels, median levels, or the like), Z-scores, the like, or combinations thereof. The counts can be raw counts or processed counts from one or more samples (e.g., a test sample, a sample from a pregnant female). In some embodiments counts are obtained from one or more samples obtained from one or more subjects.

In some embodiments a normalization method (e.g., the type of normalization method) is selected according to a regression (e.g., a regression analysis) and/or a correlation coefficient. A regression analysis refers to a statistical technique for estimating a relationship among variables (e.g., counts and GC content). In some embodiments a regression is generated according to counts and a measure of GC content for each portion of multiple portions of a reference genome.

A suitable measure of GC content can be used, non-limiting examples of which include a measure of guanine, cytosine, adenine, thymine, purine (GC), or pyrimidine (AT or ATU) content, melting temperature ($T_m$) (e.g., denaturation temperature, annealing temperature, hybridization temperature), a measure of free energy, the like or combinations thereof. A measure of guanine (G), cytosine (C), adenine (A), thymine (T), purine (GC), or pyrimidine (AT or ATU) content can be expressed as a ratio or a percentage. In some embodiments any suitable ratio or percentage is used, non-limiting examples of which include GC/AT, GC/total nucleotide, GC/A, GC/T, AT/total nucleotide, AT/GC, AT/G, AT/C, G/A, C/A, G/T, G/A, G/AT, C/T, the like or combinations thereof. In some embodiments a measure of GC content is a ratio or percentage of GC to total nucleotide content. In some embodiments a measure of GC content is a ratio or percentage of GC to total nucleotide content for sequence reads mapped to a portion of reference genome. In certain embodiments the GC content is determined according to and/or from sequence reads mapped to each portion of a reference genome and the sequence reads are obtained from a sample. In some embodiments a measure of GC content is not determined according to and/or from sequence reads. In certain embodiments, a measure of GC content is determined for one or more samples obtained from one or more subjects.

In some embodiments generating a regression comprises generating a regression analysis or a correlation analysis. A suitable regression can be used, non-limiting examples of which include a regression analysis, (e.g., a linear regression analysis), a goodness of fit analysis, a Pearson's correlation analysis, a rank correlation, a fraction of variance unexplained, Nash-Sutcliffe model efficiency analysis, regression model validation, proportional reduction in loss, root mean square deviation, the like or a combination thereof. In some embodiments a regression line is generated. In certain embodiments generating a regression comprises generating a linear regression. In certain embodiments generating a regression comprises generating a non-linear regression (e.g., an LOESS regression, an LOWESS regression).

In some embodiments a regression determines the presence or absence of a correlation (e.g., a linear correlation), for example between counts and a measure of GC content. In some embodiments a regression (e.g., a linear regression) is generated and a correlation coefficient is determined. In some embodiments a suitable correlation coefficient is determined, non-limiting examples of which include a coefficient of determination, an $R^2$ value, a Pearson's correlation coefficient, or the like.

In some embodiments goodness of fit is determined for a regression (e.g., a regression analysis, a linear regression). Goodness of fit sometimes is determined by visual or mathematical analysis. An assessment sometimes includes determining whether the goodness of fit is greater for a non-linear regression or for a linear regression. In some embodiments a correlation coefficient is a measure of a goodness of fit. In some embodiments an assessment of a goodness of fit for a regression is determined according to a correlation coefficient and/or a correlation coefficient cutoff value. In some embodiments an assessment of a goodness of fit comprises comparing a correlation coefficient to a correlation coefficient cutoff value. In some embodiments an assessment of a goodness of fit for a regression is indicative of a linear regression. For example, in certain embodiments, a goodness of fit is greater for a linear regression than for a non-linear regression and the assessment of the goodness of fit is indicative of a linear regression. In some embodiments an assessment is indicative of a linear regression and a linear regression is used to normalized the counts. In some embodiments an assessment of a goodness of fit for a regression is indicative of a non-linear regression. For example, in certain embodiments, a goodness of fit is greater for a non-linear regression than for a linear regression and the assessment of the goodness of fit is indicative of a non-linear regression. In some embodiments an assessment is indicative of a non-linear regression and a non-linear regression is used to normalized the counts.

In some embodiments an assessment of a goodness of fit is indicative of a linear regression when a correlation coefficient is equal to or greater than a correlation coefficient cutoff. In some embodiments an assessment of a goodness of fit is indicative of a non-linear regression when a correlation coefficient is less than a correlation coefficient cutoff. In some embodiments a correlation coefficient cutoff is predetermined. In some embodiments a correlation coefficient cutoff is about 0.5 or greater, about 0.55 or greater, about 0.6 or greater, about 0.65 or greater, about 0.7 or greater, about 0.75 or greater, about 0.8 or greater, about 0.85 or greater, about 0.9 or greater, or about 0.95 or greater.

In some embodiments a specific type of regression is selected (e.g., a linear or non-linear regression) and, after the regression is generated, counts are normalized by subtracting the regression from the counts. In some embodiments subtracting a regression from the counts provides normalized counts with reduced bias (e.g., GC bias). In some embodiments a linear regression is subtracted from the counts. In some embodiments a non-linear regression (e.g., a LOESS, GC-LOESS, LOWESS regression) is subtracted from the counts. Any suitable method can be used to subtract a regression line from the counts. For example, if counts x are derived from portion i (e.g., a portion i) comprising a GC content of 0.5 and a regression line determines counts y at a GC content of 0.5, then x-y=normalized counts for portion i. In some embodiments counts are normalized prior to and/or after subtracting a regression. In some embodiments, counts normalized by a hybrid normalization approach are used to generate levels, Z-scores, levels and/or profiles of a genome or a part thereof. In certain embodiments, counts normalized by a hybrid normalization approach are analyzed by methods described herein to determine the presence or absence of a genetic variation or genetic alteration (e.g., copy number alteration).

In some embodiments a hybrid normalization method comprises filtering or weighting one or more portions before or after normalization. A suitable method of filtering portions, including methods of filtering portions (e.g., portions of a reference genome) described herein can be used. In some embodiments, portions (e.g., portions of a reference genome) are filtered prior to applying a hybrid normalization method. In some embodiments, only counts of sequencing reads mapped to selected portions (e.g., portions selected according to count variability) are normalized by a hybrid normalization. In some embodiments counts of sequencing reads mapped to filtered portions of a reference genome (e.g., portions filtered according to count variability) are removed prior to utilizing a hybrid normalization method. In some embodiments a hybrid normalization method comprises selecting or filtering portions (e.g., portions of a reference genome) according to a suitable method (e.g., a method described herein). In some embodiments a hybrid normalization method comprises selecting or filtering portions (e.g., portions of a reference genome) according to an uncertainty value for counts mapped to each of the portions for multiple test samples. In some embodiments a hybrid normalization method comprises selecting or filtering portions (e.g., portions of a reference genome) according to count variability. In some embodiments a hybrid normalization method comprises selecting or filtering portions (e.g., portions of a reference genome) according to GC content, repetitive elements, repetitive sequences, introns, exons, the like or a combination thereof.

Profiles

In some embodiments, a processing step comprises generating one or more profiles (e.g., profile plot) from various aspects of a data set or derivation thereof (e.g., product of one or more mathematical and/or statistical data processing steps known in the art and/or described herein). The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a part or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a portion. In certain embodiments, a data point in a profile includes results of data manipulation for groups of portions. In some embodiments, groups of portions may be adjacent to one another, and in certain embodiments, groups of portions may be from different parts of a chromosome or genome.

Data points in a profile derived from a data set can be representative of any suitable data categorization. Non-limiting examples of categories into which data can be grouped to generate profile data points include: portions based on size, portions based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile (e.g., a genomic profile, a chromosome profile, a profile of a part of a chromosome) often is a collection of normalized or non-normalized counts for two or more portions. A profile often includes at least one level, and often comprises two or more levels (e.g., a profile often has multiple levels). A level generally is for a set of portions having about the same counts or normalized counts. Levels are described in greater detail herein. In certain embodiments, a profile comprises one or more portions, which portions can be weighted, removed, filtered, normalized, adjusted, averaged, derived as a mean, added, subtracted, processed or transformed by any combination thereof. A profile often comprises normalized counts mapped to portions defining two or more levels, where the counts are further normalized according to one of the levels by a suitable method. Often counts of a profile (e.g., a profile level) are associated with an uncertainty value.

A profile comprising one or more levels is sometimes padded (e.g., hole padding). Padding (e.g., hole padding) refers to a process of identifying and adjusting levels in a profile that are due to copy number alterations (e.g., microduplications or microdeletions in a patient's genome, maternal microduplications or microdeletions). In some embodiments, levels are padded that are due to microduplications or microdeletions in a tumor or a fetus. Microduplications or microdeletions in a profile can, in some embodiments, artificially raise or lower the overall level of a profile (e.g., a profile of a chromosome) leading to false positive or false negative determinations of a chromosome aneuploidy (e.g., a trisomy). In some embodiments, levels in a profile that are due to microduplications and/or deletions are identified and adjusted (e.g., padded and/or removed) by a process sometimes referred to as padding or hole padding.

A profile comprising one or more levels can include a first level and a second level. In some embodiments a first level is different (e.g., significantly different) than a second level. In some embodiments a first level comprises a first set of portions, a second level comprises a second set of portions and the first set of portions is not a subset of the second set of portions. In certain embodiments, a first set of portions is different than a second set of portions from which a first and second level are determined. In some embodiments a profile can have multiple first levels that are different (e.g., significantly different, e.g., have a significantly different value) than a second level within the profile. In some embodiments a profile comprises one or more first levels that are significantly different than a second level within the profile and one or more of the first levels are adjusted. In some embodiments a first level within a profile is removed from the profile or adjusted (e.g., padded). A profile can comprise multiple levels that include one or more first levels significantly different than one or more second levels and often the majority of levels in a profile are second levels, which second levels are about equal to one another. In some embodiments greater than 50%, greater than 60%, greater than 70%, greater than 80%, greater than 90% or greater than 95% of the levels in a profile are second levels.

A profile sometimes is displayed as a plot. For example, one or more levels representing counts (e.g., normalized counts) of portions can be plotted and visualized. Non-limiting examples of profile plots that can be generated include raw count (e.g., raw count profile or raw profile), normalized count, portion-weighted, z-score, p-value, area ratio versus fitted ploidy, median level versus ratio between fitted and measured minority species fraction, principal components, the like, or combinations thereof. Profile plots allow visualization of the manipulated data, in some embodiments. In certain embodiments, a profile plot can be utilized to provide an outcome (e.g., area ratio versus fitted ploidy, median level versus ratio between fitted and measured minority species fraction, principal components). The terms "raw count profile plot" or "raw profile plot" as used herein refer to a plot of counts in each portion in a region normalized to total counts in a region (e.g., genome, portion, chromosome, chromosome portions of a reference genome or a part of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions, e.g., assumptions described herein. In certain embodiments, a test profile often centers around a predetermined value representative of the absence of a copy number alteration, and often deviates from a predetermined value in areas corresponding to the genomic location in which the copy number alteration is located in the test subject, if the test subject possessed the copy number alteration. In test subjects at risk for, or suffering from a medical condition associated with a copy number alteration, the numerical value for a selected portion is expected to vary significantly from the predetermined value for non-affected genomic locations. Depending on starting assumptions (e.g., fixed ploidy or optimized ploidy, fixed fraction of cancer cell nucleic acid or optimized fraction of cancer cell nucleic acid, fixed fetal fraction or optimized fetal fraction, or combinations thereof) the predetermined threshold or cutoff value or threshold range of values indicative of the presence or absence of a copy number alteration can vary while still providing an outcome useful for determining the presence or absence of a copy number alteration. In some embodiments, a profile is indicative of and/or representative of a phenotype.

In some embodiments, the use of one or more reference samples that are substantially free of a copy number alteration in question can be used to generate a reference count profile (e.g., a reference median count profile), which may result in a predetermined value representative of the absence of the copy number alteration, and often deviates from a predetermined value in areas corresponding to the genomic location in which the copy number alteration is located in the test subject, if the test subject possessed the copy number alteration. In test subjects at risk for, or suffering from a medical condition associated with a copy number alteration, the numerical value for the selected portion or sections is expected to vary significantly from the predetermined value for non-affected genomic locations. In certain embodiments, the use of one or more reference samples known to carry the copy number alteration in question can be used to generate a reference count profile (a reference median count profile), which may result in a predetermined value representative of the presence of the copy number alteration, and often deviates from a predetermined value in areas corresponding to the genomic location in which a test subject does not carry the copy number alteration. In test subjects not at risk for, or suffering from a medical condition associated with a copy number alteration, the numerical value for the selected portion or sections is expected to vary significantly from the predetermined value for affected genomic locations.

By way of a non-limiting example, normalized sample and/or reference count profiles can be obtained from raw sequence read data by (a) calculating reference median counts for selected chromosomes, portions or parts thereof from a set of references known not to carry a copy number alteration, (b) removal of uninformative portions from the reference sample raw counts (e.g., filtering); (c) normalizing the reference counts for all remaining portions of a reference genome to the total residual number of counts (e.g., sum of remaining counts after removal of uninformative portions of a reference genome) for the reference sample selected chromosome or selected genomic location, thereby generating a normalized reference subject profile; (d) removing the corresponding portions from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered portions in (b), can be included between (c) and (d).

In some embodiments a read density profile is determined. In some embodiments a read density profile comprises at least one read density, and often comprises two or more read densities (e.g., a read density profile often comprises multiple read densities). In some embodiments, a read density profile comprises a suitable quantitative value (e.g., a mean, a median, a Z-score, or the like). A read density profile often comprises values resulting from one or more read densities. A read density profile sometimes comprises values resulting from one or more manipulations of read densities based on one or more adjustments (e.g., normalizations). In some embodiments a read density profile comprises unmanipulated read densities. In some embodiments, one or more read density profiles are generated from various aspects of a data set comprising read densities, or a derivation thereof (e.g., product of one or more mathematical and/or statistical data processing steps known in the art and/or described herein). In certain embodiments, a read density profile comprises normalized read densities. In some embodiments a read density profile comprises adjusted read densities. In certain embodiments a read density profile comprises raw read densities (e.g., unmanipulated, not adjusted or normalized), normalized read densities, weighted read densities, read densities of filtered portions, z-scores of read densities, p-values of read densities, integral values of read densities (e.g., area under the curve), average, mean or median read densities, principal components, the like, or combinations thereof. Often read densities of a read density profile and/or a read density profile is associated with a measure of uncertainty (e.g., a MAD). In certain embodiments, a read density profile comprises a distribution of median read densities. In some embodiments a read density profile comprises a relationship (e.g., a fitted relationship, a regression, or the like) of a plurality of read densities. For example, sometimes a read density profile comprises a relationship between read densities (e.g., read densities value) and genomic locations (e.g., portions, portion locations). In some embodiments, a read density profile is generated using a static window process, and in certain embodiments, a read density profile is generated using a sliding window process. In some embodiments a read density profile is sometimes printed and/or displayed (e.g., displayed as a visual representation, e.g., a plot or a graph).

In some embodiments, a read density profile corresponds to a set of portions (e.g., a set of portions of a reference genome, a set of portions of a chromosome or a subset of portions of a part of a chromosome). In some embodiments a read density profile comprises read densities and/or counts associated with a collection (e.g., a set, a subset) of portions. In some embodiments, a read density profile is determined for read densities of portions that are contiguous. In some embodiments, contiguous portions comprise gaps comprising regions of a reference sequence and/or sequence reads that are not included in a density profile (e.g., portions removed by a filtering). Sometimes portions (e.g., a set of portions) that are contiguous represent neighboring regions of a genome or neighboring regions of a chromosome or gene. For example, two or more contiguous portions, when aligned by merging the portions end to end, can represent a sequence assembly of a DNA sequence longer than each portion. For example two or more contiguous portions can represent an intact genome, chromosome, gene, intron, exon or part thereof. Sometimes a read density profile is determined from a collection (e.g., a set, a subset) of contiguous portions and/or non-contiguous portions. In some cases, a read density profile comprises one or more portions, which portions can be weighted, removed, filtered, normalized, adjusted, averaged, derived as a mean, added, subtracted, processed or transformed by any combination thereof.

A read density profile is often determined for a sample and/or a reference (e.g., a reference sample). A read density profile is sometimes generated for an entire genome, one or more chromosomes, or for a part of a genome or a chromosome. In some embodiments, one or more read density profiles are determined for a genome or part thereof. In some embodiments, a read density profile is representative of the entirety of a set of read densities of a sample, and in certain embodiments, a read density profile is representative of a part or subset of read densities of a sample. That is, sometimes a read density profile comprises or is generated from read densities representative of data that has not been filtered to remove any data, and sometimes a read density profile includes or is generated from data points representative of data that has been filtered to remove unwanted data.

In some embodiments a read density profile is determined for a reference (e.g., a reference sample, a training set). A read density profile for a reference is sometimes referred to herein as a reference profile. In some embodiments a reference profile comprises a read densities obtained from one or more references (e.g., reference sequences, reference samples). In some embodiments a reference profile comprises read densities determined for one or more (e.g., a set of) known euploid samples. In some embodiments a reference profile comprises read densities of filtered portions. In some embodiments a reference profile comprises read densities adjusted according to the one or more principal components.

Performing a Comparison

In some embodiments, a processing step comprises preforming a comparison (e.g., comparing a test profile to a reference profile). Two or more data sets, two or more relationships and/or two or more profiles can be compared by a suitable method. Non-limiting examples of statistical methods suitable for comparing data sets, relationships and/or profiles include Behrens-Fisher approach, bootstrapping, Fisher's method for combining independent tests of significance, Neyman-Pearson testing, confirmatory data analysis, exploratory data analysis, exact test, F-test, Z-test, T-test, calculating and/or comparing a measure of uncertainty, a null hypothesis, counternulls and the like, a chi-square test, omnibus test, calculating and/or comparing level of significance (e.g., statistical significance), a meta analysis, a multivariate analysis, a regression, simple linear regression, robust linear regression, the like or combinations of the foregoing. In certain embodiments comparing two or more data sets, relationships and/or profiles comprises determining and/or comparing a measure of uncertainty. A "measure of uncertainty" as used herein refers to a measure of significance (e.g., statistical significance), a measure of error, a measure of variance, a measure of confidence, the like or a combination thereof. A measure of uncertainty can be a value (e.g., a threshold) or a range of values (e.g., an interval, a confidence interval, a Bayesian confidence interval, a threshold range). Non-limiting examples of a measure of uncertainty include p-values, a suitable measure of deviation (e.g., standard deviation, sigma, absolute deviation, mean absolute deviation, the like), a suitable measure of error (e.g., standard error, mean squared error, root mean squared error, the like), a suitable measure of variance, a suitable standard score (e.g., standard deviations, cumulative percentages, percentile equivalents, Z-scores, T-scores, R-scores, standard nine (stanine), percent in stanine, the like), the like or combinations thereof. In some embodiments determining the level of significance comprises determining a measure of uncertainty (e.g., a p-value). In certain embodiments, two or more data sets, relationships and/or profiles can be analyzed and/or compared by utilizing multiple (e.g., 2 or more) statistical methods (e.g., least squares regression, principal component analysis, linear discriminant analysis, quadratic discriminant analysis, bagging, neural networks, support vector machine models, random forests, classification tree models, K-nearest neighbors, logistic regression and/or loss smoothing) and/or any suitable mathematical and/or statistical manipulations (e.g., referred to herein as manipulations).

In some embodiments, a processing step comprises a comparison of two or more profiles (e.g., two or more read density profiles). Comparing profiles may comprise comparing profiles generated for a selected region of a genome. For example, a test profile may be compared to a reference profile where the test and reference profiles were determined for a region of a genome (e.g., a reference genome) that is substantially the same region. Comparing profiles sometimes comprises comparing two or more subsets of portions of a profile (e.g., a read density profile). A subset of portions of a profile may represent a region of a genome (e.g., a chromosome, or region thereof). A profile (e.g., a read density profile) can comprise any amount of subsets of portions. Sometimes a profile (e.g., a read density profile) comprises two or more, three or more, four or more, or five or more subsets. In certain embodiments, a profile (e.g., a read density profile) comprises two subsets of portions where each portion represents regions of a reference genome that are adjacent. In some embodiments, a test profile can be compared to a reference profile where the test profile and reference profile both comprise a first subset of portions and a second subset of portions where the first and second subsets represent different regions of a genome. Some subsets of portions of a profile may comprise copy number alterations and other subsets of portions are sometimes substantially free of copy number alterations. Sometimes all subsets of portions of a profile (e.g., a test profile) are substantially free of a copy number alteration. Sometimes all subsets of portions of a profile (e.g., a test profile) comprise a copy number alteration. In some embodiments a test profile can comprise a first subset of portions that comprise a copy number alteration and a second subset of portions that are substantially free of a copy number alteration.

In certain embodiments, comparing two or more profiles comprises determining and/or comparing a measure of uncertainty for two or more profiles. Profiles (e.g., read density profiles) and/or associated measures of uncertainty are sometimes compared to facilitate interpretation of mathematical and/or statistical manipulations of a data set and/or to provide an outcome. A profile (e.g., a read density profile) generated for a test subject sometimes is compared to a profile (e.g., a read density profile) generated for one or more references (e.g., reference samples, reference subjects, and the like). In some embodiments, an outcome is provided by comparing a profile (e.g., a read density profile) from a test subject to a profile (e.g., a read density profile) from a reference for a chromosome, portions or parts thereof, where a reference profile is obtained from a set of reference subjects known not to possess a copy number alteration (e.g., a reference). In some embodiments an outcome is provided by comparing a profile (e.g., a read density profile) from a test subject to a profile (e.g., a read density profile) from a reference for a chromosome, portions or parts thereof, where a reference profile is obtained from a set of reference subjects known to possess a specific copy number alteration (e.g., a chromosome aneuploidy, a microduplication, a microdeletion).

In certain embodiments, a profile (e.g., a read density profile) of a test subject is compared to a predetermined value representative of the absence of a copy number alteration, and sometimes deviates from a predetermined value at one or more genomic locations (e.g., portions) corresponding to a genomic location in which a copy number alteration is located. For example, in test subjects (e.g., subjects at risk for, or suffering from a medical condition associated with a copy number alteration), profiles are expected to differ significantly from profiles of a reference (e.g., a reference sequence, reference subject, reference set) for selected portions when a test subject comprises a copy number alteration in question. Profiles (e.g., read density profiles) of a test subject are often substantially the same as profiles (e.g., read density profiles) of a reference (e.g., a reference sequence, reference subject, reference set) for selected portions when a test subject does not comprise a copy number alteration in question. Profiles (e.g., read density profiles) may be compared to a predetermined threshold and/or threshold range. The term "threshold" as used herein refers to any number that is calculated using a qualifying data set and serves as a limit of diagnosis of a copy number alteration (e.g., an aneuploidy, a microduplication, a microdeletion, and the like). In certain embodiments a threshold is exceeded by results obtained by methods described herein and a subject is diagnosed with a copy number alteration. In some embodiments, a threshold value or range of values may be calculated by mathematically and/or statistically manipulating sequence read data (e.g., from a reference and/or subject). A predetermined threshold or threshold range of values indicative of the presence or absence of a copy number alteration can vary while still providing an outcome useful for determining the presence or absence of a copy number alteration. In certain embodiments, a profile (e.g., a read density profile) comprising normalized read densities and/or normalized counts is generated to facilitate classification and/or providing an outcome. An outcome can be provided based on a plot of a profile (e.g., a read density profile) comprising normalized counts (e.g., using a plot of such a read density profile).

Decision Analysis

In some embodiments, a determination of an outcome (e.g., making a call) or a determination of the presence or absence of a copy number alteration (e.g., chromosome aneuploidy, microduplication, microdeletion) is made according to a decision analysis. Certain decision analysis features are described in International Patent Application Publication No. WO 2014/190286, which is incorporated by reference herein. For example, a decision analysis sometimes comprises applying one or more methods that produce one or more results, an evaluation of the results, and a series of decisions based on the results, evaluations and/or the possible consequences of the decisions and terminating at some juncture of the process where a final decision is made. In some embodiments a decision analysis is a decision tree. A decision analysis, in some embodiments, comprises coordinated use of one or more processes (e.g., process steps, e.g., algorithms). A decision analysis can be performed by a person, a system, an apparatus, software (e.g., a module), a computer, a processor (e.g., a microprocessor), the like or a combination thereof. In some embodiments a decision analysis comprises a method of determining the presence or absence of a copy number alteration (e.g., chromosome aneuploidy, microduplication or microdeletion) with reduced false negative and reduced false positive determinations, compared to an instance in which no decision analysis is utilized (e.g., a determination is made directly from normalized counts). In some embodiments a decision analysis comprises determining the presence or absence of a condition associated with one or more copy number alterations.

In some embodiments a decision analysis comprises generating a profile for a genome or a region of a genome (e.g., a chromosome or part thereof). A profile can be generated by any suitable method, known or described herein. In some embodiments, a decision analysis comprises a segmenting process. Segmenting can modify and/or transform a profile thereby providing one or more decomposition renderings of a profile. A profile subjected to a segmenting process often is a profile of normalized counts mapped to portions in a reference genome or part thereof. As addressed herein, raw counts mapped to the portions can be normalized by one or more suitable normalization processes (e.g., LOESS, GC-LOESS, principal component normalization, or combination thereof) to generate a profile that is segmented as part of a decision analysis. A decomposition rendering of a profile is often a transformation of a profile. A decomposition rendering of a profile is sometimes a transformation of a profile into a representation of a genome, chromosome or part thereof.

In certain embodiments, a segmenting process utilized for the segmenting locates and identifies one or more levels within a profile that are different (e.g., substantially or significantly different) than one or more other levels within a profile. A level identified in a profile according to a segmenting process that is different than another level in the profile, and has edges that are different than another level in the profile, is referred to herein as a level for a discrete segment. A segmenting process can generate, from a profile of normalized counts or levels, a decomposition rendering in which one or more discrete segments can be identified. A discrete segment generally covers fewer portions than what is segmented (e.g., chromosome, chromosomes, autosomes).

In some embodiments, segmenting locates and identifies edges of discrete segments within a profile. In certain embodiments, one or both edges of one or more discrete segments are identified. For example, a segmentation process can identify the location (e.g., genomic coordinates, e.g., portion location) of the right and/or the left edges of a discrete segment in a profile. A discrete segment often comprises two edges. For example, a discrete segment can include a left edge and a right edge. In some embodiments, depending upon the representation or view, a left edge can be a 5'-edge and a right edge can be a 3'-edge of a nucleic acid segment in a profile. In some embodiments, a left edge can be a 3'-edge and a right edge can be a 5'-edge of a nucleic acid segment in a profile. Often the edges of a profile are known prior to segmentation and therefore, in some embodiments, the edges of a profile determine which edge of a level is a 5'-edge and which edge is 3'-edge. In some embodiments one or both edges of a profile and/or discrete segment is an edge of a chromosome.

In some embodiments, the edges of a discrete segment are determined according to a decomposition rendering generated for a reference sample (e.g., a reference profile). In some embodiments a null edge height distribution is determined according to a decomposition rendering of a reference profile (e.g., a profile of a chromosome or part thereof). In certain embodiments, the edges of a discrete segment in a profile are identified when the level of the discrete segment is outside a null edge height distribution. In some embodiments, the edges of a discrete segment in a profile are identified according a Z-score calculated according to a decomposition rendering for a reference profile.

In some instances, segmenting generates two or more discrete segments (e.g., two or more fragmented levels, two or more fragmented segments) in a profile. In some embodiments, a decomposition rendering derived from a segmenting process is over-segmented or fragmented and comprises multiple discrete segments. Sometimes discrete segments generated by segmenting are substantially different and sometimes discrete segments generated by segmenting are substantially similar. Substantially similar discrete segments (e.g., substantially similar levels) often refers to two or more adjacent discrete segments in a segmented profile each having a level that differs by less than a predetermined level of uncertainty. In some embodiments, substantially similar discrete segments are adjacent to each other and are not separated by an intervening segment. In some embodiments, substantially similar discrete segments are separated by one or more smaller segments. In some embodiments substantially similar discrete segments are separated by about 1 to about 20, about 1 to about 15, about 1 to about 10 or about 1 to about 5 portions where one or more of the intervening portions have a level significantly different than the level of each of the substantially similar discrete segments. In some embodiments, the level of substantially similar discrete segments differs by less than about 3 times, less than about 2 times, less than about 1 time or less than about 0.5 times a level of uncertainty. Substantially similar discrete segments, in some embodiments, comprise a median level that differs by less than 3 MAD (e.g., less than 3 sigma), less than 2 MAD, less than 1 MAD or less than about 0.5 MAD, where a MAD is calculated from a median level of each of the segments. Substantially different discrete segments, in some embodiments, are not adjacent or are separated by 10 or more, 15 or more or 20 or more portions. Substantially different discrete segments generally have substantially different levels. In certain embodiments, substantially different discrete segments comprises levels that differ by more than about 2.5 times, more than about 3 times, more than about 4 times, more than about 5 times, more than about 6 times a level of uncertainty. Substantially different discrete segments, in some embodiments, comprise a median level that differs by more than 2.5 MAD (e.g., more than 2.5 sigma), more than 3 MAD, more than 4 MAD, more than about 5 MAD or more than about 6 MAD, where a MAD is calculated from a median level of each of the discrete segments.

In some embodiments, a segmentation process comprises determining (e.g., calculating) a level (e.g., a quantitative value, e.g., a mean or median level), a level of uncertainty (e.g., an uncertainty value), Z-score, Z-value, p-value, the like or combinations thereof for one or more discrete segments in a profile or part thereof. In some embodiments a level (e.g., a quantitative value, e.g., a mean or median level), a level of uncertainty (e.g., an uncertainty value), Z-score, Z-value, p-value, the like or combinations thereof are determined (e.g., calculated) for a discrete segment.

Segmenting can be performed, in full or in part, by one or more decomposition generating processes. A decomposition generating process may provide, for example, a decomposition rendering of a profile. Any decomposition generating process described herein or known in the art may be used. Non-limiting examples of a decomposition generating process include circular binary segmentation (CBS) (see e.g., Olshen et al. (2004) Biostatistics 5(4):557-72; Venkatraman, E S, Olshen, A B (2007) Bioinformatics 23(6):657-63); Haar wavelet segmentation (see e.g., Haar, Alfred (1910) Mathematische Annalen 69(3):331-371); maximal overlap discrete wavelet transform (MODWT) (see e.g., Hsu et al. (2005) Biostatistics 6 (2):211-226); stationary wavelet (SWT) (see e.g., Y. Wang and S. Wang (2007) International Journal of Bioinformatics Research and Applications 3(2): 206-222); dual-tree complex wavelet transform (DTCWT) (see e.g., Nguyen et al. (2007) Proceedings of the 7th IEEE International Conference, Boston Mass., on Oct. 14-17, 2007, pages 137-144); maximum entropy segmentation, convolution with edge detection kernel, Jensen Shannon Divergence, Kullback-Leibler divergence, Binary Recursive Segmentation, a Fourier transform, the like or combinations thereof.

In some embodiments, segmenting is accomplished by a process that comprises one process or multiple sub-processes, non-limiting examples of which include a decomposition generating process, thresholding, leveling, smoothing, polishing, the like or combination thereof. Thresholding, leveling, smoothing, polishing and the like can be performed in conjunction with a decomposition generating process, for example.

In some embodiments, a decision analysis comprises identifying a candidate segment in a decomposition rendering. A candidate segment is determined as being the most significant discrete segment in a decomposition rendering. A candidate segment may be the most significant in terms of the number of portions covered by the segment and/or in terms of the absolute value of the level of normalized counts for the segment. A candidate segment sometimes is larger and sometimes substantially larger than other discrete segments in a decomposition rendering. A candidate segment can be identified by a suitable method. In some embodiments, a candidate segment is identified by an area under the curve (AUC) analysis. In certain embodiments, where a first discrete segment has a level and/or covers a number of portions substantially larger than for another discrete segment in a decomposition rendering, the first segment comprises a larger AUC. Where a level is analyzed for AUC, an absolute value of a level often is utilized (e.g., a level corresponding to normalized counts can have a negative value for a deletion and a positive value for a duplication). In certain embodiments, an AUC is determined as an absolute value of a calculated AUC (e.g., a resulting positive value). In certain embodiments, a candidate segment, once identified (e.g., by an AUC analysis or by a suitable method) and optionally after it is validated, is selected for a z-score calculation, or the like, to determine if the candidate segment represents a genetic variation or genetic alteration (e.g., an aneuploidy, microdeletion or microduplication).

In some embodiments, a decision analysis comprises a comparison. In some embodiments, a comparison comprises comparing at least two decomposition renderings. In some embodiments, a comparison comprises comparing at least two candidate segments. In certain embodiments, each of the at least two candidate segments is from a different decomposition rendering. For example, a first candidate segment can be from a first decomposition rendering and a second candidate segment can be from a second decomposition rendering. In some embodiments, a comparison comprises determining if two decomposition renderings are substantially the same or different. In some embodiments, a comparison comprises determining if two candidate segments are substantially the same or different. Two candidate segments can be determined as substantially the same or different by a suitable comparison method, non-limiting examples of which include by visual inspection, by comparing levels or Z-scores of the two candidate segments, by comparing the edges of the two candidate segments, by overlaying either the two candidate segments or their corresponding decomposition renderings, the like or combinations thereof.

Classifications and Uses Thereof

Methods described herein can provide an outcome indicative of presence or absence of genomic instability for a test sample. Methods described herein sometimes provide an outcome indicative of a genotype and/or presence or absence of a genetic variation/alteration in a genomic region for a test sample (e.g., providing an outcome determinative of the presence or absence of a genetic variation). Methods described herein sometimes provide an outcome indicative of a phenotype and/or presence or absence of a medical condition for a test sample (e.g., providing an outcome determinative of the presence or absence of a medical condition and/or phenotype). An outcome often is part of a classification process, and a classification (e.g., classification of presence or absence of genomic instability, a genotype, a phenotype, a genetic variation and/or a medical condition for a test sample) sometimes is based on and/or includes an outcome. An outcome and/or classification sometimes is based on and/or includes a result of data processing for a test sample that facilitates determining presence or absence of genomic instability, a genotype, a phenotype, a genetic variation, genetic alteration, and/or a medical condition in a classification process (e.g., a statistic value (e.g., standard score (e.g., z-score)). An outcome and/or classification sometimes includes or is based on a score determinative of, or a call of, presence or absence of genomic instability, a genotype, a phenotype, a genetic variation, genetic alteration, and/or a medical condition. In certain embodiments, an outcome and/or classification includes a conclusion that predicts and/or determines presence or absence of genomic instability, a genotype, a phenotype, a genetic variation, genetic alteration, and/or a medical condition in a classification process.

A genotype and/or genetic variation often includes a gain, a loss and/or alteration of a region comprising one or more nucleotides (e.g., duplication, deletion, fusion, insertion, short tandem repeat (STR), mutation, single nucleotide alteration, reorganization, substitution or aberrant methylation) that results in a detectable change in the genome or genetic information for a test sample. A genotype and/or genetic variation often is in a particular genomic region (e.g., chromosome, portion of a chromosome (i.e., sub-chromosome region), STR, polymorphic region, translocated region, altered nucleotide sequence, the like or combinations of the foregoing). A genetic variation sometimes is a copy number alteration for a particular region, such as a trisomy or monosomy for chromosome region, or a microduplication or microdeletion event for a particular region (e.g., gain or loss of a region of about 10 megabases or less (e.g., about 9 megabases or less, 8 megabases or less, 7 megabases or less, 6 megabases or less, 5 megabases or less, 4 megabases or less, 3 megabases or less, 2 megabases or less or 1 megabase or less)), for example. A copy number alteration sometimes is expressed as having no copy or one, two, three or four or more copies of a particular region (e.g., chromosome, sub-chromosome, STR, microduplication or microdeletion region).

Presence or absence of genomic instability, a genotype, a phenotype, a genetic variation and/or a medical condition can be determined by transforming, analyzing and/or manipulating sequence reads that have been mapped to genomic portions (e.g., counts, counts of genomic portions of a reference genome). In certain embodiments, an outcome and/or classification is determined according to normalized counts, read densities, read density profiles, and the like, and can be determined by a method described herein. An outcome and/or classification sometimes includes one or more scores and/or calls that refer to the probability that genomic instability, or a particular genotype, phenotype, genetic variation, or medical condition, is present or absent for a test sample. The value of a score may be used to determine, for example, a variation, difference, or ratio of mapped sequence reads that may correspond to genomic instability, a genotype, phenotype, genetic variation, or medical condition. For example, calculating a positive score for genomic instability, or a selected genotype, phenotype, genetic variation, or medical condition, from a data set, with respect to a reference genome, can lead to a classification of genomic instability, or the genotype, phenotype, genetic variation, or medical condition, for a test sample.

Any suitable expression of an outcome and/or classification can be provided. An outcome and/or classification sometimes is based on and/or includes one or more numerical values generated using a processing method described herein in the context of one or more considerations of probability. Non-limiting examples of values that can be utilized include a sensitivity, specificity, standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, ploidy value, fitted minority species fraction, area ratio, median level, the like or combination thereof. In some embodiments, an outcome and/or classification comprises a read density, a read density profile and/or a plot (e.g., a profile plot). In certain embodiments, multiple values are analyzed together, sometimes in a profile for such values (e.g., z-score profile, p-value profile, chi value profile, phi value profile, result of a t-test, value profile, the like, or combination thereof). A consideration of probability can facilitate determining whether a subject is at risk of having, or has, genomic instability, a genotype, phenotype, genetic variation and/or medical condition, and an outcome and/or classification determinative of the foregoing sometimes includes such a consideration.

In certain embodiments, an outcome and/or classification is based on and/or includes a conclusion that predicts and/or determines a risk or probability of the presence or absence of genomic instability, a genotype, phenotype, genetic variation and/or medical condition for a test sample. A conclusion sometimes is based on a value determined from a data analysis method described herein (e.g., a statistics value indicative of probability, certainty and/or uncertainty (e.g., standard deviation, median absolute deviation (MAD), measure of certainty, measure of confidence, measure of certainty or confidence that a value obtained for a test sample is inside or outside a particular range of values, measure of uncertainty, measure of uncertainty that a value obtained for a test sample is inside or outside a particular range of values, coefficient of variation (CV), confidence level, confidence interval (e.g., about 95% confidence interval), standard score (e.g., z-score), chi value, phi value, result of a t-test, p-value, sensitivity, specificity, the like or combination thereof). An outcome and/or classification sometimes is expressed in a laboratory test report (described in greater detail hereafter) for particular test sample as a probability (e.g., odds ratio, p-value), likelihood, or risk factor, associated with the presence or absence of genomic instability, a genotype, phenotype, genetic variation and/or medical condition. An outcome and/or classification for a test sample sometimes is provided as "positive" or "negative" with respect a genomic instability, or a particular genotype, phenotype, genetic variation and/or medical condition. For example, an outcome and/or classification sometimes is designated as "positive" in a laboratory test report for a particular test sample where presence of genomic instability, a genotype, phenotype, genetic variation and/or medical condition is determined, and sometimes an outcome and/or classification is designated as "negative" in a laboratory test report for a particular test sample where absence of genomic instability, a genotype, phenotype, genetic variation and/or medical condition is determined. An outcome and/or classification sometimes is determined and sometimes includes an assumption used in data processing.

An outcome and/or classification sometimes is based on or is expressed as a value in or out of a cluster, value over or under a threshold value, value within a range (e.g., a threshold range), and/or a value with a measure of variance or confidence. In some embodiments, an outcome and/or classification is based on or is expressed as a value above or below a predetermined threshold or cutoff value and/or a measure of uncertainty, confidence level or confidence interval associated with the value. In certain embodiments, a predetermined threshold or cutoff value is an expected level or an expected level range. In some embodiments, a value obtained for a test sample is a standard score (e.g., z-score), where presence of genomic instability, a genotype, phenotype, genetic variation and/or medical condition is determined when the absolute value of the score is greater than a particular score threshold (e.g., threshold between about 2 and about 5; between about 3 and about 4), and where the absence of genomic instability, a genotype, phenotype, genetic variation and/or medical condition is determined when the absolute value of the score is less than the particular score threshold. In certain embodiments, an outcome and/or classification is based on or is expressed as a value that falls within or outside a predetermined range of values (e.g., a threshold range) and the associated uncertainty or confidence level for that value being inside or outside the range. In some embodiments, an outcome and/or classification comprises a value that is equal to a predetermined value (e.g., equal to 1, equal to zero), or is equal to a value within a predetermined value range, and its associated uncertainty or confidence level for that value being equal or within or outside the range. An outcome and/or classification sometimes is graphically represented as a plot (e.g., profile plot). An outcome and/or classification sometimes comprises use of a reference value or reference profile, and sometimes a reference value or reference profile is obtained from one or more reference samples (e.g., reference sample(s) euploid for a selected part of a genome (e.g., region)).

In some embodiments, an outcome and/or classification is based on or includes use of a measure of uncertainty between a test value or profile and a reference value or profile for a selected region. In some embodiments, a determination of the presence or absence of genomic instability, a genotype, phenotype, genetic variation and/or medical condition is according to the number of deviations (e.g., sigma) between a test value or profile and a reference value or profile for a selected region (e.g., a chromosome, or part thereof). A measure of deviation often is an absolute value or absolute measure of deviation (e.g., mean absolute deviation or median absolute deviation (MAD)). In some embodiments, the presence of genomic instability, a genotype, phenotype, genetic variation and/or medical condition is determined when the number of deviations between a test value or profile and a reference value or profile is about 1 or greater (e.g., about 1.5, 2, 2.5, 2.6, 2.7, 2.8, 2.9, 3, 3.1, 3.2, 3.3, 3.4, 3.5, 3.6, 3.7, 3.8, 3.9, 4, 5 or 6 deviations or greater). In certain embodiments, presence of genomic instability, a genotype, phenotype, genetic variation and/or medical condition is determined when a test value or profile and a reference value or profile differ by about 2 to about 5 measures of deviation (e.g., sigma, MAD), or more than 3 measures of deviation (e.g., 3 sigma, 3 MAD). A deviation of greater than three between a test value or profile and a reference value or profile often is indicative of a non-euploid test subject (e.g., presence of a genetic variation (e.g., presence of trisomy, monosomy, microduplication, microdeletion) for a selected region. Test values or profiles significantly above a reference profile, which reference profile is indicative of euploidy, sometimes are determinative of a trisomy, sub-chromosome duplication or microduplication. Test values or profiles significantly below a reference profile, which reference profile is indicative of euploidy, sometimes are determinative of a monosomy, sub-chromosome deletion or microdeletion. In some embodiments, the absence of genomic instability, a genotype, phenotype, genetic variation and/or medical condition is determined when the number of deviations between a test value or profile and reference value or profile for a selected region of a genome is about 3.5 or less (e.g., about less than about 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1 or less). In certain embodiments, absence of genomic instability, a genotype, phenotype, genetic variation and/or medical condition is determined when a test value or profile differs from a reference value or profile by less than three measures of deviation (e.g., 3 sigma, 3 MAD). In some embodiments, a measure of deviation of less than three between a test value or profile and reference value or profile (e.g., 3-sigma for standard deviation) often is indicative of a region that is euploid (e.g., absence of a genetic variation). A measure of deviation between a test value or profile for a test sample and a reference value or profile for one or more reference subjects can be plotted and visualized (e.g., z-score plot).

In some embodiments, an outcome and/or classification is determined according to a call zone. In certain embodiments, a call is made (e.g., a call determining presence or absence of genomic instability, a genotype, phenotype, genetic variation and/or medical condition) when a value (e.g., a profile, a read density profile and/or a measure of uncertainty) or collection of values falls within a pre-defined range (e.g., a zone, a call zone). In some embodiments, a call zone is defined according to a collection of values (e.g., profiles, read density profiles, measures or determination of probability and/or measures of uncertainty) obtained from a particular group of samples. In certain embodiments, a call zone is defined according to a collection of values that are derived from the same chromosome or part thereof. In some embodiments, a call zone for determining presence or absence of genomic instability, a genotype, phenotype, genetic variation and/or medical condition is defined according a measure of uncertainty (e.g., high level of confidence or low measure of uncertainty) and/or a quantification of a minority nucleic acid species (e.g., about 1% minority species or greater (e.g., about 2, 3, 4, 5, 6, 7, 8, 9, 10% or more minority nucleic acid species)) determined for a test sample. A minority nucleic acid species quantification sometimes is a fraction or percent of cancer cell nucleic acid or fetal nucleic acid (i.e., fetal fraction) ascertained for a test sample. In some embodiments, a call zone is defined by a confidence level or confidence interval (e.g., a confidence interval for 95% level of confidence). A call zone sometimes is defined by a confidence level, or confidence interval based on a particular confidence level, of about 90% or greater (e.g., about 91, 92, 93, 94, 95, 96, 97, 98, 99, 99.1, 99.2, 99.3, 99.4, 99.5, 99.6, 99.7, 99.8, 99.9% or greater). In some embodiments, a call is made using a call zone and additional data or information. In some embodiments, a call is made without using a call zone. In some embodiments, a call is made based on a comparison without the use of a call zone. In some embodiments, a call is made based on visual inspection of a profile (e.g., visual inspection of read densities).

In some embodiments, a classification or call is not provided for a test sample when a test value or profile is in a no-call zone. In some embodiments, a no-call zone is defined by a value (e.g., collection of values) or profile that indicates low accuracy, high risk, high error, low level of confidence, high measure of uncertainty, the like or combination thereof. In some embodiments, a no-call zone is defined, in part, by a minority nucleic acid species quantification (e.g., a minority nucleic acid species of about 10% or less (e.g., about 9%, 8%, 7%, 6%, 5%, 4%, 3%, 2%, 1.5%, 1% or less minority nucleic acid species)). An outcome and/or classification generated for determining presence or absence of genomic instability, a genotype, phenotype, genetic variation and/or medical condition sometimes includes a null result. A null result sometimes is a data point between two clusters; sometimes is a numerical value with a standard deviation that encompasses values for both the presence and absence of genomic instability, a genotype, phenotype, genetic variation and/or medical condition; and sometimes is a data set with a profile plot that is not similar to profile plots for subjects having or free from genomic instability, or a genotype, phenotype, genetic variation or medical condition under investigation. In some embodiments, an outcome and/or classification indicative of a null result is considered a determinative result, and the determination can include a conclusion of the need for additional information and/or a repeat of data generation and/or analysis for determining the presence or absence of genomic instability, a genotype, phenotype, genetic variation and/or medical condition.

There typically are four types of classifications generated in a classification process: true positive, false positive, true negative and false negative. The term "true positive" as used herein refers to presence of genomic instability, a genotype, phenotype, genetic variation, or medical condition correctly determined for a test sample. The term "false positive" as used herein refers to presence of genomic instability, a genotype, phenotype, genetic variation, or medical condition incorrectly determined for a test sample. The term "true negative" as used herein refers to absence of genomic instability, a genotype, phenotype, genetic variation, or medical condition correctly determined for a test sample. The term "false negative" as used herein refers to absence of genomic instability, a genotype, phenotype, genetic variation, or medical condition incorrectly determined for a test sample. Two measures of performance for a classification process can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, a laboratory test report generated for a classification process includes a measure of test performance (e.g., sensitivity and/or specificity) and/or a measure of confidence (e.g., a confidence level, confidence interval). A measure of test performance and/or confidence sometimes is obtained from a clinical validation study performed prior to performing a laboratory test for a test sample. In certain embodiments, one or more of sensitivity, specificity and/or confidence are expressed as a percentage. In some embodiments, a percentage expressed independently for each of sensitivity, specificity or confidence level, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). A confidence interval expressed for a particular confidence level (e.g., a confidence level of about 90% to about 99.9% (e.g., about 95%)) can be expressed as a range of values, and sometimes is expressed as a range or sensitivities and/or specificities for a particular confidence level. Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome and/or classification is not due to chance) in certain embodiments is expressed as a standard score (e.g., z-score), a p-value, or result of a t-test. In some embodiments, a measured variance, confidence level, confidence interval, sensitivity, specificity and the like (e.g., referred to collectively as confidence parameters) for an outcome and/or classification can be generated using one or more data processing manipulations described herein. Specific examples of generating an outcome and/or classification and associated confidence levels are described, for example, in International Patent Application Publication Nos. WO 2013/052913, WO 2014/190286 and WO 2015/051163, the entire content of which is incorporated herein by reference, including all text, tables, equations and drawings.

An outcome and/or classification for a test sample often is ordered by, and often is provided to, a health care professional or other qualified individual (e.g., physician or assistant) who transmits an outcome and/or classification to a subject from whom the test sample is obtained. In certain embodiments, an outcome and/or classification is provided using a suitable visual medium (e.g., a peripheral or component of a machine, e.g., a printer or display). A classification and/or outcome often is provided to a healthcare professional or qualified individual in the form of a report. A report typically comprises a display of an outcome and/or classification (e.g., a value, or an assessment or probability of presence or absence of genomic instability, a genotype, phenotype, genetic variation and/or medical condition), sometimes includes an associated confidence parameter, and sometimes includes a measure of performance for a test used to generate the outcome and/or classification. A report sometimes includes a recommendation for a follow-up procedure (e.g., a procedure that confirms the outcome or classification). A report sometimes includes a visual representation of a chromosome or portion thereof (e.g., a chromosome ideogram or karyogram), and sometimes shows a visualization of a duplication and/or deletion region for a chromosome (e.g., a visualization of a whole chromosome for a chromosome deletion or duplication; a visualization of a whole chromosome with a deleted region or duplicated region shown; a visualization of a portion of chromosome duplicated or deleted; a visualization of a portion of a chromosome remaining in the event of a deletion of a portion of a chromosome) identified for a test sample.

A report can be displayed in a suitable format that facilitates determination of presence or absence of genomic instability, a genotype, a phenotype, a genetic variation and/or a medical condition by a health professional or other qualified individual. Non-limiting examples of formats suitable for use for generating a report include digital data, a graph, a 2D graph, a 3D graph, and 4D graph, a picture (e.g., a jpg, bitmap (e.g., bmp), pdf, tiff, gif, raw, png, the like or suitable format), a pictograph, a chart, a table, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, or combination of the foregoing.

A report may be generated by a computer and/or by human data entry, and can be transmitted and communicated using a suitable electronic medium (e.g., via the internet, via computer, via facsimile, from one network location to another location at the same or different physical sites), or by another method of sending or receiving data (e.g., mail service, courier service and the like). Non-limiting examples of communication media for transmitting a report include auditory file, computer readable file (e.g., pdf file), paper file, laboratory file, medical record file, or any other medium described in the previous paragraph. A laboratory file or medical record file may be in tangible form or electronic form (e.g., computer readable form), in certain embodiments. After a report is generated and transmitted, a report can be received by obtaining, via a suitable communication medium, a written and/or graphical representation comprising an outcome and/or classification, which upon review allows a healthcare professional or other qualified individual to make a determination as to presence or absence of genomic instability, a genotype, phenotype, genetic variation and/or or medical condition for a test sample.

An outcome and/or classification may be provided by and obtained from a laboratory (e.g., obtained from a laboratory file). A laboratory file can be generated by a laboratory that carries out one or more tests for determining presence or absence of genomic instability, a genotype, a phenotype, a genetic variation and/or a medical condition for a test sample. Laboratory personnel (e.g., a laboratory manager) can analyze information associated with test samples (e.g., test profiles, reference profiles, test values, reference values, level of deviation, patient information) underlying an outcome and/or classification. For calls pertaining to presence or absence of genomic instability, a genotype, a phenotype, a genetic variation and/or a medical condition that are close or questionable, laboratory personnel can re-run the same procedure using the same (e.g., aliquot of the same sample) or different test sample from a test subject. A laboratory may be in the same location or different location (e.g., in another country) as personnel assessing presence or absence of genomic instability, phenotype, genetic variation and/or medical condition from the laboratory file. For example, a laboratory file can be generated in one location and transmitted to another location in which the information for a test sample therein is assessed by a healthcare professional or other qualified individual, and optionally, transmitted to the subject from which the test sample was obtained. A laboratory sometimes generates and/or transmits a laboratory report containing a classification of presence or absence of genomic instability, a genotype, phenotype, a genetic variation and/or a medical condition for a test sample. A laboratory generating a laboratory test report sometimes is a certified laboratory, and sometimes is a laboratory certified under the Clinical Laboratory Improvement Amendments (CLIA).

An outcome and/or classification sometimes is a component of a diagnosis for a subject, and sometimes an outcome and/or classification is utilized and/or assessed as part of providing a diagnosis for a test sample. For example, a healthcare professional or other qualified individual may analyze an outcome and/or classification and provide a diagnosis based on, or based in part on, the outcome and/or classification. In some embodiments, determination, detection or diagnosis of a medical condition, disease, syndrome or abnormality comprises use of an outcome and/or classification determinative of presence or absence of genomic instability, a genotype, a phenotype, a genetic variation and/or a medical condition. In some embodiments, an outcome and/or classification based on counted mapped sequence reads, normalized counts and/or transformations thereof is determinative of presence or absence of genomic instability, a genotype and/or a genetic variation. In certain embodiments, a diagnosis comprises a determination of presence or absence of a condition, syndrome or abnormality. In certain instances, a diagnosis comprises a determination of a genetic variation as the nature and/or cause of genomic instability and/or a medical condition, disease, syndrome or abnormality. Thus, provided herein are methods for diagnosing presence or absence of genomic instability, a genotype, phenotype, a genetic variation and/or a medical condition for a test sample according to an outcome or classification generated by methods described herein, and optionally according to generating and transmitting a laboratory report that includes a classification for presence or absence of genomic instability, a genotype, phenotype, a genetic variation and/or a medical condition for the test sample.

An outcome and/or classification sometimes is a component of health care and/or treatment of a subject. An outcome and/or classification sometimes is utilized and/or assessed as part of providing a treatment for a subject from whom a test sample was obtained. For example, an outcome and/or classification indicative of presence or absence of genomic instability, a genotype, a phenotype, a genetic variation, and/or a medical condition is a component of health care and/or treatment of a subject from whom a test sample was obtained. Medical care, treatment and or diagnosis can be in any suitable area of health, such as medical treatment of subjects for prenatal care, cell proliferative conditions, cancer and the like, for example. An outcome and/or classification determinative of presence or absence of genomic instability, a genotype, a phenotype, a genetic variation, and/or a medical condition, disease, syndrome or abnormality by methods described herein sometimes is independently verified by further testing. Any suitable type of further test to verify an outcome and/or classification can be utilized, non-limiting examples of which include blood level test (e.g., serum test), biopsy, scan (e.g., CT scan, MRI scan), invasive sampling (e.g., amniocentesis or chorionic villus sampling), karyotyping, microarray assay, ultrasound, sonogram, and the like, for example.

A healthcare professional or qualified individual can provide a suitable healthcare recommendation based on the outcome and/or classification provided in a laboratory report. In some embodiments, a recommendation is dependent on the outcome and/or classification provided (e.g., cancer, stage and/or type of cancer, Down's syndrome, Turner syndrome, medical conditions associated with genetic variations in T13, medical conditions associated with genetic variations in T18). Non-limiting examples of recommendations that can be provided based on an outcome or classification in a laboratory report includes, without limitation, surgery, radiation therapy, chemotherapy, genetic counseling, after-birth treatment solutions (e.g., life planning, long term assisted care, medicaments, symptomatic treatments), pregnancy termination, organ transplant, blood transfusion, further testing described in the previous paragraph, the like or combinations of the foregoing. Thus, methods for treating a subject and methods for providing health care to a subject sometimes include generating a classification for presence or absence of genomic instability, a genotype, phenotype, a genetic variation and/or a medical condition for a test sample by a method described herein, and optionally generating and transmitting a laboratory report that includes a classification of presence or absence of genomic instability, a genotype, phenotype, a genetic variation and/or a medical condition for the test sample.

Generating an outcome and/or classification can be viewed as a transformation of nucleic acid sequence reads from a test sample into a representation of a subject's cellular nucleic acid. For example, transmuting sequence reads of nucleic acid from a subject by a method described herein, and generating an outcome and/or classification can be viewed as a transformation of relatively small sequence read fragments to a representation of relatively large and complex structure of nucleic acid in the subject. In some embodiments, an outcome and/or classification results from a transformation of sequence reads from a subject into a representation of an existing nucleic acid structure present in the subject (e.g., a genome, a chromosome, chromosome segment, mixture of circulating cell-free nucleic acid fragments in the subject).

In some embodiments, a method herein comprises treating a subject when the presence of a genetic alteration or genetic variation is determined for a test sample from the subject. In some embodiments, treating a subject comprises performing a medical procedure when the presence of a genetic alteration or genetic variation is determined for a test sample. In some embodiments, a medical procedure includes an invasive diagnostic procedure such as, for example, amniocentesis, chorionic villus sampling, biopsy, and the like. For example, a medical procedure comprising amniocentesis or chorionic villus sampling may be performed when the presence of a fetal aneuploidy is determined for a test sample from a pregnant female. In another example, a medical procedure comprising a biopsy may be performed when presence of a genetic alteration indicative of or associated with the presence of cancer is determined for a test sample from a subject. An invasive diagnostic procedure may be performed to confirm a determination of the presence of a genetic alteration or genetic variation and/or may be performed to further characterize a medical condition associated with a genetic alteration or genetic variation, for example. In some embodiments, a medical procedure may be performed as a treatment of a medical condition associated with a genetic alteration or genetic variation. Treatments may include one or more of surgery, radiation therapy, chemotherapy, pregnancy termination, organ transplant, cell transplant, blood transfusion, medicaments, symptomatic treatments, and the like, for example.

In some embodiments, a method herein comprises treating a subject when the absence of a genetic alteration or genetic variation is determined for a test sample from the subject. In some embodiments, treating a subject comprises performing a medical procedure when the absence of a genetic alteration or genetic variation is determined for a test sample. For example, when the absence of a genetic alteration or genetic variation is determined for a test sample, a medical procedure may include health monitoring, retesting, further screening, follow-up examinations, and the like. In some embodiments, a method herein comprises treating a subject consistent with a euploid pregnancy or normal pregnancy when the absence of a fetal aneuploidy, genetic variation or genetic alteration is determined for a test sample from a pregnant female. For example, a medical procedure consistent with a euploid pregnancy or normal pregnancy may be performed when the absence of a fetal aneuploidy, genetic variation or genetic alteration is determined for a test sample from a pregnant female. A medical procedure consistent with a euploid pregnancy or normal pregnancy may include one or more procedures performed as part of monitoring health of the fetus and/or the mother, or monitoring feto-maternal well-being. A medical procedure consistent with a euploid pregnancy or normal pregnancy may include one or more procedures for treating symptoms of pregnancy which may include, for example, one or more of nausea, fatigue, breast tenderness, frequent urination, back pain, abdominal pain, leg cramps, constipation, heartburn, shortness of breath, hemorrhoids, urinary incontinence, varicose veins and sleeping problems. A medical procedure consistent with a euploid pregnancy or normal pregnancy may include one or more procedures performed throughout the course of prenatal care for assessing potential risks, treating complications, addressing preexisting medical conditions (e.g., hypertension, diabetes), and monitoring the growth and development of the fetus, for example. Medical procedures consistent with a euploid pregnancy or normal pregnancy may include, for example, complete blood count (CBC) monitoring, Rh antibody testing, urinalysis, urine culture monitoring, rubella screening, hepatitis B and hepatitis C screening, sexually transmitted infection (STI) screening (e.g., screening for syphilis, chlamydia, gonorrhea), human immunodeficiency virus (HIV) screening, tuberculosis (TB) screening, alpha-fetoprotein screening, fetal heart rate monitoring (e.g., using an ultrasound transducer), uterine activity monitoring (e.g., using toco transducer), genetic screening and/or diagnostic testing for genetic disorders (e.g., cystic fibrosis, sickle cell anemia, hemophilia A), glucose screening, glucose tolerance testing, treatment of gestational diabetes, treatment of prenatal hypertension, treatment of preeclampsia, group B streptococci (GBS) blood type screening, group B strep culture, treatment of group B strep (e.g., with antibiotics), ultrasound monitoring (e.g., routine ultrasound monitoring, level II ultrasound monitoring, targeted ultrasound monitoring), non-stress test monitoring, biophysical profile monitoring, amniotic fluid index monitoring, serum testing (e.g., plasma protein-A (PAPP-A), alpha-fetoprotein (AFP), human chorionic gonadotropin (hCG), unconjugated estriol (uE3), and inhibin-A (inhA) testing), genetic testing, amniocentesis diagnostic testing and chorionic villus sampling (CVS) diagnostic testing.

In some embodiments, a method herein comprises treating a subject consistent with having no cancer when the absence of a genetic variation or genetic alteration is determined for a test sample from a subject. In certain embodiments, a medical procedure consistent with a healthy prognosis may be performed when absence of a genetic alteration or genetic variation associated with cancer is determined for a test sample. For example, medical procedures consistent with a healthy prognosis include without limitation monitoring health of the subject from whom a test sample was tested, performing a secondary test (e.g., a secondary screening test), performing a confirmatory test, monitoring one or more biomarkers associated with cancer (e.g., prostate specific antigen (PSA) in males), monitoring blood cells (e.g., red blood cells, white blood cells, platelets), monitoring one or more vital signs (e.g., heart rate, blood pressure), and/or monitoring one or more blood metabolites (e.g., total cholesterol, HDL (high-density lipoprotein), LDL (low-density lipo-protein), triglycerides, total cholesterol/HDL ratio, glucose, fibrinogen, hemoglobin, dehydroepiandrosterone (DHEA), homocysteine, C-reactive protein, hormones (e.g., thyroid stimulating hormone, testosterone, estrogen, estradiol), creatine, salt (e.g., potassium, calcium), and the like). In some embodiments, a method herein comprises performing no medical procedure, and sometimes no medical procedure that includes invasive sampling, when the absence of a genetic alteration or genetic variation is determined for a test sample.

Machines, Software and Interfaces

Certain processes and methods described herein (e.g., mapping, counting, normalizing, range setting, adjusting, categorizing and/or determining sequence reads, counts, levels and/or profiles) often cannot be performed without a computer, microprocessor, software, module or other machine. Methods described herein typically are computer-implemented methods, and one or more portions of a method sometimes are performed by one or more processors (e.g., microprocessors), computers, systems, apparatuses, or machines (e.g., microprocessor-controlled machine).

Computers, systems, apparatuses, machines and computer program products suitable for use often include, or are utilized in conjunction with, computer readable storage media. Non-limiting examples of computer readable storage media include memory, hard disk, CD-ROM, flash memory device and the like. Computer readable storage media generally are computer hardware, and often are non-transitory computer-readable storage media. Computer readable storage media are not computer readable transmission media, the latter of which are transmission signals per se.

Provided herein is a system comprising one or more processors and non-transitory machine readable storage medium; a set of genomic portions stored on the non-transitory machine readable medium, each of the set of genomic portions coupled to a copy number alteration quantification for a test sample. The genomic portions comprise portions of a reference genome to which sequence reads obtained for sample nucleic acid from the test subject have been mapped and a copy number alteration quantification coupled to each genomic portion has been determined from a quantification of sequence reads mapped to the genomic portion. The system further comprises program instructions to determine a presence or absence of genomic instability for the test subject according to the copy number alteration quantifications coupled to the filtered genomic portions, and the program instructions are stored on the non-transitory machine readable storage medium for execution by the one or more processors.

The system of the disclosure may further comprise program instructions to adjust the quantified sequence reads for each of the genomic portions by an adjustment process that reduces experimental bias, wherein the adjustment process generates a normalized quantification of sequence reads for each of the genomic portions wherein the program instructions are stored on the non-transitory machine readable storage medium for execution by the one or more processors.

The system may further comprise program instructions to generate a genomic instability classification for the test sample according to the normalized quantification of sequence reads for each of the genomic portions, wherein the program instructions are stored on the non-transitory machine readable storage medium for execution by the one or more processors.

Provided herein is a system comprising one or more processors and non-transitory machine readable storage medium. In some embodiments, the system comprises a set of genomic portions each coupled to a copy number alteration quantification for a test sample, wherein the genomic portions comprise portions of a reference genome to which sequence reads obtained for sample nucleic acid from the test subject have been mapped, the copy number alteration quantification coupled to each genomic portion has been determined from a quantification of sequence reads mapped to the genomic portion, and the set of genomic portions are stored on the non-transitory machine readable storage medium. The system may comprise program instructions to filter from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and the second subset of portions. The system may further comprise program instructions to determine a presence or absence of genomic instability for the test subject according to the copy number alteration quantifications coupled to the filtered genomic portions, wherein the program instructions are stored on the non-transitory machine readable storage medium for execution by the one or more processors.

In some embodiments, the system further comprises program instructions for transforming the set of filtered genomic portions to a reduced set of parameters, wherein the transforming comprises: performing a principal component transformation that yields principal components for the test sample, and determining a distance from a common principal component origin for the test sample. The system may also comprise program instructions for determining a distance between the principal components of the test sample from a common principal component origin.

Also provided herein is a system comprising: one or more processors and non-transitory machine readable storage medium; a set of genomic portions of a reference genome to which sequence reads obtained for sample nucleic acid from the test subject have been mapped, and for which the sequence reads mapped to the genomic portions have been quantified, wherein the set of genomic portions are stored on the non-transitory machine readable storage medium. The system may further comprise program instructions to adjust the quantified sequence reads for each of the genomic portions by an adjustment process that reduces experimental bias, wherein the adjustment process generates a normalized quantification of sequence reads for each of the genomic portions. The system may further comprise program instructions to generate a genomic instability classification for the test sample according to the normalized quantification of sequence reads for each of the genomic portions. These program instructions may be stored on the non-transitory machine readable storage medium for execution by the one or more processors. In some cases, the program instructions to reduce experimental bias is according to a GC normalized quantification of sequence reads.

Provided herein is a non-transitory machine readable storage medium comprising: a set of genomic portions each coupled to a copy number alteration quantification for a test sample. The genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion. The non-transitory machine readable storage medium further comprises program instructions that when executed by one or more processors cause the one or more processors to perform a method comprising determining presence or absence of genomic instability for the test subject according to the copy number alteration qualifications coupled to the genomic portions.

Provided herein are computer readable storage media with an executable program stored thereon, where the program instructs a microprocessor to perform a method described herein. Provided also are computer readable storage media with an executable program module stored thereon, where the program module instructs a microprocessor to perform part of a method described herein. Also provided herein are systems, machines, apparatuses and computer program products that include computer readable storage media with an executable program stored thereon, where the program instructs a microprocessor to perform a method described herein. Provided also are systems, machines and apparatuses that include computer readable storage media with an executable program module stored thereon, where the program module instructs a microprocessor to perform part of a method described herein.

In some embodiments, the disclosure provides a non-transitory machine readable storage medium comprising program instructions that when executed by one or more processors cause the one or more processors to perform a method, the method comprising: filtering from a set of genomic portions, each of which is coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion, (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and the second subset of portions; and determining presence or absence of genomic instability for the test subject according to the copy number alteration qualifications coupled to the filtered genomic portions.

In some embodiments, the non-transitory machine readable storage medium further comprises: program Instructions for transforming the set of filtered genomic portions to a reduced set of parameters, wherein the transforming comprises: performing a principal component transformation that yields principal components for the test sample, and determining a distance from a common principal component origin for the test sample; and
determining a distance between the principal components of the test sample from a common principal component origin.

The non-transitory machine readable storage medium may further comprise program instructions that when executed by one or more processors cause the one or more processors to perform a method comprising: adjusting the quantified sequence reads for each of the genomic portions by an adjustment process that reduces experimental bias, wherein the adjustment process generates a normalized quantification of sequence reads for each of the genomic portions.

Also provided herein is a non-transitory machine readable storage medium comprising: program instructions that when executed by one or more processors cause the one or more processors to perform a method comprising: adjusting the quantified sequence reads for each of a set of genomic portions by an adjustment process that reduces experimental bias, wherein the set of genomic portions of a reference genome to which sequence reads obtained for sample nucleic acid from the test subject have been mapped, and for which the sequence reads mapped to the genomic portions have been quantified, and wherein the adjustment process generates a normalized quantification of sequence reads for each of the genomic portions; and generating a genomic instability classification for the test sample according to the normalized quantification of sequence reads for each of the genomic portions. In some embodiments, the program instructions to reduce experimental bias is according to a GC normalized quantification of sequence reads.

Thus, also provided are computer program products. A computer program product often includes a computer usable medium that includes a computer readable program code embodied therein, the computer readable program code adapted for being executed to implement a method or part of a method described herein. Computer usable media and readable program code are not transmission media (i.e., transmission signals per se). Computer readable program code often is adapted for being executed by a processor, computer, system, apparatus, or machine.

In some embodiments, methods described herein (e.g., quantifying, counting, filtering, normalizing, transforming, clustering and/or determining sequence reads, counts, levels, profiles and/or outcomes) are performed by automated methods. In some embodiments, one or more steps of a method described herein are carried out by a microprocessor and/or computer, and/or carried out in conjunction with memory. In some embodiments, an automated method is embodied in software, modules, microprocessors, peripherals and/or a machine comprising the like, that perform methods described herein. As used herein, software refers to computer readable program instructions that, when executed by a microprocessor, perform computer operations, as described herein.

Sequence reads, counts, levels and/or profiles sometimes are referred to as "data" or "data sets." In some embodiments, data or data sets can be characterized by one or more features or variables (e.g., sequence based (e.g., GC content, specific nucleotide sequence, the like), function specific (e.g., expressed genes, cancer genes, the like), location based (genome specific, chromosome specific, portion or portion-specific), the like and combinations thereof). In certain embodiments, data or data sets can be organized into a matrix having two or more dimensions based on one or more features or variables. Data organized into matrices can be organized using any suitable features or variables. In certain embodiments, data sets characterized by one or more features or variables sometimes are processed after counting.

Machines, software and interfaces may be used to conduct methods described herein. Using machines, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing machine and a sequencing apparatus or machine, where the sequencing apparatus or machine is configured to receive physical nucleic acid and generate sequence reads, and the computing apparatus is configured to process the reads from the sequencing apparatus or machine. The computing machine sometimes is configured to determine a classification outcome from the sequence reads.

A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses, computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output components may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus or machine may serve as data that can be input via an input device. In certain embodiments, mapped sequence reads may serve as data that can be input via an input device. In certain embodiments, nucleic acid fragment size (e.g., length) may serve as data that can be input via an input device. In certain embodiments, output from a nucleic acid capture process (e.g., genomic region origin data) may serve as data that can be input via an input device. In certain embodiments, a combination of nucleic acid fragment size (e.g., length) and output from a nucleic acid capture process (e.g., genomic region origin data) may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process or part of a process described herein, and software can include one or more modules for performing such processes (e.g., sequencing module, logic processing module, data display organization module). The term "software" refers to computer readable program instructions that, when executed by a computer, perform computer operations. Instructions executable by the one or more microprocessors sometimes are provided as executable code, that when executed, can cause one or more microprocessors to implement a method described herein.

A module described herein can exist as software, and instructions (e.g., processes, routines, subroutines) embodied in the software can be implemented or performed by a microprocessor. For example, a module (e.g., a software module) can be a part of a program that performs a particular process or task. The term "module" refers to a self-contained functional unit that can be used in a larger machine or software system. A module can comprise a set of instructions for carrying out a function of the module. A module can transform data and/or information. Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an machine, peripheral, component or another module. A module can perform one or more of the following non-limiting functions: mapping sequence reads, providing counts, assembling portions, providing or determining a level, providing a count profile, normalizing (e.g., normalizing reads, normalizing counts, and the like), providing a normalized count profile or levels of normalized counts, comparing two or more levels, providing uncertainty values, providing or determining expected levels and expected ranges (e.g., expected level ranges, threshold ranges and threshold levels), providing adjustments to levels (e.g., adjusting a first level, adjusting a second level, adjusting a profile of a chromosome or a part thereof, and/or padding), providing identification (e.g., identifying a copy number alteration, genetic variation/genetic alteration or aneuploidy), categorizing, plotting, and/or determining an outcome, for example. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

A machine, in some embodiments, comprises at least one microprocessor for carrying out the instructions in a module. Sequence read quantifications (e.g., counts) sometimes are accessed by a microprocessor that executes instructions configured to carry out a method described herein. Sequence read quantifications that are accessed by a microprocessor can be within memory of a system, and the counts can be accessed and placed into the memory of the system after they are obtained. In some embodiments, a machine includes a microprocessor (e.g., one or more microprocessors) which microprocessor can perform and/or implement one or more instructions (e.g., processes, routines and/or subroutines) from a module. In some embodiments, a machine includes multiple microprocessors, such as microprocessors coordinated and working in parallel. In some embodiments, a machine operates with one or more external microprocessors (e.g., an internal or external network, server, storage device and/or storage network (e.g., a cloud)). In some embodiments, a machine comprises a module (e.g., one or more modules). A machine comprising a module often is capable of receiving and transferring one or more of data and/or information to and from other modules.

In certain embodiments, a machine comprises peripherals and/or components. In certain embodiments, a machine can comprise one or more peripherals or components that can transfer data and/or information to and from other modules, peripherals and/or components. In certain embodiments, a machine interacts with a peripheral and/or component that provides data and/or information. In certain embodiments, peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., iPads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like), the world wide web (www), the internet, a computer and/or another module.

Software comprising program instructions often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash memory devices (e.g., flash drives), RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more microprocessors in certain embodiments. A microprocessor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A microprocessor may implement software in a system. In some embodiments, a microprocessor may be programmed to automatically perform a task described herein that a user could perform. Accordingly, a microprocessor, or algorithm conducted by such a microprocessor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation or genetic alteration.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

FIG. 1 illustrates a non-limiting example of a computing environment 110 in which various systems, methods, algorithms, and data structures described herein may be implemented. The computing environment 110 is only one example of a suitable computing environment and is not intended to suggest any limitation as to the scope of use or functionality of the systems, methods, and data structures described herein. Neither should computing environment 110 be interpreted as having any dependency or requirement relating to any one or combination of components illustrated in computing environment 110. A subset of systems, methods, and data structures shown in FIG. 1 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 110 of FIG. 1 includes a general purpose computing device in the form of a computer 120, including a processing unit 121, a system memory 122, and a system bus 123 that operatively couples various system components including the system memory 122 to the processing unit 121. There may be only one or there may be more than one processing unit 121, such that the processor of computer 120 includes a single central-processing unit (CPU), or a plurality of processing units, commonly referred to as a parallel processing environment. The computer 120 may be a conventional computer, a distributed computer, or any other type of computer.

The system bus 123 may be any of several types of bus structures including a memory bus or memory controller, a peripheral bus, and a local bus using any of a variety of bus architectures. The system memory may also be referred to as simply the memory, and includes read only memory (ROM) 124 and random access memory (RAM). A basic input/output system (BIOS) 126, containing the basic routines that help to transfer information between elements within the computer 120, such as during start-up, is stored in ROM 124. The computer 120 may further include a hard disk drive interface 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media.

The hard disk drive 127, magnetic disk drive 128, and optical disk drive 130 are connected to the system bus 123 by a hard disk drive interface 132, a magnetic disk drive interface 133, and an optical disk drive interface 134, respectively. The drives and their associated computer-readable media provide nonvolatile storage of computer-readable instructions, data structures, program modules and other data for the computer 120. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 129, optical disk 131, ROM 124, or RAM, including an operating system 135, one or more application programs 136, other program modules 137, and program data 138. A user may enter commands and information into the personal computer 120 through input devices such as a keyboard 140 and pointing device 142. Other input devices (not shown) may include a microphone, joystick, game pad, satellite dish, scanner, or the like. These and other input devices are often connected to the processing unit 121 through a serial port interface 146 that is coupled to the system bus, but may be connected by other interfaces, such as a parallel port, game port, or a universal serial bus (USB). A monitor 147 or other type of display device is also connected to the system bus 123 via an interface, such as a video adapter 148. In addition to the monitor, computers typically include other peripheral output devices (not shown), such as speakers and printers.

The computer 120 may operate in a networked environment using logical connections to one or more remote computers, such as remote computer 149. These logical connections may be achieved by a communication device coupled to or a part of the computer 120, or in other manners. The remote computer 149 may be another computer, a server, a router, a network PC, a client, a peer device or other common network node, and typically includes many or all of the elements described above relative to the computer 120, although only a memory storage device 150 has been illustrated in FIG. 1. The logical connections depicted in FIG. 1 include a local-area network (LAN) 151 and a wide-area network (WAN) 152. Such networking environments are commonplace in office networks, enterprise-wide computer networks, intranets and the Internet, which all are types of networks.

When used in a LAN-networking environment, the computer 120 is connected to the local network 151 through a network interface or adapter 153, which is one type of communications device. When used in a WAN-networking environment, the computer 120 often includes a modem 154, a type of communications device, or any other type of communications device for establishing communications over the wide area network 152. The modem 154, which may be internal or external, is connected to the system bus 123 via the serial port interface 146. In a networked environment, program modules depicted relative to the personal computer 120, or portions thereof, may be stored in the remote memory storage device. It is appreciated that the network connections shown are non-limiting examples and other communications devices for establishing a communications link between computers may be used.

Transformations

As noted above, data sometimes is transformed from one form into another form. The terms "transformed," "transformation," and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's nucleic acid.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, fragment size (e.g., length of CCF fragments, reads or a suitable representation thereof (e.g., FRS)), fragment sequence, identification of a copy number alteration, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principal component analysis of derived quantities; and the like or combinations thereof.

Genetic Variations/Genetic Alterations and Medical Conditions

The presence or absence of a genetic variation can be determined using a method or apparatus described herein. A genetic variation also may be referred to as a genetic alteration, and the terms are often used interchangeably herein and in the art. In certain instances, "genetic alteration" may be used to describe a somatic alteration whereby the genome in a subset of cells in a subject contains the alteration (such as, for example, in tumor or cancer cells). In certain instances, "genetic variation" may be used to describe a variation inherited from one or both parents (such as, for example, a genetic variation in a fetus).

In certain embodiments, the presence or absence of one or more genetic variations or genetic alterations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation or genetic alteration is a chromosome abnormality or copy number alteration (e.g., aneuploidy, duplication of one or more chromosomes, loss of one or more chromosomes, partial chromosome abnormality or mosaicism (e.g., loss or gain of one or more regions of a chromosome), translocation, inversion, each of which is described in greater detail herein). Non-limiting examples of genetic variations/genetic alterations include one or more copy number alterations/variations, deletions (e.g., microdeletions), duplications (e.g., microduplications), insertions, mutations (e.g., single nucleotide variations, single nucleotide alterations), polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 50,000 kilobases (kb) in length (e.g., about 10 bp, 50 bp, 100 bp, 500 bp, 1 kb, 5 kb, 10 kb, 50 kb, 100 kb, 500 kb, 1000 kb, 5000 kb or 10,000 kb in length).

A genetic variation or genetic alteration is sometime a deletion. In certain instances, a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a region of a chromosome, an allele, a gene, an intron, an exon, any non-coding region, any coding region, a part thereof or combination thereof. A deletion can comprise a microdeletion. A deletion can comprise the deletion of a single base.

A genetic variation or genetic alteration is sometimes a duplication. In certain instances, a duplication is a mutation (e.g., a genetic aberration) in which a part of a chromosome or a sequence of DNA is copied and inserted back into the genome. In certain embodiments, a genetic duplication (e.g., duplication) is any duplication of a region of DNA. In some embodiments, a duplication is a nucleic acid sequence that is repeated, often in tandem, within a genome or chromosome. In some embodiments, a duplication can comprise a copy of one or more entire chromosomes, a region of a chromosome, an allele, a gene, an intron, an exon, any non-coding region, any coding region, part thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation or genetic alteration is sometimes an insertion. An insertion is sometimes the addition of one or more nucleotide base pairs into a nucleic acid sequence. An insertion is sometimes a microinsertion. In certain embodiments, an insertion comprises the addition of a region of a chromosome into a genome, chromosome, or part thereof. In certain embodiments, an insertion comprises the addition of an allele, a gene, an intron, an exon, any non-coding region, any coding region, part thereof or combination thereof into a genome or part thereof. In certain embodiments, an insertion comprises the addition (e.g., insertion) of nucleic acid of unknown origin into a genome, chromosome, or part thereof. In certain embodiments, an insertion comprises the addition (e.g., insertion) of a single base.

As used herein a "copy number alteration" generally is a class or type of genetic variation, genetic alteration or chromosomal aberration. A copy number alteration also may be referred to as a copy number variation, and the terms are often used interchangeably herein and in the art. In certain instances, "copy number alteration" may be used to describe a somatic alteration whereby the genome in a subset of cells in a subject contains the alteration (such as, for example, in tumor or cancer cells). In certain instances, "copy number variation" may be used to describe a variation inherited from one or both parents (such as, for example, a copy number variation in a fetus). A copy number alteration can be a deletion (e.g., microdeletion), duplication (e.g., a microduplication) or insertion (e.g., a microinsertion). Often, the prefix "micro" as used herein sometimes is a region of nucleic acid less than 5 Mb in length. A copy number alteration can include one or more deletions (e.g., microdeletion), duplications and/or insertions (e.g., a microduplication, microinsertion) of a part of a chromosome. In certain embodiments, a duplication comprises an insertion. In certain embodiments, an insertion is a duplication. In certain embodiments, an insertion is not a duplication.

In some embodiments, a copy number alteration is a copy number alteration from a tumor or cancer cell. In some embodiments, a copy number alteration is a copy number alteration from a non-cancer cell. In certain embodiments, a copy number alteration is a copy number alteration within the genome of a subject (e.g., a cancer patient) and/or within the genome of a cancer cell or tumor in a subject. A copy number alteration can be a heterozygous copy number alteration where the variation (e.g., a duplication or deletion) is present on one allele of a genome. A copy number alteration can be a homozygous copy number alteration where the alteration is present on both alleles of a genome. In some embodiments, a copy number alteration is a heterozygous or homozygous copy number alteration. In some embodiments, a copy number alteration is a heterozygous or homozygous copy number alteration from a cancer cell or non-cancer cell. A copy number alteration sometimes is present in a cancer cell genome and a non-cancer cell genome, a cancer cell genome and not a non-cancer cell genome, or a non-cancer cell genome and not a cancer cell genome.

In some embodiments, a copy number alteration is a fetal copy number alteration. Often, a fetal copy number alteration is a copy number alteration in the genome of a fetus. In some embodiments, a copy number alteration is a maternal and/or fetal copy number alteration. In certain embodiments, a maternal and/or fetal copy number alteration is a copy number alteration within the genome of a pregnant female (e.g., a female subject bearing a fetus), a female subject that gave birth or a female capable of bearing a fetus. A copy number alteration can be a heterozygous copy number alteration where the alteration (e.g., a duplication or deletion) is present on one allele of a genome. A copy number alteration can be a homozygous copy number alteration where the alteration is present on both alleles of a genome. In some embodiments, a copy number alteration is a heterozygous or homozygous fetal copy number alteration. In some embodiments, a copy number alteration is a heterozygous or homozygous maternal and/or fetal copy number alteration. A copy number alteration sometimes is present in a maternal genome and a fetal genome, a maternal genome and not a fetal genome, or a fetal genome and not a maternal genome.

"Ploidy" is a reference to the number of chromosomes present in a subject. In certain embodiments, "ploidy" is the same as "chromosome ploidy." In humans, for example, autosomal chromosomes are often present in pairs. For example, in the absence of a genetic variation or genetic alteration, most humans have two of each autosomal chromosome (e.g., chromosomes 1-22). The presence of the normal complement of 2 autosomal chromosomes in a human is often referred to as euploid or diploid. "Microploidy" is similar in meaning to ploidy. "Microploidy" often refers to the ploidy of a part of a chromosome. The term "microploidy" sometimes is a reference to the presence or absence of a copy number alteration (e.g., a deletion, duplication and/or an insertion) within a chromosome (e.g., a homozygous or heterozygous deletion, duplication, or insertion, the like or absence thereof).

A genetic variation or genetic alteration for which the presence or absence is identified for a subject is associated with a medical condition in certain embodiments. Thus, technology described herein can be used to identify the presence or absence of one or more genetic variations or genetic alterations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations/genetic alterations, medical conditions and states are described hereafter.

Chromosome Abnormalities

In some embodiments, the presence or absence of a chromosome abnormality can be determined by using a method and/or apparatus described herein. Chromosome abnormalities include, without limitation, copy number alterations, and a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality" or "aneuploidy" as used herein refer to a deviation between the structure of the subject chromosome and a normal homologous chromosome. The term "normal" refers to the predominate karyotype or banding pattern found in healthy individuals of a particular species, for example, a euploid genome (e.g., diploid in humans, e.g., 46,XX or 46,XY). As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a region of a chromosome. The term "euploid," in some embodiments, refers a normal complement of chromosomes.

The term "monosomy" as used herein refers to lack of one chromosome of the normal complement. Partial monosomy can occur in unbalanced translocations or deletions, in which only a part of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47,XYY in Jacobs Syndrome). In some embodiments, a trisomy is a duplication of most or all of an autosome. In certain embodiments, a trisomy is a whole chromosome aneuploidy resulting in three instances (e.g., three copies) of a particular type of chromosome (e.g., instead of two instances (e.g., a pair) of a particular type of chromosome for a euploid).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

In some embodiments, the disclosure provides a method of determining whether a test sample comprises trisomies, e.g., trisomy 21, trisomy 18 or trisomy 13. The method comprises providing a set of genomic portions each coupled to a copy number alteration quantification for the test sample. The genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion. The method further comprises filtering, by a computing device, from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and/or the second subset of portions. The method then transforms the set of filtered genomic portions to a reduced set of parameters by performing a principal component transformation of the set of filtered genomic portions that yields principal components for the test sample. The produced principal components can be represented in a principal component space, which contains a common principal component origin. Trisomy samples are typically grouped together and follow distinct patterns or directions, e.g., they form a vector in a two dimensional principal component space, a plane in a three dimensional principal component space, or a hyperplane in a n-dimension principal component space.

Medical Disorders and Medical Conditions

Methods described herein can be applicable to any suitable medical disorder or medical condition. Non-limiting examples of medical disorders and medical conditions include cell proliferative disorders and conditions, wasting disorders and conditions, degenerative disorders and conditions, autoimmune disorders and conditions, pre-eclampsia, chemical or environmental toxicity, liver damage or disease, kidney damage or disease, vascular disease, high blood pressure, and myocardial infarction.

In some embodiments, a cell proliferative disorder or condition sometimes is a cancer, tumor, neoplasm, metastatic disease, the like or combination thereof. A cell proliferative disorder or condition sometimes is a disorder or condition of the liver, lung, spleen, pancreas, colon, skin, bladder, eye, brain, esophagus, head, neck, ovary, testes, prostate, the like or combination thereof. Non-limiting examples of cancers include hematopoietic neoplastic disorders, which are diseases involving hyperplastic/neoplastic cells of hematopoietic origin (e.g., arising from myeloid, lymphoid or erythroid lineages, or precursor cells thereof), and can arise from poorly differentiated acute leukemias (e.g., erythroblastic leukemia and acute megakaryoblastic leukemia). Certain myeloid disorders include, but are not limited to, acute promyeloid leukemia (APML), acute myelogenous leukemia (AML) and chronic myelogenous leukemia (CML). Certain lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Certain forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. A cell proliferative disorder sometimes is a non-endocrine tumor or endocrine tumor. Illustrative examples of non-endocrine tumors include, but are not limited to, adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor sometimes is an islet cell tumor.

In some embodiments, the disclosure provides a method to determine if a test sample comprising a cancer. The method comprises providing a set of genomic portions each coupled to a copy number alteration quantification for the test sample. The genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion. The method further comprises filtering, by a computing device, from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and/or the second subset of portions. The method then transforms the set of filtered genomic portions to a reduced set of parameters by performing a principal component transformation of the set of filtered genomic portions that yields principal components for the test sample. The produced principal components can be represented in a principal component space, which contains a common principal component origin. The distance between the principal components of the test sample from the common principal component origin can be determined and compared with a predetermined threshold. These tumor samples with anomalous CNA events demonstrated outlier behavior lying outside of the central cloud and thus the distance as determined above are typically greater than the predetermined threshold. In some cases, the distance is a Mahalanobis distance and the predetermined threshold greater than 300, e.g., greater than 400, greater than 450, greater than 500, or about 500 (i.e., cutoff log 10 Mahalanobis distance between 2 and 3).

In some embodiments, a wasting disorder or condition, or degenerative disorder or condition, is cirrhosis, amyotrophic lateral sclerosis (ALS), Alzheimer's disease, Parkinson's disease, multiple system atrophy, atherosclerosis, progressive supranuclear palsy, Tay-Sachs disease, diabetes, heart disease, keratoconus, inflammatory bowel disease (IBD), prostatitis, osteoarthritis, osteoporosis, rheumatoid arthritis, Huntington's disease, chronic traumatic encephalopathy, chronic obstructive pulmonary disease (COPD), tuberculosis, chronic diarrhea, acquired immune deficiency syndrome (AIDS), superior mesenteric artery syndrome, the like or combination thereof.

In some embodiments, an autoimmune disorder or condition is acute disseminated encephalomyelitis (ADEM), Addison's disease, alopecia areata, ankylosing spondylitis, antiphospholipid antibody syndrome (APS), autoimmune hemolytic anemia, autoimmune hepatitis, autoimmune inner ear disease, bullous pemphigoid, celiac disease, Chagas disease, chronic obstructive pulmonary disease, Crohns Disease (a type of idiopathic inflammatory bowel disease "IBD"), dermatomyositis, diabetes mellitus type 1, endometriosis, Goodpasture's syndrome, Graves' disease, Guillain-Barré syndrome (GBS), Hashimoto's disease, hidradenitis suppurativa, idiopathic thrombocytopenic purpura, interstitial cystitis, Lupus erythematosus, mixed connective tissue disease, morphea, multiple sclerosis (MS), myasthenia gravis, narcolepsy, euromyotonia, pemphigus vulgaris, pernicious anaemia, polymyositis, primary biliary cirrhosis, rheumatoid arthritis, schizophrenia, scleroderma, Sjögren's syndrome, temporal arteritis (also known as "giant cell arteritis"), ulcerative colitis (a type of idiopathic inflammatory bowel disease "IBD"), vasculitis, vitiligo, Wegener's granulomatosis, the like or combination thereof.

Preeclampsia

In some embodiments, the presence or absence of preeclampsia is determined by using a method or apparatus described herein. Preeclampsia is a condition in which hypertension arises in pregnancy (e.g., pregnancy-induced hypertension) and is associated with significant amounts of protein in the urine. In certain instances, preeclampsia may be associated with elevated levels of extracellular nucleic acid and/or alterations in methylation patterns. For example, a positive correlation between extracellular fetal-derived hypermethylated RASSF1A levels and the severity of preeclampsia has been observed. In certain instances, increased DNA methylation is observed for the H19 gene in preeclamptic placentas compared to normal controls.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods, machines and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g., strain).

Use of Cell Free Nucleic Acid

In certain instances, nucleic acid from abnormal or diseased cells associated with a particular condition or disorder is released from the cells as circulating cell-free nucleic acid (CCF-NA). For example, cancer cell nucleic acid is present in CCF-NA, and analysis of CCF-NA using methods provided herein can be used to determining whether a subject has, or is at risk of having, cancer. Analysis of the presence or absence of cancer cell nucleic acid in CCF-NA can be used for cancer screening, for example. In certain instances, levels of CCF-NA in serum can be elevated in patients with various types of cancer compared with healthy patients. Patients with metastatic diseases, for example, can sometimes have serum DNA levels approximately twice as high as non-metastatic patients. Accordingly, methods described herein can provide an outcome by processing sequencing read counts obtained from CCF-NA extracted from a sample from a subject (e.g., a subject having, suspected of having, predisposed to, or suspected as being predisposed to, a particular condition or disease).

Markers

In certain instances, a polynucleotide in abnormal or diseased cells is modified with respect to nucleic acid in normal or non-diseased cells (e.g., single nucleotide alteration, single nucleotide variation, copy number alteration, copy number variation). In some instances, a polynucleotide is present in abnormal or diseased cells and not present in normal or non-diseased cells, and sometimes a polynucleotide is not present in abnormal or diseased cells and is present in normal or non-diseased cells. Thus, a marker sometimes is a single nucleotide alteration/variation and/or a copy number alteration/variation (e.g., a differentially expressed DNA or RNA (e.g., mRNA)). For example, patients with metastatic diseases may be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Accordingly, methods described herein sometimes provide an outcome based on determining the presence or absence of a particular marker, and sometimes an outcome is presence or absence of a particular type of condition (e.g., a particular type of cancer).

Certain methods described herein may be performed in conjunction with methods described, for example in International Patent Application Publication No. WO 2013/052913, International Patent Application Publication No. WO 2013/052907, International Patent Application Publication No. WO 2013/055817, International Patent Application Publication No. WO 2013/109981, International Patent Application Publication No. WO 2013/177086, International Patent Application Publication No. WO 2013/192562, International Patent Application Publication No. WO 2014/116598, International Patent Application Publication No. WO 2014/055774, International Patent Application Publication No. WO 2014/190286, International Patent Application Publication No. WO 2014/205401, International Patent Application Publication No. WO 2015/051163, International Patent Application Publication No. WO 2015/138774, International Patent Application Publication No. WO 2015/054080, International Patent Application Publication No.

WO 2015/183872, International Patent Application Publication No. WO 2016/019042, and International Patent Application Publication No. WO 2016/057901, the entire content of each is incorporated herein by reference, including all text, tables, equations and drawings.

EXAMPLES

The examples hereafter illustrates certain embodiments and do not limit the technology. An automated process was developed that identifies biological samples having genomic instability, which is a feature common to samples from subjects having cancer or tumors as shown below. This automated classification assesses copy number alteration (CNA) characteristics for samples by reducing noise and enriching information in higher dimensions.

Figure 2:
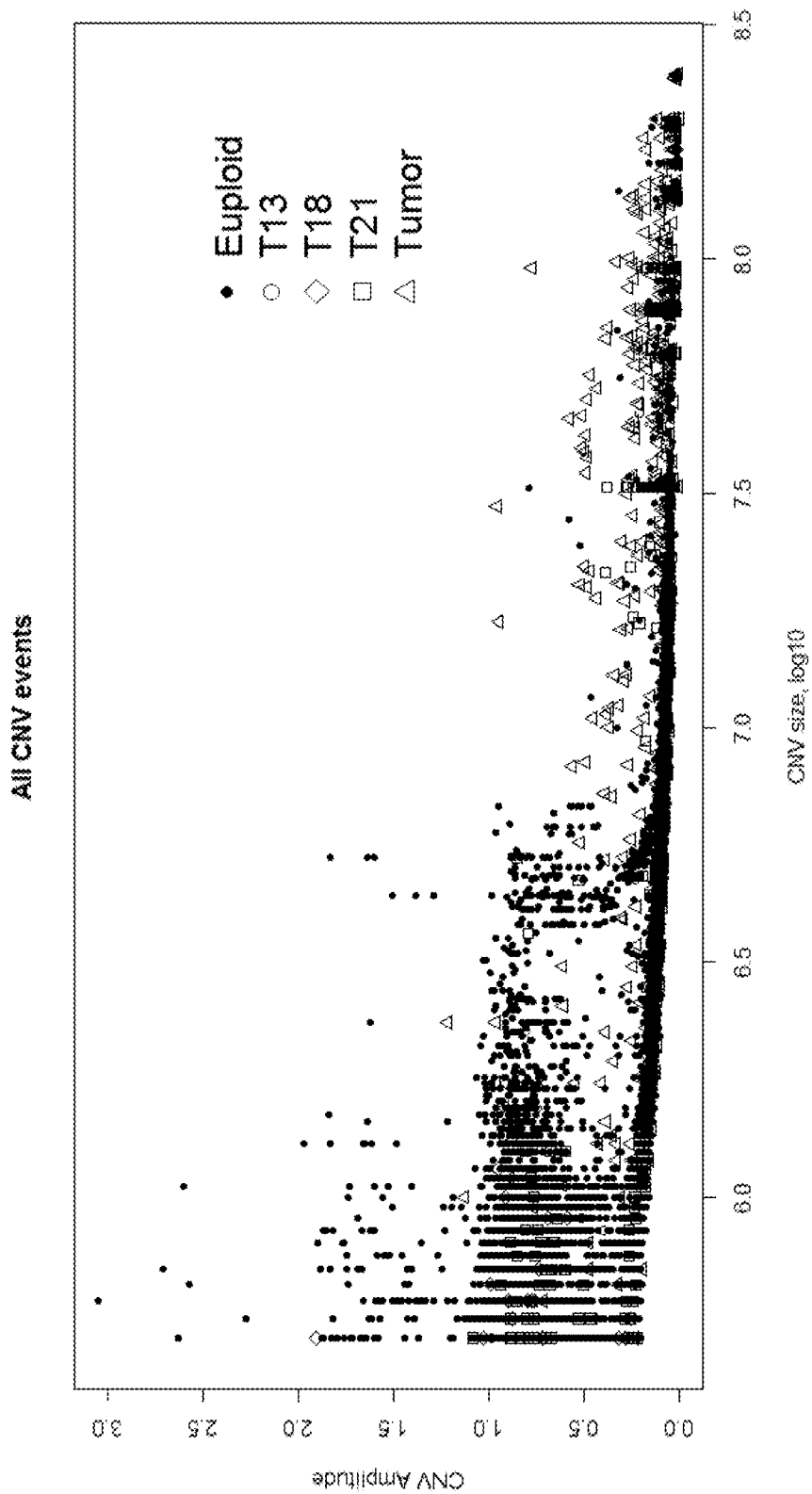
FIG. 2 shows copy number alteration (CNA) size compared against CNA elevation for samples.

FIG. 2 highlights observed copy number alterations (CNAs) according to amplitude and length observed in 27K CLIA samples processed through MaterniT21 tests. As observed in tumor-related samples, the genome profiles contained many CNAs with varying sizes and frequencies (see, triangle data points in FIG. 2).

The automated genomic instability classification process developed includes multiple steps, as described below. The process was constructed by assembling scripts written in R programming language. R build-in functions for LOESS and PCA were utilized and R package {DNAcopy} was used for CBS segmentation. The R package "Matrix" was utilized for filtering bins based on consistently presented CNAs in normal samples. The R package "igraph" was used for filtering based on selecting representative bins from clusters. The R package "irlba" was used for efficient singular value decomposition (SVD). The R function "mahalanobis" was used for mahalanobis distance calculations.

Example 1: Generating Genomic Portion CNA Quantifications

After sequencing sample nucleic acid, mapping sequencing reads to bins in a reference genome (i.e., consecutive 50 kilobase bins) and counting reads in each bin, counts in each bin were normalized to correct for bias, such as GC bias and other types of bias. An SPCA method was utilized to correct for bias, as described in Zhao et al., Clin. Chem. 61:4: 608-616 (2015).

Next, the bias-corrected bin counts were segmented using a circular binary segmentation (CBS) analyses for detection of CNA. The CBS segmentation provided segments, a z-score for each of the segments and a confidence value for each of the segments, as described in Zhao et al., Clin. Chem. 61:4: 608-616 (2015) and Lefkowitz et al., American Journal of Obstetrics & Gynecology 1.e1 (2016).

Example 2: Filtering Genomic Portions and Coupled CNA Quantifications

After segments were identified and quantified by CBS, systematic biases such as normalization artifacts and repetitive elements were filtered using two filtering processes, in which several bins, and counts associated with those bins, were removed. These filtering processes were applied to reduce noise and remove information redundancy.

Figure 3:
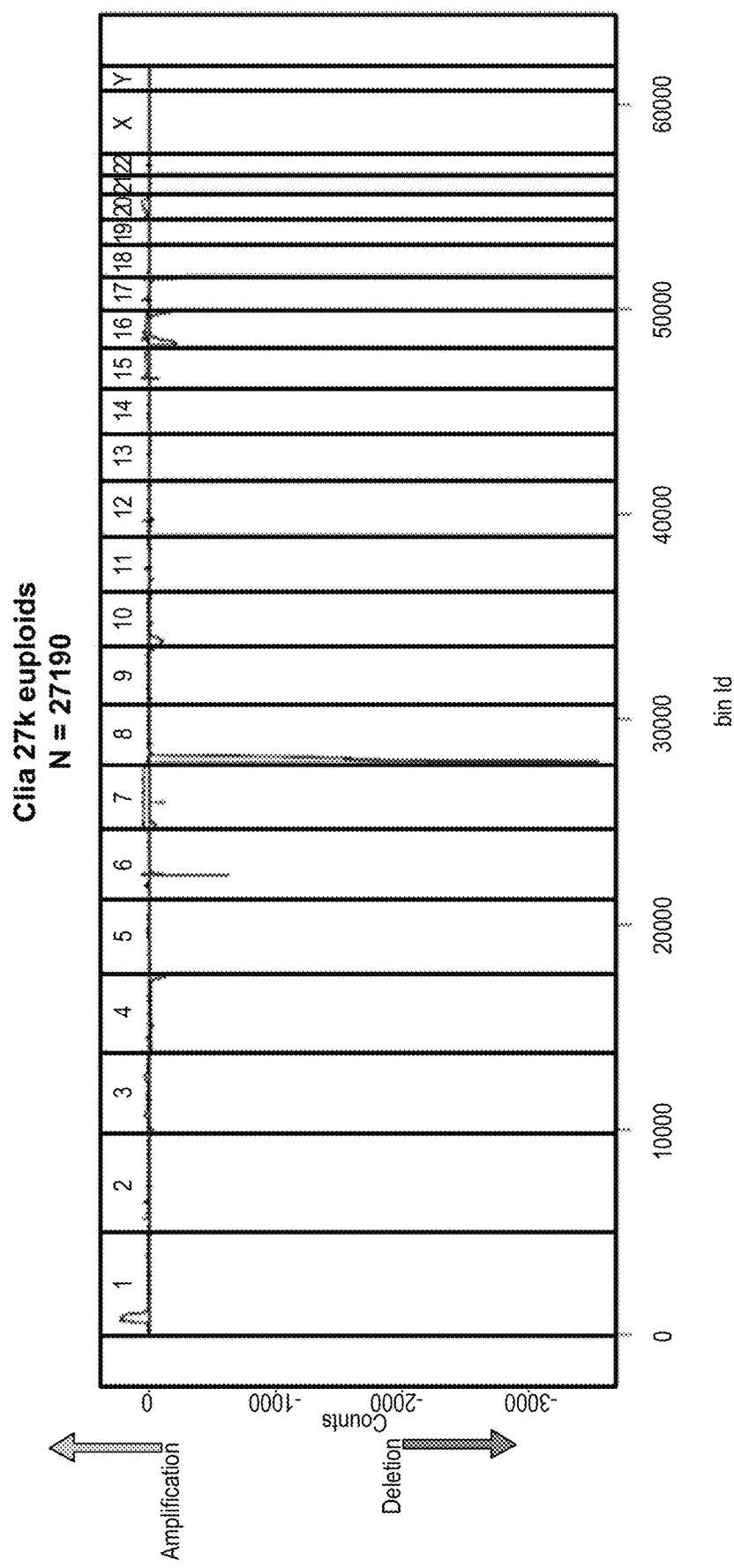
FIG. 3 shows a copy number alteration (CNA) baseline as observed from the 27K CLIA euploid samples.

In the first filtering process, certain bins identified as consistently influenced by bias were removed from segments, and the remaining bins were subjected to a second filtering process. In the first filtering process, bins frequently affected by CNA events in the 27K CLIA euploid samples were filtered (i.e., remove CNA baseline caused by normalization artifacts). As part of the first filtering process, CNAs detected by CBS were further filtered for high-quality events according to the following criteria (i) CNA |z-score| greater than 3, (ii) CNA confidence greater than 0.99, (iii) affected CNA size greater than or equal to 0.5 Mb, and (iv) CNA is located on any autosome except for chromosome 19. The total number of CNA events per bin (bin size equals to 50 kilobases) were counted among all 27K CLIA euploid samples (FIG. 3). In FIG. 3, positive counts represent the number of copy number amplification events while negative counts represent the number of copy number deletion events. It can be seen from FIG. 3 that some bins were frequently affected by copy number amplification or deletion events. Without being limited by theory, it appears these CNA hotspots were usually caused by alignment or normalization artifacts, or reflected the CNA events common to a normal population. Since the goal was to detect cancer samples and cancer-related CNA events, the CNA hotspots commonly observed in the euploid samples were filtered out prior to further analysis. About 10,200 bins from five (5) chromosomes were excluded after this first filtering processes.

Figure 4:
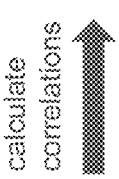
FIG. 4 shows pairwise bin correlations that were calculated based on a Circular Binary Segmentation (CBS) z-score matrix (left table), where rows represent samples with CNAs and columns represent bins.
Figure 5:
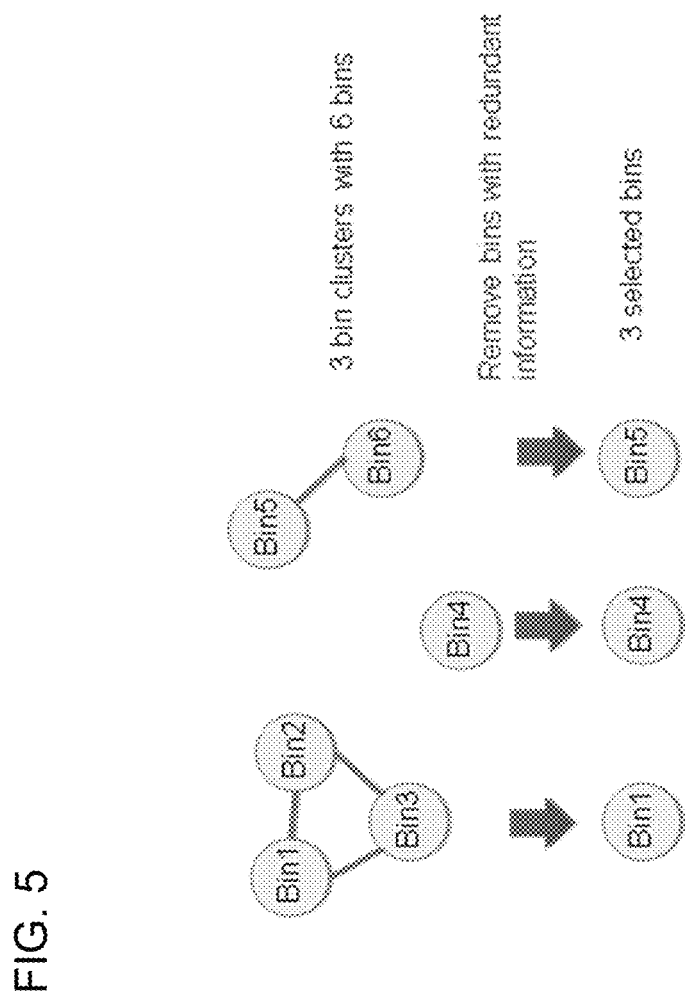
FIG. 5 illustrates filtering of chromosome bins (i.e., genomic portions) to reduce information redundancy. In this illustration, connected nodes represent bins that are almost perfectly correlated (correlation>0.999). Only one bin is selected from each correlation cluster (i.e., connected subgraph) to reduce feature dimension as well as information redundancy.

In the second filtering process, highly correlated bins were removed to reduce information redundancy. Pairwise bin correlations were calculated using CBS z-scores, where the z-score for each segment obtained from the CBS process was assigned to each corresponding bin within each segment (FIG. 4). In FIG. 4, the correlation between bin1 and bin2, for example, is the correlation of the two corresponding column vectors. Assuming bin1 and bin2 have exactly the same CNA events, the correlation is 1 (right table). Bins were clustered together if the correlation was higher than 0.999, and the bins in one correlation cluster thereby represented similar information. One bin was selected from each cluster to represent each correlation cluster (FIG. 5). This second filtering process greatly reduced the number of features in the analysis, prevented over-fitting, and still maintained a significant amount of the information contained in the original data set.

Figure 6:
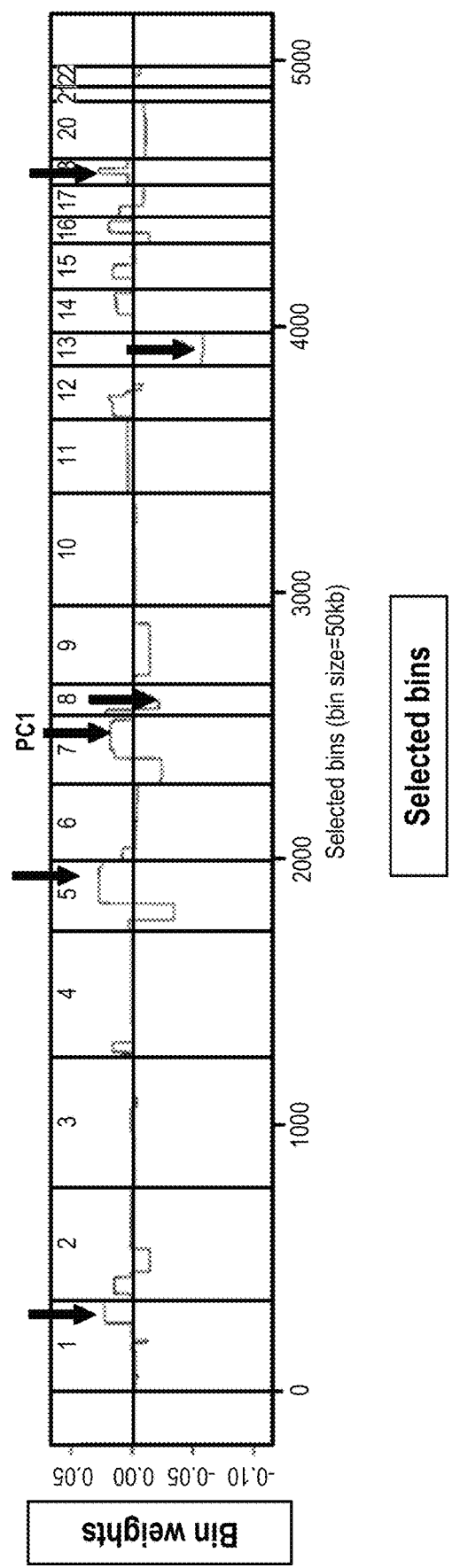
FIG. 6 illustrates that principal components (PCs) can be viewed as a weighted combination of different chromosome bins. For example, the first principal component (PC1) is enriched by bins from chr1, 5, 7, 8, 13 and chr18 as pinpointed by the arrows.
Figure 7:
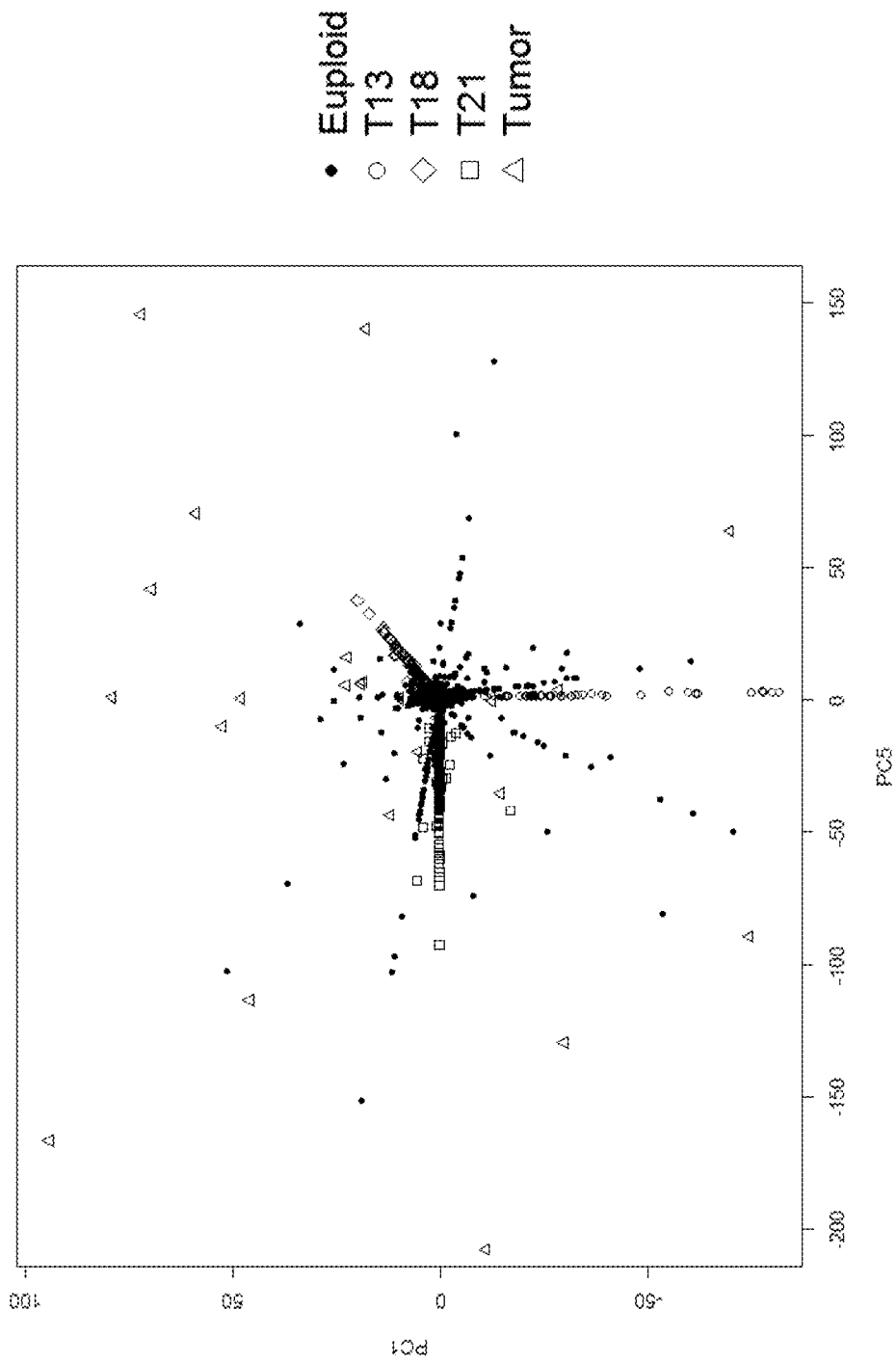
FIG. 7 shows the first and fifth PC projections of individual samples. Samples identified as having tumor-related CNA effects are represented by triangles. Samples identified as having trisomy 13, 18, and 21 are represented by open circles, diamonds and squares, respectively.

Example 3: Principal Component Transformation and Normalized Distance Determinations The reduced set of bins (i.e., bin counts) remaining after the two filtering processes then was reduced into fewer parameters, and a normalized distance was determined from the fewer parameters. Principal component analysis (PCA) was utilized to reduce the filtered bin counts into a principal component (PC) space. The principal components (PC) can be viewed as a weighted combination of different bins (FIG. 6) and thus contain highly-enriched information in a higher dimension space. As FIG. 7 illustrates, trisomy samples were grouped together along distinct directions and many tumor samples with anomalous CNA events demonstrated outlier behavior lying outside of the central cloud.

From the principal components, a Mahalanobis distance to the PC origin was calculated for each sample. The Mahalanobis distance normalized the distance along each PC by the corresponding variance. The top twenty (20) principal components were selected for the Mahalanobis distance calculation since they together captured more than 70% of the variability in the data set. The top 20 principal components were determined by ranking principal components in decreasing order according to their corresponding eigenvalues of matrix sigma, where sigma is a covariance matrix of x, and where x denotes the CBS z-score matrix in which samples are in rows and bins are in columns. A logarithmically-transformed Mahalanobis distance (i.e., log 10 transformed Mahalonobis distance) was determined for each sample.

Example 4: Classification

Figure 8:
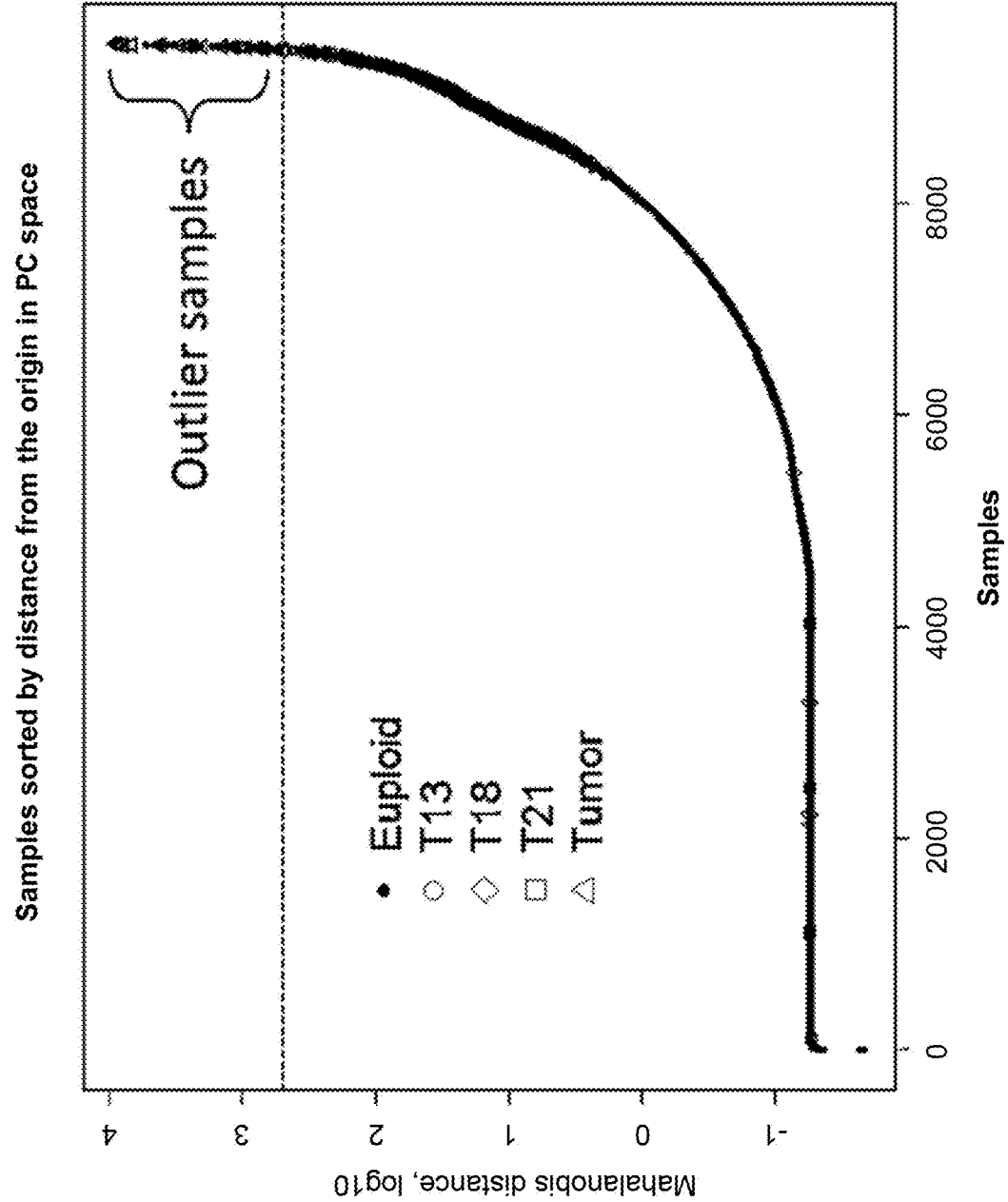
FIG. 8 shows Mahalanobis distances for a set of samples.

A cutoff Mahalanobis distance of about 500 (i.e., cutoff log 10 Mahalanobis distance between 2 and 3) was determined according to known tumor samples in a training set (FIG. 8). According to this assay, test samples having a Mahalanobis distance value above the cutoff value (e.g., Mahalanobis distance above 500) are classified as having genomic instability, and thereby are identified as cancer candidate samples. Test samples having a Mahalanobis distance value below the cutoff value (e.g., Mahalanobis distance below 500) are classified as not having genomic instability, and thereby are identified as not being cancer candidate samples. The classification is reported to a healthcare professional who ordered the test for which the classification method described here is performed. According to the test classification, a healthcare professional can determine whether further testing should be recommend to the subject. Among the 27K CLIA samples, there were 7 confirmed tumor samples. The PCA algorithm with outlier detection identified 55 outliers, including 5 out of 7 confirmed tumor samples. The 5 identified tumor samples have 5 to 24 CNA events and have extreme z-scores on chr13, chr18 and chr21.

Before this classification system was developed, cancer candidate samples were classified by visual inspection. A laboratory director typically can make this type of classification by visual inspection at a rate of about two (2) samples per minute (i.e., one sample every 30 seconds). The classification system here can make this type of classification at a rate of 100 samples per second when running on a standard desktop computer.

Example 5: Genomic Instability Number Determinations

Plasma samples were obtained at different time points for patients diagnosed with a cancer and on consistent immunotherapy regimens in the period of time shown in FIG. 19 to FIG. 25. Circulating cell-free DNA (ccf-DNA) was isolated from the plasma samples and subjected to genome-wide highly multiplexed sequencing. Sequencing reads included 27-36 base pair inserts and 8-15 base pair barcodes. Sequencing data were processed as described previously (Jensen et al., High-throughput massively parallel sequencing for fetal aneuploidy detection from maternal plasma, *PLoS ONE* 8(3):e57381 (2013); Lefkowitz et al., Clinical validation of a noninvasive prenatal test for genome-wide detection of fetal copy number variants, *Am J Obst Gyn* 215:227.e1-227.e16 (2016)). Briefly, raw base calls are converted to sequence read data and aligned to a human genomic reference. The genome reference was partitioned into 50 kilobase segments (i.e., bins) and the total sum of all sequencing reads mapped to each partition was calculated on a sample-specific basis. Alternative partitioning approaches known in the art can be used in place of non-overlapping 50 kilobase bins (e.g., sliding window bins of the same or different size; non-overlapping bins of different size). Bins identified as poor quality based on composition and historical performance behavior were excluded. For the remaining 50034 bins in autosomes, data were corrected for bin-level GC content and sequencing read coverage via GC-LOESS correction and were normalized by principal components analysis (PCA). The resulting normalized bin counts were non-negative real values scaled to a value of 1.0 for an average bin (i.e., a bin having an average normalized bin count).

Figure 17:
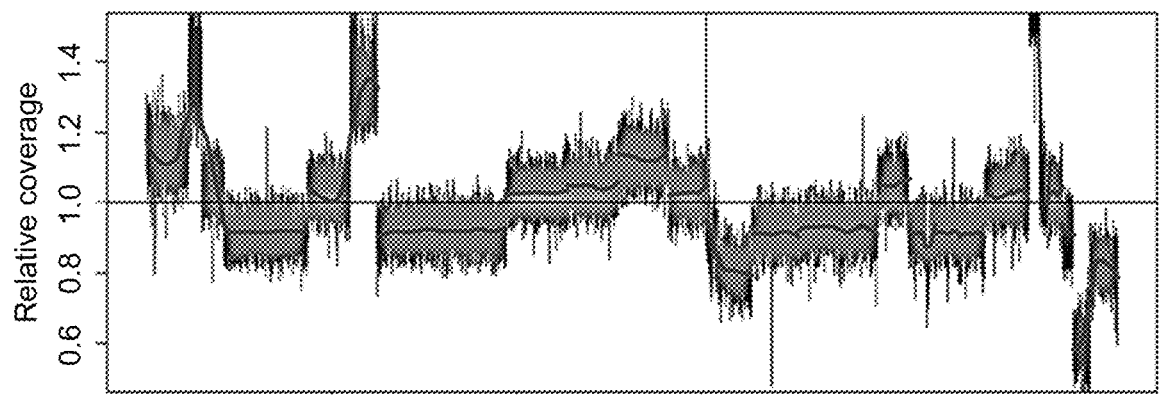
FIG. 17 shows a genome profile with chromosome specific shading for a subject having genomic instability.

Normalized bin counts were further modified using a secondary LOESS fit to correct for and smooth stochastic variation in the data. Each genomic bin was reassigned a smoothed value in which a value of 1.0 was expected for an average bin. FIG. 17 shows an example of such secondary LOESS adjusted bin counts for a sample in a genome profile with chromosome-specific shading. The secondary LOESS adjusted count was considered a corrected bin coverage assessment for each bin according to the equation below. A genomic instability number (GIN) was then calculated as a non-negative, continuously distributed, real number representing the sum of absolute deviation from expectation for all 50034 autosomal partitions. This calculation is summarized by the equation below.

$$GIN = \Sigma_{n=1}^{50034} |\text{Corrected bin coverage} - 1|$$

Figure 18:
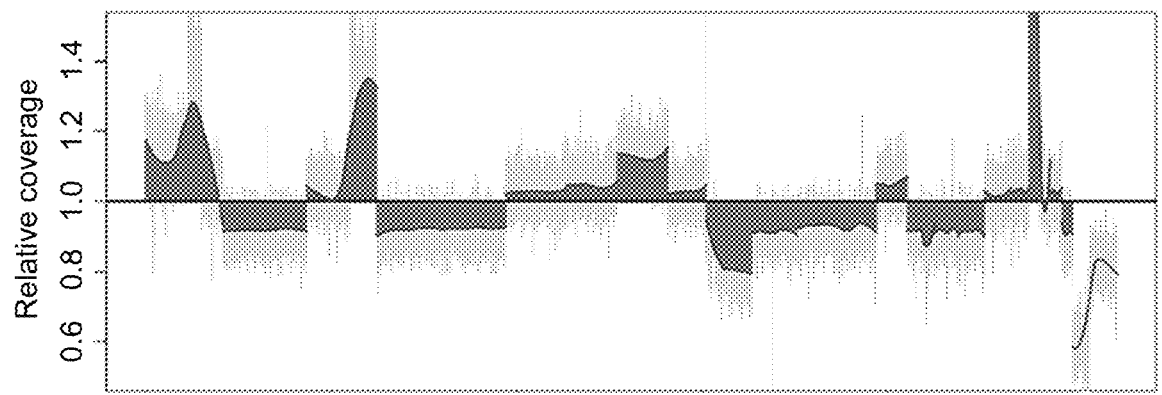
FIG. 18 shows a genome profile deviation from expectation highlighted illustrating how a genomic instability number can be generated.

FIG. 18 shows a genome profile with deviation from expectation highlighted. Increasing GIN values were expected to be indicative of increasing disruption to normal genomic profiles.

Copy number alteration (CNA) events were identified using the algorithm and approach described in Lefkowitz et al. 2016 cited above. Briefly, segments were identified by applying a segmentation process to the bin counts normalized by GC-LOESS and PCA, and a z-score was calculated for each segment identified as a CNA event by the segmentation process. A heuristic framework was applied to assign a confidence classifier to all identified copy number alteration events. Copy number alteration events with a z-score of greater than 7 and having a size greater than 10 megabases were classified as high confidence events. Copy number alteration events with a z-score greater than 7 and having a size between 4 and 10 megabases were classified as intermediate confidence events. All other CNA events were disregarded as low confidence events.

Figure 19:
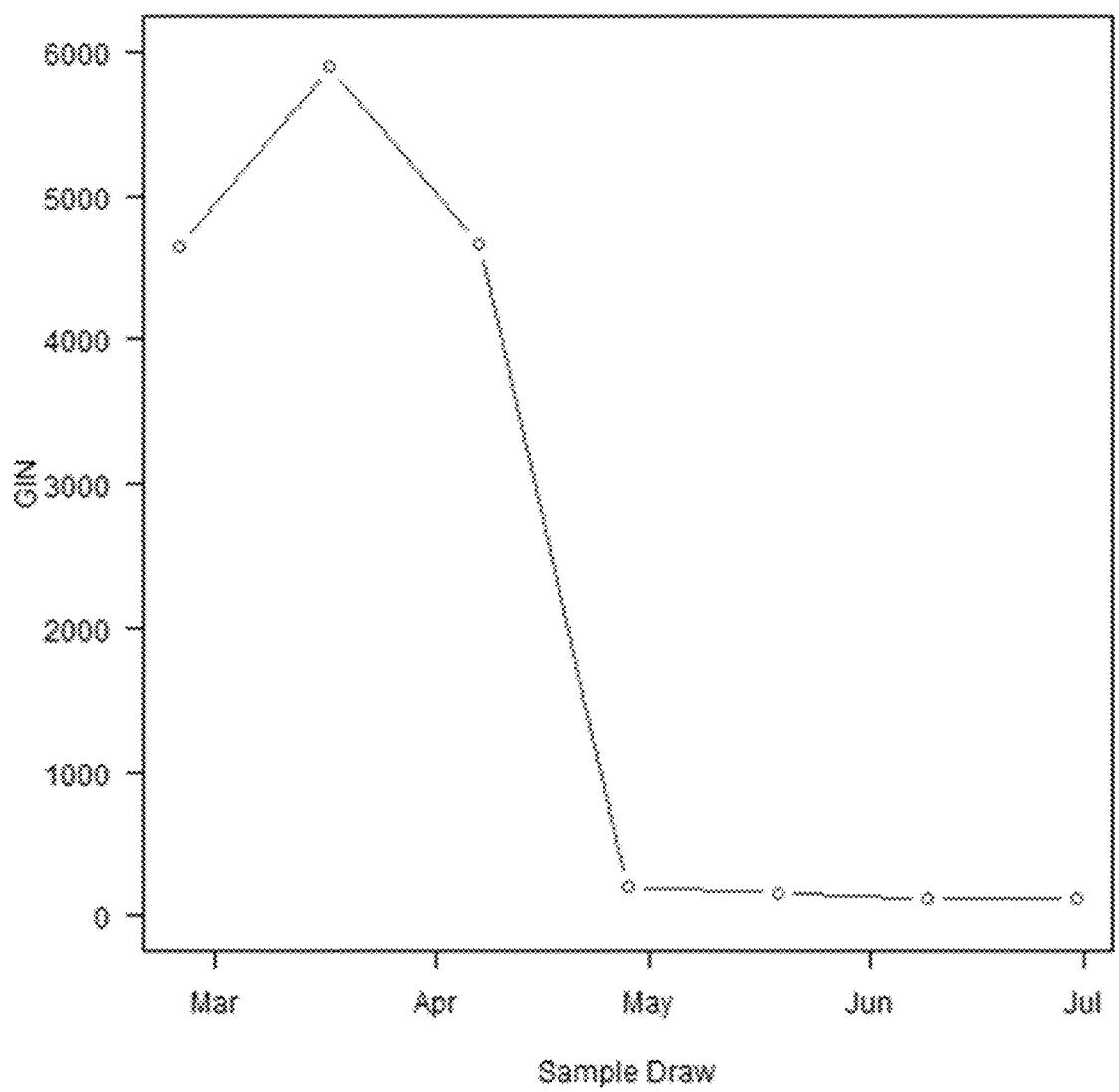
FIGS. 19 to 25 show genomic instability numbers generated for subjects diagnosed with a cell proliferative disorder undergoing treatment with therapeutics to treat their disease.
Figure 20:
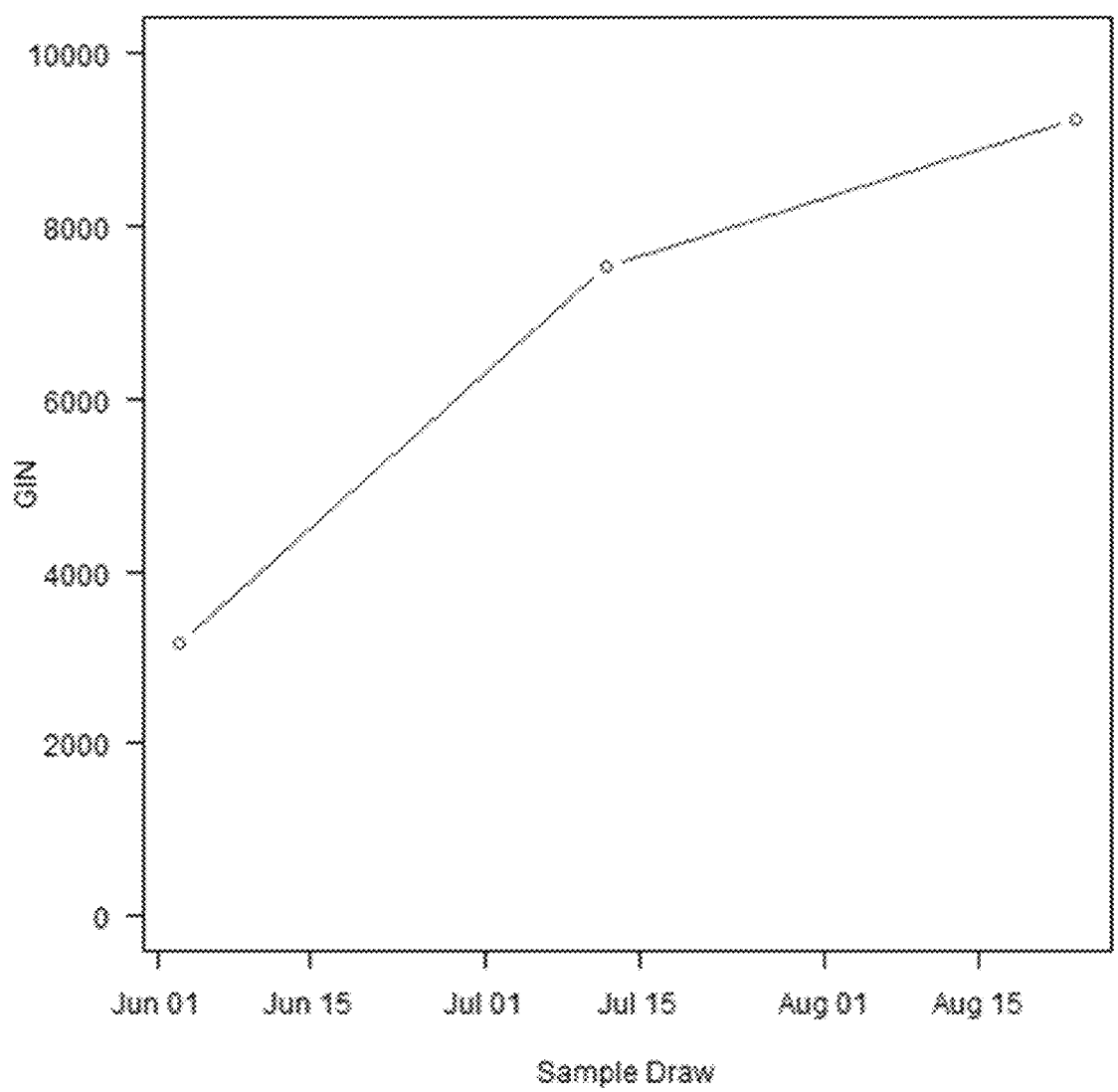
Figure 21:
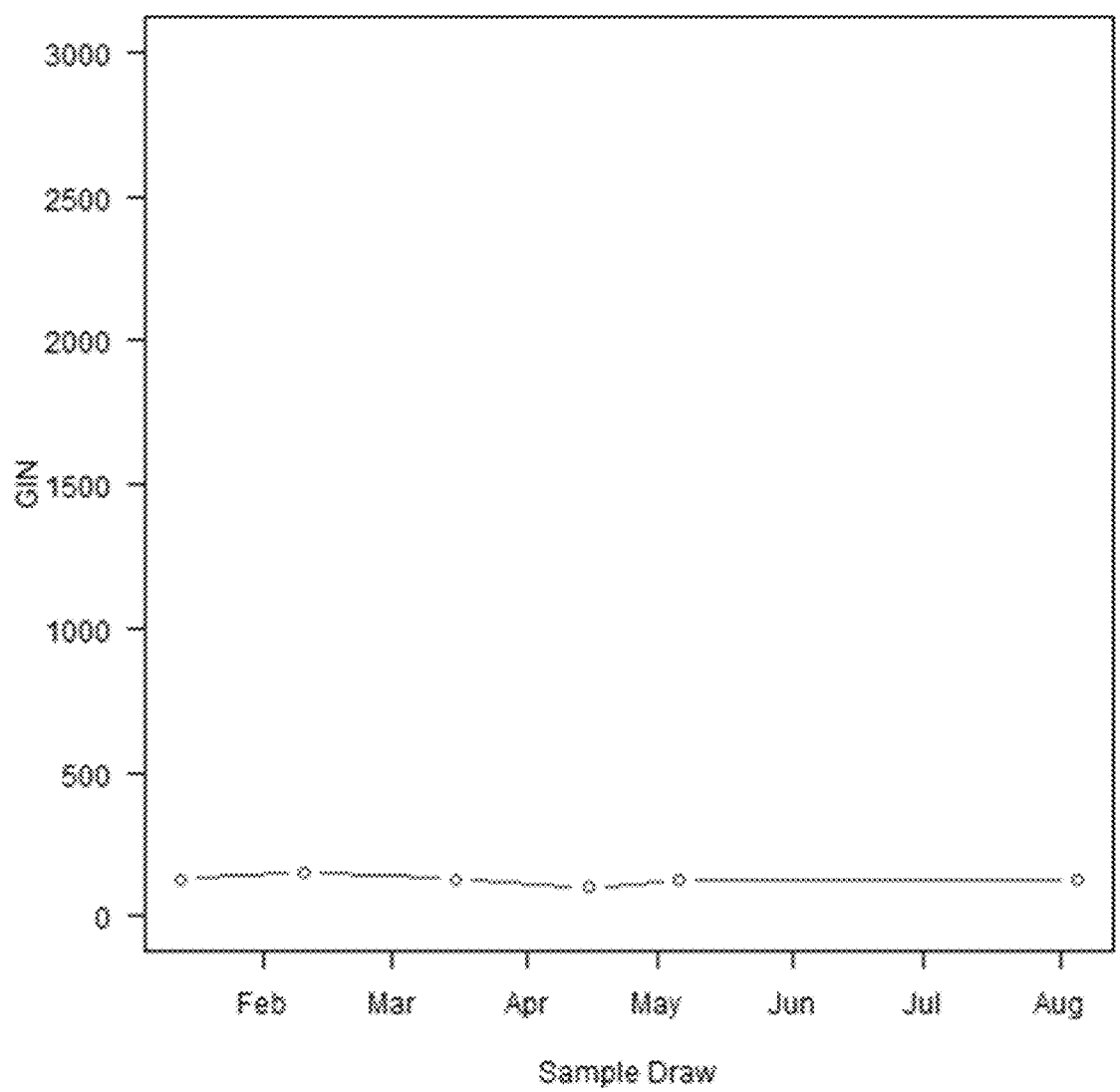
Figure 22:
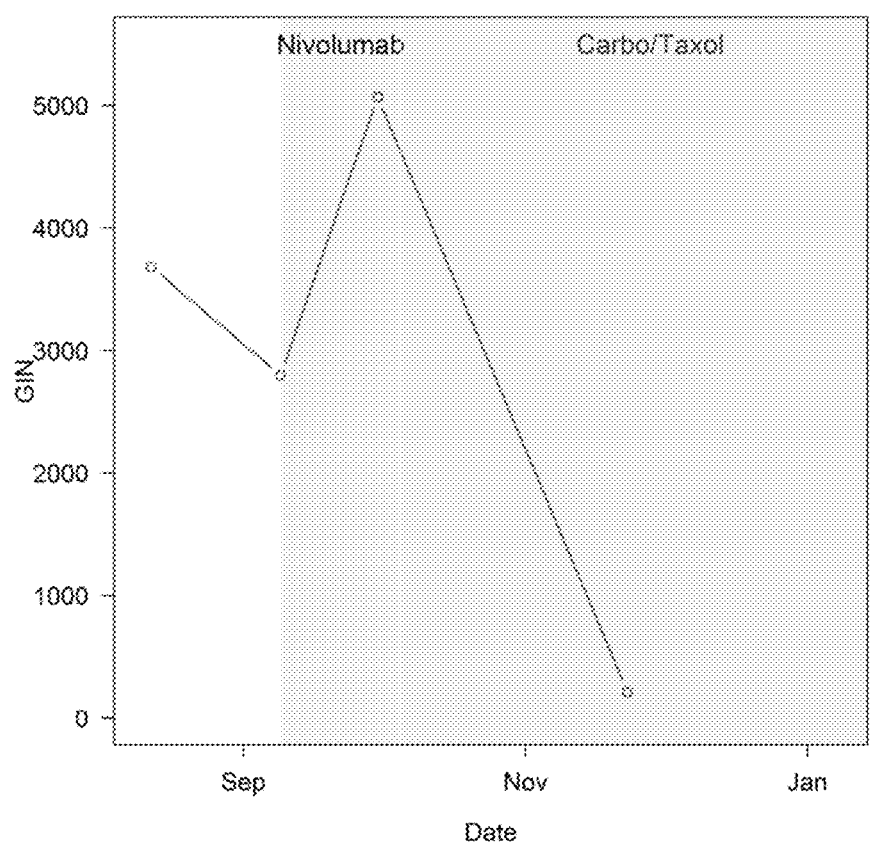

Example 6: Use of Genomic Instability Number as an Indicator for Clinical Effectiveness FIG. 19 to FIG. 25 show GIN values determined for samples obtained from cancer patients during immunotherapy. FIG. 19 shows a fluctuation in GIN values for a cutaneous squamous cell carcinoma (cSCC) patient treated with Pembrolizumab, indicating a response to therapy. FIG. 20 shows a fluctuation in GIN values for a colorectal adenocarcinoma patient treated with Nivolumab and radiation, consistent with disease progression. FIG. 21 shows low GIN values for a melanoma patient treated in which no CNAs were detected by sequencing ccf-DNA. FIG. 22 shows a fluctuation in GIN values for a patient having metastatic ovarian cancer involving liver treated with Nivolumab and radiation, consistent with progression, and then treated with Carboplatin and Taxol, consistent with a clinical response to the latter therapy.

Figure 23:
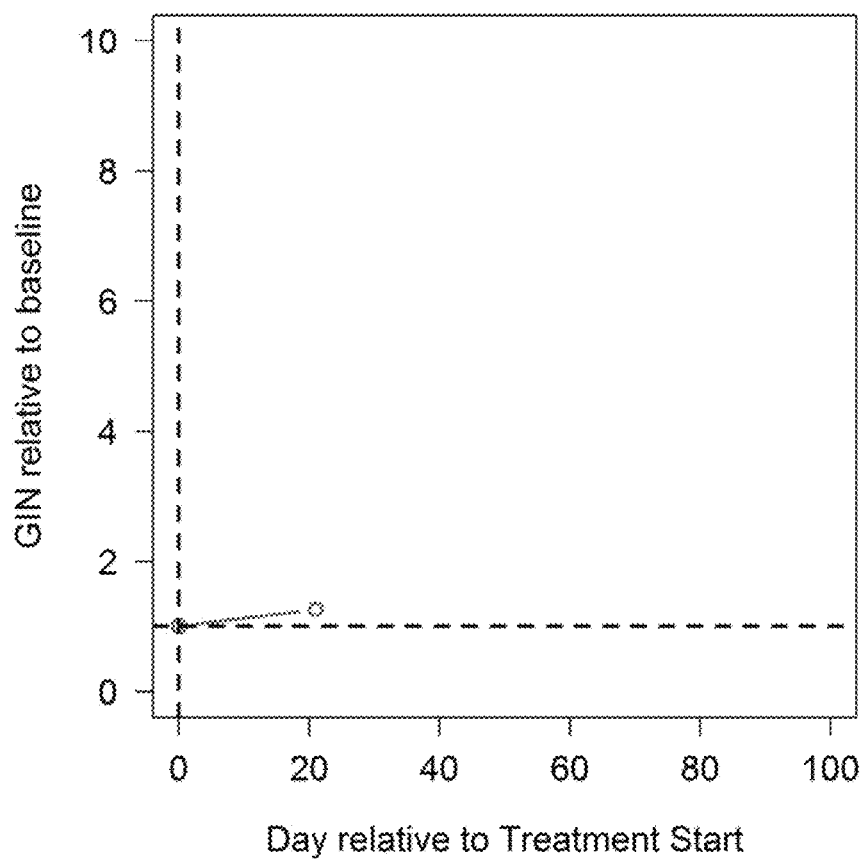
Figure 24:
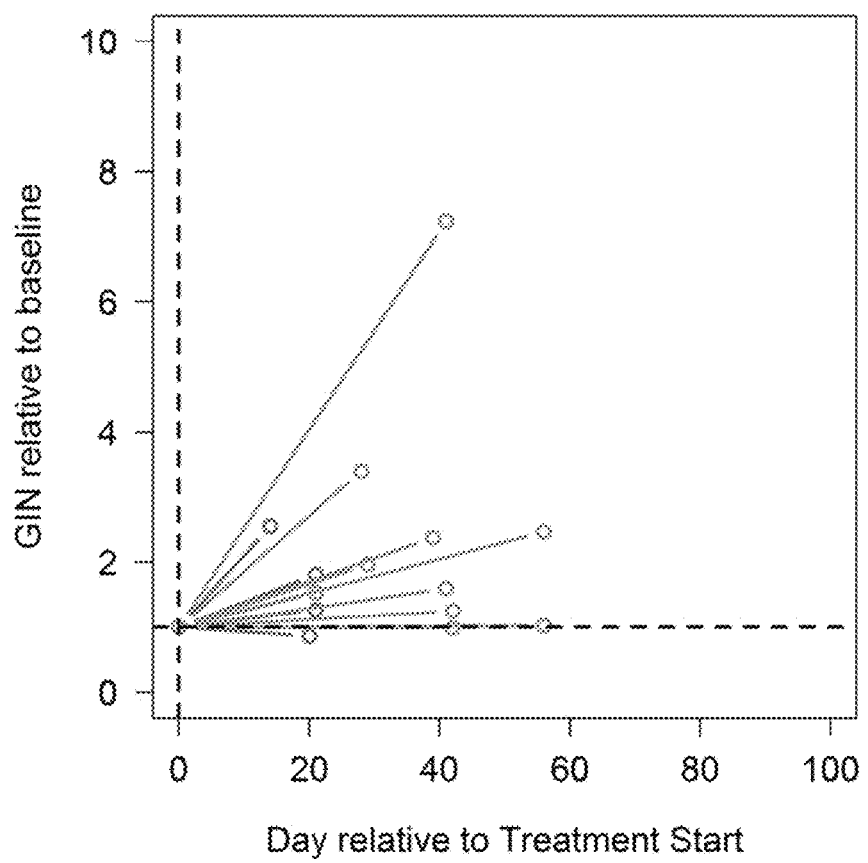
Figure 25:
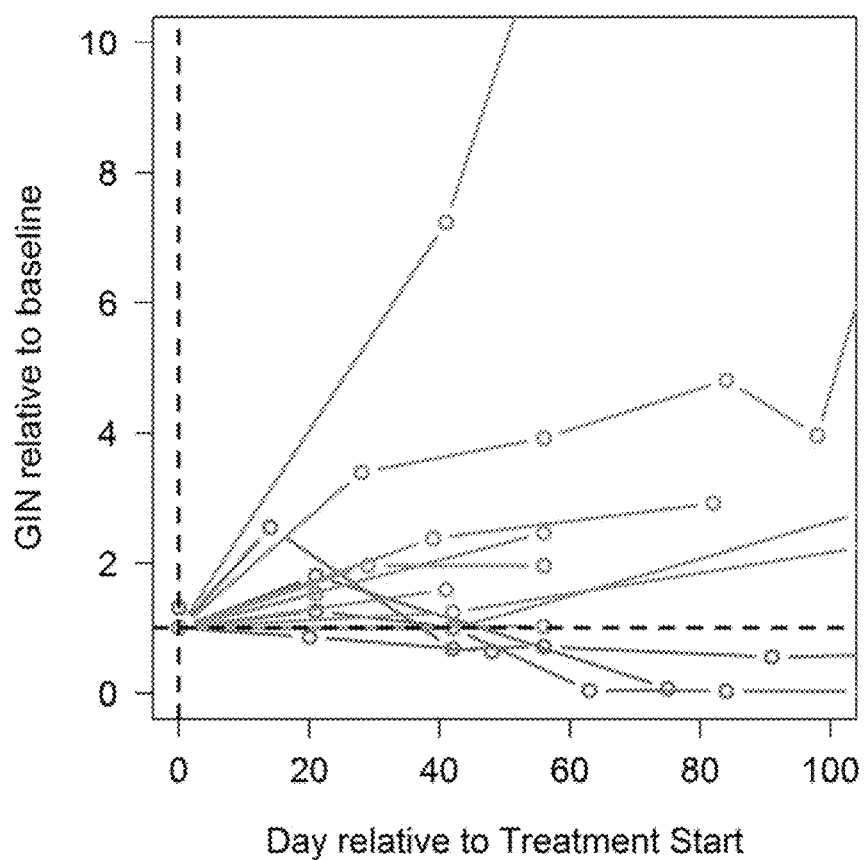

FIG. 23 to FIG. 25 show GIN values for fourteen (14) cancer patients at different times during immunotherapy. The patients in the group shared the following: detectable copy number variations, longitudinal sampling, and a change in disease status when receiving immunotherapy. Four (4) patients showed a partial response (PR) or a complete response (CR). Cancer in ten (10) patients progressed. Collection times were variable and the median time to first collection was 34 days. Thirteen (13) of the fourteen (14) patients showed an increase in GIN values at first collection after the start of treatment. Patients who responded reached an inflection point where their GIN values decreased, while patients who progressed did not. Patients who progressed showed an additional increase in the GIN value. GIN values from patients with a positive response often were below respective baseline values 6-8 weeks after the start of treatment.

LISTING OF EMBODIMENTS

Provided hereafter is a listing of non-limiting examples of embodiments of the technology.

A1. A method for determining presence or absence of genomic instability for a test subject, comprising:
  (a) providing a set of genomic portions each coupled to a copy number alteration quantification for a test sample, wherein:
    the genomic portions comprise portions of a reference genome to which sequence reads obtained for sample nucleic acid from the test subject have been mapped, and
    the copy number alteration quantification coupled to each genomic portion has been determined from a quantification of sequence reads mapped to the genomic portion;
  (b) filtering from the set of genomic portions genomic portions identified as having one or more features, thereby generating a set of filtered genomic portions not containing the genomic portions having the features; and
  (c) generating a classification for presence or absence of genomic instability for the test subject according to the copy number alteration quantifications coupled to the filtered genomic portions.

A1.1. The method of embodiment A1, wherein the filtering in (b) comprises filtering from the set of genomic portions:
  (i) a first subset of portions associated with copy number alterations consistently presented in a reference set of samples, and/or
  (ii) a second subset of portions other than representative portions derived from groups of portions identified by a clustering process applied to a reference set of samples,
  thereby generating a set of filtered genomic portions not containing the first subset of portions and/or the second subset of portions.
  (c) transforming the set of filtered genomic portions to a reduced set of parameters, which parameters in the reduced set are different than parameters of the set of filtered genomic portions; and
  (d) determining presence or absence of genomic instability for the test subject according to the reduced set of parameters.

A1.2. The method of embodiment A1 or A1.1, wherein generating the classification comprises transforming the set of filtered genomic portions to a reduced set of parameters, which parameters in the reduced set are different than parameters of the set of filtered genomic portions; and determining presence or absence of genomic instability for the test subject according to the reduced set of parameters.

A2. The method of embodiment A1.2, wherein the reduced set of parameters contains fewer dimensions than dimensions of the set of filtered genomic portions.

A3. The method of embodiment A1.2 or A1.3, wherein the transforming comprises performing a principal component transformation that yields principal component values for the test sample.

A4. The method of embodiment A3, wherein the principal component transformation is performed for the test sample with input principal component portion weights obtained from a set of training samples.

A5. The method of embodiment A4, wherein the input principal component portion weights from the set of training samples are obtained by a process comprising:
  (A) providing a set of genomic portions each coupled to a copy number alteration quantification for each training sample in the set of training samples, wherein:
    the genomic portions comprise portions of a reference genome to which sequence reads obtained for nucleic acid from each training sample have been mapped, and the copy number alteration quantification coupled to each genomic portion has been determined from a quantification of sequence reads mapped to the genomic portion;
  (B) filtering from the set of genomic portions a subset of portions having selected features, thereby generating a set of filtered genomic portions not containing the subset of portions having the selected features;
  (C) performing a principal component transformation on the set of filtered genomic portions that yields principal component portion weights from the training set of samples.

A6. The method of embodiment A5, comprising:
  generating a matrix comprising the training samples and the set of filtered genomic portions for the training samples; and
  performing the principal component transformation on the matrix.

A7. The method of any one of embodiments A4 to A6, wherein the set of training samples comprises or consists of samples classified as not having genomic instability.

A7.1. The method of any one of embodiments A4 to A7, wherein (C) yields a weight for each portion for each principal component.

A8. The method of any one of embodiments A5 to A7.1, wherein the filtering in (B) comprises filtering from the set of genomic portions for the training samples:
  (i) a first subset of portions associated with copy number alterations consistently presented in a reference set of samples, and/or
  (ii) a second subset of portions other than representative portions derived from groups of portions identified by a clustering process applied to a reference set of samples,
thereby generating a set of filtered genomic portions not containing the first subset of portions and/or the second subset of portions A9. The method of any one of embodiments A1.2 to A8, comprising determining a distance from a common principal component origin for the test sample.

A10. The method of embodiment A9, wherein the distance for the test sample is determined for a sub-group of the principal component values.

A11. The method of embodiment A10, wherein the sub-group of principal components consists of top-ranked principal component values.

A12. The method of embodiment A11, wherein the sub-group of principal component values consists of about 10 to about 30 principal component values.

A13. The method of any one of embodiments A9 to A12, wherein the distance is a Euclidian distance.

A14. The method of any one of embodiments A9 to A12, wherein the distance is a normalized distance, and determining the presence or absence of genomic instability is based on the normalized distance.

A15. The method of embodiment A14, wherein the normalized distance is generated according to variance of principal components for the set of training samples.

A16. The method of embodiment A14 or A15, wherein the normalized distance is a Mahalanobis distance.

A17. The method of any one of embodiments A14 to A16, wherein determining the presence or absence of genomic instability for the test subject comprises:
  determining the presence of genomic instability for the test subject according to a normalized distance above a cutoff value; and
  determining the absence of genomic instability for the test subject according to a normalized distance below the cutoff value.

A18. The method of any one of embodiments A1.1 to A17, wherein the clustering process comprises:
  (A) providing a set of genomic portions each coupled to a copy number alteration quantification for each sample in the reference set of samples, wherein:
    the genomic portions comprise portions of a reference genome to which sequence reads obtained for nucleic acid from each sample in the reference set of samples have been mapped, and
    the copy number alteration quantification coupled to each genomic portion has been determined from a quantification of sequence reads mapped to the genomic portion;
  (B) clustering genomic portions according to the copy number alteration quantification coupled to each of the portions for each sample in the reference set of samples, thereby generating groups of portions, and
  (C) selecting a representative genomic portion from each of the groups.

A19. The method of embodiment A18, comprising, prior to (A), filtering from the set of genomic portions a first subset of portions associated with copy number alterations consistently presented in the reference set of samples, thereby providing a set of filtered genomic portions for each sample in the reference set of samples, and performing (B) and (C) on the set of filtered genomic portions.

A20. The method of embodiment A18 or A19, wherein the clustering comprises:
  generating a matrix comprising the genomic portions and the samples in the reference set of samples;
  generating pair-wise correlation values from the matrix, wherein there is one correlation value for each pair of the portions; and
  clustering the portions into groups according to the correlation values.

A21. The method of embodiment A20, wherein each of the groups consists of portions that are correlated to one another according to the correlation value for each pair.

A22. The method of embodiment A21, wherein each of the groups consists of portions correlated with a correlation value of 0.999 or greater.

A23. The method of any one of embodiments A1 to A22, wherein (b) consists of filtering from the set of genomic portions:
  (i) a first subset of portions associated with copy number alterations consistently presented in a reference set of samples, or
  (ii) a second subset of portions other than representative portions derived from groups of portions identified by a clustering process applied to a reference set of samples,
thereby generating a set of filtered genomic portions not containing the first subset of portions or the second subset of portions.

A24. The method of any one of embodiments A1 to A22, wherein (b) consists of filtering from the set of genomic portions:
  (i) a first subset of portions associated with copy number alterations consistently presented in a reference set of samples, and
  (ii) a second subset of portions other than representative portions derived from groups of portions identified by a clustering process applied to a reference set of samples,
thereby generating a set of filtered genomic portions not containing the first subset of portions and the second subset of portions.

B1. A method for determining presence or absence of genomic instability for a test subject, comprising:
  (a) providing a set of genomic portions each coupled to a copy number alteration quantification for a test sample, wherein:
    the genomic portions comprise portions of a reference genome to which sequence reads obtained for sample nucleic acid from the test subject have been mapped, and
    the copy number alteration quantification coupled to each genomic portion has been determined from a quantification of sequence reads mapped to the genomic portion;
  (b) filtering from the set of genomic portions a subset of portions having selected features, thereby generating a set of filtered genomic portions not containing the subset of portions having the selected features;
  (c) transforming the set of filtered genomic portions to a reduced set of parameters, wherein the transforming comprises:
    performing a principal component transformation that yields principal component values for the test sample, and
    determining a distance from a common principal component origin for the test sample; and
  (d) determining presence or absence of genomic instability for the test subject according to the distance.

B2. The method of embodiment B1, wherein the filtering in (b) comprises filtering from the set of genomic portions a subset of portions associated with copy number alterations consistently presented in a reference set of samples, thereby generating the set of filtered genomic portions, wherein the set of filtered genomic portions does not contain the subset of portions.

B3. The method of embodiment B1, wherein the filtering in (b) comprises filtering a subset of portions other than representative portions derived from groups of portions identified by a clustering process applied to a reference set of samples, thereby generating the set of filtered genomic portions, wherein the set of filtered genomic portions does not contain the subset of portions.

B4. The method of any one of embodiments B1 to B3, wherein the filtering in (b) comprises filtering from the set of genomic portions:
  (i) a first subset of portions associated with copy number alterations consistently presented in a reference set of samples, and (ii) a second subset of portions other than representative portions derived from groups of portions identified by a clustering process applied to a reference set of samples, thereby generating the set of filtered genomic portions, wherein the set of filtered genomic portions does not contain the first subset of portions and the second subset of portions.

B5. The method of embodiment B3 or B4, wherein the clustering process comprises:
- (A) providing a set of genomic portions each coupled to a copy number alteration quantification for each sample in the reference set of samples, wherein:
  - the genomic portions comprise portions of a reference genome to which sequence reads obtained for nucleic acid from each sample in the reference set of samples have been mapped, and
  - the copy number alteration quantification coupled to each genomic portion has been determined from a quantification of sequence reads mapped to the genomic portion;
- (B) clustering genomic portions according to the copy number alteration quantification coupled to each of the portions for each sample in the reference set of samples, thereby generating groups of portions, and
- (C) selecting a representative genomic portion from each of the groups.

B6. The method of embodiment B5, comprising, prior to (A), filtering from the set of genomic portions a first subset of portions associated with copy number alterations consistently presented in the reference set of samples, thereby providing a set of filtered genomic portions for each sample in the reference set of samples, and performing (B) and (C) on the set of filtered genomic portions.

B7. The method of embodiment B5 or B6, wherein the clustering comprises:
- generating a matrix comprising the genomic portions and the samples in the reference set of samples;
- generating pair-wise correlation values from the matrix, wherein there is one correlation value for each pair of the portions; and
- clustering the portions into groups according to the correlation values.

B7.1. The method of embodiment B7, wherein each of the groups consists of portions that are correlated to one another according to the correlation value for each pair.

B7.2. The method of embodiment B7.1, wherein each of the groups consists of portions correlated with a correlation value of 0.999 or greater.

B8. The method of any one of embodiments B1 to B7.2, wherein the principal component transformation is performed for the test sample with input principal component portion weights obtained from a set of training samples.

B9. The method of embodiment B8, wherein the input principal components from the set of training samples are obtained by a process comprising:
- (A) providing a set of genomic portions each coupled to a copy number alteration quantification for each training sample in the set of training samples, wherein:
  - the genomic portions comprise portions of a reference genome to which sequence reads obtained for nucleic acid from each training sample have been mapped, and the copy number alteration quantification coupled to each genomic portion has been determined from a quantification of sequence reads mapped to the genomic portion;
- (B) filtering from the set of genomic portions a subset of portions having selected features, thereby generating a set of filtered genomic portions not containing the subset of portions having the selected features;
- (C) performing a principal component transformation on the set of filtered genomic portions that yields principal component portion weights from the training set of samples.

B10. The method of embodiment B9, comprising:
- generating a matrix comprising the training samples and the set of filtered genomic portions for the training samples; and
- performing the principal component transformation on the matrix.

B11. The method of any one of embodiments B8 to B10, wherein the set of training samples comprises or consists of samples classified as not having genomic instability.

B12. The method of any one of embodiments B8 to B10, wherein (C) yields a weight for each portion for each principal component.

B13. The method of any one of embodiments B9 to B12, wherein the filtering in (B) comprises filtering from the set of genomic portions for the training samples:
- (i) a first subset of portions associated with copy number alterations consistently presented in a reference set of samples, and/or
- (ii) a second subset of portions other than representative portions derived from groups of portions identified by a clustering process applied to a reference set of samples, thereby generating a set of filtered genomic portions not containing the first subset of portions and/or the second subset of portions B14. The method of any one of embodiments B1 to B13, wherein the distance for the test sample is determined for a sub-group of the principal component values.

B15. The method of embodiment B14, wherein the sub-group of principal components consists of top-ranked principal component values.

B16. The method of embodiment B15, wherein the sub-group of principal component values consists of about 10 to about 30 principal component values.

B17. The method of any one of embodiments B1 to B16, wherein the distance is a Euclidian distance.

B18. The method of any one of embodiments B1 to B16, wherein the distance is a normalized distance, and determining presence or absence of genomic instability for the test subject according to the normalized distance.

B19. The method of embodiment B18, wherein the normalized distance is generated according to variance of principal components for the set of training samples.

B19. The method of embodiment B18 or B19, wherein the normalized distance is a Mahalanobis distance.

B20. The method of any one of embodiments B1 to B19, wherein the determining in (d) comprises:
- determining the presence of genomic instability for the test subject according to a distance or normalized distance above a cutoff value; and
- determining the absence of genomic instability for the test subject according to a distance or normalized distance below the cutoff value.

C1. A method for determining presence or absence of genomic instability for a test subject, comprising:
- (a) providing a set of genomic portions each coupled to a copy number alteration quantification for a test sample, wherein:

the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion;

(b) filtering from the set of genomic portions:
  (i) a first subset of portions associated with copy number alterations consistently presented in a reference set of samples, and
  (ii) a second subset of portions other than representative portions derived from groups of portions identified by a clustering process applied to a reference set of samples,
  thereby generating a set of filtered genomic portions not containing the first subset of portions and the second subset of portions;

(c) transforming the set of filtered genomic portions to a reduced set of parameters, wherein the transforming comprises:
  performing a principal component transformation that yields principal components for the test sample, and
  determining a distance from a common principal component origin for the test sample; and (d) determining presence or absence of genomic instability for the test subject according to the distance.

C2. The method of embodiment C1, wherein the clustering process comprises:
  (A) providing a set of genomic portions each coupled to a copy number alteration quantification for each sample in the reference set of samples, wherein:
    the genomic portions comprise portions of a reference genome to which sequence reads obtained for nucleic acid from each sample in the reference set of samples have been mapped, and
    the copy number alteration quantification coupled to each genomic portion has been determined from a quantification of sequence reads mapped to the genomic portion;
  (B) clustering genomic portions according to the copy number alteration quantification coupled to each of the portions for each sample in the reference set of samples, thereby generating groups of portions, and
  (C) selecting a representative genomic portion from each of the groups.

C3. The method of embodiment C2, comprising, prior to (A), filtering from the set of genomic portions a first subset of portions associated with copy number alterations consistently presented in the reference set of samples, thereby providing a set of filtered genomic portions for each sample in the reference set of samples, and performing (B) and (C) on the set of filtered genomic portions.

C4. The method of embodiment C2 or C3, wherein the clustering comprises:
  generating a matrix comprising the genomic portions and the samples in the reference set of samples;
  generating pair-wise correlation values from the matrix, wherein there is one correlation value for each pair of the portions; and
  clustering the portions into groups according to the correlation values.

C4.1. The method of embodiment C4, wherein each of the groups consists of portions that are correlated to one another according to the correlation value for each pair.

C4.2. The method of embodiment C4.1, wherein each of the groups consists of portions correlated with a correlation value of 0.999 or greater.

C5. The method of any one of embodiments C1 to C4.2, wherein the principal component transformation is performed for the test sample with input principal component portion weights obtained from a set of training samples.

C6. The method of embodiment C5, wherein the input principal components from the set of training samples are obtained by a process comprising:
  (A) providing a set of genomic portions each coupled to a copy number alteration quantification for each training sample in the set of training samples, wherein:
    the genomic portions comprise portions of a reference genome to which sequence reads obtained for nucleic acid from each training sample have been mapped, and
    the copy number alteration quantification coupled to each genomic portion has been determined from a quantification of sequence reads mapped to the genomic portion;
  (B) filtering from the set of genomic portions a subset of portions having selected features, thereby generating a set of filtered genomic portions not containing the subset of portions having the selected features;
  (C) performing a principal component transformation on the set of filtered genomic portions that yields principal component portion weights from the training set of samples.

C7. The method of embodiment C6, comprising:
  generating a matrix comprising the training samples and the set of filtered genomic portions for the training samples; and
  performing the principal component transformation on the matrix.

C8. The method of any one of embodiments C5 to C7, wherein the set of training samples comprises or consists of samples classified as not having genomic instability.

C9. The method of any one of embodiments C5 to C8, wherein (C) yields a weight for each portion for each principal component.

C10. The method of any one of embodiments C6 to C9, wherein the filtering in (B) comprises filtering from the set of genomic portions for the training samples:
  (i) a first subset of portions associated with copy number alterations consistently presented in a reference set of samples, and/or
  (ii) a second subset of portions other than representative portions derived from groups of portions identified by a clustering process applied to a reference set of samples,
thereby generating a set of filtered genomic portions not containing the first subset of portions and/or the second subset of portions C11. The method of any one of embodiments C1 to 010, wherein the distance for the test sample is determined for a sub-group of the principal component values.

C12. The method of embodiment C11, wherein the sub-group of principal components consists of top-ranked principal component values.

C13. The method of embodiment C12, wherein the sub-group of principal component values consists of about 10 to about 30 principal component values.

C14. The method of any one of embodiments C1 to C13, wherein the distance is a Euclidian distance.

C15. The method of any one of embodiments C1 to C13, wherein the distance is a normalized distance and determining the presence or absence of genomic instability is according to the normalized distance.

C16. The method of embodiment C15, wherein the normalized distance is generated according to variance of principal components for the set of training samples.

C17. The method of embodiment C15 or C16, wherein the normalized distance is a Mahalanobis distance.

C18. The method of any one of embodiments C1 to C17, wherein the determining in (d) comprises:
 determining the presence of genomic instability for the test subject according to a normalized distance above a cutoff value; and
 determining the absence of genomic instability for the test subject according to a normalized distance below the cutoff value.

C19. The method of any one of embodiments C1 to C18, wherein (b) consists of filtering from the set of genomic portions:
 (i) a first subset of portions associated with copy number alterations consistently presented in a reference set of samples, or
 (ii) a second subset of portions other than representative portions derived from groups of portions identified by a clustering process applied to a reference set of samples,
thereby generating a set of filtered genomic portions not containing the first subset of portions or the second subset of portions.

C20. The method of any one of embodiments C1 to C19, wherein (b) consists of filtering from the set of genomic portions:
 (i) a first subset of portions associated with copy number alterations consistently presented in a reference set of samples, and
 (ii) a second subset of portions other than representative portions derived from groups of portions identified by a clustering process applied to a reference set of samples,
thereby generating a set of filtered genomic portions not containing the first subset of portions and the second subset of portions.

D1. The method of any one of embodiments A1 to C20, wherein the reference set of samples comprises samples classified as not having genomic instability.

D2. The method of any one of embodiments A1 to C20, wherein the reference set of samples consists of samples classified as not having genomic instability.

D3. The method of any one of embodiments A1 to D2, wherein the test subject is a female.

D4. The method of embodiment D3, wherein the female is a human female.

D5. The method of embodiment D3 or D4, wherein the female is a pregnant female.

D6. The method of any one of embodiments A1 to D2, wherein the test subject is a male.

D6.1. The method of embodiment D6, wherein the test subject is a human male.

D7. The method of any one of embodiments A1 to D6.1, wherein the genomic portions are of fixed length.

D8. The method of embodiment D7, wherein the genomic portions are of equal length.

D9. The method of embodiment D8, wherein the genomic portions are about 50 kilobases in length.

D10. The method of any one of embodiments A1 to D9, wherein at least two of the genomic portions are of unequal length.

D11. The method of any one of embodiments A1 to D10, wherein the genomic portions do not overlap.

D12. The method of embodiment D11, wherein the 3' ends of the genomic portions abut the 5' ends of adjacent genomic portions.

D13. The method of any one of embodiments A1 to D10, wherein at least two of the genomic portions overlap.

D14. The method of any one of embodiments A1 to D13, comprising generating the sequence reads from the nucleic acid sample by a sequencing process.

D15. The method of embodiment D14, wherein the sequence process is a genome-wide sequencing process.

D16. The method of embodiment D14 or D15, wherein the sequencing process comprises sequencing by synthesis.

D17. The method of any one of embodiments A1 to D16, comprising obtaining the sequence reads and mapping the sequence reads to the genomic portions, thereby providing sequence reads mapped to the genomic portions.

D18. The method of any one of embodiments A1 to D17, comprising obtaining sequence reads mapped to the genomic portions and quantifying the sequence reads mapped to each of the genomic portions, thereby generating a quantification of the sequence reads mapped to the genomic portions.

D19. The method of embodiment D19, wherein the quantification of the sequence reads mapped to each of the genomic portions is a count or read density.

D20. The method of any one of embodiments A1 to D19, comprising normalizing the quantification of sequence reads mapped to the genomic portions, thereby generating a normalized quantification of sequence reads mapped to the genomic portions.

D21. The method of embodiment D20, wherein the normalizing comprises a guanine-cytosine GC normalization process.

D22. The method of embodiment D21, wherein the normalization process comprises LOESS, GCRM or combination thereof.

D23. The method of any one of embodiments D20 to D22, wherein the normalizing comprises adjusting the quantification of sequence reads, or the normalized quantification of sequence reads, mapped to the genomic portions by principal component portion weights derived from a training set of samples, thereby generating an adjusted quantification of sequence reads mapped to the genomic portions.

D24. The method of any one of embodiments D20 to D23, wherein certain genomic portions are filtered prior to, or after, the normalizing or the adjusting.

D25. The method of embodiment D24, wherein the filtering is based on mappability, repeat masking or combination thereof.

D26. The method of embodiment D25, wherein filtering is based on variation of the quantification of sequence reads mapped to genomic portions across multiple reference samples, consistently no reads mapped to genomic portions across multiple reference samples, or combination thereof.

D27. The method of any one of embodiments A1 to D26, wherein the copy number alteration quantification coupled to each of the genomic portions for the test sample is obtained by a process comprising a segmentation process.

D28. The method of embodiment D27, wherein the segmentation process comprises a circular binary segmentation (CBS) process.

D29. The method of embodiment D27 or D28, wherein the copy number alteration quantification is z-score.

D30. The method of embodiment D29, wherein the z-score for each genomic portion is the z-score for a segment identified by the segmentation process that includes the genomic portion.

D31. The method of embodiment D29 or D30, wherein the z-score is determined according to:

$$z\text{-score} = (S_{scr} - S_{mcr})/\text{MAD}$$

wherein:
the $S_{scr}$ is a test sample count representation of a segment, wherein the $S_{scr}$ is the total normalized counts in the segment divided by the total normalized autosome counts for the test sample;
the $S_{mcr}$ is a median count representation for the segment generated for a reference set of samples; and
the MAD is a median absolute deviation determined for the count representation of the segment for the reference set of samples.

D32. The method of any one of embodiments A1 to D31, wherein (b), (c) and/or (d) are performed by a computer.

D33. The method of embodiment D32, wherein (b), (c) and/or (d) are performed by one or more processors in the computer.

D34. The method of embodiment D32 or D33, wherein (b), (c) and/or (d) are performed according to instructions stored in memory and implemented by the computer.

D35. The method of any one of embodiments A1 to D34, wherein the determining in (d):
generates a determination for each test sample in a group of test samples, and
is performed at a rate of about 80 determinations or more per second.

D36. The method of any one of embodiments A1 to D35, wherein the sample nucleic acid from the test subject is circulating cell free nucleic acid.

D37. The method of embodiment D36, wherein the circulating cell free nucleic acid is from blood plasma or blood serum from the test subject.

E1. A system, comprising one or more processors and memory, which memory comprises instructions for the one or more processors to perform a method of any one of embodiments A1 to D37.

E2. A machine, comprising one or more processors and memory, which memory comprises instructions for the one or more processors to perform a method of any one of embodiments A1 to D37.

E3. A computer program product in a computer readable storage medium, the product comprising: programmed instructions for the computer to perform a method of any one of embodiments A1 to D37.

F1. A method for generating a genomic instability classification for sample nucleic acid from a subject, comprising:
(a) providing a set of genomic portions of a reference genome to which sequence reads obtained for sample nucleic acid from a subject have been mapped, and for which the sequence reads mapped to the genomic portions have been quantified;
(b) adjusting the quantified sequence reads for each of the genomic portions by an adjustment process that reduces experimental bias, thereby providing an adjusted quantification of sequence reads for each of the genomic portions; and
(c) generating a genomic instability classification for the test sample according to the adjusted quantification of sequence reads for the genomic portions.

G1. The method of embodiment F1, wherein the generating in (c) comprises modifying the adjusted quantification of sequence reads according to a baseline adjusted quantification of sequence reads for each of the genomic portions, thereby providing a modified product for each of the genomic portions.

G1.1. The method of embodiment F1 of G1, wherein the generating in (c) comprises subtracting a baseline adjusted quantification of sequence reads from the adjusted quantification of sequence reads for each of the genomic portions, thereby providing a subtraction product for each of the genomic portions.

G2. The method of embodiment G1 or G1.1, comprising determining the absolute value of the modified product or the subtraction product for each of the genomic portions.

G3. The method of any one of embodiments G1, G1.1 or G2, wherein the baseline is (i) an average adjusted quantification of sequence reads for the genomic portions, (ii) a centered value of the adjusted quantification of sequence reads for the genomic portions, (iii) or a representative value of the adjusted quantification of sequence reads for the genomic portions.

G4. The method of embodiment G3, wherein the average is a mean, median or mode of the adjusted quantification of sequence reads for the genomic portions.

G5. The method of embodiment G3 or G4, comprising scaling the adjusted quantification of sequence reads for the genomic portions to the average, centered value or representative value.

G6. The method of any one of embodiments G1 to G5, wherein the generating in (c) comprises summing the modified products, absolute values of the modified products, subtraction products or absolute values of the subtraction products for the genomic portions, thereby providing a genomic instability number.

G7. The method of embodiment G6, wherein the genomic instability classification is based on the genomic instability number.

G8. The method of embodiment G6, wherein the genomic instability classification is the genomic instability number.

G9. The method of any one of embodiments G6 to G8, wherein the magnitude of the genomic instability number is based on the number of copy number variations in the sample nucleic acid, the magnitude of the copy number variations in the sample nucleic acid, and the portion of nucleic acid in the sample nucleic acid bearing each of the copy number variations.

G10. The method of any one of embodiments G6 to G9, wherein:
presence of genomic instability is classified according to a genomic instability number above a cutoff value; and
absence of genomic instability is classified according to a genomic instability number below the cutoff value.

H1. The method of embodiment F1, comprising identifying the presence of a copy number alteration.

H2. The method of embodiment H1, wherein the copy number alteration is identified according to a copy number alteration quantification coupled to the genomic portions.

H3. The method of embodiment H1 or H2, wherein the copy number alteration is identified according to a copy number alteration quantification obtained for genomic portions by a process comprising a segmentation process.

H4. The method of embodiment H3, wherein the segmentation process comprises a circular binary segmentation (CBS) process.

H5. The method of any one of embodiments H2 to H4, wherein the copy number alteration quantification is a z-score.

H6. The method of embodiment H5, wherein the z-score for each genomic portion is the z-score for a segment identified by the segmentation process that includes the genomic portion.

H7. The method of embodiment H5 or H6, wherein the z-score is determined according to:

$$z\text{-score} = (S_{scr} - S_{mcr})/\text{MAD}$$

wherein:
- the $S_{scr}$ is a test sample count representation of a segment, wherein the $S_{scr}$ is the total normalized counts in the segment divided by the total normalized autosome counts for the test sample;
- the $S_{mcr}$ is a median count representation for the segment generated for a reference set of samples; and
- the MAD is a median absolute deviation determined for the count representation of the segment for the reference set of samples.

H8. The method of any one of embodiments H1 to H7, comprising:
(i) filtering from the set of genomic portions a subset of portions having selected features, thereby generating a set of filtered genomic portions not containing the subset of portions having the selected features;
(ii) transforming the set of filtered genomic portions to a reduced set of parameters, wherein the transforming comprises:
  performing a principal component transformation that yields principal component values for the sample nucleic acid, and
  determining a distance from a common principal component origin for the sample nucleic acid; and
(iii) classifying genomic instability for the subject according to the distance.

H9. The method of embodiment H8, wherein the filtering in (i) comprises filtering from the set of genomic portions a subset of portions associated with copy number alterations consistently presented in a reference set of samples, thereby generating the set of filtered genomic portions, wherein the set of filtered genomic portions does not contain the subset of portions.

H10. The method of embodiment H8, wherein the filtering in (i) comprises filtering a subset of portions other than representative portions derived from groups of portions identified by a clustering process applied to a reference set of samples, thereby generating the set of filtered genomic portions, wherein the set of filtered genomic portions does not contain the subset of portions.

H11. The method of any one of embodiments H8 to H10, wherein the filtering in (i) comprises filtering from the set of genomic portions:
(i) a first subset of portions associated with copy number alterations consistently presented in a reference set of samples, and
(ii) a second subset of portions other than representative portions derived from groups of portions identified by a clustering process applied to a reference set of samples,
thereby generating the set of filtered genomic portions, wherein the set of filtered genomic portions does not contain the first subset of portions and the second subset of portions.

H12. The method of embodiment H10 or H11, wherein the clustering process comprises:
(A) providing a set of genomic portions each coupled to a copy number alteration quantification for each sample in the reference set of samples, wherein:
  the genomic portions comprise portions of a reference genome to which sequence reads obtained for nucleic acid from each sample in the reference set of samples have been mapped, and
  the copy number alteration quantification coupled to each genomic portion has been determined from a quantification of sequence reads mapped to the genomic portion;
(B) clustering genomic portions according to the copy number alteration quantification coupled to each of the portions for each sample in the reference set of samples, thereby generating groups of portions, and
(C) selecting a representative genomic portion from each of the groups.

H13. The method of embodiment H12, comprising, prior to (A), filtering from the set of genomic portions a first subset of portions associated with copy number alterations consistently presented in the reference set of samples, thereby providing a set of filtered genomic portions for each sample in the reference set of samples, and performing (B) and (C) on the set of filtered genomic portions.

H14. The method of embodiment H12 or H13, wherein the clustering comprises:
generating a matrix comprising the genomic portions and the samples in the reference set of samples;
generating pair-wise correlation values from the matrix, wherein there is one correlation value for each pair of the portions; and
clustering the portions into groups according to the correlation values.

H15. The method of embodiment H14, wherein each of the groups consists of portions that are correlated to one another according to the correlation value for each pair.

H16. The method of embodiment H15, wherein each of the groups consists of portions correlated with a correlation value of 0.999 or greater.

H17. The method of any one of embodiments H8 to H17, wherein the principal component transformation is performed for the test sample with input principal component portion weights obtained from a set of training samples.

H18. The method of embodiment H17, wherein the input principal components from the set of training samples are obtained by a process comprising:
(A) providing a set of genomic portions each coupled to a copy number alteration quantification for each training sample in the set of training samples, wherein:
  the genomic portions comprise portions of a reference genome to which sequence reads obtained for nucleic acid from each training sample have been mapped, and
  the copy number alteration quantification coupled to each genomic portion has been determined from a quantification of sequence reads mapped to the genomic portion;
(B) filtering from the set of genomic portions a subset of portions having selected features, thereby generating a set of filtered genomic portions not containing the subset of portions having the selected features;
(C) performing a principal component transformation on the set of filtered genomic portions that yields principal component portion weights from the training set of samples.

H19. The method of embodiment H18, comprising:
generating a matrix comprising the training samples and the set of filtered genomic portions for the training samples; and
performing the principal component transformation on the matrix.

H20. The method of any one of embodiments H17 to H19, wherein the set of training samples comprises or consists of samples classified as not having genomic instability.

H21. The method of any one of embodiments H17 to H19, wherein (C) yields a weight for each portion for each principal component.

H22. The method of any one of embodiments H17 to H21, wherein the filtering in (B) comprises filtering from the set of genomic portions for the training samples:
  (1) a first subset of portions associated with copy number alterations consistently presented in a reference set of samples, and/or
  (2) a second subset of portions other than representative portions derived from groups of portions identified by a clustering process applied to a reference set of samples,
thereby generating a set of filtered genomic portions not containing the first subset of portions and/or the second subset of portions H23. The method of any one of embodiments H8 to H22, wherein the distance for the test sample is determined for a sub-group of the principal component values.

H24. The method of embodiment H23, wherein the sub-group of principal components consists of top-ranked principal component values.

H25. The method of embodiment H24, wherein the sub-group of principal component values consists of about 10 to about 30 principal component values.

H26. The method of any one of embodiments H8 to H25, wherein the distance is a Euclidian distance.

H27. The method of any one of embodiments H8 to H25, wherein the distance is a normalized distance, and determining presence or absence of genomic instability for the test subject according to the normalized distance.

H28. The method of embodiment H27, wherein the normalized distance is generated according to variance of principal components for the set of training samples.

H29. The method of embodiment H18 or H19, wherein the normalized distance is a Mahalanobis distance.

H30. The method of any one of embodiments H27 to H29, wherein the genomic instability classification in (iii) is based on the normalized distance.

H31. The method of any one of embodiments H8 to H30, wherein the genomic instability classification in (iii) is the distance or the normalized distance.

H32. The method of any one of embodiments H8 to H31, wherein:
  presence of genomic instability is classified in (iii) for the subject according to a distance or normalized distance above a cutoff value; and
  absence of genomic instability is classified in (iii) for the subject according to a distance or normalized distance below the cutoff value.

H33. The method of any one of embodiments H8 to H32, wherein a classification is generated for each sample in a group of samples at a rate of about 80 classifications or more per second.

J1. The method of any one of embodiments F1 to H33, wherein:
  the subject is diagnosed with a cell proliferative condition; and
  the subject is selected for a treatment of the cell proliferative condition according to the genomic instability classification.

J2. The method of any one of embodiments F1 to J1, wherein:
  the subject is diagnosed with a cell proliferative condition;
  the subject is undergoing a treatment of the cell proliferative condition; and
  the subject is identified as a responder or non-responder to the treatment according to the genomic instability classification.

J3. The method of embodiment J2, wherein the genomic instability classification is generated for the subject at two or more time points during the treatment.

J4. The method of embodiment J2 or J3, wherein:
  the subject is identified as a responder to the treatment if after a time point of about 6 weeks to about 8 weeks of treatment the genomic instability classification is less than a threshold value; or
  the subject is identified as a non-responder to the treatment if after the time point of treatment the genomic instability classification is greater than the threshold value.

J5. The method of embodiment J5, wherein the genomic instability classification is a genomic instability number or is based on a genomic instability number.

J6. The method of any one of embodiments J1 to J5, wherein the cell proliferative disorder is a cancer.

J7. The method of embodiment J6, wherein the cancer is a solid tumor cancer.

J8. The method of any one of embodiments J1 to J8, wherein the treatment comprises administering an immunotherapeutic.

J9. The method of embodiment J8, wherein the immunotherapeutic comprises a checkpoint inhibitor.

K1. The method of any one of embodiments F1 to J9, wherein the subject is a female.

K2. The method of embodiment K1, wherein the female is a human female.

K3. The method of any one of embodiments F1 to J9, wherein the subject is a male.

K4. The method of embodiment K3, wherein the subject is a human male.

K5. The method of any one of embodiments K1 to K4, wherein the subject has been diagnosed with a cell proliferative disorder.

K6. The method of any one of embodiments K1 to K5, wherein the genomic portions are of fixed length.

K7. The method of embodiment K6, wherein the genomic portions are of equal length.

K8. The method of embodiment K7, wherein the genomic portions are about 50 kilobases in length.

K9. The method of any one of embodiments K1 to K8, wherein at least two of the genomic portions are of unequal length.

K10. The method of any one of embodiments K1 to K9, wherein the genomic portions do not overlap.

K11. The method of embodiment K10, wherein the 3' ends of the genomic portions abut the 5' ends of adjacent genomic portions.

K12. The method of any one of embodiments K1 to K9, wherein at least two of the genomic portions overlap.

K13. The method of any one of embodiments K1 to K12, comprising generating the sequence reads from the nucleic acid sample by a sequencing process.

K14. The method of embodiment K13, wherein the sequence process is a genome-wide sequencing process.

K15. The method of embodiment K13 or K14, wherein the sequencing process comprises sequencing by synthesis.

K16. The method of any one of embodiments K1 to K15, comprising obtaining the sequence reads and mapping the sequence reads to the genomic portions, thereby providing sequence reads mapped to the genomic portions.

K17. The method of any one of embodiments K1 to K16, comprising obtaining sequence reads mapped to the genomic portions and quantifying the sequence reads mapped to each of the genomic portions, thereby generating a quantification of the sequence reads mapped to the genomic portions.

K18. The method of embodiment K17, wherein the quantification of the sequence reads mapped to each of the genomic portions is a count or read density.

K19. The method of any one of embodiments K1 to K18, wherein the adjusting in (b) comprises normalizing the quantification of sequence reads by a guanine-cytosine (GC) normalizing process that generates a GC normalized quantification of sequence reads for each of the genomic portions, whereby the adjusted quantification of sequence reads in (b) is the GC normalized quantification of sequence reads.

K20. The method of embodiment K19, wherein the GC normalizing process comprises LOESS, GCRM or combination thereof.

K21. The method of embodiment K19 or K20, wherein the adjusting in (b) comprises normalizing the quantification of sequence reads, or the GC normalized quantification of sequence reads, mapped to the genomic portions by principal component (PC) portion weights derived from a training set of samples, thereby generating a PC normalized quantification of sequence reads mapped to the genomic portions, whereby the adjusted quantification of sequence reads in (b) is the PC normalized quantification of sequence reads.

K22. The method of embodiment K21, wherein the set of training samples are samples classified as having an absence of genomic instability.

K23. The method of any one of embodiments K19 to K22, wherein the adjusting in (b) comprises normalizing the GC normalized quantification of sequence reads or the PC normalized quantification of sequence reads by a secondary GC normalizing process, thereby generating a smoothed quantification of sequence reads, whereby the adjusted quantification of sequence reads in (b) is the smoothed quantification of sequence reads.

K24. The method of embodiment K23, wherein the secondary GC normalizing process comprises LOESS, GCRM or combination thereof.

K25. The method of any one of embodiments K1 to K24, wherein certain genomic portions are filtered prior to, or after, the normalizing and/or the adjusting.

K26. The method of embodiment K25, wherein the set of genomic portions provided in (a) are filtered.

K27. The method of embodiment K25 or K26, wherein the filtering is based on mappability, repeat masking or combination thereof.

K28. The method of embodiment K27, wherein filtering is based on variation of the quantification of sequence reads mapped to genomic portions across multiple reference samples, consistently no reads mapped to genomic portions across multiple reference samples, or combination thereof.

K29. The method of any one of embodiments K26 to K28, wherein about 75% to about 95% of all genomic portions in autosomes remain after filtering.

K30. The method of embodiment K29, wherein about 80% to about 90% of all genomic portions in autosomes remain after filtering.

K31. The method of any one of embodiments K26 to K28, wherein about 75% to about 95% of all genomic portions in the genome remain after filtering.

K32. The method of embodiment K31, wherein about 80% to about 90% of all genomic portions in the genome remain after filtering.

K33. The method of any one of embodiments F1 to K32, wherein (b) and/or (c) are performed by a computer.

K34. The method of embodiment K33, wherein (b) and/or (c) are performed by one or more processors in the computer.

K35. The method of embodiment K33 or K34, wherein (b) and/or (c) are performed according to instructions stored in memory and implemented by the computer.

K36. The method of any one of embodiments F1 to K35, wherein the sample nucleic acid from the subject is circulating cell free nucleic acid.

K37. The method of embodiment K36, wherein the circulating cell free nucleic acid is from blood plasma or blood serum from the subject.

L1. A system, comprising one or more processors and memory, which memory comprises programmed instructions for the one or more processors to perform a method of any one of embodiments F1 to K37.

L2. A machine, comprising one or more processors and memory, which memory comprises programmed instructions for the one or more processors to perform a method of any one of embodiments F1 to K37.

L3. A computer program product in a computer readable storage medium, the product comprising: programmed instructions for a computer to perform a method of any one of embodiments F1 to K37.

Additional non-limiting embodiments of the technology are provided below.

M1. A method of determining presence or absence of genomic instability for a test subject, comprising:
  providing a set of genomic portions each coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion;
  filtering, by a computing device, from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and/or the second subset of portions; and
  determining, by the computing device, presence or absence of genomic instability for the test subject according to the copy number alteration quantifications coupled to the filtered genomic portions.

M2. The method of embodiment M1, wherein the determining comprises:
transforming the set of filtered genomic portions to a reduced set of parameters, wherein the transforming comprises:

performing a principal component transformation of the set of filtered genomic portions that yields principal components for the test sample, and determining a distance between the principal components of the test sample from a common principal component origin.

M3. The method of embodiment M2, wherein the distance is generated using more than three principal component values.

M4. The method of any of embodiments M2 to M3, wherein the determining yields a weight for each portion for each principal component.

M5. The method of any of embodiments M2 to M4, wherein the distance is a Euclidian distance.

M6. The method of any of embodiments M2 tp M6, wherein the distance is a normalized distance generated according to variance of principal components for a set of training samples, and determining the presence or absence of genomic instability is based on the normalized distance.

M7. The method of any of embodiments M1 to M6, wherein the normalized distance is a Mahalanobis distance.

M8. The method of any one of embodiments M2 to M7, wherein the determining comprises:
determining the presence of genomic instability for the test subject according to a normalized distance above a cutoff value; and
determining the absence of genomic instability for the test subject according to a normalized distance below the cutoff value.

M9. The method of any one of embodiments M2 to M8, wherein the reduced set of parameters contains fewer dimensions than dimensions of the set of filtered genomic portions.

M10. The method of any one of embodiments M2 to M9, wherein the transforming yields a weight for each portion for each principal component.

M11. The method of any one of embodiments M2 to M10, wherein the principal component transformation of the set of filtered genomic portions is performed for the test sample with the input principal component portion weights from a set of training samples.

M12. The method of embodiment M12, wherein the set of training samples comprises or consists of samples classified as not having genomic instability.

M13. The method of any one of embodiments M11 to M12, wherein the input principal component portion weights from the set of training samples are obtained by a process comprising:
providing a set of genomic portions each coupled to a copy number alteration quantification for each training sample in the set of training samples, wherein the genomic portions comprise portions of a reference genome to which sequence reads obtained for nucleic acid from each training sample have been mapped, and the copy number alteration quantification coupled to each genomic portion has been determined from a quantification of sequence reads mapped to the genomic portion;
filtering, by the computing device, from the set of genomic portions a subset of portions having selected features, thereby generating a set of filtered genomic portions not containing the subset of portions having the selected features: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and/or the second subset of portions; and
performing, by the computing device, a principal component transformation on the set of filtered genomic portions that yields principal component portion weights from the training set of samples.

M14. The method of any of embodiments M1 to M13, wherein the clustering process comprises: providing a set of genomic portions each coupled to a copy number alteration quantification for each sample in the reference set of samples, wherein:
the genomic portions comprise portions of a reference genome to which sequence reads obtained for nucleic acid from each sample in the reference set of samples have been mapped, and
the copy number alteration quantification coupled to each genomic portion has been determined from a quantification of sequence reads mapped to the genomic portion; clustering, by the computing device, genomic portions according to the copy number alteration quantification coupled to each of the portions for each sample in the reference set of sample, thereby generating groups of portions; and
selecting, by the computing device, a representative genomic portion from each of the groups.

M15. The method of any of embodiments M1 to M14, wherein the clustering comprises:
generating, by the computing device, a matrix comprising the genomic portions and the samples in the reference set of samples;
generating, by the computing device, pair-wise correlation values from the matrix, wherein there is one correlation value for each pair of the portions; and
clustering, by the computing device, the portions into groups according to the correlation values.

M16. The method of embodiment M15, wherein each of the groups consists of portions that are correlated to one another according to the correlation value for each pair.

M17. The method of any one of embodiments M15 to M16, wherein each of the groups consists of portions correlated with a correlation value of 0.999 or greater.

M18. The method of any one of embodiments M2 to M17, wherein the distance for the test sample is determined for a sub-group of the principal component values that consists of top-ranked about 10 to about 30 principal component values.

M19. The method of any one of embodiments M1 to M18, wherein the copy number alteration quantification coupled to each of the genomic portions for the test sample is obtained by a process comprising a segmentation process.

M20. The method of embodiment M19, wherein the segmentation process comprises a circular binary segmentation (CBS) process.

M21. The method of any one of embodiments M19 to M20, wherein the copy number alteration quantification is a z-score.

M22. The method of embodiment M21, wherein the z-score for each genomic portion is the z-score for a segment identified by the segmentation process that includes the genomic portion.

M23. The method of any of embodiments M21 to M22, wherein the z-score is determined according to:

$$z\text{-score}=(S_{scr}-S_{mcr})/\text{MAD}$$

wherein:

the Sscr is a test sample count representation of a segment, and the Sscr is the total normalized counts in the segment divided by the total normalized autosome counts for the test sample;

the Smcr is a median count representation for the segment generated for a reference set of samples; and the MAD is a median absolute deviation determined for the count representation of the segment for the reference set of samples.

M24. The method of any of embodiments M2 to M23, where performing the principal component transformation forms a principal component space.

M25. The method of any of embodiments M1 to M24, wherein test sample is determined as comprising a cancer when the distance of the sample from the common principal component origin shared by a plurality of samples in the principal component space is greater than a pre-determined threshold.

M26. The method of embodiment M25, wherein the distance is a Mahalanobis distance and the threshold is greater than 300.

M27. The method of any of embodiments M1 to M26, wherein the test sample is determined as comprising trisomy 21, trisomy 18 or trisomy 13, when the sample is among a group of samples that follow a distinct pattern, wherein the distinct pattern is a vector in a two dimensional principal component space, a plane in a three dimensional principal component space, or a hyperplane in a n-dimension principal component space.

M28. A method for generating a genomic instability classification for sample nucleic acid from a test subject, comprising:
 providing a set of genomic portions of a reference genome to which sequence reads obtained for sample nucleic acid from the test subject have been mapped, and for which the sequence reads mapped to the genomic portions have been quantified;
 adjusting, by a computing device, the quantified sequence reads for each of the genomic portions by an adjustment process that reduces experimental bias, thereby providing an adjusted quantification of sequence reads for each of the genomic portions; and
 generating, by the computing device, a genomic instability classification for the test sample according to the adjusted quantification of sequence reads for the genomic portions.

M29. The method of embodiment M28, wherein the generating comprises modifying the adjusted quantification of sequence reads according to a baseline adjusted quantification of sequence reads for each of the genomic portions, thereby providing a modified product for each of the genomic portions.

M30. The method of any one of embodiments M28 to M29, wherein the generating comprises subtracting a baseline adjusted quantification of sequence reads from the adjusted quantification of sequence reads for each of the genomic portions, thereby providing a subtraction product for each of the genomic portions.

M31. The method of embodiment M30, further comprising determining, by the computing device, the absolute value of the modified product or the subtraction product for each of the genomic portions.

M32. The method of any one of embodiments M28 to M31 wherein the baseline is (i) an average adjusted quantification of sequence reads for the genomic portions, (ii) a centered value of the adjusted quantification of sequence reads for the genomic portions, or (iii) a representative value of the adjusted quantification of sequence reads for the genomic portions.

M33. The method of embodiment M32, wherein the average is a mean, median or mode of the adjusted quantification of sequence reads for the genomic portions.

M34. The method of any one of embodiments M32 to M33, further comprising scaling, by the computing device, the adjusted quantification of sequence reads for the genomic portions to the average, centered value or representative value.

M35. The method of any one of embodiments M28 to M34, wherein the generating comprises summing the modified products, absolute values of the modified products, subtraction products or absolute values of the subtraction products for the genomic portions, thereby providing a genomic instability number.

M36. The method of embodiment M35, wherein the genomic instability classification is based on the genomic instability number.

M37. The method of embodiment M35, wherein the genomic instability classification is the genomic instability number.

M38. The method of any one of embodiments M35 to M37, wherein the magnitude of the genomic instability number is based on the number of copy number variations in the sample nucleic acid, the magnitude of the copy number variations in the sample nucleic acid, and the portion of nucleic acid in the sample nucleic acid bearing each of the copy number variations.

M39. The method of any one of embodiments M35 to M38, wherein:
 a presence of genomic instability is classified according to a genomic instability number above a cutoff value; and
 an absence of genomic instability is classified according to a genomic instability number below the cutoff value.

M40. The method of embodiments M28 to M39, wherein the method comprises identifying a copy number alteration coupled to the genomic portions according to a copy number alteration quantification obtained for the genomic portions.

M41. The method of embodiment M39, wherein the copy number alteration quantification is a z-score.

M42. The method of any one of embodiments M28 to M41, comprising:
 filtering, by the computing device, from the set of genomic portions a subset of portions having selected features, thereby generating a set of filtered genomic portions not containing the subset of portions having the selected features;
 transforming, by the computing device, the set of filtered genomic portions to a reduced set of parameters, wherein the transforming comprises:
 performing a principal component transformation that yields principal component values for the sample nucleic acid, and
 determining a distance from a common principal component origin for the sample nucleic acid; and
 classifying, by the computing device, genomic instability for the subject according to the distance.

M43. The method of embodiment M42, wherein the filtering comprises filtering from the set of genomic portions:
 (i) a first subset of portions associated with copy number alterations consistently presented in a reference set of samples, and (ii) a second subset of portions other than representative portions derived from groups of portions identified by a clustering process applied to a reference set of samples, thereby generating the set of filtered genomic portions, wherein the set of filtered genomic portions does not contain the first subset of portions and the second subset of portions.

M44. The method of any one of embodiments M28 to M43, wherein the subject is diagnosed with a cell proliferative condition according to the genomic instability classification and the subject is selected for a treatment of the cell proliferative condition according to the genomic instability classification.

M45. The method of embodiment M44, wherein the genomic instability classification is generated for the subject at two or more time points during the treatment; and (i) the subject is identified as a responder to the treatment if after a time point of about 6 weeks to about 8 weeks of treatment the genomic instability classification is less than a threshold value, or (ii) the subject is identified as a non-responder to the treatment if after the time point of treatment the genomic instability classification is greater than the threshold value.

M46. The method of embodiment M45, wherein the genomic instability classification is a genomic instability number or is based on a genomic instability number.

M47. The method of any one of embodiments M44 to M46, wherein the cell proliferative disorder is a cancer.

M48. The method of any one of embodiments M44 to M47, wherein the treatment comprises administering an immunotherapeutic.

M49. The method of embodiment M48, wherein the immunotherapeutic comprises a checkpoint inhibitor.

M50. The method of any of embodiments M1 to M49, wherein the genomic portions are about 50 kilobases in length.

M51. The method of any of embodiments M1 to M50, wherein the genomic portions do not overlap.

M52. The method of embodiment M51, wherein the 3' ends of the genomic portions abut the 5' ends of adjacent genomic portions.

M53. The method of any of embodiments M1 to M52, further comprising generating, by the computing device, the sequence reads from the nucleic acid sample by a sequencing process.

M54. The method of any of embodiments M1 to M53, wherein the quantification of the sequence reads mapped to each of the genomic portions is a count or read density.

M55. The method of any one of embodiments M3 to M54, wherein the adjusting comprises normalizing the quantification of sequence reads by a guanine-cytosine (GC) normalizing process that generates a GC normalized quantification of sequence reads for each of the genomic portions, whereby the adjusted quantification of sequence reads in (b) is the GC normalized quantification of sequence reads.

M56. The method of embodiment M55, wherein the GC normalizing process comprises LOESS, GCRM or combination thereof.

M57. The method of any of embodiments M1 to M56, comprising:
obtaining the sequence reads and mapping the sequence reads to the genomic portions, thereby providing sequence reads mapped to the genomic portions; and
quantifying, by the computing device, the sequence reads mapped to each of the genomic portions, thereby generating a quantification of the sequence reads mapped to the genomic portions.

M58. The method of any of embodiments M1 to M57, wherein the set of genomic portions provided are filtered.

M59. The method of embodiment M58, wherein the filtering is based on mappability, repeat masking or combination thereof.

M60. The method of any one of embodiments M58 to M59, wherein filtering is based on variation of the quantification of sequence reads mapped to genomic portions across multiple reference samples, consistently no reads mapped to genomic portions across multiple reference samples, or combination thereof.

M61. The method of any one of the embodiments M1 to M61, wherein the sample nucleic acid from the subject is circulating cell free nucleic acid.

N1. A system comprising:
one or more processors and non-transitory machine readable storage medium;
a set of genomic portions each coupled to a copy number alteration quantification for a test sample, wherein the genomic portions comprise portions of a reference genome to which sequence reads obtained for sample nucleic acid from the test subject have been mapped, the copy number alteration quantification coupled to each genomic portion has been determined from a quantification of sequence reads mapped to the genomic portion, and the set of genomic portions are stored on the non-transitory machine readable storage medium;
program instructions to filter from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and the second subset of portions; and
program instructions to determine a presence or absence of genomic instability for the test subject according to the copy number alteration quantifications coupled to the filtered genomic portions, wherein the program instructions are stored on the non-transitory machine readable storage medium for execution by the one or more processors.

N2. The system of embodiment N1, further comprising:
program instructions for transforming the set of filtered genomic portions to a reduced set of parameters, wherein the transforming comprises performing a principal component transformation that yields principal components for the test sample, and
determining a distance from a common principal component origin for the test sample; and program instructions for determining a distance between the principal components of the test sample from a common principal component origin.

O1. A non-transitory machine readable storage medium comprising:
a set of genomic portions each coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion; and program instructions that when executed by one or more processors cause the one or more processors to perform a method comprising:

filtering from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and the second subset of portions; and determining presence or absence of genomic instability for the test subject according to the copy number alteration qualifications coupled to the filtered genomic portions.

O2. The non-transitory machine readable storage medium of embodiment O1, wherein the medium further comprises:

program Instructions for transforming the set of filtered genomic portions to a reduced set of parameters, wherein the transforming comprises performing a principal component transformation that yields principal components for the test sample; and determining a distance from a common principal component origin for the test sample; and determining a distance between the principal components of the test sample from a common principal component origin.

P1. A system comprising:

one or more processors and non-transitory machine readable storage medium;

a set of genomic portions of a reference genome to which sequence reads obtained for sample nucleic acid from the test subject have been mapped, and for which the sequence reads mapped to the genomic portions have been quantified, wherein the set of genomic portions are stored on the non-transitory machine readable storage medium;

program instructions to adjust the quantified sequence reads for each of the genomic portions by an adjustment process that reduces experimental bias, wherein the adjustment process generates a normalized quantification of sequence reads for each of the genomic portions; and program instructions to generate a genomic instability classification for the test sample according to the normalized quantification of sequence reads for each of the genomic portions, wherein the program instructions are stored on the non-transitory machine readable storage medium for execution by the one or more processors.

P2. The system of embodiment P1, wherein the program instructions to reduce experimental bias is according to a GC normalized quantification of sequence reads.

Q1. A non-transitory machine readable storage medium comprising:

a set of genomic portions of a reference genome to which sequence reads obtained for sample nucleic acid from the test subject have been mapped, and for which the sequence reads mapped to the genomic portions have been quantified;

program instructions that when executed by one or more processors cause the one or more processors to perform a method comprising:

adjusting the quantified sequence reads for each of the genomic portions by an adjustment process that reduces experimental bias, wherein the adjustment process generates a normalized quantification of sequence reads for each of the genomic portions; and generating a genomic instability classification for the test sample according to the normalized quantification of sequence reads for each of the genomic portions.

Q2. The medium of embodiment Q1, wherein the instructions to reduce experimental bias is according to a GC normalized quantification of sequence reads.

R1. A method of determining presence or absence of genomic instability for a test subject, comprising:

providing a set of genomic portions each coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion; and determining, by a computing device, presence or absence of genomic instability for the test subject according to the copy number alteration quantifications coupled to the genomic portions.

R2. The method of embodiment R1, further comprising filtering, by the computing device, from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and/or the second subset of portions R3. The method of any of embodiments R1 to R2, further comprising adjusting, by the computing device, the quantified sequence reads for each of the genomic portions by an adjustment process that reduces experimental bias, thereby providing an adjusted quantification of sequence reads for each of the genomic portions.

R4. The method of any of embodiments R1 to R3, further comprising generating, by the computing device, a genomic instability classification for the test sample according to the adjusted quantification of sequence reads for the genomic portions.

R5. The method of any of embodiments R1 to R4, wherein the determining comprises:

transforming the set of genomic portions to a reduced set of parameters, wherein the transforming comprises performing a principal component transformation of the set of genomic portions that yields principal components for the test sample, and determining a distance between the principal components of the test sample from a common principal component origin.

R6. The method of embodiment R5, wherein the distance is a normalized distance generated according to variance of principal components for a set of training samples, and determining the presence or absence of genomic instability is based on the normalized distance.

R7. The method of embodiment R6, wherein the set of training samples comprises or consists of samples classified as not having genomic instability.

R8. The method of any of embodiments R5 to R7, wherein performing the principal component transformation forms a principal component space.

R9. The method of any of embodiments R1 to R8, wherein test sample is determined as comprising a cancer when the distance of the sample from the common principal component origin shared by a plurality of samples in the principal component space is greater than a pre-determined threshold.

R10. The method of embodiment R9, wherein the distance is a Mahalanobis distance and the threshold is greater than 300.

R11. The method of any of embodiments R1 to R10, wherein the test sample is determined as comprising trisomy 21, trisomy 18 or trisomy 13, when the sample is among a group of samples that follow a distinct pattern, wherein the distinct pattern is a vector in a two dimensional principal component space, a plane in a three dimensional principal component space, or a hyperplane in a n-dimension principal component space.

R12. The method of any of embodiments R5 to R10, wherein the reduced set of parameters contains fewer dimensions than dimensions of the set of filtered genomic portions.

R13. The method of any of embodiments R5 to R12, wherein the clustering comprises:
  generating, by the computing device, a matrix comprising the genomic portions and the samples in the reference set of samples;
  generating, by the computing device, pair-wise correlation values from the matrix, wherein there is one correlation value for each pair of the portions; and
  clustering, by the computing device, the portions into groups according to the correlation values.

R14. The method of any one of embodiments R1 to R13, wherein the copy number alteration quantification coupled to each of the genomic portions for the test sample is obtained by a process comprising a segmentation process.

R15. The method of embodiment R14, wherein the segmentation process comprises a circular binary segmentation (CBS) process.

R16. The method of any of embodiments R14 to R15, wherein the copy number alteration quantification is a z-score.

R17. The method of embodiment R16, wherein the z-score for each genomic portion is the z-score for a segment identified by the segmentation process that includes the genomic portion.

R18. The method of embodiment R17, wherein the z-score is determined according to:

$$z\text{-score}=(S_{scr}-S_{mcr})/\text{MAD}$$

wherein:
  the Sscr is a test sample count representation of a segment, and the Sscr is the total normalized counts in the segment divided by the total normalized autosome counts for the test sample;
  the Smcr is a median count representation for the segment generated for a reference set of samples; and
  the MAD is a median absolute deviation determined for the count representation of the segment for the reference set of samples.

R19. The method of any of embodiments R3 to R18, wherein generating a genomic instability classification comprises modifying the adjusted quantification of sequence reads according to a baseline adjusted quantification of sequence reads for each of the genomic portions, thereby providing a modified product for each of the genomic portions.

R20. The method of any of embodiments R4 to R19, wherein the generating a genomic instability classification comprises subtracting a baseline adjusted quantification of sequence reads from the adjusted quantification of sequence reads for each of the genomic portions, thereby providing a subtraction product for each of the genomic portions.

R21. The method of any of embodiments R19 to R20, further comprising determining, by the computing device, the absolute value of the modified product or the subtraction product for each of the genomic portions.

R22. The method of any of embodiments R19 to R21 wherein the baseline is (i) an average adjusted quantification of sequence reads for the genomic portions, (ii) a centered value of the adjusted quantification of sequence reads for the genomic portions, or (iii) a representative value of the adjusted quantification of sequence reads for the genomic portions.

R23. The method of any of embodiments R3 to R22, further comprising scaling, by the computing device, the adjusted quantification of sequence reads for the genomic portions to the average, centered value or representative value.

R24. The method of any of embodiments R3 to R23, wherein the generating a genomic instability classification comprises summing the modified products, absolute values of the modified products, subtraction products or absolute values of the subtraction products for the genomic portions, thereby providing a genomic instability number.

R25. The method of any of embodiments R3 to R24, wherein the adjusting comprises normalizing the quantification of sequence reads by a guanine-cytosine (GC) normalizing process that generates a GC normalized quantification of sequence reads for each of the genomic portions, whereby the adjusted quantification of sequence reads in (b) is the GC normalized quantification of sequence reads.

R26. The method of any of embodiments R1 to R25, wherein the subject is diagnosed with a cell proliferative condition according to the genomic instability classification, and the subject is selected for a treatment of the cell proliferative condition according to the genomic instability classification.

R27. The method of embodiment R26, wherein the genomic instability classification is generated for the subject at two or more time points during the treatment, and (i) the subject is identified as a responder to the treatment if after a time point of about 6 weeks to about 8 weeks of treatment the genomic instability classification is less than a threshold value, or (ii) the subject is identified as a non-responder to the treatment if after the time point of treatment the genomic instability classification is greater than the threshold value.

R28. The method of any one of embodiments R26 to R27, wherein the cell proliferative disorder is a cancer.

R29. The method of any one of embodiments R26 to R27, wherein the treatment comprises administering at least one of an immunotherapeutic or a checkpoint inhibitor.

R30. The method of any one of embodiments R1 to R29, wherein the sample nucleic acid from the subject is circulating cell free nucleic acid.

S1. A system comprising:
  one or more processors and non-transitory machine readable storage medium;
  a set of genomic portions each coupled to a copy number alteration quantification for a test sample, wherein the genomic portions comprise portions of a reference genome to which sequence reads obtained for sample nucleic acid from the test subject have been mapped, the copy number alteration quantification coupled to each genomic portion has been determined from a quantification of sequence reads mapped to the genomic portion, and the set of genomic portions are stored on the non-transitory machine readable storage medium; and program instructions to determine a presence or absence of genomic instability for the test subject according to the copy number alteration quantifications coupled to the filtered genomic portions, wherein the program instructions are stored on the non-transitory machine readable storage medium for execution by the one or more processors.

S2. The system of embodiment S1, further comprising:

program instructions to filter from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and the second subset of portions wherein the program instructions are stored on the non-transitory machine readable storage medium for execution by the one or more processors.

S3. The system of any one of embodiments S31 to S32, further comprising:

program instructions for transforming the set of filtered genomic portions to a reduced set of parameters, wherein the transforming comprises performing a principal component transformation that yields principal components for the test sample, and determining a distance from a common principal component origin for the test sample; and program instructions for determining a distance between the principal components of the test sample from a common principal component origin wherein the program instructions are stored on the non-transitory machine readable storage medium for execution by the one or more processors.

S4. The system of any of embodiments S1 to S3, further comprising program instructions to adjust the quantified sequence reads for each of the genomic portions by an adjustment process that reduces experimental bias, wherein the adjustment process generates a normalized quantification of sequence reads for each of the genomic portions wherein the program instructions are stored on the non-transitory machine readable storage medium for execution by the one or more processors.

S5. The system of any of embodiments S1 to S4, further comprising program instructions to generate a genomic instability classification for the test sample according to the normalized quantification of sequence reads for each of the genomic portions, wherein the program instructions are stored on the non-transitory machine readable storage medium for execution by the one or more processors.

S6. The system of embodiment S5, wherein the program instructions to reduce experimental bias is according to a GC normalized quantification of sequence reads.

T1. A non-transitory machine readable storage medium comprising:

a set of genomic portions each coupled to a copy number alteration quantification for a test sample, wherein the genomic portions comprise portions of a reference genome to which sequence reads obtained for sample nucleic acid from the test subject have been mapped, and the copy number alteration quantification coupled to each genomic portion has been determined from a quantification of sequence reads mapped to the genomic portion; and program instructions that when executed by one or more processors cause the one or more processors to perform a method comprising: determining presence or absence of genomic instability for the test subject according to the copy number alteration qualifications coupled to the genomic portions.

T2. The non-transitory machine readable storage medium of claim T1, wherein the medium further comprises:

program instructions that when executed by one or more processors cause the one or more processors to perform a method comprising filtering from the set of genomic portions: (i) a first subset of portions associated with copy number alterations consistently presented in a reference set of samples, and/or (ii) a second subset of portions other than representative portions derived from groups of portions identified by a clustering process applied to a reference set of samples, thereby generating a set of filtered genomic portions not containing the first subset of portions and the second subset of portions.

T3. The non-transitory machine readable storage medium of any one of embodiments T1 to T2, wherein the medium further comprises:

program Instructions for transforming a set of genomic portions to a reduced set of parameters, wherein the transforming comprises:

performing a principal component transformation that yields principal components for the test sample, determining a distance from a common principal component origin for the test sample; and determining a distance between the principal components of the test sample from a common principal component origin.

T4. The non-transitory machine readable storage medium of any of embodiments T1 to T3, further comprising:

program instructions that when executed by one or more processors cause the one or more processors to perform a method comprising adjusting the quantified sequence reads for each of the genomic portions by an adjustment process that reduces experimental bias, wherein the adjustment process generates a normalized quantification of sequence reads for each of the genomic portions.

T5. The non-transitory machine readable storage medium of any of embodiments T1 to T4, further comprising program instructions that when executed by one or more processors cause the one or more processors to perform a method comprising generating a genomic instability classification for the test sample according to the normalized quantification of sequence reads for each of the genomic portions.

T6. The non-transitory machine readable storage medium of embodiment T5, wherein the instructions to reduce experimental bias is according to a GC normalized quantification of sequence reads.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The terms "method" and "process" are used interchangeably herein. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method of determining presence or absence of genomic instability for a subject, comprising:
   i) mapping thousands to millions of sequence reads obtained from a nucleic acid sample obtained from the subject to a set of genomic portions of a reference genome,
   ii) determining a copy number alteration quantification based on a quantification of sequence reads mapped to each genomic portion of the set;
   iii) filtering, by a computing device, from the set of genomic portions: (a) a first subset of genomic portions associated with copy number alterations presented in a reference set of samples, (b) a second subset of genomic portions that are not representative portions derived from groups of portions identified by a clustering process applied to the reference set of samples, or both (a) and (b), thereby generating a set of filtered genomic portions coupled to copy number alteration quantifications, wherein the set of filtered genomic portions do not contain the first subset of portions, do not contain the second subset of portions, or contain neither the first subset nor the second subset of genomic portions; and
   iv) determining, by a computing device, the presence or absence of genomic instability for the subject according to the copy number alteration quantifications coupled to the filtered genomic portions from the nucleic acid sample from the subject.

2. The method of claim 1, wherein step i) further comprises:
   obtaining the thousands to millions of sequence reads for the set of genomic portions of the nucleic acid sample from the subject, and generating the copy number alteration quantification for each genomic portion by quantifying the number of sequence reads mapped to the genomic portion in the nucleic acid sample.

3. The method of claim 1, wherein the clustering process comprises:
   generating, by the computing device, a matrix comprising the genomic portions and identifying information of the reference set of samples as rows and columns of the matrix;
   generating, by the computing device, pair-wise correlation values from the matrix, wherein there is one correlation value for each possible pair of the portions; and
   clustering, by the computing device, the portions into groups according to the correlation values.

4. The method of claim 1, further comprising adjusting the quantification of the sequence reads by a guanine-cytosine (GC) normalizing process that generates a GC normalized quantification of sequence reads for each of the genomic portions, thereby providing an adjusted quantification of sequence reads.

5. The method of claim 4, wherein the method further comprises modifying the adjusted quantification of sequence reads according to a baseline adjusted quantification of sequence reads for each of the genomic portions wherein said modification produces a modified quantification of sequence reads for each of the genomic portions, or
   wherein the method further comprises subtracting a baseline adjusted quantification of sequence reads from the adjusted quantification of sequence reads for each of the genomic portions, wherein said subtracting produces a subtracted quantification of sequence reads for each of the genomic portions.

6. The method of claim 5, further comprising determining, by the computing device, the absolute value of the modified quantification of sequence reads or the absolute value of the subtracted quantification of sequence reads-for each of the genomic portions.

7. The method of claim 5, wherein the baseline is (i) an average of the adjusted quantification of sequence reads for each of the genomic portions, (ii) a centered value of the adjusted quantification of sequence reads for each of the genomic portions, or (iii) a representative value of the adjusted quantification of sequence reads for each of the genomic portions.

8. The method of claim 7, further comprising scaling, by the computing device, the adjusted quantifications of sequence reads for the genomic portions to the average, centered value or representative value.

9. The method of claim 5, wherein the method comprises summing the modified quantification of sequence reads, the absolute values of the modified quantification of sequence reads, subtracted quantification of sequence reads or absolute values of the subtracted quantification of sequence reads for the genomic portions, thereby providing a genomic instability number.

10. The method of claim 9, wherein the genomic instability number is generated for the subject at two or more time points during a treatment, and
wherein the subject is identified as a responder to the treatment if after a time point of about 6 weeks to about 8 weeks of treatment the genomic instability number is less than a threshold value, or
wherein the subject is identified as a non-responder to the treatment if after the time point of treatment the genomic instability number is greater than the threshold value.

11. The method of claim 4, further comprising generating, by the computing device, a genomic instability classification for the nucleic acid sample according to the adjusted quantification of sequence reads for the genomic portions.

12. The method of claim 1,
wherein the determining the presence or absence of genomic instability further comprises:
transforming the set of filtered genomic portions each coupled with a copy number alteration quantification to a reduced set of dimensions, wherein the transforming comprises performing a principal component transformation of the set of genomic portions which transformation yields principal components for the nucleic acid sample in a principal component space, wherein the principal component space comprises a common principal component origin shared by the genomic portions of the reference set of samples, each coupled with a copy number alteration, and
determining a distance between the principal components of the nucleic acid sample and the common principal component origin.

13. The method of claim 12, wherein the distance is a normalized distance generated according to a variance of the principal components over a set of training samples, and wherein the method further comprises determining the presence or absence of genomic instability based on the normalized distance.

14. The method of claim 12, wherein the nucleic acid sample is determined as comprising a cancer when the distance of the sample from the common principal component origin shared by a plurality of samples in the principal component space is greater than a predetermined threshold.

15. The method of claim 14, wherein the distance is a Mahalanobis distance and the predetermined threshold is 300.

16. The method of claim 1, wherein the copy number alteration quantification coupled to each of the genomic portions for the nucleic acid sample is obtained by a segmentation process.

17. The method of claim 16, wherein the segmentation process comprises a circular binary segmentation (CBS) process.

18. The method of claim 16, wherein each copy number alteration quantification is a z-score.

19. The method of claim 18, wherein the z-score for each genomic portion is the z-score for a segment identified by the segmentation process, wherein the segment includes the genomic portion.

20. The method of claim 19, wherein the z-score is determined according to: z-score=(Sscr−Smcr)/MAD, wherein:
the Sscr is a total normalized counts in the segment divided by a total normalized autosome counts for the nucleic acid sample;
the Smcr is a median value of counts for the segment generated for the reference set of samples; and
the MAD is the median absolute deviation value determined for the counts of the segment for the reference set of samples.

21. The method of claim 1, wherein the subject is diagnosed with a cell proliferative disorder according to the determination of the presence or absence of genomic instability for the subject and the subject is selected for treatment of the cell proliferative disorder according to the determination of the presence or absence of genomic instability for the subject.

22. The method of claim 21, wherein the cell proliferative disorder is cancer.

23. The method of claim 21, wherein the treatment comprises administering at least one of an immunotherapeutic or a checkpoint inhibitor.

24. The method of claim 1, wherein the nucleic acid sample comprises circulating cell-free nucleic acid.

* * * * *